US010758626B2

(12) United States Patent
Birkett et al.

(10) Patent No.: US 10,758,626 B2
(45) Date of Patent: Sep. 1, 2020

(54) POLYMER CONJUGATE COMPRISING A BIOACTIVE AGENT

(71) Applicant: POLYACTIVA PTY LTD, Melbourne, Victoria (AU)

(72) Inventors: Stephen Lonsdale Birkett, West Brunswick (AU); Andrew Craig Donohue, Bentleigh East (AU); Asha Marina D'Souza, Carnegie (AU); Sarah Man Yee Ng, Berwick (AU); Adrian Sulistio, Glen Iris (AU); Russell John Tait, Balwyn (AU); David Valade, Coburg North (AU); Alan Naylor, Harston (GB); Anton Blencowe, Windsor Gardens (AU)

(73) Assignee: POLYACTIVA PTY LTD, Melbourne, Victoria (AU)

( * ) Notice: Subject to any disclaimer, the term of this patent is extended or adjusted under 35 U.S.C. 154(b) by 0 days.

(21) Appl. No.: 15/758,662

(22) PCT Filed: Sep. 9, 2016

(86) PCT No.: PCT/AU2016/050850
§ 371 (c)(1),
(2) Date: Mar. 8, 2018

(87) PCT Pub. No.: WO2017/041142
PCT Pub. Date: Mar. 16, 2017

(65) Prior Publication Data
US 2018/0303948 A1    Oct. 25, 2018

Related U.S. Application Data

(60) Provisional application No. 62/217,215, filed on Sep. 11, 2015.

(51) Int. Cl.
A61K 47/50     (2017.01)
A61K 31/4192   (2006.01)
A61K 31/4196   (2006.01)
A61K 31/47     (2006.01)
A61K 31/19     (2006.01)
A61K 47/59     (2017.01)
A61K 31/196    (2006.01)
A61K 47/60     (2017.01)
A61K 31/496    (2006.01)
A61K 31/407    (2006.01)
A61K 31/192    (2006.01)
A61K 31/606    (2006.01)
A61K 31/635    (2006.01)
A61P 29/00     (2006.01)
A61K 31/60     (2006.01)

(52) U.S. Cl.
CPC .......... A61K 47/595 (2017.08); A61K 31/192 (2013.01); A61K 31/196 (2013.01); A61K 31/407 (2013.01); A61K 31/496 (2013.01); A61K 31/606 (2013.01); A61K 31/635 (2013.01); A61K 47/60 (2017.08); A61K 31/47 (2013.01); A61K 31/60 (2013.01); A61K 2300/00 (2013.01); A61P 29/00 (2018.01)

(58) Field of Classification Search
None
See application file for complete search history.

(56) References Cited

U.S. PATENT DOCUMENTS

| 2002/0013345 | A1* | 1/2002 | Berman | ............... A61K 31/00 514/330 |
| 2014/0046018 | A1 | 2/2014 | O'Shea et al. | |
| 2014/0271527 | A1 | 9/2014 | Moreadith et al. | |

FOREIGN PATENT DOCUMENTS

| WO | WO-2006/138463 A2 | 12/2006 | |
| WO | WO 2014/000033 * | 1/2014 | ......... A61K 31/5383 |
| WO | WO-2014/000033 A1 | 1/2014 | |
| WO | WO-2014/004278 A1 | 1/2014 | |
| WO | WO 2014/134689 * | 9/2014 | ......... A61K 31/4192 |
| WO | WO-2014/134689 A1 | 9/2014 | |
| WO | WO-2015/114171 A1 | 8/2015 | |

* cited by examiner

Primary Examiner — Brian Gulledge
(74) Attorney, Agent, or Firm — Foley & Lardner LLP

(57) ABSTRACT

The present invention relates in general to polymer-bioactive agent conjugates for delivering a bioactive agent to a subject. The polymer-bioactive agent conjugates contain triazole moieties in the polymer backbone and a bioactive moiety selected from quinolones, NSAIDs and mixtures thereof. The present invention also relates to methods for preparing the polymer conjugates using click cycloaddition chemical reactions, to monomer-bioactive agent conjugates suitable for preparing the polymer conjugates, and to pharmaceutical products comprising the polymer conjugates for the post-surgical care to treat or prevent infections, provide analgesia and treat inflammation.

24 Claims, 5 Drawing Sheets

POLYMER CONJUGATE COMPRISING A BIOACTIVE AGENT

This application is the U.S. National Stage of International Application PCT/AU2016/050850, filed Sep. 9, 2016, which claims priority from U.S. Application 62/217,215 filed Sep. 11, 2015.

FIELD OF THE INVENTION

The present invention relates in general to polymer-bioactive agent conjugates for delivering a bioactive agent selected from quinolone antibiotics, non-steroidal anti-inflammatory drugs (NSAIDs) and mixtures of these drugs. The present invention also relates to methods for preparing the polymer conjugates, to monomer-bioactive agent conjugates suitable for preparing the polymer conjugates, and to pharmaceutical products comprising the polymer conjugates for the treatment or prevention of infections, provision of analgesia and treatment of inflammation, in particular for post-surgical care.

BACKGROUND

Quinolones are a family of antibiotics with broad spectrum antibacterial properties used to treat a wide range of infections, including both Gram-positive and Gram-negative bacterial infections. The basic pharmacophore, or active structure, of the quinolone class is based upon the quinoline ring system (Schaumann, R.; Rodloff, A. C. (January 2007). "Activities of Quinolones Against Obligately Anaerobic Bacteria" *Anti-infective Agents in Medicinal Chemistry (Formerly Current Medicinal Chemistry—Anti-Infective Agents)* (Bentham Science Publishers) 6 (1): 49-56). The majority of quinolones in clinical use are fluoroquinolones, which have a fluorine atom attached to the central ring system, typically at the 6-position.

Non-steroidal anti-inflammatory drugs (NSAIDs) are an important therapeutic class of drugs also commonly used in the control of inflammation and provide analgesia in a range of diseases and following surgical intervention. For example NSAIDs are increasingly being used in ophthalmology practice in treating a range of conditions and as a preventative measure following surgery. NSAID drops have been found to ameliorate pain and reduce the signs of ocular inflammation, including postoperative cells and flare within the anterior chamber following ocular surgery (Kabat and Sowka Review of Optometry (2013) June 16 and references sited therein). They have also been found to reduce the incidence of cystoid macular oedema (CME).

Many of the existing drug delivery systems are only effective at delivering drugs that have molecular masses that are only up to a few hundred Daltons, exhibit octanol-water partition coefficients that heavily favor lipids and require doses of milligrams per day or less (Prausnitz M R, Mitragotri S, Langer R. *Current status and future potential of transdermal drug delivery.* Nat Rev Drug Discov. 2004; 3:115-124). Such systems are ineffective at delivering low potency and hydrophilic drugs. Almost all antiobitics require doses of tens of milligrams per day or more and are relatively hydrophilic drugs. It is desirable to be able to deliver such antibiotics directly to the site of infection in a controlled manner over an extended period of time.

To treat eye infection fluoroquinolone antibiotics are presently formulated as eye drops, which if administered conscientiously to the affected eye will prevent infection or treat an established infection. The fluoroquinolone antibiotics are administered as eye drops, either alone (i.e. as a single agent) or in combination. For example, some pharmaceutical preparations used in post-surgical eye care, such as Ciloxan™, Zymar™, Zymaxid™, Quixan™, LQuix™ and Vigamox™ eye drops marketed by Alcon, Allergan, Allergan, Vistakon Pharmaceuticals LLC, Santen, and Alcon, respectively, Acular™, marketed by Allergan and Prolensa™ and Bromday™ eye drops marketed by ISTA Pharmaceuticals.

It is postulated that combining quinolones with non-steroidal anti-inflammatory drugs (NSAIDs), may provide an additive effect in post-surgical care by both preventing infection, providing analgesia and treating inflammation.

Unfortunately, as ocular surgery is more prevalent in the elderly many patients do not have the drop competence to administer their drops effectively, compromising therapy. A recent study by An et al showed that drop competence in the elderly is poor with only 7.4% of patients capable of administering their drops effectively following cataract surgery (An J A, Kasner O, Samek D A, Levesque V. *Evaluation of eye drop administration by inexperienced patient after cataract surgery.* J Cataract Refract Surg., 2014; 40:1857-1861). Drop competence in post-surgical drop therapy is therefore an issue.

Drug delivery systems have been developed to aid in the administration and/or sustained delivery of bioactive agents (such as drugs) to a desired site of action. One mode of delivering a drug to a subject involves the use of a polymer in association with the drug so that it can be delivered to and/or retained at a specific location.

One form of a polymer/drug delivery system utilises an admixture of a polymer with a drug, where the drug is blended with the polymer matrix. However, such admixtures generally result in poor control over the release of the drug, with a "burst effect" often occurring immediately after administration and significant changes in the physical properties of the admixture occurring as the drug is released (Sjoquist, B.; Basu, S.; Byding, P.; Bergh, K.; Stjernschantz, J. *Drug Metab. Dispos.* 1998, 26, 745.). In addition, such admixtures have limited dose loading capacity, resulting in a prohibitively large device for convenient administration to some sites in a subject. As more drugs are added the system becomes more complex and the ability to control the release of each drug more difficult.

Polymer-bioactive agent conjugates, offer one approach that has been used in an attempt to provide targeted drug delivery of NSAIDs and fluoroquinolones. Polymer-bioactive agent conjugates can be prepared by covalently reacting a bioactive agent-functionalised monomer having at least two terminal reactive functional groups, with a co-monomer of complementary terminal functionality. An example is the reaction of a drug-functionalised dihydroxy monomer with a diisocyanate co-monomer to form a polymer-drug conjugate with a polyurethane polymer backbone. However, one problem with polymerisation methods is that the NSAIDs and quinolones which contain multiple nucleophilic functional groups may react with a terminal functional group of a monomer, leading to intra-chain incorporation of the bioactive agent in the polymer. As a result, the bioactive agent becomes part of the polymer backbone structure, rather than forming a pendant group.

Systems which take advantage of the option of in chain incorporations are described in U.S. Pat. No. 6,613,807, WO2008/128193, WO94/04593 and U.S. Pat. No. 7,122,615. However, such polymer systems generally provide inefficient delivery of the drug, as release of the drug relies on breakdown of the polymer backbone. Furthermore, breakdown of the polymer backbone produces inactive intermediates. Such intermediates can complicate regulatory approval, which may require the safety of the intermediates to be demonstrated. Also this strategy does not readily allow for multiple drugs to be incorporated due to differences in reactivity and biodegradation.

For efficient delivery, bioactive agents such as drugs are ideally pendant from the backbone polymer chain. One approach for preparing pendant active agent conjugates involves the covalent attachment of bioactive agent molecules to a pre-formed polymer backbone. Examples of such polymer conjugates have been reviewed in *Nature Reviews: Drug Discovery* 2003:2, 347-360. However, this approach can also be problematic. In particular, steric and thermodynamic constraints can affect the amount of bioactive agent that can be covalently attached, and also impact on the distribution of the bioactive agent along the polymer backbone. These factors can, in turn, reduce control over the release of the bioactive agent. Furthermore, the use of a pre-formed polymer backbone provides limited scope for modification of the polymer conjugate after attachment of the bioactive agent should the properties of the conjugate need to be adjusted to improve drug release and/or to aid patient comfort, particularly in the eye.

In US2015/0150999, we have shown that NSAIDs of the aryl carboxylic acid class may be conjugated pendant to a polyurethane-ester backbone through the carboxylic acid of the NSAID. To ensure therapeutic levels of drug release the NSAID need to be conjugated to the polymer backbone via an aryl ester. It was also found that the desired level of release often called for the use of relatively high stoichiometric amounts of a hydrophilic component (e.g. PEG), which in turn limits the maximum dose load that can be achieved. Moroever, there was a risk of in-chain incorporation for any NSAID that had another nucleophilic functional group (e.g. diclofenac or bromfenac) during the step-growth polymerisation process used to make the conjugate.

Flouroquinolone-polymer conjugates have been described by Parwe et al (Parwe et al Int J Nanomed (2014) Vol 9 pp 1463-1477), Roseeuw et al (Roseeuw et al Antimcrobial Agents and Chemotherapy (2003) Vol 47(11) pp 3435-1441), Gac-Bretin et al (Gac-Bretin et al J Drug Targeting (2004) Vol 12(5) pp 297-307) and Schmidt et al (Schmidt al Bioconjugate Chem (2015) Vol 26(9) pp 1950-1962) and in all cases the fluoroquinolone is conjugated through an amine functionality opposite to the common carboxylic acid functional group of the fluoroquinolone. The precise linkage used varies with each fluoroquinolone according to the precise amine functional group of each fluoroquinolone. It would be advantageous to use the common carboxylic acid associated with the fluoroquinolone moiety so the delivery system may the broadly applicable to all fluoroquinolones of the class and ensure the rate of delivery of the fluoroquinolone is consistent across all drugs in the class.

It is also desirable to provide a polymer structure which allows manufacturers to achieve high loadings of the drugs pendant to the backbone. Polymerisation of a number of co-monomers, in addition to an active monomer, is frequently required in many systems in order to provide optimal biodegradation of the backbone and the required rate of drug release. This can result in blocks of inactive monomer and generally reduces the dose load of the active monomer units. It would be advantageous to increase the drug load by reducing the number of monomer components required to make the drug-polymer conjugate.

It is also desirable to use a polymer structure which allows manufacturers to achieve consistent stoichiometry of each monomer component used to make the final conjugate. A propensity for uneven distribution of monomer components through the final backbone exists if more than one monomer is used to make the final conjugate. For example, use of an active drug-monomer diol and PEG diol with a common diisocynate comonomer can result in block-polymer character due to differences in the reactivity of the active drug-monomer diol and PEG diol. A propensity of uneven distribution may contribute to batch-to-batch variation in manufacture of the conjugate.

It would be desirable to provide new polymer-bioactive agent conjugates, which address or ameliorate one or more disadvantages or shortcomings associated with existing materials and/or their method of manufacture, or to at least provide a useful alternative to such materials and their method of manufacture.

SUMMARY OF THE INVENTION

The present invention provides in one aspect, a polymer-bioactive agent conjugate comprising a polymer backbone comprising a plurality of triazole moieties, and a plurality of releasable bioactive agents covalently bonded to and pendant from the polymer backbone, wherein the bioactive moieties are selected from the group consisting of quinolones, NSAIDs and mixtures thereof.

Polymer-bioactive agent conjugates of the invention are obtained through the use of click chemistry, in particular through the application of variants of the Huisgen 1,3 dipolar cycloaddition of azides and alkynes. With click chemistry, at least two co-monomers of appropriate complementary terminal functionality covalently react to form the polymer-bioactive agent conjugate. At least one of the co-monomers carries a pendant bioactive agent. The triazole moieties present in the polymer backbone of the polymer-bioactive agent conjugate are reaction products obtained from the covalent coupling of terminal functional groups present on the co-monomers. Thus, the covalent reaction between the co-monomers results in the formation of a polymer-bioactive agent conjugate comprising a polymer backbone and bioactive agents pendant from the polymer backbone, together with triazole moieties in the polymer backbone structure.

In some embodiments, polymer-bioactive agent conjugates of the invention comprise a moiety of formula (I):

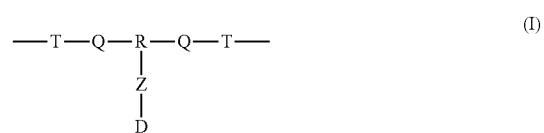

where:
T at each occurrence represents a triazole moiety;
Q is independently selected at each occurrence and may be present or absent and when present represents a linking group;
R is an optionally substituted linear or branched hydrocarbon and may comprise optionally substituted aromatic hydrocarbon or heteroaromatic hydrocarbon
Z is a cleavable linking group; and
D is the releasable bioactive agent.

In some embodiments, polymer-bioactive agent conjugates of the invention comprise a moiety of formula (Ib):

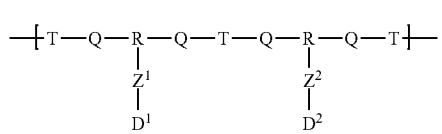

(Ib)

where:

T at each occurrence represents a triazole moiety;

Q is independently selected at each occurrence may be present or absent and when present represents a linking group;

R is an optionally substituted linear or branched hydrocarbon and may comprise optionally substituted aromatic hydrocarbon and or heteroaromatic hydrocarbon;

$Z^1$ and $Z^2$ are each cleavable linking groups that may be the same or different; and $D^1$ and $D^2$ are each the releasable bioactive agents that may be the same or different.

In formulae (I) and (Ib), the bioactive agents are independently selected from the group consisting of quinolones, NSAIDs and mixtures thereof.

Triazole moieties present in the polymer backbone of the polymer-bioactive agent conjugates, which are the product of an azideialkyne coupling, are 1,2,3-triazole moieties.

A polymer-bioactive agent conjugate according to one aspect of the invention comprises a bioactive agent selected from quinolones. The quinolone is preferably of the fluoroquinolone class. The quinolone is conjugated to the polymer backbone at the carboxyl (COOH) group of the quinolone. The quinolone may be conjugated to the polymer backbone via a range of groups which form an ester with the carbonyl of the quinolone carboxyl. In preferred set of embodiments the quinolone may be linked to the backbone via an ester selected from the group consisting of alkyl ester, aryl ester, (acyloxy)alkyl ester, [(alkoxycarbonyl)oxy]alkyl ester, and [(aryloxycarbonyl)oxy]alky ester linking groups. In a further preferred set of embodiments the quinolone may be linked to the backbone via an anhydride selected from the group consisting of alkyl anhydride and aryl anhydride linking groups.

In one set of embodiments, the bioactive agent is selected from quinolones of formula (Xi) or (Xii):

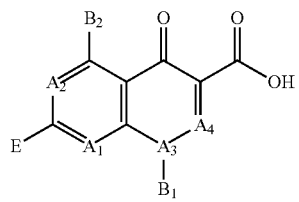

(Xi)

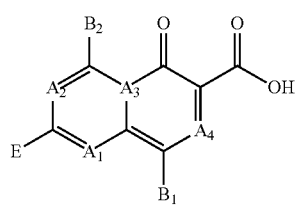

(Xii)

where:

$A_1$ is selected from N or —$CY_1$— where $Y_1$ is hydrogen, halogen (particularly chloro or fluoro), alkyl (particularly $C_1$ to $C_4$ alkyl), haloalkyl (particularly $C_1$ to $C_4$ alkyl substituted with one to three halo selected from chloro and fluoro) —O-alkyl (particularly $C_1$ to $C_4$ alkoxy), halo($C_1$ to $C_4$alkoxy) (preferable fluoroalkoxy such as difluoromethoxyl), —S-alkyl, nitrile, an amine, an amino radical, $NO_2$, and the group wherein $Y_1$ forms a bridge with $B_1$ (preferably a 3 membered bridge selected from methylene, nitrogen and oxygen and sulphur wherein the bridge is optionally substituted by $C_1$ to $C_4$ alkyl such as trimethylene optionally substituted by $C_1$ to $C_4$ alkyl);

$A_2$ is selected from N or —$CY_2$— where $Y_2$ is selected from the group consisting of hydrogen, halogen, alkyl (preferably $C_1$ to $C_4$ alkyl), —O-alkyl (preferably $C_1$ to $C_4$ alkoxy), —S-alkyl, an amine, an amino radical, $NO_2$ and the group wherein $Y_2$ forms a bridge with E (preferably a 3 membered bridge such as methylene dioxo);

$A_3$ is selected from N or —C— (preferably N;

$A_4$ is selected from the group consisting of N, —$CB_3$ wherein $B_3$ is H or together with $B_1$ forms a bridge —$B_3$—$B_1$— wherein $B_3$ is —S— and $B_1$ is —CH($B_4$)— where $B_4$ is H or methyl (preferably in the bridge forming embodiment the compound is of formula Xia and $A_3$ is N);

$B_1$ is selected from the group consisting of hydrogen, alkyl (preferably $C_1$ to $C_4$ alkyl), substituted alkyl (preferably halo-$C_1$ to $C_4$ alkyl such as fluoro $C_1$ to $C_4$ alkyl), optionally substituted cycloalkyl (preferably cyclopropyl and fluorocyclopropyl) aryl (preferably phenyl), substituted aryl (preferably haloaryl such as 4-fluorophenyl and 2,4-difluorophenyl), heteroaryl (such as pyridyl), substituted heteroaryl such as 2-pyridyl substituted with one to three substituents selected from fluoro-$C_1$ to $C_4$ alkyl and amino); —O-alkyl (preferably $C_1$ to $C_4$ alkoxy); and wherein $B_1$ may form a bridge with $A_1$ (preferably a 3 membered bridge selected from methylene, nitrogen and oxygen and sulfur wherein the bridge is optionally substituted by one or two $C_1$ to $C_4$ alkyl) or a bridge with $B_3$ (when $A_4$ is $CB_3$) wherein in the bridge —$B_3$—$B_1$— the group $B_3$ is —S— and $B_1$ is —CH($B_4$)— where $B_4$ is H or methyl (preferably in the —$B_3$—$B_1$— bridge forming embodiment the compound is of formula Xia and $A_3$ is N);

$B_2$ is hydrogen, halogen, —OH, —$CH_3$, or an amino radical

E is selected from hydrogen; halogen (preferably fluoro or chloro); alkyl (preferably $C_1$ to $C_4$ alkyl); optionally substituted aryl (preferably optionally substituted phenyl or pridyl wherein substituted phenyl and substituted pyridyl preferably comprise one to three substituents independently selected from the group consisting of $C_1$ to $C_4$ alkyl, ($C_1$ to $C_4$ alkylamino, $C_1$ to $C_4$ alkoxy and hydroxyl); alkoxy (preferably $C_1$ to $C_4$ alkoxy); amino radical preferably an optionally substituted heterocyclic or heterobicyclic of 4 to 9 constituent ring or fused ring members and comprising one or two nitrogens and optionally one of oxygen or sulfur atoms (preferred optional substituents include one to three substituents selected from the group consisting of $C_1$ to $C_4$ alkyl, spiro $C_3$ to $C_5$ cycloalkyl, amino, hydroxyl, $C_1$ to $C_4$ alkylamino, 1-methyl-7-[4-(5-methyl-2-oxo-1,3-dioxolen-4-yl)methyl, 3-(Aminomethyl)-4-methoxyimino and may optionally comprise a methylene bridge; and the group wherein $A_2$ forms a bridge with E (preferably a 3 membered bridge such as methylene dioxo).

A polymer-bioactive agent conjugate according to one aspect of the invention comprises a bioactive agent selected from non-steroidal anti-inflammatory drugs (NSAIDs). The NSAID is preferably an analogue of the carboxylic acid NSAID class. In a preferred set of embodiments the NSAID of the carboxylic acid class is conjugated to the polymer backbone at the —COOH position of the NSAID. The NSAID of the carboxylic acid class may be conjugated to the polymer backbone via an alkyl ester, aryl ester (acyloxy) alkyl ester, [(alkoxycarbonyl)oxy]alkyl ester or [(aryloxycarbonyl)oxy]alky ester linking group. In further preferred set of embodiments the NSAID of the carboxylic acid class may be conjugated to the polymer backbone via an alkyl anhydride or aryl anhydride linking group.

In some embodiments of a polymer-NSAID conjugate of the invention, D is the acid residue of a carboxylic acid NSAID of formula (XX):

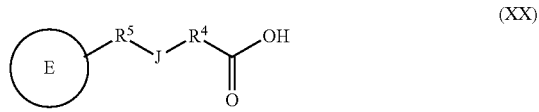

(XX)

where:

E represents an optionally substituted ring system;

J is selected from the group consisting of a bond or a functional group;

$R^4$ and $R^5$ are each independently selected from the group consisting of a bond and an optionally substituted aliphatic.

In some embodiments, a polymer-bioactive agent conjugate according to the invention is a copolymer of at least one monomer of formula (IV):

(IV)

where:

X may be the same or different at each occurrence and represents a terminal functional group comprising an alkyne or an azide;

Q is independently selected at each occurrence and may be present or absent and when present, represents a linking group;

R is an optionally substituted linear or branched hydrocarbon and may comprise optionally substituted aromatic hydrocarbon or heteroaromatic hydrocarbon Z is a cleavable linking group; and D is a bioactive agent selected from quinolones and NSAIDs;

with at least one monomer of formula (V):

(V)

where:

A may be the same or different at each occurrence and represents a group comprising a terminal functional group comprising an alkyne or an azide, wherein said terminal functional group is complementary to the terminal functional group of X;

L is an optionally substituted linker group; and n is an integer and is at least 1.

In some embodiments, the moieties of formula (I), (II), (III) and (IX) can be produced when a monomer of formula (IV) is reacted under click chemistry conditions with a monomer of formula (V). Such moieties of formula (I), (II), (III) and (IX) therefore form part of the structure of the backbone polymer chain.

In some embodiments, the monomer component of the polymer-bioactive agent conjugate according to any one of the embodiments described herein comprises at least about 33 mol % of cross-linker monomer having formula (V) wherein n is two or more. It is preferred that the theoretical average molecular weights between crosslinks ($M_c$) is lower than 2,000 g/mol and a theoretical crosslink density ($v=1/(2M_c)$) higher than 0.50 mmol/g.

Polymer-bioactive agent conjugates of the present invention may be incorporated into drug delivery systems, therapeutic devices, articles or preparations, and pharmaceutical products for post surgical care. They may be used to provide antibiotic prophylaxis, analgesia and anti-inflamatory treatment.

In another aspect, the present invention provides a pharmaceutical product as an ocular implant or drug delivery system for post-surgical care comprising a polymer-bioactive agent conjugate of any one of the embodiments described herein. The implant may be in the form of a solid article, deformable solid, hydrogel, or liquid for placement in the eye of a subject.

In another aspect, there is provided a method for the treatment or prevention of infection or treatment or prevention of inflammation in one or both eyes of a subject, the method comprising administering an article comprising a polymer-bioactive agent conjugate of any one of the embodiments described herein to an eye. In one set of embodiments, the method comprises depositing the article in the lumen of a needle and injecting the article into the eye from the needle.

In another aspect, there is provided use of a polymer-bioactive agent conjugate of any one of the embodiments described herein the manufacture of a pharmaceutical product for the treatment or prevention of infection or treatment or prevention of inflammation. In one set of embodiments, the pharmaceutical product is in the form of an ocular implant. An ocular implant comprising the polymer-bioactive agent conjugate may be injectable.

DETAILED DESCRIPTION OF THE INVENTION

In one aspect, the present invention relates to a polymer-bioactive agent conjugate comprising a polymer backbone and a plurality of releasable bioactive agents covalently bonded to and pendant from the polymer backbone. In accordance with this aspect, the polymer backbone comprises a plurality of triazole moieties. The releasable bioactive agents are selected from the group consisting of quinolones, NSAIDs, and mixtures thereof. Bioactive agents used in the polymer conjugate of the invention may also be referred to herein as "drugs" or "prodrugs".

The term "drug" refers to a substance for therapeutic use whose application (or one or more applications) involves: a chemical interaction, or physico-chemical interaction, with a subject's physiological system; or an action on an infectious agent, or on a toxin or other poison in a subject's body, or with biological material such as cells in vitro.

As used herein, the term "prodrug" refers to a derivative of the drug moiety, wherein the derivative may have little or none of the activity of the drug moiety per se yet is capable of being converted in vivo or in vitro into a bioactive moiety. An example of such derivatisation is the acetylation of one or more carboxyclic acid groups on a bioactive moiety, such that subsequent to being released in vivo the released prodrug is deactylated to produce the drug moiety. An example of an NSAID prodrug is aceclofenac. An example of a quinoline prodrug is prulifloxacin.

As used herein, the term "pharmaceutically acceptable salt" means those salts that are safe and effective for use in pharmaceutical preparations. Pharmaceutically acceptable salts include salts of basic or acidic groups present in compounds of the invention. Suitable salts may include sodium, potassium, ammonium, calcium, diethylamine and piperazine salts or acetic acid, adipic acid, ascorbic acid, aspartic acid, citric acid, hydrochloric acid, lactic acid, methane sulfonic acid, oxalic acid, phosphoric acid, sulfuric acid, tartaric acid, toluene sulfonic acid and the like. Pharmaceutically acceptable salts are described in Stahl P H, Wermuth C G, editors. 2002. Handbook of pharmaceutical salts: Properties, selection and use. Weinheim/Zurich: Wiley-VCH/VHCA.

Polymers having bioactive agents covalently attached thereto are sometimes referred to in the art as "polymer-bioactive agent conjugates". In some instances, it may be convenient to refer to a polymer-bioactive agent conjugate of the invention as a "bioactive-polymer conjugate", "polymer-drug conjugate", "drug-polymer conjugate", "polymer conjugate", or simply a "conjugate".

Polymer-bioactive agent conjugates of the invention comprise a polymer backbone comprising a plurality of triazole moieties. Each triazole moiety is incorporated in the structure of the polymer chain, and forms part of the polymer backbone. Accordingly, the polymer backbone may be considered to be a polytriazole polymer.

The triazole moieties present in the polymer backbone are 1,2,3-triazole moieties. A skilled person will understand that such triazole moieties are products of an alkyne/azide reaction cycloaddition reaction performed under "click" chemistry conditions.

As used herein, the expression forming "part of the polymer backbone" means that the triazole moiety is part of the string of atoms that are each connected so as to form the polymer chain. In embodiments where the polymer backbone has a branched structure (i.e. has one or more branches or side chains extending from a main polymer chain), the triazole moiety may be part of a side chain as well as the main chain of the polymer. However, the expression is intended to exclude polymer structures where triazole moieties are present only in the side chain.

Polymer-bioactive agent conjugates of the invention, which have a plurality of triazole moieties in its polymer backbone, can be prepared through the use of click chemistry. The term 'click chemistry' was coined by Professor K. Barry Sharpless in 2001 to describe a series of chemical reactions defined by their modular nature, high yield, stability of products in vivo, stereospecificity, high atom economy and high thermodynamic driving force. A number of 'click' reactions exist, with several of them involving a cycloaddition reaction between appropriate functional groups to generate a stable cyclic structure.

Using click chemistry, at least two co-monomers of appropriate complementary terminal functionality can covalently react to form the polymer-bioactive agent conjugate of the invention. At least one of the co-monomers carries a pendant bioactive agent. During polymerisation of the co-monomers to form the conjugate, the complementary terminal functional groups in the co-monomers react with one another and form a triazole moiety as a product of the covalent coupling. This results in the co-monomers being linked together via the triazole moiety. Therefore, the resulting polymer-bioactive agent conjugate comprises triazole moieties as a part of its polymer backbone structure.

As used herein, the terms "polymer" and "polymer backbone" encompasses all parts of the conjugate, with the exception of the bioactive agent, which in formulae shown herein below can be represented by the moieties D, $D^1$ or $D^2$. Thus, the polymer backbone would encompass the linking group Z, shown in formulae herein described, unless otherwise indicated.

Polymer-bioactive agent conjugates prepared with azide-alkyne cycloaddition click chemistry have a number of significant advantages over those prepared by other methods. One advantage of azide-alkyne cycloaddition click reactions is that it can be used to provide a simpler method for preparing polymer-bioactive conjugates containing bioactive agents that have multiple reactive functionality. In the case of quinolones and NSAIDs, these bioactive agents contain multiple nucleophilic or electrophilic functional groups. For instance, quinolones can contain Michael acceptors, hydroxy, amino and carboxy functional groups, while NSAIDs can also contain hydroxy, carboxy and amino functional groups. It would be appreciated that such reactive functional groups might otherwise need to be protected in order to avoid the possibility of undesirable intra-chain incorporation of the bioactive agent during polymer synthesis involving reaction of nucleophilic and electrophilic functional groups such as reaction of alcohols with isocyanates. As the azide-alkyne cycloaddition click reaction is almost completely orthogonal in terms of its reactivity to the reactivity exhibited by functional groups such as Michael acceptors, hydroxyl groups, amino groups and other nucleophilic centres, protecting group strategies are not required as unprotected reactive functional groups (such as hydroxyl groups and amino groups) present in a bioactive agent would take no part in any click reaction.

A further advantage of click reactions is that it can allow polymer synthesis to proceed under relatively mild conditions, for example, at lower temperatures than that used in a number of conventional step-growth polymerisation techniques.

"Conventional step-growth polymerisation" is defined as including both polycondensation and polyaddition, except where the polyaddition involves the use of an azide-alkyne cycloaddition click reaction. Examples of polycondensation include reactions to form polyesters from an acid halide and an alcohol and result in a halide acid by-product. Examples of polyaddition include reactions to form polyurethanes from the addition of a diisocyanate a dial that result in a molecular rearrangement of bonds to form a polymer without loss of any atom or molecule.

1,2,3-Triazole moieties can be produced through the reaction of co-monomers having appropriate complementary terminal functional groups comprising alkyne and/or azide functionalities, under click reaction conditions. The terms "complementary terminal functionality" and "complementary terminal functional group" as used in the context of the present invention means a terminal chemical group that is capable of reacting with another chemical group to form a covalent intermolecular bond there between.

An appropriate click reaction for the formation of 1,2-triazoles is the Huisgen 1,3-dipolar cycloaddition of azides and alkynes (thermal) which gives a mixture of the 1,4 and 1,5 regioisomers of the 1,2,3-triazole. Click reactions suitable for forming triazole moieties may also be metal catalysed. For example, a Copper(I)-catalyzed Azide-Alkyne Cycloaddition (CuAAC) variant of the Huisgen cycloaddition of azides and terminal alkynes forms 1,2,3-triazoles.

Use of a copper catalyst in the Huisgen cycloaddition reaction results in formation of a 1,4-substituted 1,2,3-triazole from azides and terminal alkynes, while use of a ruthenium catalyst enables use of terminal or internal alkynes and results in the formation of the alternate 1,5-regioisomer. The use of a silver catalyst also results in the 1,4-substituted 1,2,3-triazole. Other metals that can be used include, but are not limited to, Ni, Pt, Pd, Rh, and Ir; the regiochemistry of the 1,2,3 triazole resulting from the use of these metal catalysts is less well defined Some exemplary click functional groups have been described by W. H. Binder and R. Sachsenhofer in Macromol. Rapid Commun., 2007, 28, 15-54, the disclosure of which is incorporated herein by reference.

In addition to the thermal and metal catalysed variants of the Huisgen cycloaddition of azides and alkynes, a more recent development centres on the development of a metal-free, strain promoted azide-alkyne cycloaddition (SPAAC). In this variant, no catalyst is required as the alkyne is activated and made more reactive by incorporation of the alkyne functionality into a strained ring and/or by the selective placement of electron withdrawing functionality and heteroatoms in the vicinity of the alkyne group. The regiochemistry of this SPAAC is mixed with both 1,4 and 1,5 1,2,3 triazoles being formed.

The use of appropriately functionalised co-monomers to prepare the polymer-bioactive agent conjugate can advantageously enable the composition, structure and molecular weight of the conjugate to be controlled. In contrast, polymers prepared by conventional step-growth polymerisation may have less reproducible molecular weights and a broader molecular weight distribution. Control over the structure and/or composition of the polymer-bioactive agent conjugate may be advantageous for regulatory purposes.

In some embodiments, the polymer-bioactive conjugate comprises a moiety of formula (I):

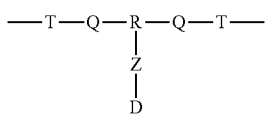

where:
T at each occurrence represents a triazole moiety;
Q is independently selected at each occurrence and may be present or absent and when present, represents a linking group;
R is an optionally substituted linear or branched hydrocarbon and may comprise optionally substituted aromatic hydrocarbon and or heteroaromatic hydrocarbon;
Z is a cleavable linking group; and
D is a releasable bioactive agent.

The polymer-bioactive agent conjugate typically comprises a plurality of moieties of formula (I), each group represented by Q, R, Z and D is independently selected and may be the same or different in each moiety.

In formula (I), the bioactive agent (represented by D) is selected from the group consisting of quinolones and NSAIDs. Examples of quinolones and NSAIDs are described herein.

Polymer-bioactive conjugates comprising a plurality of moieties of formula (I) may have moieties of formula (I) adjacent to each other or spaced apart within the polymer conjugate.

An important feature of the polymer-bioactive conjugates of the invention is that its polymer backbone comprises a plurality of triazole moieties. The triazole moieties in formula (I) are represented by the group T. Thus, the moiety of formula (I), which carries a pendant bioactive agent, is coupled to the remainder of the polymer backbone via triazole moieties.

In some embodiments, the polymer-bioactive agent conjugate comprises a polymer backbone comprising at least one triazole moiety selected from the group consisting of formula (II), (III) and (IX):

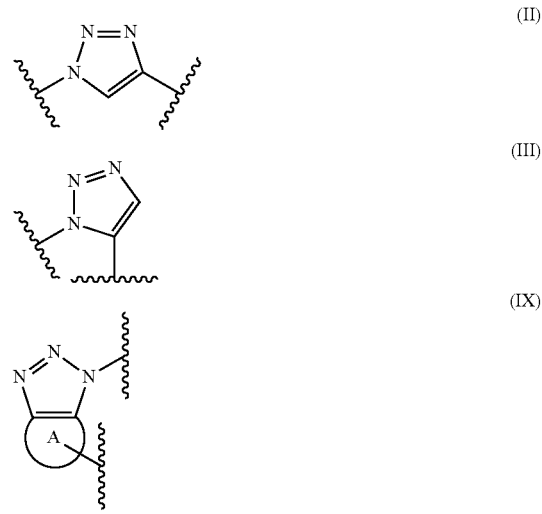

wherein in formula (IX), A represents an optionally substituted cyclic group, preferably said ring of from 7 to 9 constitutent ring members.

In some embodiments, a polymer-bioactive agent conjugate comprising a triazole moiety of formula (II) may comprise a moiety selected from formula (IIa) and (IIb):

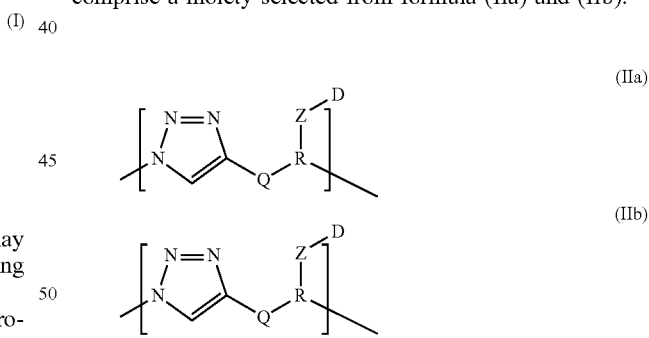

The moiety of formulae (II), (IIa) and (IIb) comprises a 1,4-substituted triazole moiety. Such a triazole moiety may be referred to herein as a 1,4-regioisomer.

In some embodiments, a polymer-bioactive agent conjugate comprising a triazole moiety of of formula (III) may comprise a moiety selected from formula (IIIa) and (IIIb):

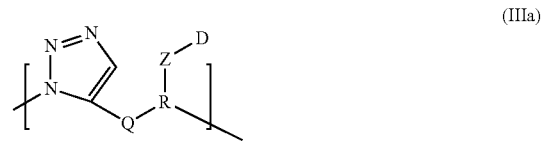

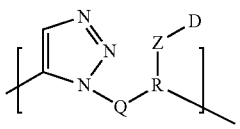
(IIIb)

The moiety of formulae (III), (IIIa) and (IIIb) comprises a 1,5-substituted triazole moiety. Such a triazole moiety may be referred to herein as a 1,5-regioisomer.

In one set of embodiments the triazole unit T is of formula IIIc

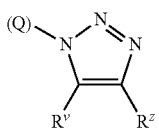
(IIIc)

wherein:
either
A. one of $R^v$ and $R^z$ is (Q) and the other is hydrogen; or
B. $R^v$ and $R^z$ together complete a ring of from 7 to 9 constitutent ring members selected from the group consisting of carbon and from 0 to 2 heteroatom groups selected from sulfur and the group N—$R^t$ wherein $R^t$ is hydrogen, $C_1$ to $C_6$ alkyl or the group (Q) and wherein the ring is optionally substituted with at least one substituent selected from the group consisting of:

hydroxyl (preferably from 0 to 2 hydroxy);
oxo (i.e. =O) (preferably 0 or 1 oxo group);
halo (preferably from 0 to 2 halo selected from chloro, bromo and fluoro and most preferably fluoro);
$C_1$ to $C_6$ alkoxy (preferably from 0 to 2 $C_1$ to $C_6$ alkoxy); and
rings fused with said ring of 7 to 9 constituent members wherein said fused rings include 0 to 3 rings each fused with said 7 to 9 membered ring and selected from benzene, cyclopropanone, and cyclopropane wherein the fused benzene and cyclopropane rings are optionally further substituted with from one to three substituents selected from the group consisting of $C_1$ to $C_6$ alkyl, halo (preferably from 0 to 2 halo selected from chloro, bromo and fluoro and most preferably fluoro) and $C_1$ to $C_6$ alkoxy; and wherein at least one ring member selected from nitrogen and carbon is substituted by the further Q polymer unit.

In some embodiments, a polymer-bioactive agent conjugate comprising a moiety of formula (IX) may comprise a moiety of formula (IXa) or (IXb):

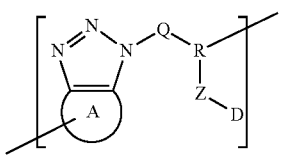
(IXa)

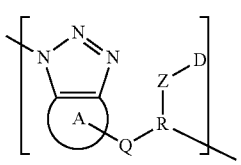
(IXb)

In formulae (IXa) and (IXb), A represents an optionally substituted cyclic group. Preferably the cyclic group comprises from 7 to 9 ring atoms. The ring atoms are each independently selected from the group consisting of C, N, O and S, preferably C, N and S. In one preference, A is C8 cycloalkyl. In one set of embodiments the ring "A" is said ring of from 7 to 9 constitutent ring members described above.

In one set of embodiments of formulae (IXa) and (IXb), A is substituted with one or more substituents selected from the group consisting of hydroxy (—OH), —Oalkyl, alkyl, halo (preferably fluoro), cycloalkyl, heterocycloalkyl, aryl and heteroaryl. Cycloalkyl, heterocycloalkyl, aryl and heteroaryl substituent groups may comprise from 3 to 6 ring atoms and may be fused to A. The optional substitutents may be located on any ring atom of the cyclic group.

In the moieties of formula (IIa), (IIb), (IIIa), (IIIb), (IIIc), (IXa) and (IXb):

Q may be present or absent and when present represents a linking group;
R is an optionally substituted linear or branched hydrocarbon and may comprise optionally substituted aryl or heteroaryl
Z is a cleavable linking group; and
D is a releasable bioactive agent selected from the group consisting of quinolones, NSAIDs, and mixtures thereof.

A further discussion of the groups Q, R, Z and D is provided below.

The polymer-bioactive agent conjugates of the invention may comprise a plurality of triazole moieties of formula (II), (III) or (IX) as herein described. The triazole moieties may be independently selected at each occurrence.

The triazole moieties present in the polymer backbone may each of the same type, or they may be a mixture of different types. For example, the triazole moieties present in the polymer conjugates may each be the same and be selected from formulae (IIa), (IIb), (IIIa), (IIIb), (IIIc), (IXa) or (IXb). Alternatively, the polymer backbone of the polymer conjugate may comprise a mixture of these types of triazole moieties.

One skilled in the relevant art would understand that depending on the monomers employed in the synthesis of the polymer-bioactive conjugate and the reaction conditions, the resulting conjugate may comprise a single type of triazole moiety selected from those of formulae (IIa), (IIb), (IIIa), (IIIb), (IIIc), (IXa) or (IXb), or it may comprise a combination of such moieties.

In some embodiments, the conjugate may comprise a triazole moiety selected from those of formula (II) and (III), and preferably comprises at least one moiety selected from formulae (IIa), (IIb), (IIIa) and (IIIb). Thus the triazole moieties present in the polymer backbone of the conjugates may each be 1,4-substituted triazole moieties, 1,5-substituted triazole moieties, or a combination of these regioisomers.

Co-monomers useful for the preparation of polymer-bioactive conjugates of the invention comprise terminal functional groups comprising an alkyne and/or an azide. One skilled in the relevant art would understand that under appropriate reaction conditions, an alkyne and an azide containing functional groups can covalently react to form a triazole moiety. Click reaction conditions have been described in for example, Chem. Rev. 2008, 108, 2952, Angew Chem Int Ed 2001, 40, 2004, Angew Chem Int Ed Engl. 2002, Jul. 15, 41(14): 2596-9, Aldrichimica Acta 2010, 43 (1) 15 and Accounts of Chemical Research 44 (9): 666-676.

In accordance with one embodiment of the polymer-bioactive agent conjugates of the invention, the triazole moieties may constitute at least 10 mol % of the polymer backbone. In some embodiments, the triazole moieties may constitute at least 20 mol % of the polymer backbone. In some embodiments, the triazole moieties may constitute at least 30 mol % of the polymer backbone.

As each triazole moiety is a reaction product from the covalent coupling of co-monomers, the proportion of triazole moieties in the polymer backbone may provide an indication of the degree of monomer incorporation in the polymer-bioactive agent conjugate.

The mol % of triazole moieties is determined on the basis of the proportion (on a molar basis) of such moieties within the polymer backbone in the conjugate.

As an example, the proportion of triazole moieties in polymer conjugates of the invention where a pendant bioactive moiety is coupled to the polymer backbone via a cleavable linking group (represented by Z in formulae described herein) may be determined by following equation:

$$\% \text{ triazole} = \left( \frac{67.05}{[MW_{monomer\text{-}bioactive\ agent\ conjugate} + MW_{(co\text{-}monomer)}] - MW_{(bioactive\ agent\text{-}1)} + 17} \right) \times 100\%$$

The polymer backbone of the conjugates of the present invention have a molecular weight of about 250 Daltons to about 10 MM Daltons, preferably from 500 Daltons to 2M Daltons.

The mol % of cross-linking density is determined on the basis of the proportion (on a molar basis) of cross-linking within the polymer backbone in the conjugate.

As an example, the cross-linking density in polymer conjugates of the invention where a pendant bioactive moiety is coupled to the polymer backbone via a cleavable linking group (represented by Z in formulae described herein) may be determined by following equation: (v=1/(2M_c)), where v is the cross-linking density and $M_c$ is the molecular weight between cross-links. When synthesising cross-linked polymers, it is desirable to achieve high cross-link densities (T. R. Hoare et al, Polymer (2008) 49, 1993-2007). High crosslink densities lead to polymers with higher physical strength, mechanical properties (I. Katime et al. J Applied Polym Sci, (2006) 102, 4016-4022), stability towards biodegradation (J. L. Holloway et al. J Control Release (2014) 191, 63-70) and, consequently, slower clearance rates. High crosslink density also allows limiting the swelling of the polymer in an aqueous environment (H. V. Chavda et al. Int J Pharm Investig. 2011 January-March; 1(1): 17-21.) and possibly the drug release rate. In contrast with hydroxyl and amine based step-growth polymerisations in which increasing the crosslink density can be detrimental to drug loading, the present invention generally allows high loading of the active to be provided. For example, cross-linked polymer conjugates may be prepared using a monomer of formula V wherein n is two or more such as from 2 to 8 and particularly 2 or 3.

The conjugates of the invention comprise a plurality of releasable bioactive agents selected from quinolones, NSAIDs and mixtures, covalently bonded to and pendant from the polymer backbone.

In some embodiments, conjugates of the invention comprise at least about 5 mol %, at least 10 mol %, at least 15 mol %, at least 20 mol %, or at least 30 mol % bioactive agent. The mol % of bioactive agent may be determined relative to the total number of moles of monomer that form the polymer conjugate.

The conjugates of the present invention can accommodate high bioactive agent loadings, minimising the amount of material required to deliver a dose of bioactive agent. Bioactive agent loadings of at least 5% by weight, at least 10% by weight, at least 15% by weight, at least 20% by weight, or at least 30% by weight, relative to the total weight of the polymer conjugate may be achieved.

In some embodiments, conjugates of the invention comprise up to 60 mol %, up to 70 mol %, up to 80 mol %, up to 90 mol % and even up to 100 mol % of conjugated bioactive agent, relative to the total number of moles of monomer that form the polymer conjugate. Those skilled in the art would appreciate that the mol % of bioactive agent may be dependent on the relative molar ratio of monomers used to form the polymer conjugate.

In some embodiments, polymer-bioactive agent conjugates of the invention comprise a moiety of formula (Ib):

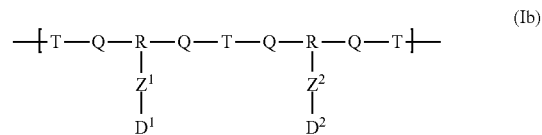

where:
T at each occurrence represents a triazole moiety;
Q is independently selected at each occurrence may be present or absent and when present represents a linking group;
R is an optionally substituted linear or branched hydrocarbon and may comprise optionally substituted aromatic hydrocarbon or heteroaromatic hydrocarbon;
$Z^1$ and $Z^2$ are each cleavable linking groups that may be the same or different; and
$D^1$ and $D^2$ are each bioactive agents that may be the same or different.

A moiety of formula (Ib) may occur when two moieties of formula (I) are covalently coupled together in the polymer conjugate.

In the moiety of formula (Ib), each T may be independently selected from a triazole moiety of formula (II), (III) or (IX). For instance, each T may be independently selected from triazole moiety of formula (IIa), (IIb), (IIIa), (IIIb), (IXa) and (IXb).

In one set of embodiments, in the moiety of formula (Ib), each T may be a 1,4-substituted triazole moiety or a 1,5-substituted triazole moiety. Alternatively, formula (Ib) may comprise a combination of such 1,4 and 1,5-regioisomers.

In the moiety of formula (Ib), each Q and R may be independently selected from any one of the moieties described herein for such groups.

The groups $Z^1$ and $Z^2$ in the moiety formula (Ib) are each cleavable linking groups, which may be the same or different at each occurrence. $Z^1$ and $Z^2$ may each be independently selected from any one of the groups described herein for the group Z. Where $Z^1$ and $Z^2$ are different, there exists the possibility that release of the bioactive agent can be further controlled.

The bioactive agents $D^1$ and $D^2$ are coupled to $Z^1$ and $Z^2$ respectively via a cleavable covalent bond. Examples of cleavable covalent bonds are described herein with reference to the linking group Z.

The linking group Z in formula (i) and groups $Z^1$ and $Z^2$ in formula (Ib) forms a link between the group R and drug D. Generally Z forms an ester at the carboxyl group of the quinolone or NSAID drug where Z is the alcohol portion of the ester and the drug is the carboxyl portion of the ester. The preferred embodiments of the groups D, Z, $Z^1$, and $Z^2$ defined in relation to Z comprising the alcohol portion and D comprising the carbonyl portion of the ester.

The groups $D^1$ and $D^2$ in the moiety of formula (Ib) are each bioactive agents, which may be the same or different at each occurrence. $D^1$ and $D^2$ may each be independently selected from any one of the bioactive agents as described herein for the group D. In accordance with the invention, $D^1$ and $D^2$ may each be independently selected from the group consisting of quinolones and NSAIDs.

In some embodiments, it may be desireable for $D^1$ and $D^2$ to be same. In such embodiments, the bioactive agents are therefore of a single type of drug (i.e. quinolones or NSAIDs only).

In some embodiments, it may be desireable for $D^1$ and $D^2$ to belong to the same class of drug, but be different bioactive agents within the same drug class. In such embodiments, the $D^1$ and $D^2$ may each be either quinolones or NSAIDs but be selected from different drugs within the class (e.g. a mixture of levofloxacin and moxifloxacin of fluoroquinolone drug class).

In some embodiments, it may be desirable for D1 and D2 to be different (i.e. a mixture of quinolones and NSAIDs). This may enable different therapeutic agents to be delivered to a subject by a single polymer conjugate. For example, the fluoroquinolone levofloxacin may be combined with the NSAID diclofenac that provides a polymer conjugate that releases levofloxacin and diclofenac from the same polymer conjugate. Alternativey, the fluoroquinolone levofloxacin may be combined with the NSAID ketorolac that provides a polymer conjugate that releases levofloxacin and ketorolac from the same polymer conjugate. Without wishing to be limited by theory, it is believed that the use of a mixture of bioactive agents may advantageously provide an enhanced therapeutic effect (e.g. an additive effect) in preventing inflammation. The combination of NSAID eye drops with antibiotic eye drops is also important to limit the damage from the host response to the infection (Textbook of Ophthalmology, Vol 1 2002 By Sunita Agarwal, Athiya Agarwal, Lucio Buratto, David J. Apple, Jorge L. Ali). Thus a mixture of different bioactive agents in the polymer conjugate may be more efficacious than a single type of bioactive agent alone.

A polymer-bioactive agent conjugate comprising a moiety of formula (Ib) may have a higher loading of bioactive agent. For example, a polymer-bioactive agent conjugate comprising formula (Ib) may comprise more than 50 mol % of bioactive agent. In some embodiments, the polymer-bioactive agent conjugate may comprise up to 60 mol %, up to 70 mol %, up to 80 mol % up to 90 mol % and even up to 100 mol % of conjugated bioactive agent, relative to the total number of moles of monomer that form the polymer conjugate.

The "bioactive agent" (also represented as "D" in certain formulae herein) employed in the polymer-bioactive agent conjugate of the invention is selected from the group consisting of quinolones, NSAIDs, and mixtures thereof.

Ophthalmic preparations of quinolone antibiotics formulated as eye drops, which if administered conscientiously to the affected eye will prevent infection or treat an established infection. The fluoroquinolone antibitoics are administered as eye drops, either alone (i.e. as a single agent) or in combination. Ophthalmic preparations of NSAIDs formulated as eye drops, which if administered conscientiously to the affected eye provides analgesia and is used to treat inflammation. It is postulated that combining quinolones with non-steroidal anti-inflammatory drugs (NSAIDs), may provide an additive effect in post-surgical care by both preventing infection, providing analgesia and treating inflammation.

Quinolones and NSAIDs bound to the polymer backbone of the conjugate of the invention are in pendant form. By being "pendant", the bioactive agents do not form part of the polymer backbone structure and as such, can be released without causing a reduction in the chain length of the polymer backbone. The pendant configuration can also ensure efficient release of the drug.

A skilled person would appreciate that bioactive agents such as quinolones and NSAIDs possess functional groups. Functional groups in a bioactive agent may be used to promote covalent coupling of the agent to the polymer backbone.

In the case of quinolones and NSAIDs, these bioactive agents comprise carboxylic acid, hydroxy and amino functional groups.

As discussed above, when a bioactive agent contains more than one such functional group, there is a potential for these functional groups to react with terminal functional groups in many monomers used in step growth polymerisation. For example, polyurethane conjugates may be formed with a diisocyanate monomer and a diol monomer. The isocyanate and hydroxyl groups in the co-monomers react to form a urethane linked polymer. The diol monomer may include a conjugated bioactive agent. In such instances, if the conjugated bioactive agent also comprises a free hydroxyl or free amine functional group, the free hydroxyl or free amine group on the bioactive agent may compete with the diol hydroxyl groups for reaction with an isocyanate group of the diisocyanate monomer. If this occurs, the bioactive agent may become incorporated in the polymer backbone of the conjugate, rather than being pendant.

As polymer-bioactive agent conjugates of the invention are prepared using click chemistry, it is an advantage of the invention that bioactive agents having multiple functional groups can be covalently coupled to the polymer backbone without the need to employ protecting group strategies, which might otherwise be used to protect certain functional groups from reaction to thereby ensure that a bioactive agent is covalently coupled to the polymer backbone in a preselected fashion.

The terms quinolone and fluoroquinolone are used herein to refer to the quinolone class of antibiotics and the narrower group of fluoroquinolone class respectively. These classes of antibiotics include compounds of formula (Xi) and (Xii) and in preferred embodiments the fluoroquinolones of formula Xia and Xiia. The formula Xii and Xiia are not quinolone compounds in a chemical sense but are analogues in which the quinolone nitrogen is replace by carbon. Nonetheless the quinolone class of antibiotics is understood in the art to include such analogues. Quinolone antibiotics can be in the form of a therapeutically active drug or a prodrug.

The quinolone, or a pharmaceutically acceptable salt thereof, is conjugated to the polymer backbone. The present invention enables the quinolone, or pharmaceutically acceptable salt thereof to be delivered to a desired site in order to produce a therapeutic effect.

Generally speaking the fluoroquinolone antibiotics are preferred a fluorine atom at the 6-position (as shown in formulae Xia and Xiia, more preferably Xia) enhances the antibacterial properties of by increased inhibitory activity of topoisomerase II, facilitating penetration of the bacterial cell wall and providing increased activity to staphylococci.

In one aspect, the present invention relates to a polymer-drug conjugate comprising a polymer backbone and a fluoroquinolone class of quinolone conjugated to the polymer backbone.

Quinolones delivered by polymer-bioactive agent conjugates of the invention comprise at least one functional group selected from the group consisting of a carboxylic acid group.

The carboxylic acid group serves as a reactive functional group for conjugation of the quinolone drug to a polymer. The drug moiety (denoted D in formulae described herein) linked to the polymer is therefore an acid residue of the alkyl ester, aryl ester, (acyloxy)alkyl ester [(alkoxycarbonyl)oxy]alkyl ester, [(aryloxycarbonyl)oxy]alkyl, alkyl anhydride or aryl anhydride ester linking group conjugating the quinolone to the polymer backbone. The moiety represented by D may therefore be a releasable quinolone.

The quinolone may be conjugated to the polymer backbone via an alkyl ester, aryl ester, (acyloxy)alkyl ester, [(alkoxycarbonyl)oxy]alkyl ester, [(aryloxycarbonyl)oxy]alkyl ester, alkyl anhydride or aryl anhydride linking group. Alkyl ester, aryl ester, (acyloxy)alkyl ester, [(alkoxycarbonyl)oxy]alkyl ester [(aryloxycarbonyl)oxy]alkyl ester, alkyl anhydride or aryl anhydride linking groups have been found to be hydrolytically labile in biological environments and can help to ensure that a sufficient amount of the drug is effectively released from the polymer conjugate to achieve therapeutic levels in the immediate vicinity of the polymer conjugate material.

As used herein, the term "acid residue" is a reference to that part of an ester such as an alkyl ester, aryl ester, (acyloxy)alkyl ester or [(alkoxycarbonyl)oxy]alkyl ester, [(aryloxycarbonyl)oxy]alkyl ester, alkyl anhydride or aryl anhydride linking group that is derived from a carboxylic acid functional group of a bioactive agent, after conjugation of the bioactive agent to the polymer backbone. The acid residue will generally have the structure —C(O)—. In the case of a quinolone, the carboxylic acid group is located at the 3 position.

Generally speaking the aryl ester, (acyloxy)alkyl ester or [(alkoxycarbonyl)oxy]alkyl ester groups are preferred. These groups generally provide more effective release of the active quilolone agents.

In one set of embodiments, the bioactive agent is selected from quinolones of formula (Xi) or (Xii) as hereinbefore described. The preferred quinolones are of formula Xi where $A_3$ is nitrogen.

The preferred compounds are of formula (Xi) wherein A3 is N.

In a preferred set of embodiments the substituent $A_2$ in formulae (Xi) or (Xii) is $CY_1$ where $Y_1$ is halogen and more specifically fluorine, that is, $A_2$ is the group C—F. In this embodiment, the bioactive agent is selected from the group of fluoroquinolones of formula (Xia) and (Xiia):

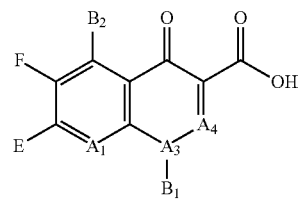

(Xia)

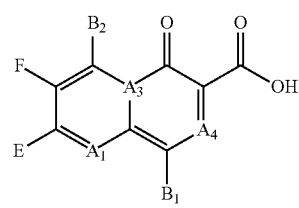

(Xiia)

wherein $A_1$ is selected from N or —$CY_1$— where $Y_1$ is selected from the group consisting of hydrogen, halogen (particularly chloro or fluoro), alkyl (particularly $C_1$ to $C_4$ alkyl), haloalkyl (particularly $C_1$ to $C_4$ alkyl substituted with from one to three halo selected from fluoro and chloro), —O-alkyl (particularly $C_1$ to $C_4$ alkoxy), haloakoxy (preferable $C_1$ to $C_4$ alkoxy substituted with from 1 to 3 fluoro such as difluoromethoxy), —S-alkyl, nitrile, an amine, an amino radical, $NO_2$, or $Y_1$ forms a bridge with $B_1$ (preferably a 3 membered bridge selected from methylene, nitrogen and oxygen and sulphur wherein the bridge is optionally substituted by $C_1$ to $C_4$ alkyl such as trimethylene optionally substituted by $C_1$ to $C_4$ alkyl);

$A_3$ is selected from —N— or —C— (preferably N);

$A_4$ is selected from the group consisting of N and —$CB_3$ wherein $B_3$ is H or together with $B_1$ form a bridge —$B_3$—$B_1$— wherein $B_3$ is —S— and $B_1$ is —$CH(B_4)$— where $B_4$ is H or methyl (preferably in the bridge forming embodiment the compound is of formula (Xia) and $A_3$ is N);

$B_1$ is selected from the group consisting of hydrogen, alkyl (preferably $C_1$ to $C_4$ alkyl), substituted alkyl (preferably halo-$C_1$ to $C_4$ alkyl such as fluoro $C_1$ to $C_4$ alkyl), optionally substituted cycloalkyl (preferably cyclopropyl and fluorocyclopropyl) aryl (preferably phenyl), substituted aryl (preferably haloaryl such as 4-fluorophenyl and 2,4-difluorophenyl), heteroaryl (such as pyridyl), substituted heteroaryl such as 2-pyridyl substituted with one to three substituents selected from fluoro $C_1$ to $C_4$ alkyl and amino) or —O-alkyl (preferably $C_1$ to $C_4$ alkoxy) when $A_3$ is —N—; and wherein $B_1$ may form a bridge with $A_1$ (preferably a 3 membered bridge selected from methylene, nitrogen and oxygen and sulfur wherein the bridge is optionally substituted by one or two $C_1$ to $C_4$ alkyl) or a bridge with $B_3$ (when $A_4$ is $CB_3$) wherein in the bridge —$B_3$—$B_1$— the group $B_3$ is —S— and $B_1$ is —$CH(B_4)$— where $B_4$ is H or methyl (preferably in the —$B_3$—$B_1$— bridge forming embodiment the compound is of formula Xia and $A_3$ is N);

$B_2$ is selected from the group consisting of hydrogen, halogen, —OH, —$CH_3$, or an amino radical;

E is selected from hydrogen; halogen (preferably fluoro or chloro); alkyl (preferably $C_1$ to $C_4$ alkyl); optionally substituted aryl (preferably optionally substituted phenyl or pridyl wherein substituted phenyl and substituted pyridyl preferably comprise one to three substituents independently selected from the group consisting of C1 to C4 alkyl, (C1 to C4 alkylamino, C1 to C4 alkoxy and hydroxyl); alkoxy (preferably $C_1$ to $C_4$ alkoxy); amino radical preferably an optionally substituted heterocyclic or heterobicyclic of 4 to 9 constituent ring or fused ring members and comprising one or two nitrogens and optionally one of oxygen or sulfur atoms (preferred optional substituents include one to three substituents selected from the group consisting of $C_1$ to $C_4$ alkyl, spiro $C_3$ to $C_5$ cycloalkyl, amino, hydroxyl, $C_1$ to $C_4$ alkylamino, 1-methyl-7-[4-(5-methyl-2-oxo-1,3-dioxolen-4-yl)methyl, 3-(Aminomethyl)-4-methoxyimino and may optionally comprise a methylene bridge; and cycloaliphatic of from 3 to 6 ring members optionally substituted with from 1 to 3 substituents selected from the group consisting of C1 to C4 alkyl, amino, $C_1$ to $C_4$ alkylamino, hydroxyl and $C_1$ to $C_4$ alkoxy In one set of embodiments the active agent comprises a quinolone typically of formula Xi or Xii and selected from the group consisting of:

alatrofloxacin, am ifloxacin avarofloxacin, balofloxacin, besifloxacin, cadazolid, cinoxacin, ciprofloxacin clinafloxacin, danofloxacin, delafloxacin, dextrofloxacin, difloxacin, DS-8587, enoxacin, enrofloxacin, finafloxacin, fleroxacin, flumequine, garenoxacin, gatifloxacin, gemifloxacin, grepafloxacin, ibafloxacin, KRP AM1977X, KRP-AM1977Y, levofloxacin, lomefloxacin, marbofloxacin, miloxacin, moxifloxacin, nadifloxacin, (S)-nadifloxacin (WCK771), nalidixic acid, nemonoxacin, norfloxacin, ofloxacin, orbifloxacin, oxolinic aicd, ozenoxacin, pazufloxacin, pefloxacin, pipemidic acid, piromidic acid, pradofloxacin, prulifloxacin, rosoxacin, rufloxacin, sarafloxacin, sitafloxacin, sparfloxacin, temafloxacin, tosufloxacin, trovafloxacin, ulifloxacin, WCK 2349, and zabofloxacin.

Some specific examples of releasable fluoroquinolones of formulae (Xia) and (Xiia): described herein are besifloxacin, moxifloxacin, ciprofloxacin, enoxacin, fleroxacin, gatifloxacin, lomefloxacin, ofloxacin, levofloxacin ((S)-ofloxacin), dextrofloxacin ((R)-ofloxacin), norfloxacin, pefloxacin, rufloxacin, balofloxacin, grepafloxacin, pazufloxacin, sparfloxacin, temafloxacin, tosufloxacin, clinafloxacin, gem ifloxacin, sitafloxacin, trovafloxacin, alatrofloxacin, cadazolid, prulifloxacin, finafloxacin, am ifloxacin, ulifloxacin, flumequine, delafloxacin, avarofloxacin (JNJ-Q2), zabofloxacin, nadifloxacin, WCK 771, (S)-nadifloxacin, WCK 2349, KRP-AM1977X, KRP-AM1977Y, DS-8587, sarafloxacin, danofloxacin, pradofloxacin, enrofloxacin, ibafloxacin, marbofloxacin, orbifloxacin, difloxacin.

In one set of embodiments the active agent comprises a quinolone typically of formula Xi or Xii and selected from the group consisting of besifloxacin, ciprofloxacin, gatifloxacin, levofloxacin and moxifloxacin.

In accordance with the invention, the quinolone is linked to the polymer backbone by the —COON position. Accordingly, when linked to the polymer backbone, the —COON forms the acid residue (—C(O)O—) of an alkyl ester, aryl ester, (acyloxy)alkyl ester, [(alkoxycarbonyl)oxy]alkyl ester [(aryloxycarbonyl)oxy]alkyl ester, alkyl anhydride or aryl anhydride linking group. In formulae described herein, the alkyl ester, aryl ester, (acyloxy)alkyl ester, [(alkoxycarbonyl)oxy]alkyl ester, [(aryloxycarbonyl)oxy]alkyl ester, alkyl anhydride or aryl anhydride linking group is formed when the quinolone (represented by D) is conjugated with the linking group Z. That is, the quinolone of formula (Xi, Xii, Xia, Xiia), together with Z, forms an alkyl ester, aryl ester or (acyloxy)alkyl ester, [(alkoxycarbonyl)oxy]alkyl ester, [(aryloxycarbonyl)oxy]alkyl ester, alkyl anhydride or aryl anhydride linking group. Some specific examples of Z are described below.

In some embodiments, 1-COOH is linked to the polymer backbone via an anhydride linkage.

In some embodiments, 1-COOH is linked to the polymer backbone via an ester linkage.

In some embodiments, 1-COOH is linked to the polymer backbone via an aryl ester linkage.

In some embodiments, 1-COOH is linked to the polymer backbone via an (acyloxy)alkyl ester, an [(alkoxycarbonyl)oxy]alkyl ester or [(aryloxycarbonyl)oxy]alkyl ester.

In the context of the present invention it may be convenient to refer to the quinolones of general formula (Xi or Xii) as the free acid form. For example the free acid form of moxifloxacin is 1-cyclopropyl-7-[(1S,6S)-2,8-diazabicyclononan-8-yl]-6-fluoro-8-methoxy-4-oxoquinoline-3-carboxylic acid. It will be understood that the groups D, $D^1$ and $D^2$ refer to the carbonyl portion of the acid and Z, $Z^1$ and $Z^2$ refer to the alcohol portion of the ester in the polymer conjugates of formulae (i) and (Ib).

Some examples of quinolones that may be delivered by the polymer-bioactive agent conjugates are cinoxacin, garenoxacin, miloxacin, nalidixic acid, nemonoxacin, oxolinic acid, ozenoxacin, pipemidic acid, piromidic acid, rosoxacin These quinolones are shown in Table 1. Such drugs are conjugated to the polymer backbone of the polymer conjugates of the invention by the carboxylic acid functional groups located at the 3-position of the quinolone.

TABLE 1

Quinolones

Quinolone cinoxacin oxolinic acid pipemidic acid

TABLE 1-continued

Quinolones

| Quinolone |
|---|
| miloxacin |
| ozenoxacin |
| nalidixic acid |
| piromidic acid |
| rosoxacin |

TABLE 1-continued

Quinolones

| Quinolone |
|---|
| nemonoxacin |
| Garenoxacin |

Preferably, the quinolone is selected from fluoroquinolones. Some examples of fluoroquinolones that may be delivered by the polymer-bioactive agent conjugates are besifloxacin, moxifloxacin, ciprofloxacin, enoxacin, fleroxacin, lomefloxacin, ofloxacin, Levofloxacin ((S)-ofloxacin), dextrofloxacin ((R)-ofloxacin), gatifloxacin, norfloxacin, pefloxacin, rufloxacin, balofloxacin, grepafloxacin, pazufloxacin, sparfloxacin, temafloxacin, tosufloxacin, clinafloxacin, gem ifloxacin, sitafloxacin, trovafloxacin, alatrofloxacin, cadazolid, prulifloxacin, finafloxacin, am ifloxacin, ulifloxacin, flumequine, delafloxacin, avarofloxacin (JNJ-Q2), zabofloxacin, Nadifloxacin, WCK 771, (S)-nadifloxacin, WCK 2349, KRP-AM1977X, KRP-AM1977Y, DS-8587, sarafloxacin, danofloxacin, pradofloxacin, enrofloxacin, ibafloxacin, marbofloxacin, orbifloxacin, difloxacin.

These fluoroquinolones are shown in Table 2. Such drugs are conjugated to the polymer backbone of the polymer conjugates of the invention by the carboxylic acid functional group located at the 6 position of the fluoroquinolone.

TABLE 2
| Fluoroquinolones |
|---|
| Quinolone |
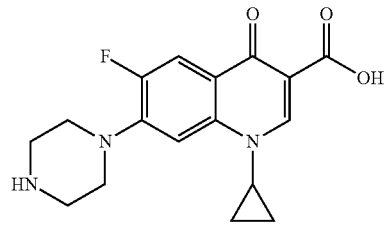
ciprofloxacin
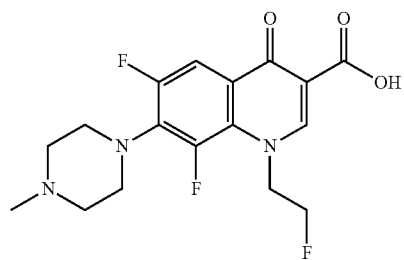
fleroxacin
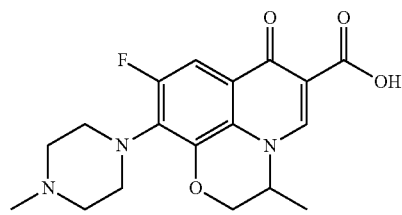
ofloxacin
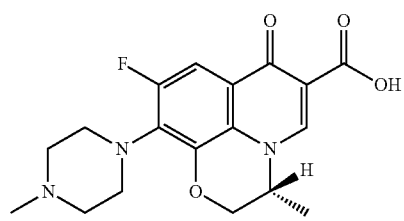
dextrofloxacin ((R)-ofloxacin)
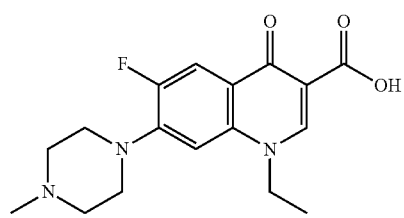
pefloxacin TABLE 2-continued
Fluoroquinolones
Quinolone
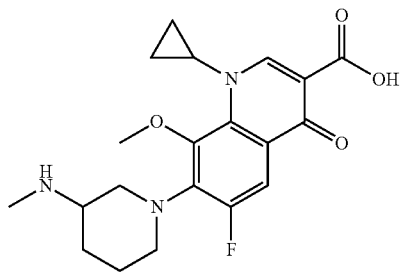
balofloxacin
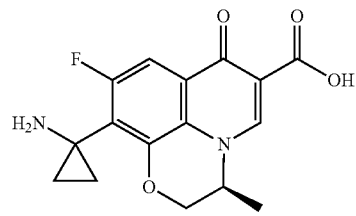
pazufloxacin
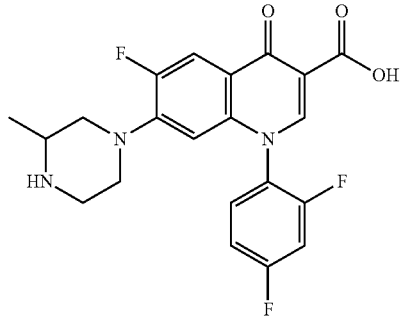
temafloxacin
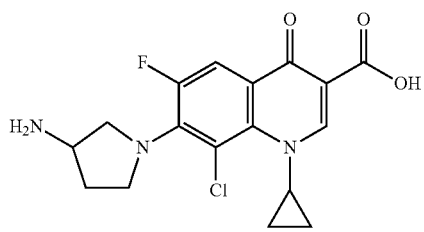
clinafloxacin TABLE 2-continued
Fluoroquinolones
Quinolone
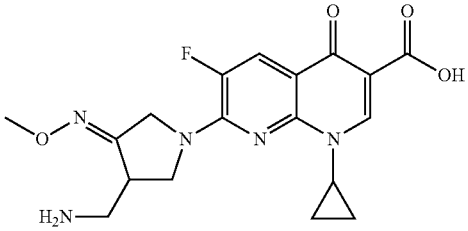
gemifloxacin
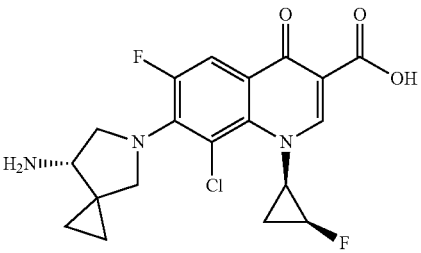
sitafloxacin
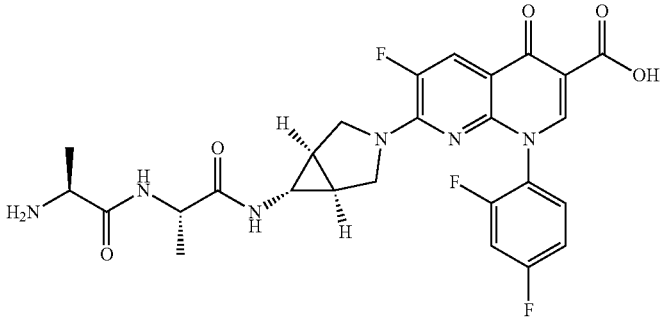
alatrofloxacin
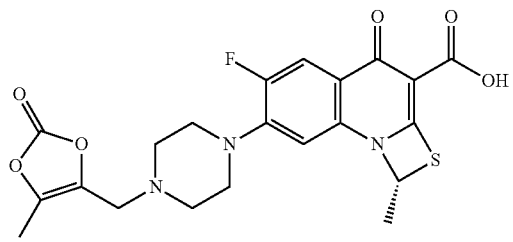
prulifloxacin TABLE 2-continued
Fluoroquinolones
Quinolone
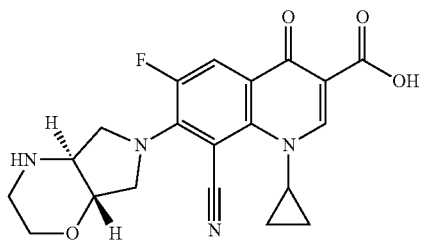
finafloxacin
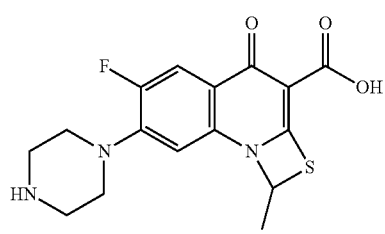
ulifloxacin
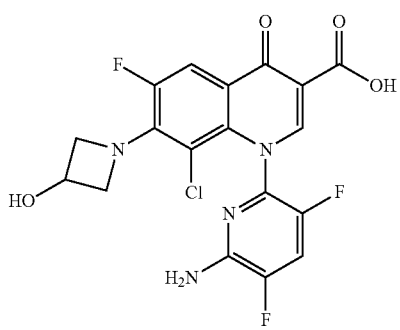
delafloxacin
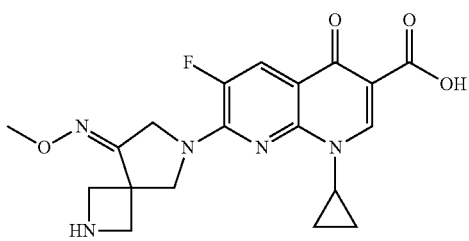
zabofloxacin
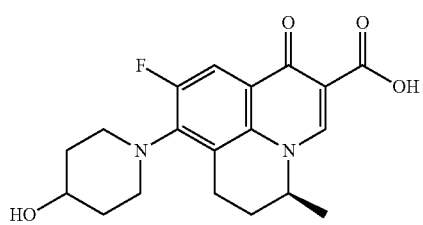
WCK 771
(S)-nadifloxacin TABLE 2-continued
| Fluoroquinolones |
|---|
| Quinolone |
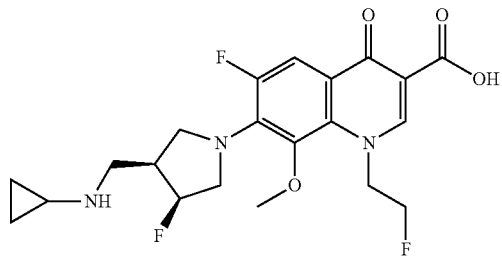
KRP-AM1977X or KRP-AM1977Y
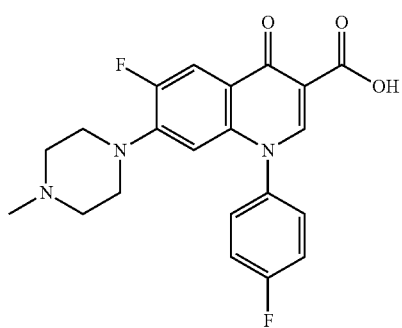
difloxacin
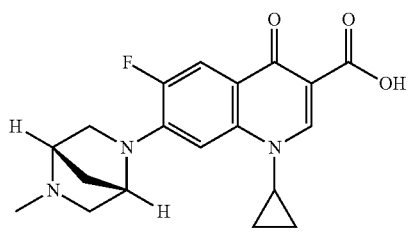
danofloxacin
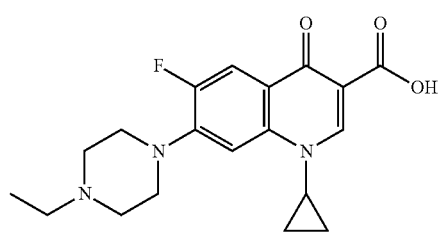
enrofloxacin TABLE 2-continued
Fluoroquinolones
Quinolone
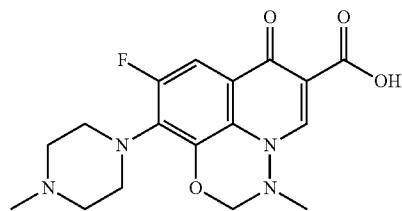
marbofloxacin
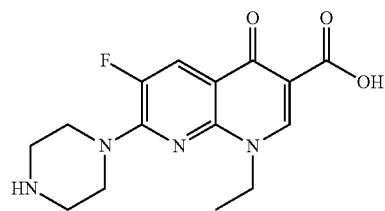
enoxacin
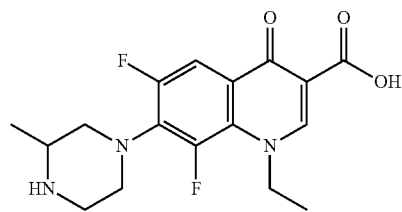
lomefloxacin
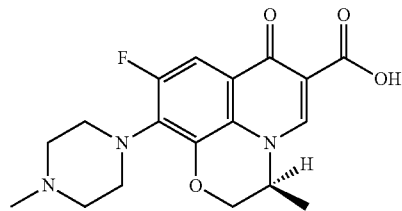
Levofloxacin ((S)-ofloxacin)
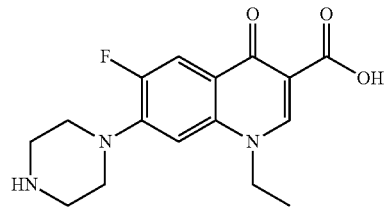
norfloxacin TABLE 2-continued
Fluoroquinolones
Quinolone
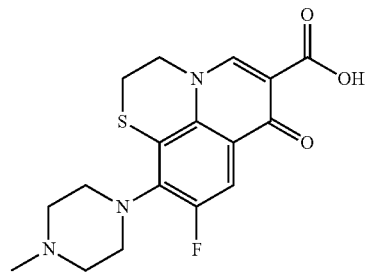
rufloxacin
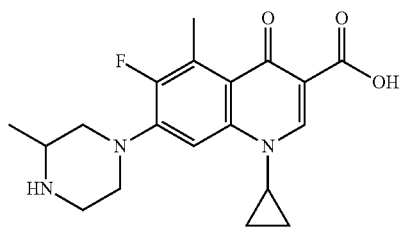
grepafloxacin
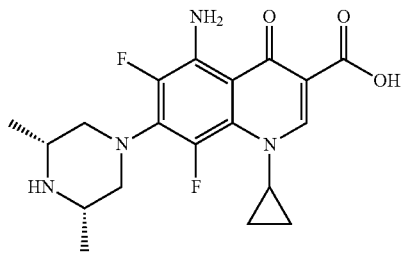
sparfloxacin
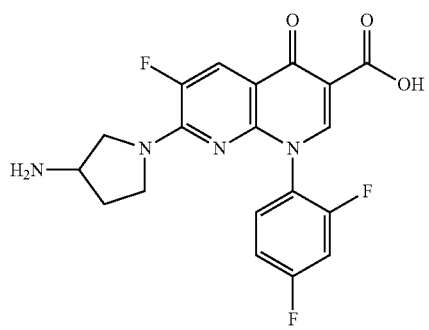
tosufloxacin TABLE 2-continued
Fluoroquinolones
Quinolone
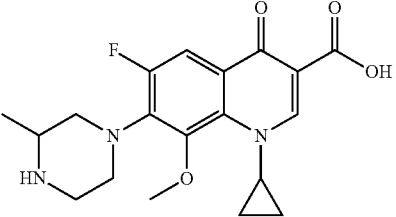
gatifloxacin
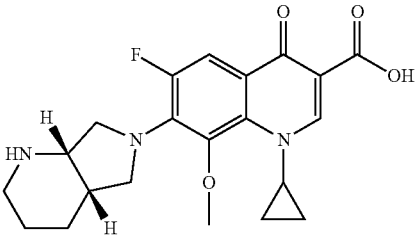
moxifloxacin
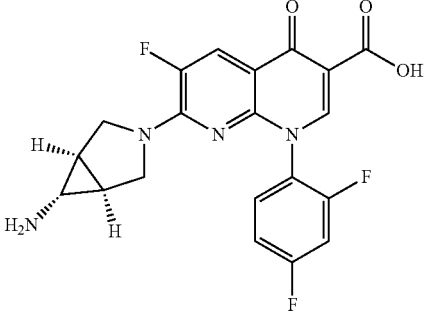
trovafloxacin
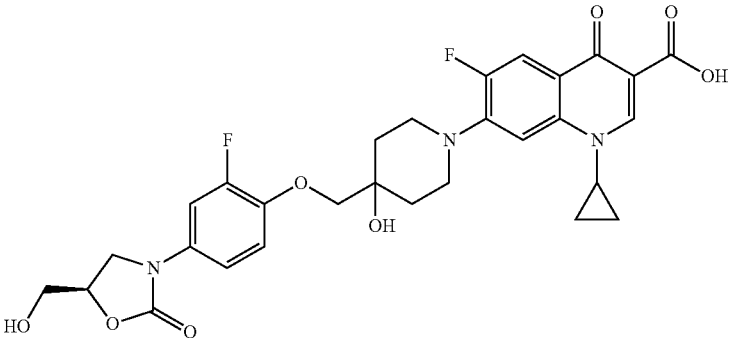
cadazolid TABLE 2-continued
Fluoroquinolones
Quinolone
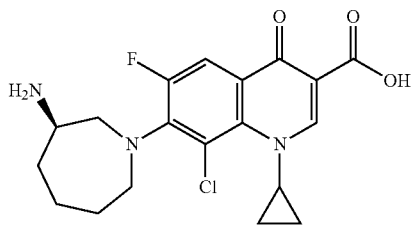
besifloxacin
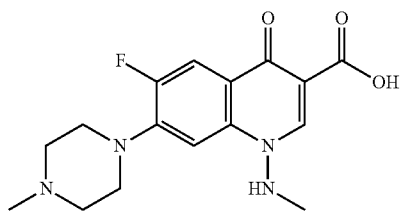
amifloxacin
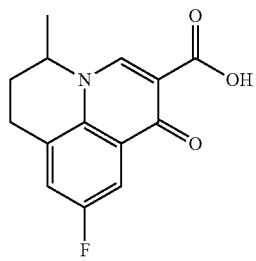
flumequine
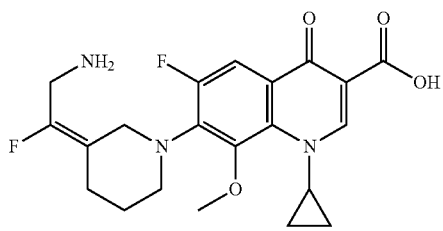
avarofloxacin (JNJ-Q2)
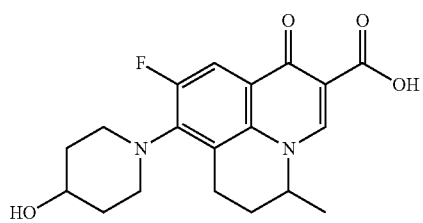
Nadifloxacin TABLE 2-continued
Fluoroquinolones
Quinolone
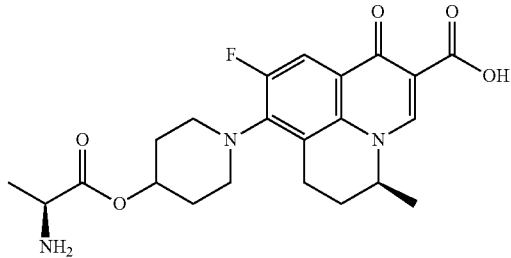
WCK 2349 a prodrug of WCK 771
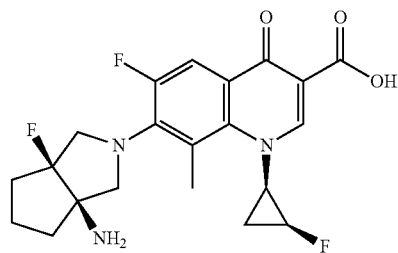
DS-8587
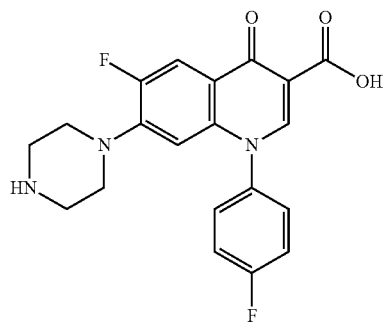
sarafloxacin
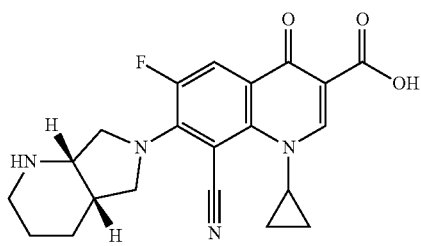
pradofloxacin TABLE 2-continued Fluoroquinolones Quinolone

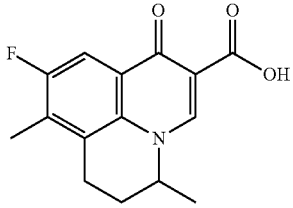

ibafloxacin

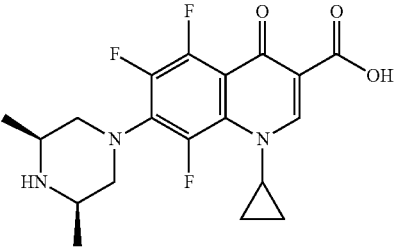

orbifloxacin

More preferably, the releasable fluoroquinolone is selected from besifloxacin, moxifloxacin, ciprofloxacin, ofloxacin, levofloxacin ((S)-ofloxacin), dextrofloxacin ((R)-ofloxacin) and gatifloxacin.

Generally, NSAIDs are an important therapeutic class of drugs typically used to suppress pain and inflammation. Drugs belonging to this class typically possess one or more of the following four major activities: analgesic (provide relief of pain by a mechanism other than reduction of inflammation), antipyretic (ability to lower elevated body temperature), anti-inflammatory (ability to reduce inflammation), and uricosuric (ability to promote excretion of uric acid, e.g., for treating gout) activities.

NSAIDs can be classified according to their chemical structure. One important class of NSAIDs are substituted carboxylic acid NSAIDs. Members in this class of NSAIDs can include acetic acid derivatives such as indole acetic acid derivatives and pyrrole acetic acid derivatives, and propionic acid derivatives as well as carboxylic acid groups substituted on aromatic rings such as in aspirin. In one embodiment the NSAID is an alkanoic acid NSAID.

For example, diclofenac is a non-steroidal anti-inflammatory drug (NSAID) having a chemical structure as illustrated below:

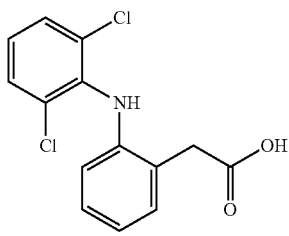 [SMILES: O=C(O)Cc1ccccc1Nc1c(Cl)cccc1Cl]

Diclofenac has anti-inflammatory, analgesic and antipyretic properties. In conventional treatments diclofenac is used for the treatment of musculoskeletal complaints and for pain management, and is often formulated in topical gels, lotions and patches, oral formulations and injectable forms for such use. For example, diclofenac can been used to treat ocular discomfort, inflammation and swelling following eye surgery, and is typically administered in eye drops for such treatment. It can also be used to treat joint inflammation and swelling associated with osteo-arthritis, and is typically administered as a topical gel or oral tablet for such treatment.

For example, ketorolac is a non-steroidal anti-inflammatory drug (NSAID) having a chemical structure as illustrated below:

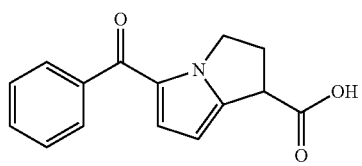 [SMILES: O=C(c1ccccc1)c1ccc2n1CCC2C(=O)O]

Ketorolac has anti-inflammatory, analgesic and antipyretic properties. In conventional treatments ketorolac is used for management of pain and inflammation, and is often formulated in topical gels, lotions and patches, eye drops, oral formulations and injectable forms for such use. For example, ketorolac can been used to treat ocular discomfort, inflammation and swelling following eye surgery, and is typically administered in eye drops for such treatment. It can also be used to treat joint inflammation and swelling associated with osteo-arthritis, and is typically administered as an intra-articular injection for such treatment.

For example, bromfenac is a non-steroidal anti-inflammatory drug (NSAID) having a chemical structure as illustrated below:

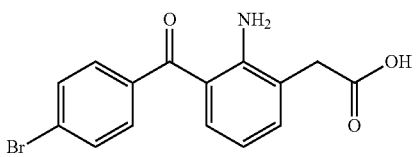 [SMILES: Nc1c(CC(=O)O)cccc1C(=O)c1ccc(Br)cc1]

Bromfenac has anti-inflammatory, analgesic and antipyretic properties. In conventional treatments bromfenac is used for the management of pain and inflammation, and is often formulated in eye drops for such use. For example, bromfenac can been used to treat discomfort, inflammation and swelling associated with cataract surgery, and is typically administered as an eye drop for such treatment.

In one aspect, the present invention relates to a polymer-NSAID conjugate comprising a biodegradable polymer backbone and a non-steroidal anti-inflammatory drug (NSAID) conjugated pendant to the polymer backbone via an aryl ester group.

As discussed above, polymer-NSAID conjugates of the invention comprise a substituted carboxylic acid NSAID conjugated to a polymer backbone. The conjugated NSAID drug moiety is represented by the group "D" in formulae described herein. The drug moiety represented by D may be a releasable NSAID analogue.

In some embodiments D is the acid residue of a substituted carboxylic acid NSAID of formula (XX) referred to above.

In accordance with the invention, the NSAID is linked to the polymer backbone by the 1-COOH position. Accordingly, when linked to the polymer backbone, the 1-COOH forms the acid residue (—C(O)O—) of an alkyl ester, aryl ester, (acyloxy)alkyl ester, [(alkoxycarbonyl)oxy]alkyl ester, [(aryloxycarbonyl)oxy]alkyl ester, alkyl anhydride or aryl anhydride linking group. In formulae described herein, the alkyl ester, aryl ester, (acyloxy)alkyl ester, [(alkoxycarbonyl)oxy]alkyl ester, [(aryloxycarbonyl)oxy]alkyl ester, alkyl anhydride or aryl anhydride linking group is formed when the NSAID (represented by D) is conjugated with the linking group Z. That is, the NSAID of formula (XX), together with Z, forms an alkyl ester, aryl ester, (acyloxy)alkyl ester, [(alkoxycarbonyl)oxy]alkyl ester, [(aryloxycarbonyl)oxy]alkyl ester, alkyl anhydride or aryl anhydride linking group. Some specific examples of Z are described below.

In preferred embodiments, 1-COOH is linked to the polymer backbone via an anhydride linkage.

In preferred embodiments, 1-COOH is linked to the polymer backbone via an ester linkage.

In some embodiments, 1-COOH is linked to the polymer backbone via an aryl ester linkage.

In some embodiments, 1-COOH is linked to the polymer backbone via an (acyloxy)alkyl ester, [(alkoxycarbonyl)oxy]alkyl ester or [(aryloxycarbonyl)oxy]alkyl ester linkage.

In general aryl esters (acyloxy)alkyl esters and [(alkoxycarbonyl)oxy]alkyl esters provide more advantageous release of the active NSAID agent.

In formula (XX), the moiety "E" represents an optionally substituted ring system. In some embodiments, E is selected from the group consisting of an optionally substituted alicyclic ring system (which may be a non-aromatic carbocyclic or non-aromatic heterocyclic) and an optionally substituted aryl ring system (which may be carbocyclic aryl or heterocyclic aryl). Suitable ring systems may contain from 5 to 16 ring members, from 5 to 12 ring members, or from 5 to 6 ring members.

In formula (XX), the moiety "J" is selected from the group consisting of a bond or a functional group. When J is a bond, it is suitably a single covalent bond. When J is a functional group, it is preferred that J be an ester functional group (—O(CO)—).

In formula (XX), $R^4$ and $R^5$ are each independently selected from the group consisting of a bond and optionally substituted aliphatic.

In some embodiments, $R^4$ is optionally substituted aliphatic. Suitable aliphatic may be linear or branched $C_1$ to $C_3$, (preferably $C_1$ to $C_2$) hydrocarbyl (e.g. methylene or ethylene hydrocarbyl). Suitable optional substituents may include linear or branched $C_1$ to $C_3$ alkyl, preferably $C_1$ alkyl (methyl).

In some embodiments, $R^5$ is an optionally substituted aliphatic. Suitable aliphatic may be linear or branched $C_1$ to $C_3$, (preferably $C_1$ to $C_2$) hydrocarbyl (e.g. methylene or ethylene hydrocarbyl). Suitable optional substituents may include linear or branched $C_1$ to $C_3$ alkyl, preferably $C_1$ alkyl (methyl).

In some embodiments, $R^5$ is a bond.

In some embodiments, D is the acid residue of a substituted NSAID having a structure of formula (XXa):

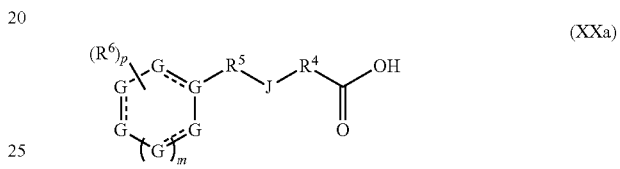

(XXa)

where:

G at each occurrence is independently selected from the group consisting of a carbon atom and a heteroatom;

— represents an optional bond;

$R^6$ is a substituent group;

p represents the number of substituent groups and is an integer in the range of from 0 to 5;

m is 0 or 1; and $R^4$, $R^5$ and J are as defined in formula (XX).

In some embodiments of formula (XXa) $R^4$ is an optionally substituted $C_1$-$C_2$ hydrocarbyl, and J and $R^5$ each represent a bond. Such compounds may be represented by compounds of formula (XXb) or (XXc):

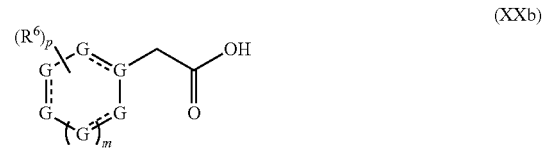

(XXb)

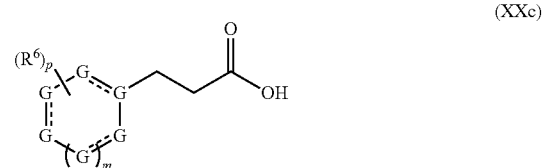

(XXc)

where: G, $R^6$, p and m are as defined herein.

A skilled person would be able to ascertain the chemical structure of a variety of substituted carboxylic acid NSAIDs. Examples of substituted carboxylic acid NSAIDs that may be delivered by polymer-NSAID conjugates of the invention are shown in Table 1. It will be understood that in the conjugates of formulae (I) and (Ib) the releasable bioactive agent D, $D^1$, $D^2$ is represented as the carbonyl portion of the acid ester and the linker Z, $Z^1$, $Z^2$ is the alcohol portion of the ester.

Specific examples of suitable NSAIDs for conjugation at the carboxyl group include those shown in Table 3.

TABLE 3

| Name | Structure |
|---|---|
| Aceclofenac | 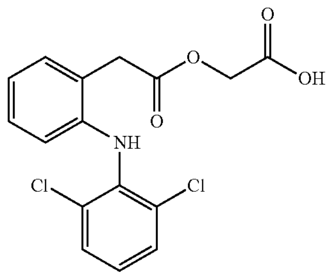 [SMILES: O=C(O)COC(=O)Cc1ccccc1Nc1c(Cl)cccc1Cl] |
| Acetylsalicyl salicyclic acid | 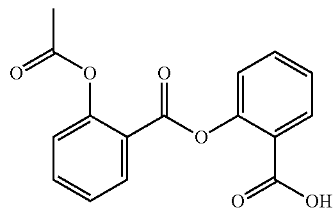 [SMILES: CC(=O)Oc1ccccc1C(=O)Oc1ccccc1C(=O)O] |
| Alclofenac | 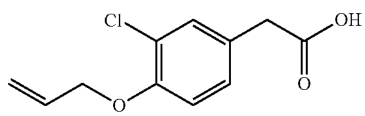 |
| Amfenac | 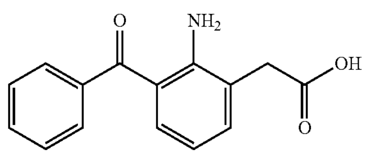 [SMILES: Nc1c(CC(=O)O)cccc1C(=O)c1ccccc1] |
| Balsalazide | 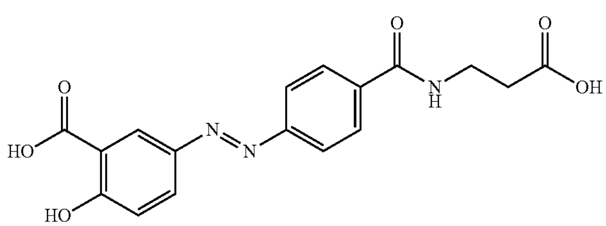 [SMILES: O=C(O)CCNC(=O)c1ccc(/N=N/c2ccc(O)c(C(=O)O)c2)cc1] |
| Benoxaprofen | 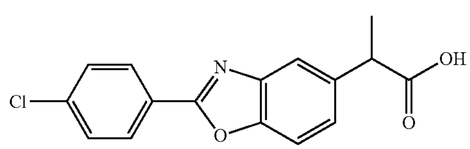 [SMILES: CC(C(=O)O)c1ccc2oc(-c3ccc(Cl)cc3)nc2c1] |
| Bromfenac | 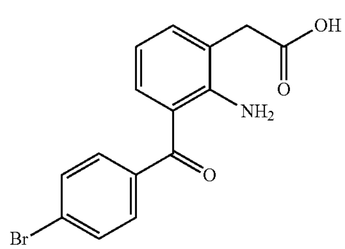 [SMILES: Nc1c(CC(=O)O)cccc1C(=O)c1ccc(Br)cc1] |
| Bucloxic Acid | 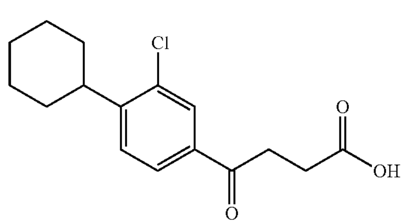 [SMILES: O=C(O)CCC(=O)c1ccc(C2CCCCC2)c(Cl)c1] |

TABLE 3-continued

| Name | Structure |
|---|---|
| Carprofen | 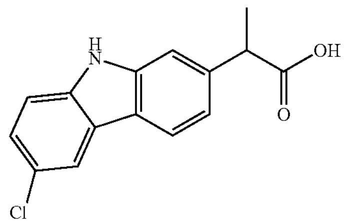 [SMILES: CC(C(=O)O)c1ccc2c(c1)[nH]c1ccc(Cl)cc12] |
| Cinmetacin | 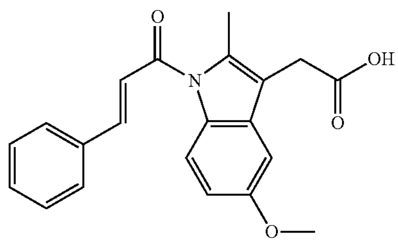 [SMILES: COc1ccc2c(c1)c(CC(=O)O)c(C)n2C(=O)/C=C/c1ccccc1] |
| Clometacin | 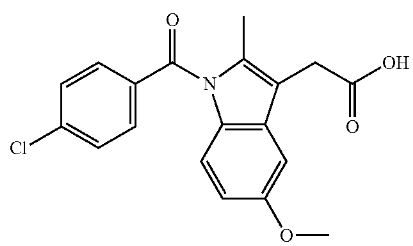 [SMILES: COc1ccc2c(c1)c(CC(=O)O)c(C)n2C(=O)c1ccc(Cl)cc1] |
| Clopirac | 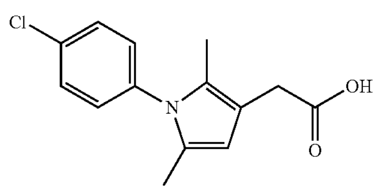 [SMILES: Cc1cc(CC(=O)O)c(C)n1-c1ccc(Cl)cc1] |
| Dexketoprofen | 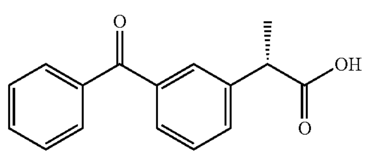 [SMILES: C[C@H](C(=O)O)c1cccc(C(=O)c2ccccc2)c1] |
| Diclofenac | 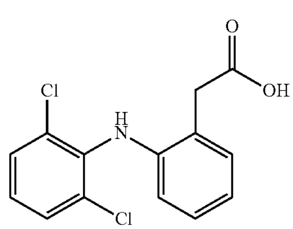 [SMILES: O=C(O)Cc1ccccc1Nc1c(Cl)cccc1Cl] |
| Dipyrocetyl | 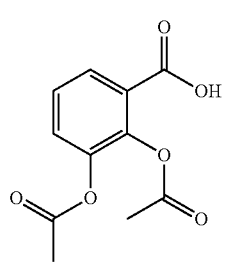 [SMILES: CC(=O)Oc1cccc(C(=O)O)c1OC(C)=O] |

TABLE 3-continued

| Name | Structure |
|---|---|
| Etodolac | 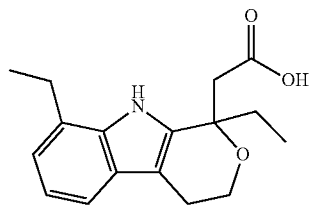 [SMILES: CCc1cccc2c3c([nH]c12)C(CC)(CC(=O)O)OCC3] |
| Fenbufen | 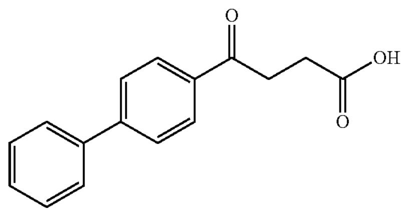 [SMILES: O=C(O)CCC(=O)c1ccc(-c2ccccc2)cc1] |
| Fendosal | 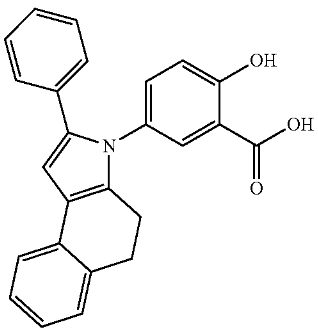 [SMILES: O=C(O)c1cc(-n2c(-c3ccccc3)cc3c2CCc2ccccc2-3)ccc1O] |
| Fentiazac | 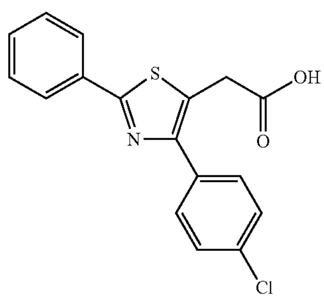 [SMILES: O=C(O)Cc1sc(-c2ccccc2)nc1-c1ccc(Cl)cc1] |
| Flunixin | 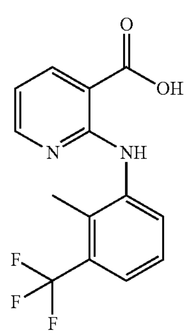 |
| Flurbiprofen | 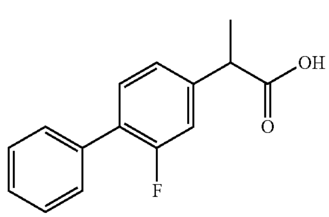 [SMILES: CC(C(=O)O)c1ccc(-c2ccccc2)c(F)c1] |

TABLE 3-continued

| Name | Structure |
|---|---|
| Gentisic acid | *(structure: 2,5-dihydroxybenzoic acid)* |
| Ibuprofen | *(structure)* |
| Indoprofen | *(structure)* |
| Isoxepac | *(structure)* |
| Ketorolac | *(structure)* |
| Lonazolac | *(structure)* |
| Lumiracoxib | *(structure)* |

TABLE 3-continued

| Name | Structure |
|---|---|
| Mefenamic Acid | 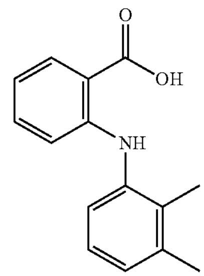 [SMILES: Cc1cccc(Nc2ccccc2C(=O)O)c1C] |
| 6-Methoxy-2-naphthyl-acetic acid | 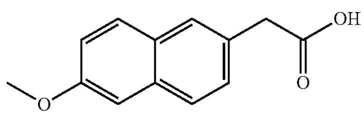 [SMILES: COc1ccc2cc(CC(=O)O)ccc2c1] |
| Mofezolac | 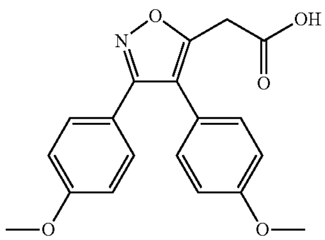 |
| Niflumic Acid | 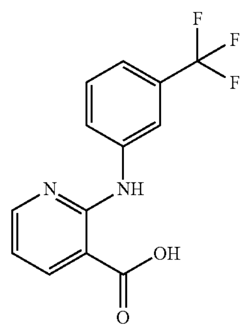 [SMILES: O=C(O)c1cccnc1Nc1cccc(C(F)(F)F)c1] |
| Oxaprozin | 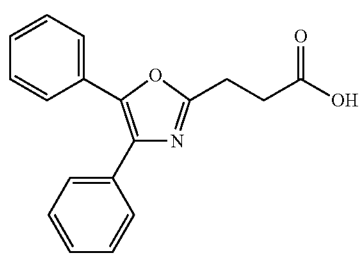 [SMILES: O=C(O)CCc1nc(-c2ccccc2)c(-c2ccccc2)o1] |
| Pirprofen | 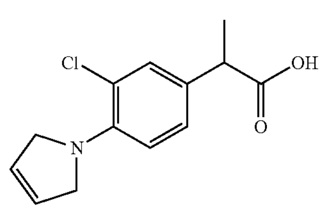 [SMILES: CC(C(=O)O)c1ccc(N2CC=CC2)c(Cl)c1] |
| Protizinic Acid | 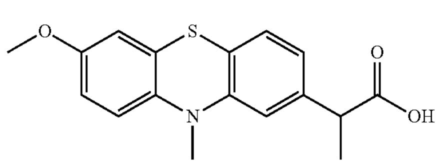 [SMILES: COc1ccc2c(c1)Sc1ccc(C(C)C(=O)O)cc1N2C] |

TABLE 3-continued

| Name | Structure |
|---|---|
| Salsalate | 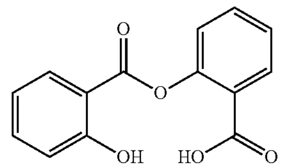 [SMILES: O=C(Oc1ccccc1C(=O)O)c1ccccc1O] |
| Sulfasalazine | 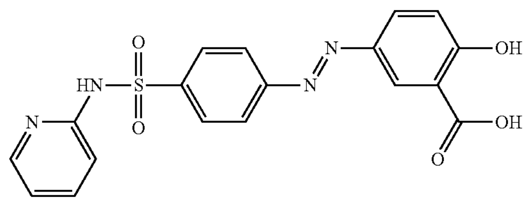 [SMILES: O=C(O)c1cc(/N=N/c2ccc(S(=O)(=O)Nc3ccccn3)cc2)ccc1O] |
| Tiaprofenic Acid | 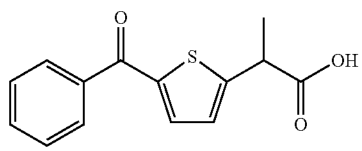 [SMILES: CC(C(=O)O)c1ccc(C(=O)c2ccccc2)s1] |
| Tolmetin | 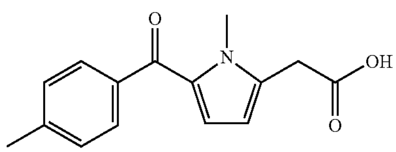 [SMILES: Cc1ccc(C(=O)c2ccc(CC(=O)O)n2C)cc1] |
| Zaltoprofen | 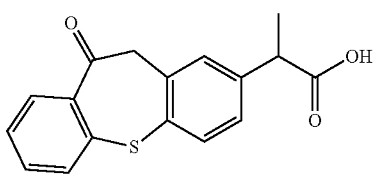 [SMILES: CC(C(=O)O)c1ccc2c(c1)CC(=O)c1ccccc1S2] |
| Acemetacin | 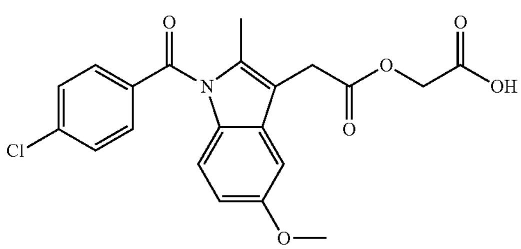 [SMILES: COc1ccc2c(c1)c(CC(=O)OCC(=O)O)c(C)n2C(=O)c1ccc(Cl)cc1] |
| Actarit | 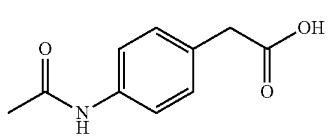 |
| Alminoprofen | 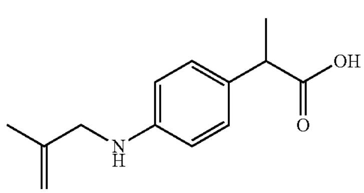 [SMILES: C=C(C)CNc1ccc(C(C)C(=O)O)cc1] |

TABLE 3-continued

| Name | Structure |
|---|---|
| Aspirin | 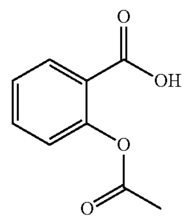 |
| Bendazac | 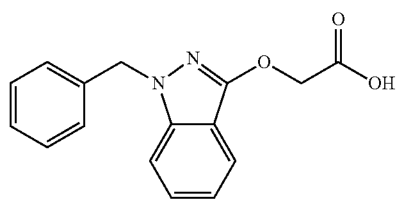 [SMILES: O=C(O)COc1nn(Cc2ccccc2)c2ccccc12] |
| Bermoprofen | 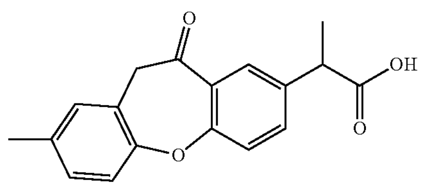 [SMILES: Cc1ccc2c(c1)CC(=O)c1cc(C(C)C(=O)O)ccc1O2] |
| 5-Bromosalicyclic acid acetate | 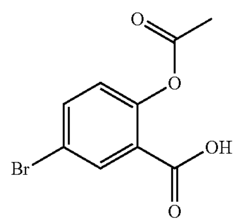 |
| Butibufen | 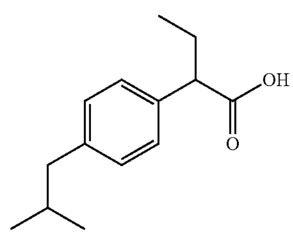 [SMILES: CCC(C(=O)O)c1ccc(CC(C)C)cc1] |
| Cinchophen | 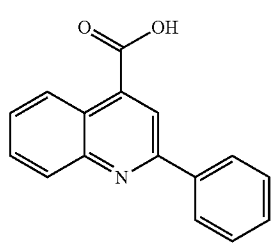 [SMILES: O=C(O)c1cc(-c2ccccc2)nc2ccccc12] |
| Clidanac | 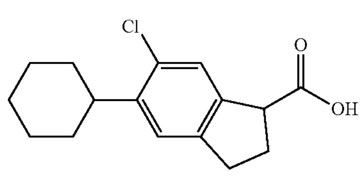 [SMILES: O=C(O)C1CCc2cc(C3CCCCC3)c(Cl)cc21] |

TABLE 3-continued

| Name | Structure |
|---|---|
| Clonixin | 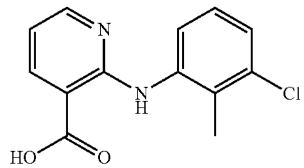 [SMILES: Cc1c(Cl)cccc1Nc1ncccc1C(=O)O] |
| Dexibuprofen | 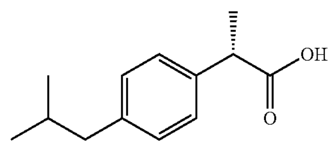 |
| Diacerein | 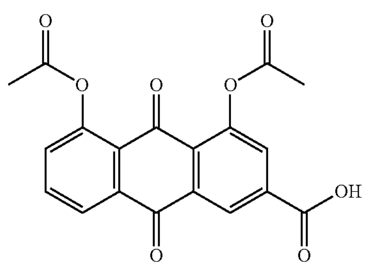 [SMILES: CC(=O)Oc1cccc2c1C(=O)c1c(OC(C)=O)cc(C(=O)O)cc1C2=O] |
| Diflunisal | 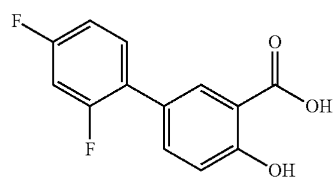 [SMILES: O=C(O)c1cc(-c2ccc(F)cc2F)ccc1O] |
| Enfenamic Acid | 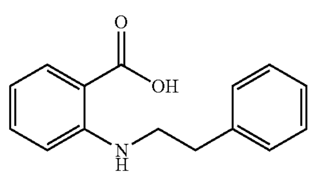 [SMILES: O=C(O)c1ccccc1NCCc1ccccc1] |
| Felbinac | 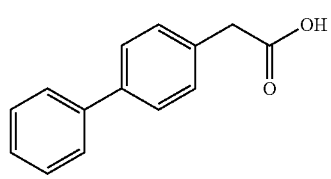 [SMILES: O=C(O)Cc1ccc(-c2ccccc2)cc1] |
| Fenclozic Acid | 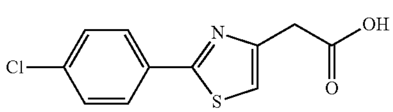 [SMILES: O=C(O)Cc1csc(-c2ccc(Cl)cc2)n1] |
| Fenoprofen | 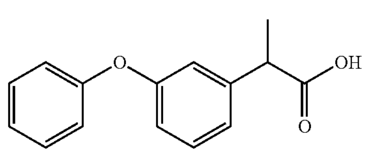 [SMILES: CC(C(=O)O)c1cccc(Oc2ccccc2)c1] |

TABLE 3-continued
| Name | Structure |
|---|---|
| Flufenamic Acid | 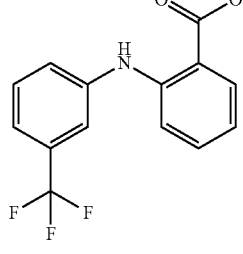 |
| Flunoxaprofen | 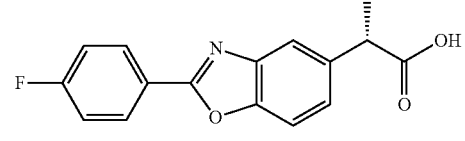 |
| Fosfosal | 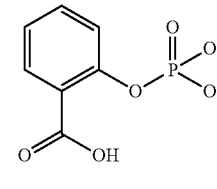 |
| Ibufenac | 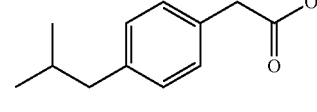 |
| Indomethacin | 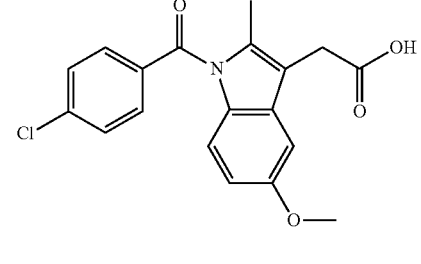 [SMILES: COc1ccc2c(c1)c(CC(=O)O)c(C)n2C(=O)c1ccc(Cl)cc1] |
| Isofezolac | 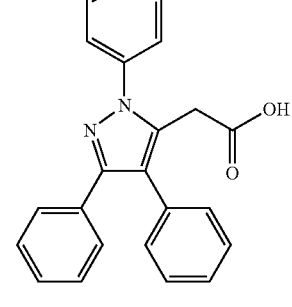 |
| Ketoprofen | 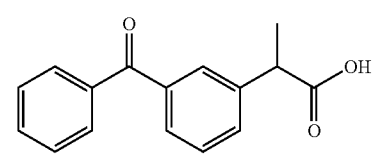 [SMILES: CC(C(=O)O)c1cccc(C(=O)c2ccccc2)c1] |

TABLE 3-continued

| Name | Structure |
| --- | --- |
| Licofelone | 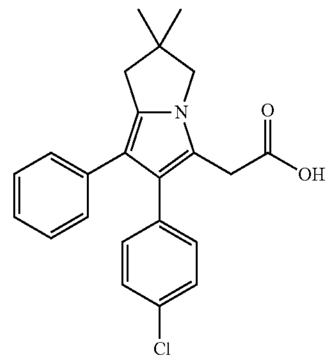 [SMILES: CC1(C)Cc2c(-c3ccccc3)c(-c3ccc(Cl)cc3)c(CC(=O)O)n2C1] |
| Loxoprofen | 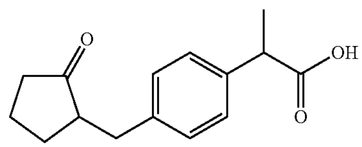 [SMILES: CC(C(=O)O)c1ccc(CC2CCCC2=O)cc1] |
| Meclofenamic Acid | 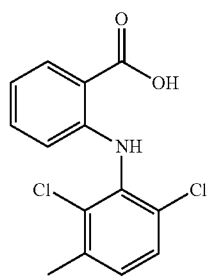 [SMILES: Cc1ccc(Cl)c(Nc2ccccc2C(=O)O)c1Cl] |
| Mesalamine | 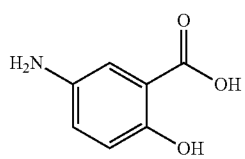 [SMILES: Nc1ccc(O)c(C(=O)O)c1] |
| Metiazinic Acid | 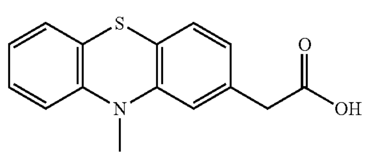 [SMILES: CN1c2ccccc2Sc2ccc(CC(=O)O)cc21] |
| Naproxen | 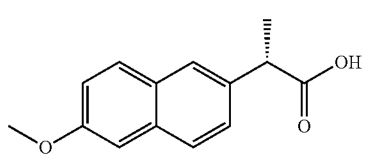 [SMILES: COc1ccc2cc([C@H](C)C(=O)O)ccc2c1] |
| Olsalazine | 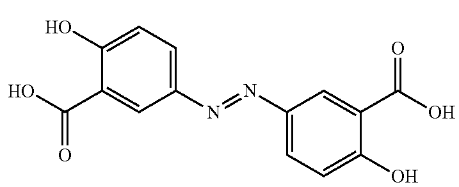 [SMILES: O=C(O)c1cc(/N=N/c2ccc(O)c(C(=O)O)c2)ccc1O] |

TABLE 3-continued

| Name | Structure |
|---|---|
| Pirazolac | 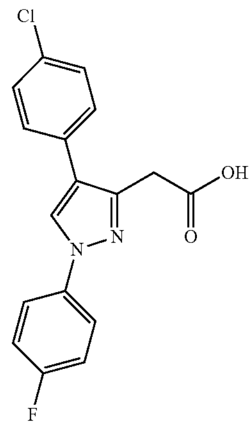 [SMILES: O=C(O)Cc1nn(-c2ccc(F)cc2)cc1-c1ccc(Cl)cc1] |
| Pranoprofen | 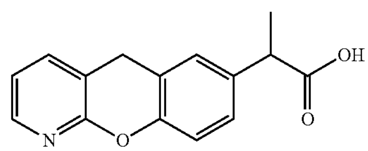 [SMILES: CC(C(=O)O)c1ccc2c(c1)Cc1cccnc1O2] |
| Salicylamide O-acetic acid | 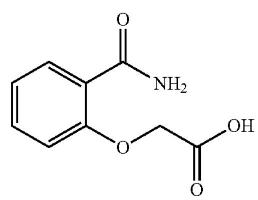 [SMILES: NC(=O)c1ccccc1OCC(=O)O] |
| Sulindac | 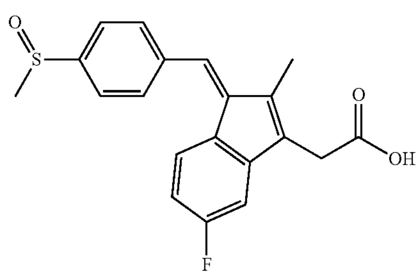 [SMILES: CC1=C(CC(=O)O)c2cc(F)ccc2/C1=C\c1ccc(S(C)=O)cc1] |
| Suprofen | 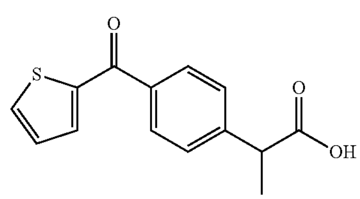 [SMILES: CC(C(=O)O)c1ccc(C(=O)c2cccs2)cc1] |
| Tolfenamic Acid | 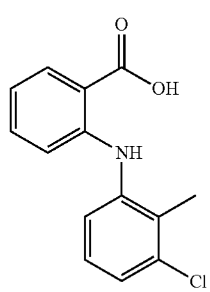 [SMILES: Cc1c(Cl)cccc1Nc1ccccc1C(=O)O] |

TABLE 3-continued

| Name | Structure |
|---|---|
| Ximoprofen | 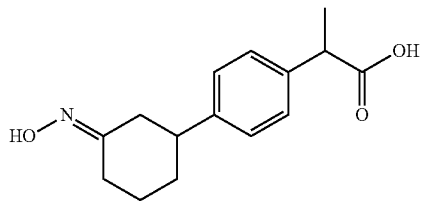 [SMILES: CC(C(=O)O)c1ccc(C2CCC/C(=N\O)C2)cc1] |
| Zomepirac | 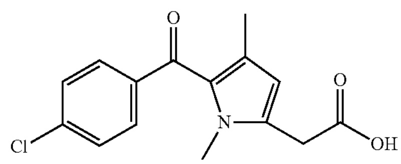 [SMILES: Cc1cc(CC(=O)O)n(C)c1C(=O)c1ccc(Cl)cc1] |

Substituted carboxylic acid NSAIDs such as those listed in Table 1 may be acetic acid or propionic acid derivatives. The present invention is generally applicable to the class of substituted carboxylic acid NSAID due to the structural similarity of the drug compounds in the carboxylic acid group that conjugates the drug to the aryl ester linkage. The performance of the polymer-NSAID conjugates of the invention in terms of release of the drug is therefore applicable across the range of drugs in this class.

In some specific embodiments of a polymer-NSAID conjugate of the invention, D is the acid residue of an carboxylic acid NSAID selected from the group consisting of aceclofenac, alminoprofen, amfenac, bromfenac, carprofen, diclofenac, enfenamic acid, etodolac, flufenamic acid, meclofenamic acid, mefenamic acid, niflumic acid, tolfenamic acid, bendazac, benoxaprofen, bermoprofen, bucloxic acid, butibufen, cinmetacin, clidanac, clopirac, dexibuprofen, dexketoprofen, felbinac, fenbufen, fenclozic acid, fenoprofen, fentiazac, flunoxaprofen, flunixin, flurbiprofen, ibuprofen, indomethacin, isofezolac, isoxepac, ketoprofen, licofelone, lonazolac, loxoprofen, lumiracoxib, metiazinic acid, mofezolac, naproxen, oxaprozin, pirazolac, pirprofen, pranoprofen, protizinic acid, sulindac, suprofen, tiaprofenic acid, tolmetin, bermoprofen, bucloxic acid, isoxepac, ketoprofen, loxoprofen, zaltoprofen, balsalazide, fendosal, olsalazine, ximoprofen, mesalamine, sulfasalazine, acetylsalicylsalicylic acid, alclofenac, aspirin, benoxaprofen, 5-bromosalicylic acid acetate, cinchophen, diacerein, dipyrocetyl, fosfosal, ibufenac, indoprofen, clometacin, ketorolac, zomepirac, actarit, clonixin, salicylamide O-acetic acid, diflunisal, gentisic acid, and salsalate.

In particular embodiments, D is the acid residue of a carboxylic acid NSAID selected from the group that have more than one nuceophilic moiety within the molecule consisting of aceclofenac, alminoprofen, amfenac, balsalazide, bromfenac, carprofen, clonixin, diclofenac, enfenamic acid, etodolac, flufenamic acid, flunixin, fosfosal, gentrisic acid, lumiracoxib, meclofenamic acid, mefenamic acid, mesalamine, niflumic acid, salicylamide o-acetic acid, salsalate, sulfasalazine, tolfenamic acid, ximoprofen.

In particular embodiments, D is the acid residue of a carboxylic acid NSAID selected from the group consisting of diclofenac, ketorolac and indomethacin.

In particular embodiments, D is the acid residue of a carboxylic acid NSAID that contains another nucleophilic moiety. In preferred set of embodiments, D is the acid residue of a carboxylic acid NSAID selected from the group consisting of diclofenac and bromfenac.

In one set of embodiments, polymer-bioactive agent conjugates of the invention comprise a moiety of formula (I):

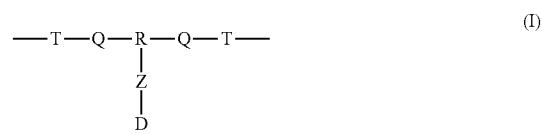

where:
T at each occurrence represents a triazole moiety;
Q is independently selected at each occurrence and may be present or absent and when present represents a linking group;
R is an optionally substituted linear or branched hydrocarbon and may comprise optionally substituted aromatic hydrocarbon or heteroaromatic hydrocarbon;
Z is a cleavable linking group; and
D is a releasable bioactive agent selected from a quinolone of formula (X) and/or a NSAID of formula (XX).

Quinolones and NSAIDs bound to polymer conjugates of the invention are releasable bioactive agents. The term "releasable" as used herein in connection with bioactive agents mean that the bioactive agents are capable of being covalently decoupled or cleaved from the polymer backbone so as to be released into an environment in a biologically active or physiologically active form. For example, the bioactive agents are capable of being released or cleaved from the Z (or $Z^1$ and $Z^2$) group defined in general formulae (I), (Ib), (IIa), (IIb), (IIIa), (IIIb), (IV), (IXa) and (IXb) above. Release of the bioactive agents may be promoted by the conjugates being exposed to physiological conditions or a biological environment. Upon being released, the bioactive agent is bioactive or will be converted in vivo or in vitro to a bioactive form (e.g. as in the case of a prodrug bioactive agent).

The ability of the bioactive agents to be releasable will generally be a result of the bioactive agents each being coupled to the polymer backbone in pendant form via a cleavable linking group, which is represented by the moiety "Z" or $Z^1$ and $Z^2$ in formulae described herein. The cleavable linking group may couple the bioactive agent to the polymer backbone directly, or through a spacer moiety. Cleavage of the cleavable linking group will therefore promote release of the bioactive agent. Some specific examples of Z are described below.

In one embodiment, the quinolones and NSAIDs are released such that they do not include a residue derived from the polymer backbone or linking group Z. By this it is meant that each bioactive agent is released in their substantially original form (i.e. before being conjugated) and are essentially free from, for example, fragments of oligomer or polymer derived from the polymer backbone and/or group(s) linking the bioactive agent to the polymer backbone. Accordingly, in this respect, the linking group Z in formulae described herein is considered to be a part of the polymer backbone of the conjugate.

In the moieties of formulae (I), (Ib), (IIa), (IIb), (IIIa), (IIIb), (IV) (IXa), and (IXb), the bioactive agent (D) or $D^1$ and $D^2$ is coupled to R through a cleavable linking group denoted by Z or $Z^1$ and $Z^2$. As used herein "linking group" refers to a generally divalent substituent group that couples D to R. The substituent group is cleavable so that the bioactive agent is releasable.

In some embodiments, the cleavable linking group represented by Z is a cleavable covalent bond that directly couples the bioactive agent to the polymer backbone.

In other embodiments, the cleavable linking group represented by Z comprises a spacer moiety and a cleavable covalent bond. The spacer moiety is attached to the polymer backbone while the cleavable covalent bond couples the spacer moiety to the bioactive agent. In some embodiments of a polymer-bioactive conjugate of the invention, it is a proviso that Z does not include a triazole moiety. Thus, polymer conjugates of the invention do not include bioactive agents coupled to the polymer backbone via a product of a click chemistry reaction.

The covalent bond coupling the bioactive agent (D) with the linking group (Z) is not a carbon-carbon bond. Accordingly, the cleavable covalent bond will generally form part of a functional group selected from: alkyl esters; aryl esters; and (acyloxy)alkyl ester, [(alkoxycarbonyl)oxy]alkyl esters [(aryloxycarbonyl)oxy]alkyl ester, alkyl anhydride or aryl anhydride. Of these functional groups, aryl esters and (acyloxy)alkyl esters or [(alkoxycarbonyl)oxy]alkyl esters are preferred. A skilled person would recognise that such groups are capable of being cleaved, for example hydrolytically, enzymatically, and/or by radical mechanisms, so as to release the bioactive agent.

The present invention preferably employs a group selected from alkyl ester, aryl ester, (acyloxy)alkyl ester, [(alkoxycarbonyl)oxy]alkyl ester [(aryloxycarbonyl)oxy] alkyl ester, alkyl anhydride or aryl anhydride linking groups to conjugate the bioactive agent to the polymer backbone as such linking groups have been found to be hydrolytically labile in biological environments. Such linking groups may also be generally more labile than other groups or moieties that may be present in the polymer-bioactive agent conjugate, such as for example, biodegradable moieties that may be present in the polymer backbone of polymer conjugates of some embodiments of the invention. Alkyl ester, aryl ester, (acyloxy)alkyl ester, [(alkoxycarbonyl)oxy]alkyl ester [(aryloxycarbonyl)oxy]alkyl, alkyl anhydride or aryl anhydride ester linking groups may further help to ensure that a sufficient amount of the drug is effectively released from the polymer conjugate to achieve therapeutic levels in the immediate vicinity of the polymer conjugate material.

The NSAIDs particularly useful in the polymer-bioactive conjugates of the invention comprise a carboxyl group or salt thereof. The carboxyl may be an alkanoic carboxyl, as is the case in a great many NSAIDS or may be an aromatic substituent as in the case of aspirin and clonixin. When the bioactive agent is a NSAID, the cleavable covalent bond forms part of an alkyl ester, aryl ester or (acyloxy)alkyl ester, [(alkoxycarbonyl)oxy]alkyl ester, [(aryloxycarbonyl)oxy] alkyl ester, alkyl anhydride or aryl anhydride group as the bioactive agent is conjugated to the polymer backbone via the carboxylic acid (—COOH) moiety of the substituted carboxylic acid.

When present, the quinolones of formula (X) and the NSAIDs of formula (XX) as shown above are each coupled to the polymer backbone by the group Z.

When the bioactive agent is a quinolone of formula (Xi or Xii) or NSAID of formula (XX or XXa), the drug and linker Z form an ester such as an alkyl ester, aryl ester or (acyloxy) alkyl ester, [(alkoxycarbonyl)oxy]alkyl ester [(aryloxycarbonyl)oxy]alkyl ester, alkyl anhydride or aryl anhydride linking group. Accordingly, in formula (X or Xa) or (XX or XXa), the active quinolone or NSAID is covalently linked to Z so as to form the carbonyl part of an ester linkage with Z, $Z^1$ $Z^2$ forming the alcohol portion of the ester linkage. The ester may be an alkyl ester, aryl ester, an (acyloxy)alkyl ester, [(alkoxycarbonyl)oxy]alkyl ester, or [(aryloxycarbonyl)oxy]alkyl ester linkage. In such embodiments, the quinolone or NSAID will comprise the acid residue (carbonyl portion) of the ester, while Z will comprise the alcohol residue of the ester. Upon hydrolysis or cleavage of the ester, (acyloxy)alkyl ester or [(alkoxycarbonyl)oxy]alkyl ester or [(aryloxycarbonyl)oxy]alkyl ester linking group, a carboxylic acid group will then form on the quinolone or NSAID. The anhydride may be an alkyl anhydride or aryl anhydride linkage. In such embodiments, the quinolone or NSAID will comprise the acid residue (carbonyl portion) of the ester, while Z will comprise the other acid residue of the anhydride. Upon hydrolysis or cleavage of the anhydride, a carboxylic acid group will then form on the quinolone or NSAID and on the alkyl or aryl group that forms part of Z.

Breakdown of the cleavable covalent bond can be promoted hydrolytically (i.e. hydrolytic cleavage) and may take place in the presence of water and an acid or a base. In some embodiments the cleavage may take place in the presence of one or more hydrolytic enzymes or other endogenous biological compounds that catalyze or at least assist in the cleavage process. For example, an ester bond may be hydrolytically cleaved to produce a carboxylic acid and an alcohol.

At the very least the bioactive agent will be releasable from the conjugate per se. However, as further described below, the polymer backbone may also biodegrade in vivo or in vitro such that the polymer backbone breaks into lower molecular weight fragments, with the bioactive agent remaining tethered to such a fragment(s) via Z. In that case, the bioactive agent will nevertheless still be capable of being released or cleaved from Z, which may or may not still be associated with the polymer conjugate per se.

In some embodiments the linker may be branched. Where the linker is branched, two or more releasable bioactive agents may be appended to the linker moiety.

Some specific examples of spacer moieties that may form part of Z include: —O—; and optionally substituted: —O—Ar—C(O)O—; —O—Ar—C(O)—$NR^a$; —O—Ar—; —O—Ar—; —O(O)O—$C_1$-$C_{18}$alkylene-O—; —O—$C_1$-$C_{18}$alkylene-O—; —O—$C_1$-$C_{18}$alkylene-$NR^a$—; —OC(O)—$C_1$-$C_{18}$alkylene-O—; —C(O)—$C_1$-$C_{18}$alkylene-O—; and where $R^a$ is as defined above.

In one form of the invention, exemplary spacer moieties include: —O—; —C(O)—; and —OC(O)—C$_{1-18}$alkylene-C(O)—, such as —OC(O)—C$_{2-3}$alkylene-C(O)—, —O—C$_{5-6}$Ar—C(O)O and —C(O)O—C$_{5-6}$Ar—C(O)O—.

The choice of spacer moieties will determine the spacing of the bioactive agents from the polymer backbone. The skilled artisan would be capable of selecting the appropriate spacer moiety based on an evaluation of steric constraints, phase chemistry and surface chemistry. For example, larger bioactive agents can be advantageously spaced from the monomer by the choice of a longer spacer moiety.

In some embodiments of a polymer conjugate of the invention, the bioactive agent (D) is a quinolone of formula (Xi), or Xii, (preferably of formula (Xi) where A$_3$ is N) wherein the COOH is an acid residue (—C(O)—) of an and Z is of a formula selected from the group consisting of:

(R) —O— (D);                                                    (i)

(R) -J-Ar—O— (D);                                               (ii)

(R) -J-C$_1$-C$_{12}$alkylene-O— (D);                           (iii)

(R) -J-Ar-J-C$_1$-C$_{12}$alkylene-O— (D);                      (iv)

(R) -J-C$_1$-C$_{12}$alkylene-J-Ar—O— (D);                      (v)

(R) -J-C$_1$-C$_{12}$alkylene-J-Ar-Q-C$_1$-C$_{12}$alkylene-O—
(D);                                                             (vi)

wherein:

(R) indicates the end of the linking group bonded to the R group in the polymer backbone and (D) indicates the end of the linking group bonded to the quinolone drug;

Ar is optionally substituted aromatic or heteroaromatic hydrocarbon; and

J is selected from the group consisting of —O—, —C(O)—, —O—C(O)—, —O—C(O)—O—, —C(O)—O—, —C(O)OC(O)—, —C(O)NR$^a$C(O)—, —OC(O)NR$^a$—, —NR$^a$C(O)O—, —NR$^a$—, —NR$^a$C(O)NR$^a$—, —NR$^a$C(O)—, —C(O)NR$^a$—, —S—, —O—C(S)—, —C(S)—O—, —S—C(O)—, —C(O)—S—, —NR$^a$C(S)—, and —C(S)NR$^a$—, where R$^a$ is hydrogen or C$_1$ to C$_6$ alkyl.

Preferred J is selected from the group consisting of —O—, —C(O)—, —O—C(O)—, O—C(O)—O—.

Preferred alkylene may be straight or branched chain alkylene and preferred C1-C12alkylene include C1 to C4 straight chain alkylene (preferably methylene) substituted by C$_1$ to C4 alkyl (preferably methyl).

In some embodiments of a polymer conjugate of the invention, the bioactive agent (D) is a NSAID of formula (XX), wherein the 1-COOH is an acid residue (—C(O)O—) of an alkyl ester, aryl ester or (acyloxy)alkyl ester, [(alkoxycarbonyl)oxy]alkyl ester or [(aryloxycarbonyl)oxy]alkyl ester linking group and Z is of a formula selected from the group consisting of:

(R) —O— (D);                                                    (i)

(R) -J-Ar—O— (D);                                               (ii)

(R) -J-C$_1$-C$_{12}$alkylene-O— (D);                           (iii)

(R) -J-Ar-J-C$_1$-C$_{12}$alkylene-O— (D);                      (iv)

(R) -J-C$_1$-C$_{12}$alkylene-J-Ar—O— (D);                      (v)

(R) -J-C$_1$-C$_{12}$alkylene-J-Ar-Q-C$_1$-C$_{12}$alkylene-O—
(D);                                                             (vi)

wherein:

(R) indicates the end of the linking group bonded to the R group in the polymer backbone and (D) indicates the end of the linking group bonded to the NSAID drug;

Ar is optionally substituted aromatic or heteroaromatic hydrocarbon; and

J is selected from the group consisting of —O—, —C(O)—, —O—C(O)—, O—C(O)—O—, —C(O)—O—, —C(O)OC(O)—, —C(O)NR$^a$C(O)—, —OC(O)NR$^a$—, —NR$^a$C(O)O—, —NR$^a$—, —NR$^a$C(O)NR$^a$—, —NR$^a$C(O)—, —C(O)NR$^a$—, —S—, —O—C(S)—, —C(S)—O—, —S—C(O)—, —C(O)—S—, —NR$^a$C(S)—, and —C(S)NR$^a$—, where R$^a$ is hydrogen or C$_1$ to C$_6$ alkyl.

Preferred J is selected from the group consisting of —O—, —C(O)—, —O—C(O)—, O—C(O)—O—.

Preferred alkylene may be straight or branched chain alkylene and preferred C1-C12alkylene include C1 to C4 straight chain alkylene (preferably methylene) substituted by C$_1$ to C4 alkyl (preferably methyl).

The terms "aromatic hydrocarbon" and "heteroaromatic hydrocarbon", including indefinition of R and Z (in connection with the group "Ar") denotes any ring system comprising at least one aromatic or heteroaromatic ring. The aromatic hydrocarbon or heteroaromatic hydrocarbon may be optionally substituted by one or more optional substituents as described herein.

The aromatic hydrocarbon or heteroaromatic hydrocarbon may comprise a suitable number of ring members. In some embodiments, the aromatic hydrocarbon or heteroaromatic hydrocarbon comprises from 5 to 12 ring members. The term "ring members" denotes the atoms forming part of the ring system. In an aryl group, the ring atoms are each carbon. In a heteroaromatic hydrocarbon group one or more of the rings atoms are heteroatoms. Examples of heteroatoms are O, N, S, P and Se, particularly O, N and S. When two or more heteroatoms are present in a heteroaromatic hydrocarbon group, the heteroatoms may be the same or different at each occurrence.

Suitable aromatic hydrocarbon may be selected from the group consisting of phenyl, biphenyl, naphthyl, tetrahydronaphthyl, idenyl, azulenyl, and the like.

Suitable heteroaromatic hydrocarbon may be selected from the group consisting of furanyl, thiophenyl, 2H-pyrrolyl, pyrrolinyl, oxazolinyl, thiazolinyl, indolinyl, imidazolidinyl, imidazolinyl, pyrazolyl, pyrazolinyl, isoxazolidinyl, isothiazolinyl, oxadiazolinyl, triazolinyl, thiadiazolinyl, tetrazolinyl, pyridinyl, pyridazinyl, pyrimidinyl, pyrazinyl, triazenyl, indolyl, isoindolinyl, benzimidazolyl, benzoxazolyl, quinolinyl, isoquinolinyl, and the like.

In some embodiments of the invention, Ar is an optionally substituted C$_{5-12}$ aromatic hydrocarbon. In some embodiments Ar is optionally substituted phenyl (C$_6$ aromatic hydrocarbon). In some specific embodiments, Ar is para or meta substituted phenyl. In some specific embodiments, Ar is optionally substituted pyridyl (C$_5$ heteroaromatic).

In some embodiments of a polymer-bioactive agent conjugate of the invention, when the bioactive agent (D in formula (I) or D$_1$, D$_2$ in formula (II)) is a quinolone or NSAID linked via COOH to the polymer backbone, then linking group (Z in formula (I) and Z$_1$, Z$_2$ in formula (II)) is of a formula selected from the group consisting of:

(R) —O— (D);

(R) —OC(O)—Ar—O— (D);

(R) —NHC(O)—Ar—O— (D);

(R) —C(O)O—$C_{1-12}$alkylene-O— (D);

(R) —OC(O)—$C_1$-$C_{12}$alkylene-O— (D).

(R) —OC(O)— (D);

In one embodiment, when the quinolone is linked via COOH to the polymer backbone, then Z is —O—; —O—$C_6$-aryl-C(O)O—; —O—$C_6$-aryl-C(O)NH.

In some embodiments of a polymer-bioactive agent conjugate of the invention, when the bioactive agent (D) is a fluoroquinolone linked via COOH to the polymer backbone, then Z is of a formula selected from the group consisting of:

(R) —O— (D);

(R) —OC(O)—Ar—O— (D);

(R) —NHC(O)—Ar—O— (D);

(R) —C(O)O—$C_{1-12}$alkylene-O— (D);

(R) —OC(O)—$C_1$-$C_{12}$alkylene-O— (D).

(R) —OC(O)— (D);

In one embodiment, when the fluoroquinolone is linked via COOH to the polymer backbone, then Z is —O—; —OC(O)—; —O—$C_6$-aryl-C(O)O—; and —O—$C_6$-aryl-C(O)NH—.

Preferred embodiments when alkyl, acetal.

Further preferred embodiments when aryl, more particularly PHB, MHB & pyridoxine.

Conjugates of the invention may, in addition to moieties of formula (I) or (Ib), comprise a linker segment as a part of its polymer backbone structure. The linker segment may be coupled to one or more moieties of formula (I) or (Ib). Each coupling to a moiety of formula (I) or (Ib) occurs via a triazole moiety. Thus, when present, the linker segment may be used to space apart moieties of formula (I) or (Ib) in the conjugates.

As used herein, the term "linker segment" refers to a segment that is generally a divalent.

The presence of a linker segment can be advantageous, as it enables the physical properties of the conjugates to be adjusted by selection of a desired linker segment, thus providing avenues for macromolecules tailored for use in particular applications. For example, hard segments and/or soft segments may be incorporated into the polymer backbone of the conjugates through the selection of an appropriate linker segment.

The linker segment may be introduced to the polymer backbone of the polymer-bioactive agent conjugate by polymerising a monomer comprising a pendant bioactive agent with a co-monomer comprising a linker moiety. In such embodiments the linker segment may be derived from the linker moiety of the co-monomer.

In some embodiments, the linker segment may be selected from the group consisting of optionally substituted linear or branched aliphatic hydrocarbon, optionally substituted carbocyclyl, optionally substituted heterocyclyl, optionally substituted aryl, optionally substituted heteroaryl, an optionally substituted polymeric linker segment, and combinations thereof.

Optionally substituted linear or branched aliphatic hydrocarbon linker segments may be selected from optionally substituted $C_1$ to $C_{20}$, $C_1$ to $C_{10}$ or $C_1$ to $C_6$ linear or branched aliphatic hydrocarbons. The aliphatic hydrocarbons may be saturated or unsaturated hydrocarbon. Optionally substituted aliphatic hydrocarbon linker segments may be derived from fatty acids (such as acetic acid, propionic acid, butyric acid, valeric acid and caproic acid), sugar alcohols (such as xylitol and mannitol), and amino acids (such as glutamic acid and lysine).

Optionally substituted carbocyclyl linker segments may comprise from 3 to 12, 3 to 8 or 5 to 6 carbon ring members.

Optionally substituted heterocyclyl linker segments may comprise from 3 to 12, 3 to 8 or 5 to 6 ring members and 1, 2, 3, 4 or more heteroatoms as a part of the ring. The heterotoms may be independently selected from the group consisting of O, N and S.

Optionally substituted aryl linker segments may comprise from 3 to 12, 3 to 8 or 5 to 6 carbon ring members and at least one unsaturation.

Optionally substituted heteroaryl linker segments may comprise from 3 to 12, 3 to 8 or 5 to 6 ring members and 1, 2, 3, 4 or more heteroatoms as a part of the ring. The heterotoms may be independently selected from the group consisting of O, N and S. The heteroaryl linker segment also comprises at least one unsaturation.

Optionally substituted polymeric linker segments may comprise any suitable polymer or copolymer. In some embodiments, it can be desirable for the polymer to be biocompatible and/or biodegradable. One skilled in the relevant art would be able to select suitable biocompatible and/or biodegradable polymers. Exemplary biocompatible polymers may be selected from polyethers, polyesters, polyamides, polyurethanes, and copolymers thereof. Copolymers may be for example, poly(ether-esters), polyurethane-ethers), poly(urethane-esters), polyester-amides) and the like. Preferred biocompatible polymers are polyethers, polyesters, polyurethanes, and copolymers thereof.

Exemplary polyethers may be polymers of $C_2$ to $C_4$ alkylene diols, such as polyethylene glycol and polypropylene glycol, preferably polyethylene glycol.

Exemplary polyesters may be polycaprolactone, polylactic acid), poly(glycolic acid) and polylactic-co-glycolic acid).

In one form, the polymeric linker segment may comprise a biodegradable polymer. Suitable biodegradable polymers may comprise at least one biodegradable moiety selected from the group consisting of an ester, an amide, a urethane (carbamate), a urea and a disulfide moiety, preferably an ester or urethane moiety. Biodegradable polymers used in the polymeric linker segment may have a combination of such moieties.

The linker segment may modify the properties of the conjugate and influence bioactive agent release. For example, a polyether linker segment (e.g. polyethylene glycol) may make the conjugate more hydrophilic. Without wishing to be limited by theory, it is believed that a conjugate comprising a hydrophilic segment as part of its polymer backbone could promote release of the bioactive agent. This may be advantageous where more rapid release of the bioactive agent is desired. Conversely, a conjugate comprising a hydrophobic segment as part of its backbone might delay release of the bioactive agent. A hydrophobic segment could be introduced by incorporation of a hydrophobic polymeric linker (e.g. a polycarpolactone linking moiety) into the conjugate.

In one set of embodiments, the polymer-bioactive agent conjugate comprises a polyether segment as part of the polymer backbone. The polyether segment may be derived from polyethylene glycol (PEG). In some embodiments, the polyether segment is derived from a PEG having a molecular weight in the range of from about 200 to 10,000, preferably from about 200 to about 3,000.

The polyether segment may be incorporated in the monomer of formula (V) by providing a linker L comprising a polyether which may be straight chain when n is 1 or branched and comprise three of more groups terminal groups "A" when n is 2 or more. Options are described hereafter with reference to formula Va and Vb wherein the group may be a polyether such as PEG.

In some embodiments, the triazole moieties in the polymer backbone may provide hard segments, which influence the properties of the polymer-bioactive agent conjugates.

In some embodiments, it may be desirable for polymer-bioctive agent conjugates of one or more embodiments of the invention to be biodegradable.

By being "biodegradable" in the context of the invention is meant that the polymer undergoes with the passage of time substantial degradation under physiological conditions or in a biological environment. In other words, the polymer has a molecular structure that is susceptible to break down (i.e. a reduction in molecular weight) by chemical decomposition in a biological environment (e.g. within a subject or in contact with biological material such as blood, tissue etc), as opposed to physical degradation. Such chemical decomposition will typically be via the hydrolysis of labile or biodegradable moieties that form part of the molecular structure of the polymer.

The presence of a biodegradable polymeric linker segment in the polymer backbone may confer biodegradability to the polymer conjugates of the invention.

Labile or cleavable functional groups present in the polymer backbone may also be susceptible to degradation, leading to the production of lower molecular weight fragments upon erosion of the polymer conjugates.

Biodegradable polymer conjugates of the invention may comprise a combination of degradable groups. For example, the conjugates may comprise a biodegradable polymeric linker, as well as cleavable functional groups, as part of the polymer backbone.

In some embodiments, polymer-bioactive agent conjugates of the invention may be formed by reacting a monomer of formula (IV):

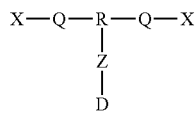 (IV)

where:
X may be the same or different at each occurrence and represents a terminal functional group comprising an alkyne or an azide functionality;
Q is independently selected at each occurrence and may be present or absent and when present, represents a linking group;
R is an optionally substituted linear or branched hydrocarbon and may comprise optionally substituted aromatic hydrocarbon or heteroaromatic hydrocarbon;
Z is a cleavable linking group; and
D is a bioactive agent selected from the group consisting of quinolones and NSAIDs,
with at least one monomer of complementary functionality.

In some embodiments, polymer-bioactive agent conjugates of the invention may be formed by reacting at least one monomer of formula (IV):

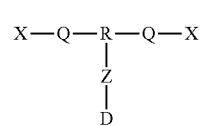 (IV)

where X, Q, R, Z and D are as herein defined, with a monomer of complementary functionality.

In the monomer of formula (IV), the groups Q, R, Z and D may be selected from any one of the moieties as described herein for such groups.

In one set of embodiments, the monomer of complementary functionality may be a monomer of formula (V):

$$A\text{-}L\text{-}[\text{-}A]_n$$ (V)

where:
A may be the same or different at each occurrence and represents a group comprising a terminal functional group selected from the group consisting of an alkyne and an azide, wherein said terminal functional group is complementary to the terminal functional group of X;
L is an optionally substituted linker group; and
n is an integer and is at least 1.

In some embodiments, polymer-bioactive agent conjugates of the invention are formed with a monomer of formula (V), where L is a linker group comprising a linker moiety selected from the group consisting of optionally substituted linear or branched aliphatic hydrocarbon, optionally substituted carbocyclyl, optionally substituted heterocyclyl, optionally substituted aryl, optionally substituted heteroaryl, and an optionally substituted polymeric segment.

In some embodiments of a monomer of formula (V), L comprises a biodegradable polymer. Biodegradable polymers may include at least one biodegradable moiety selected from the group consisting of an ester, an amide, a urethane, a urea and a disulfide moiety.

In some embodiments of a monomer of formula (V), L comprises a polymer selected from the group consisting of a polyether, a polyester, a polyamide, a polyurethane, and copolymers thereof.

In some embodiments of a monomer of formula (V), L comprises a functional group selected from the group consisting of an amide, ether, ester, urethane, urea, and carbonate ester.

In some embodiments of a monomer of formula (V), n is 1 or 2.

In another set of embodiments, the monomer of complementary functionality may be a further monomer of formula (IV). In such embodiments at least two monomers of formula (IV) may react together, provided the monomers of formula (IV) have complementary terminal functionality.

In some embodiments monomers of formula (IV) having complementary terminal functionality may be homofunctional. That is, each of the co-monomers may comprise one type of terminal functional group. The terminal functional groups of the co-monomers would be complementary and capable of reacting with one another to form a triazole moiety. For example, one co-monomer of formula (IV) may comprise a terminal functional group comprising an alkyne functionality while the other co-monomer of formula (IV) comprises a terminal functional group comprising an azide functionality. These co-monomers would be able to copolymerise under appropriate conditions to form a polymer conjugate having triazole moieties in the polymer backbone.

Examples of complementary monomers of formula (IV) that are capable of copolymerising to form a polymer-bioactive agent conjugate are shown in formula (IVa) and formula (IVb):

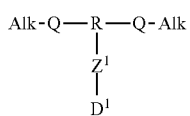

(IVa)

where:

Alk represents a terminal functional group comprising an alkyne functionality;

Q is independently selected at each occurrence and may be present or absent and when present, represents a linking group;

R is an optionally substituted linear or branched hydrocarbon and may comprise optionally substituted aromatic hydrocarbon or heteroaromatic hydrocarbon;

$Z^1$ is a cleavable linking group; and $D^1$ is a bioactive agent selected from the group consisting of quinolones and NSAIDs,

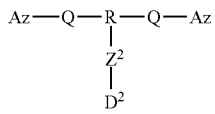

(IVb)

where:

Az represents a terminal functional group comprising an azide functionality;

Q is independently selected at each occurrence and may be present or absent and when present, represents a linking group;

R is an optionally substituted linear or branched hydrocarbon and may comprise optionally substituted aromatic hydrocarbon or heteroaromatic hydrocarbon;

$Z^2$ is a cleavable linking group; and $D^2$ is a bioactive agent selected from the group consisting of quinolones and NSAIDs.

One skilled in the art would appreciate that the terminal functional groups represented by Alk and Az in formulae (IVa) and (IVb) may be reversed. That is, the group Az may be present on formula (IVa) and the group Alk may be present on formula (IVb) in some embodiments.

The terminal functional groups represented by Alk and Az on the co-monomers of formula (IVa) and (IVb) can react to produce a triazole moiety. The triazole moiety may be of formula (II), (III) or (IX) as described herein.

A polymer-bioactive agent conjugate of the invention produced from the copolymerisation of monomers of formula (IVa) and (IVb) may comprise a moiety of formula (Ib) as described herein. The monomers of formula (IVa) and (Vb) may react with one another in a mole ratio of 1:1.

The terminal functional groups represented by Alk in formulae described herein may be straight chain aliphatic or cycloaliphatic groups comprising an alkyne functionality. Cycloaliphatic terminal functional groups may comprise from 4 to 12 ring members, preferably from 7 to 8 ring members. Cycloaliphatic alkyne containing terminal functional groups may be advantageous in strain-promoted catalyst free cycloadditions with azides to form triazole moieties.

A monomer-bioactive agent conjugate of formula (IVa) that may be used in preparing the polymer conjugates of the invention may have one of the following structures, (IVai) and (IVaii), where the alkyne functionality is part of a terminal functional group as a terminal alkyne or an internal alkyne:

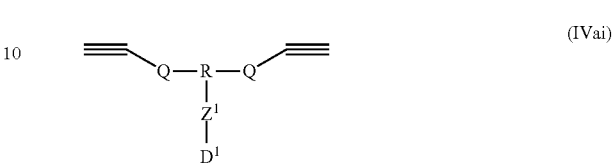

(IVai)

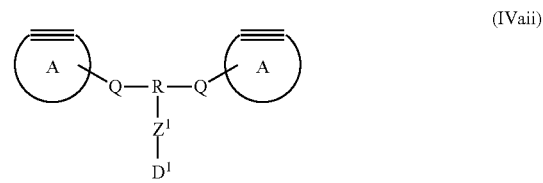

(IVaii)

A monomer-bioactive agent conjugate of formula (IVb) that may be used in preparing the polymer conjugates of the invention may have the following structure (IVbi):

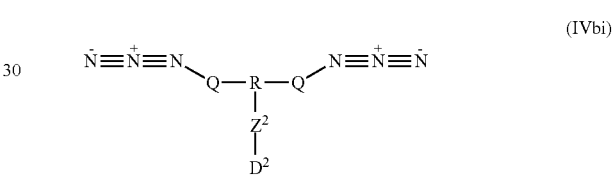

(IVbi)

In monomers of formula (IVa) and (IVb), the groups Q and R may be independently selected at each occurrence from any one of the moieties described herein for such groups.

The groups $Z^1$ and $Z^2$ in the monomers of formula (IVa) and (IVb) respectively are each cleavable linking groups, which may be the same or different. $Z^1$ and $Z^2$ may each be independently selected from any one of the groups described herein for Z.

The groups $D^1$ and $D^2$ in the monomers of formula (IVa) and (IVb) respectively are each bioactive agents, which may be the same or different. $D^1$ and $D^2$ may each be independently selected from any one of the groups described herein for D.

In some embodiments monomers of formula (IV) having complementary terminal functionality may be heterofunctional and comprise at least two different types of terminal functional groups. The terminal functional groups on the different monomers would be complementary and capable of reacting with one another to produce a triazole moiety. The trizole moiety may be selected from any of the formulae described herein for such moieties. A heterofunctional monomer may polymerise with itself (homopolymerise) or with another monomer of complementary functionality (co-polymerise) under appropriate conditions to form a polymer-bioactive agent conjugate.

An example of a monomer of formula (IV) that can polymerise to form a polymer-bioactive agent conjugate is shown in formula (IVc):

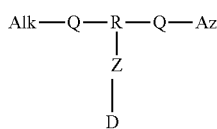

(IVc)

where:
Alk represents a terminal functional group comprising an alkyne functionality;
Az represents a terminal functional group comprising an azide functionality;
Q is independently selected at each occurrence and may be present or absent and when present, represents a linking group;
R is an optionally substituted linear or branched hydrocarbon and may comprise optionally substituted aromatic hydrocarbon or heteroaromatic hydrocarbon;
Z is a cleavable linking group; and
D is a bioactive agent selected from the group consisting of quinolones and NSAIDs Depending on the monomers used to prepare the polymer-bioactive agent conjugate, in some embodiments the polymer-bioactive conjugate of the invention may comprise a repeating unit of formula (VIa) or formula (VIb):

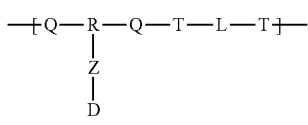

(VIa)

(VIb)

wherein in (VIa) and (VIb), T, Q, R, Z, D and L are as defined herein.

A repeating unit of formula (VIa) or (VIb) may occur when a monomer of formula (IV) reacts with a complementary monomer of formula (V).

In some embodiments, the polymer-bioactive conjugate of the invention may comprise a repeating unit of formula (VIc):

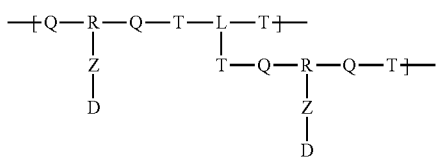

(VIc)

wherein T, Q, R, $Z^1$, $Z^2$, $D^1$ and $D^2$ are as defined herein.

A repeating unit of formula (VIc) may occur when two complementary monomers of formula (IV) react together.

A monomer which has a bioactive agent pendantly attached thereto is referred to herein as a monomer-bioactive agent conjugate. An example of a monomer-bioactive agent conjugate is shown in formula (IV), as illustrated above.

In another aspect, the present invention provides a monomer-bioactive agent conjugate of formula (IV):

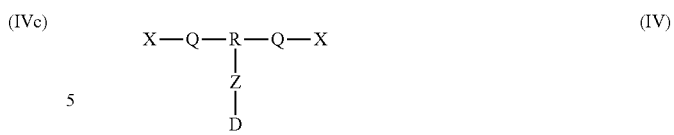

(IV)

where:
X may be the same or different at each occurrence and represents a terminal functional group comprising an alkyne or an azide functionality;
Q is independently selected at each occurrence and may be present or absent and when present, represents a linking group;
R is an optionally substituted linear or branched hydrocarbon and may comprise optionally substituted aromatic hydrocarbon or heteroaromatic hydrocarbon;
Z is a cleavable linking group; and
D is a bioactive agent selected from the group consisting of quinolones and NSAIDs.

In the monomer-bioactive agent conjugate of formula (IV) each X represents a group comprising a terminal functional group comprising an alkyne or azide functionality. The terminal functional group in X may be the same or different at each occurrence. Where the terminal functional groups (X) are the same, the monomer will generally be a diazide or dialkynyl monomer.

One skilled in the relevant art would understand that the terms "alkyne" and "azide" represent the following structures:

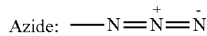

In one set of embodiments, the terminal functional group represented by X may comprise an optionally substituted straight chain aliphatic comprising an alkyne functionality. In such embodiments, X may comprise the alkyne functionality as a terminal alkyne. In one set of embodiments, group X comprises a terminal alkyne functionality. A terminal alkyne functionality may have a structure represented as follows:

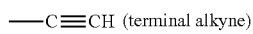

In one set of embodiments, the terminal functional group represented by X comprises an optionally substituted cyclic group comprising an alkyne functionality. In such embodiments, the alkyne functionality may be regarded as an internal alkyne, as the alkyne functionality would be part of the ring structure of the cyclic group. An internal alkyne may have a structure represented as follows:

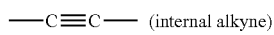

Internal alkynes contained in a cyclic group may be activated for participation in cycloaddition reactions by the presence of one or more substituent groups (e.g. electron withdrawing groups) present on the cyclic structure or by means of ring strain in the cyclic structure.

In one set of embodiments when X comprises an optionally substituted cyclic group comprising an alkyne functionality, the group may have a structure of formula (XV):

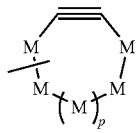

(XV)

where:
each M represents a ring atom and is independently selected from the group consisting of carbon (C), nitrogen (N), oxygen (O) and sulphur (S), with the proviso that at least 3 M is carbon; and
p is 1, 2 or 3, preferably p is 2.

In one embodiment, p is 1 and least one M is selected from the group consisting of N, O and S, preferably S.

In another embodiment, p is 2 and each M is carbon (C) or at least one M is selected from the group consisting of N, O and S, preferably S.

In another embodiment, p is 3 and each M is carbon (C).

Optional substituents that may be present in formula (XV) may be selected from the group consisting of hydroxy (—OH), —Oalkyl, alkyl, halo (preferably fluoro), cycloalkyl, heterocycloalkyl, aryl and heteroaryl. Cycloalkyl, heterocycloalkyl, aryl and heteroaryl substituent groups may each independently comprise from 3 to 6 ring atoms and may be fused to the cyclic group. The optional substituents may be located on any ring atom of the cyclic group. In one preference, one or more optional substituents are located at a ring atom ortho to the alkyne functionality.

In one set of embodiments X comprises a cycloalkyne of formula XVI

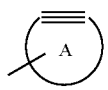

XVI wherein the cycloalkyne comprises from 7 to 9 constituent ring members selected from carbon and optionally including one or two heteroatom groups selected from sulfur and the group N—R$^t$ wherein R$^t$ is hydrogen, $C_1$ to $C_6$ alkyl or the group (Q) and wherein the ring is optionally substituted with at least one substituent selected from the group consisting of
hydroxy (preferably from 0 to 2 hydroxy);
oxo (i.e. =O) (preferably 0 or 1 oxo);
halo (preferably from 0 to 2 halo selected from chloro, bromo and fluoro and most preferably fluoro);
$C_1$ to $C_6$ alkoxy (preferably from 0 to 2 $C_1$ to $C_6$ alkoxy); and
rings fused with said ring of 7 to 9 constituent members wherein said fused rings include 0 to 3 rings each fused with said 7 to 9 membered ring and selected from benzene, cyclopropanone, and cyclopropane wherein the fused benzene and cyclopropane rings are optionally further substituted with from one to three substituents selected from the group consisting of $C_1$ to $C_6$ alkyl, halo (preferably from 0 to 2 halo selected from chloro, bromo and fluoro and most preferably fluoro) and $C_1$ to $C_6$ alkoxy; and wherein at least one ring member selected from nitrogen and carbon is bonded to Q.

The moiety "0" present in formulae (I), (Ib), (IIa), (IIb), (IIIa), (IIIb), (IV), (IXa) and (IXb) defined herein may be present or absent at each occurrence. When present, Q represents a linking group, and is independently selected at each occurrence. Examples of Q that may be present in formulae (I), (Ib), (IIa), (IIb), (IIIa), (IIIb), (IV), (IXa) and (IXb) are described below.

In some embodiments of formulae (I), (Ib), (IIa), (IIb), (IIIa), (IIIb), (IV), (IXa) or (IXb), two Q are present and each Q is attached to the group "R". In other embodiments of formulae (I), (Ib), (IIa), (IIb), (IIIa), (IIIb), (IV), (IXa) or (IXb), one Q is present and one Q is absent.

In one set of embodiments, the linking group Q present in formulae defined herein may comprise a linking moiety. In some embodiments, the linking moiety may be an optionally substituted aliphatic moiety. A suitable aliphatic linking moiety may be selected from a saturated $C_1$ to $C_{20}$, $C_1$ to $C_{10}$ or $C_1$ to $C_6$ straight or branched aliphatic moiety. The aliphatic moiety may be optionally substituted by one or more substituents.

In monomer-bioactive agent conjugates described herein, the presence of a linking group Q connected to a terminal functional group comprising an alkyne or azide functionality may facilitate polymerisation of the monomer by reducing steric crowding around the terminal functional group.

In some embodiments, in the monomer of formula (IV), each Q-X is a group of formula (VII):

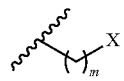

where:
X is a terminal functional group comprising an alkyne or an azide functionality; and
m is an integer in the range of from 0 to 10.

In some embodiments of formula (VII), m is an integer in the range of from 1 to 5.

In some embodiments the linking group Q present in formulae defined herein may comprise a functional group. The functional group may be present in addition to the linking moiety. Thus, the linking moiety and the functional group together form the linking group Q.

In one set of embodiments Q comprises a functional group selected from the group consisting of an amide, ether, ester, urethane, urea, and carbonate ester functional group.

In some embodiments, the linking group Q may be represented by formula (VIII):

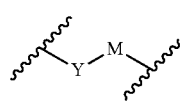

(VIII)

where:
Y represents a functional group; and
M represents a linking moiety.

In one embodiment, M may be an optionally substituted aliphatic linking moiety.

In monomers of formula (IV), when Q comprises a functional group, the group Q-X may be represented by formula (VIIIa):

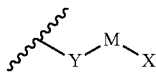
(VIIIa)

where:
Y is a functional group;
M is a linking moiety; and
X is a terminal functional group comprising an alkyne or an azide functionality.

In some embodiments, M is an optionally substituted saturated $C_1$ to $C_{20}$, $C_1$ to $C_{10}$ or $C_1$ to $C_6$ straight or branched aliphatic linking moiety.

In some embodiments the group Q-X in monomers of formula (IV) may be represented by formula (VIIIb):

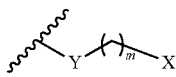
(VIIIb)

where:
Y is a functional group;
X is a terminal functional group comprising an alkyne or an azide functionality; and
m is an integer in the range of from 0 to 10.

In some embodiments of formula (VIIIb), m is an integer in the range of from 1 to 5.

The functional group represented by Y in formulae (VIII), (VIIIa) and (VIIIb) may be selected from the group consisting of an amide, ether, ester, urethane, urea, and carbonate ester functional group.

In some embodiments, in the monomer of formula (IV), Q is present and each Q-X is independently selected from the following group:

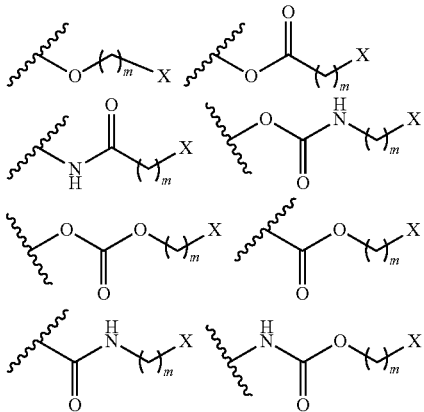

When a monomer-bioactive agent conjugate having a linking group Q is used to prepare polymer conjugates of the invention, the linking group Q becomes incorporated into the polymer backbone. Thus any linking moieties and functional groups present in Q become part of the backbone of the polymer conjugate.

When Q comprises a functional group (represented by Y in formulae defined herein) such as an amide, ether, ester, urethane, urea, and carbonate ester functional group, such functional groups will generally be cleavable functional groups and can provide points for erosion or degradation in the polymer backbone when a monomer-bioactive agent conjugate comprising such groups is used to form the polymer conjugate. The presence of cleavable groups derived from the functional groups in the polymer backbone can facilitate breakdown of the polymer conjugate, allowing formation of lower molecular weight polymer fragments.

The moiety "R" present in formulae (I), (Ib), (IIa), (IIb), (IIIa), (IIIb), (IV), (IXa) and (IXb) described herein represents an optionally substituted linear or branched hydrocarbon. In some embodiments the hydrocarbon may have between 1 and 12 carbon atoms, for example between 1 and 6 carbon atoms or 2 or 3 carbon atoms. The hydrocarbon may be partially or completely saturated or unsaturated (including moieties that are aromatic). Specific examples of R include a moiety having one of the following structures:

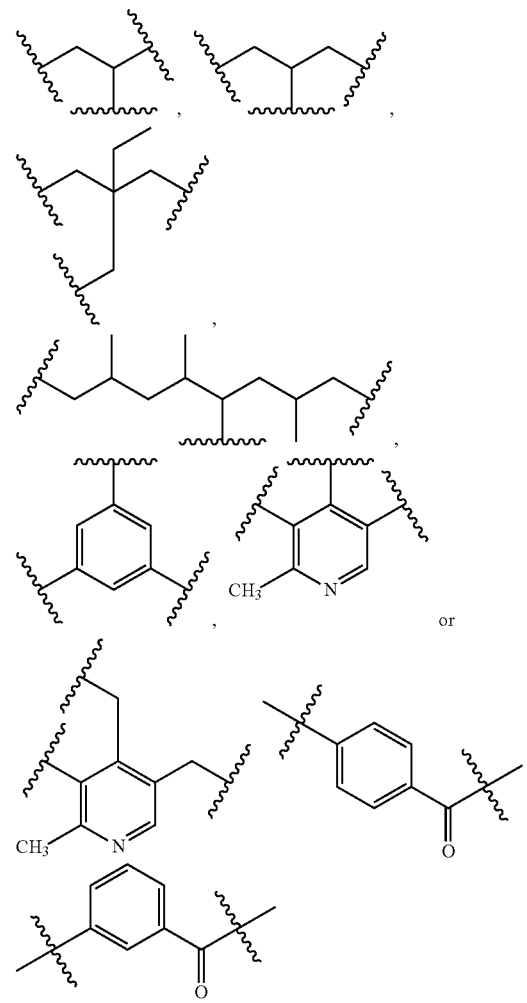

One skilled in the art would appreciate that when a monomer-bioactive agent conjugate comprising a moiety "R" is polymerised to form a polymer-bioactive agent conjugate, then R becomes part of the polymer backbone of the conjugate.

The moiety "Z" present in monomer-bioactive conjugates of formula (IV) represents a cleavable linking group as described herein.

The moiety "D" present in monomer-bioactive agent conjugates of formula (IV) represents a releasable bioactive agent as described herein. While the bioactive agent is releasable while conjugated to the monomer, it would be understood however that the bioactive agent is only intended to be released after the monomer-bioactive agent conjugate has reacted to form the polymer conjugate.

Examples of dialkynyl monomer conjugates with quinolones as the pendant conjugated bioactive agent linked through the carboxylic acid are shown below:

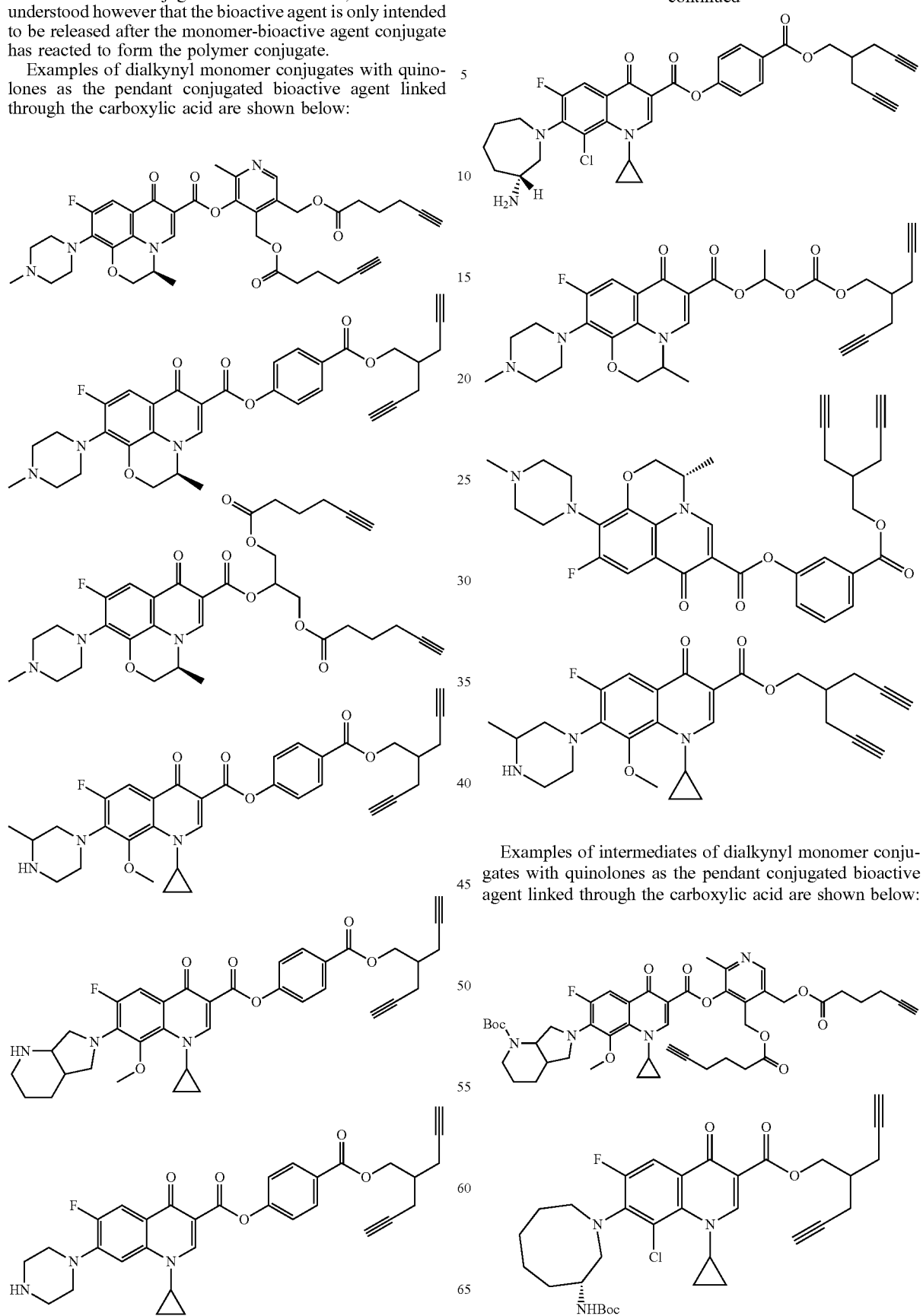

Examples of intermediates of dialkynyl monomer conjugates with quinolones as the pendant conjugated bioactive agent linked through the carboxylic acid are shown below:

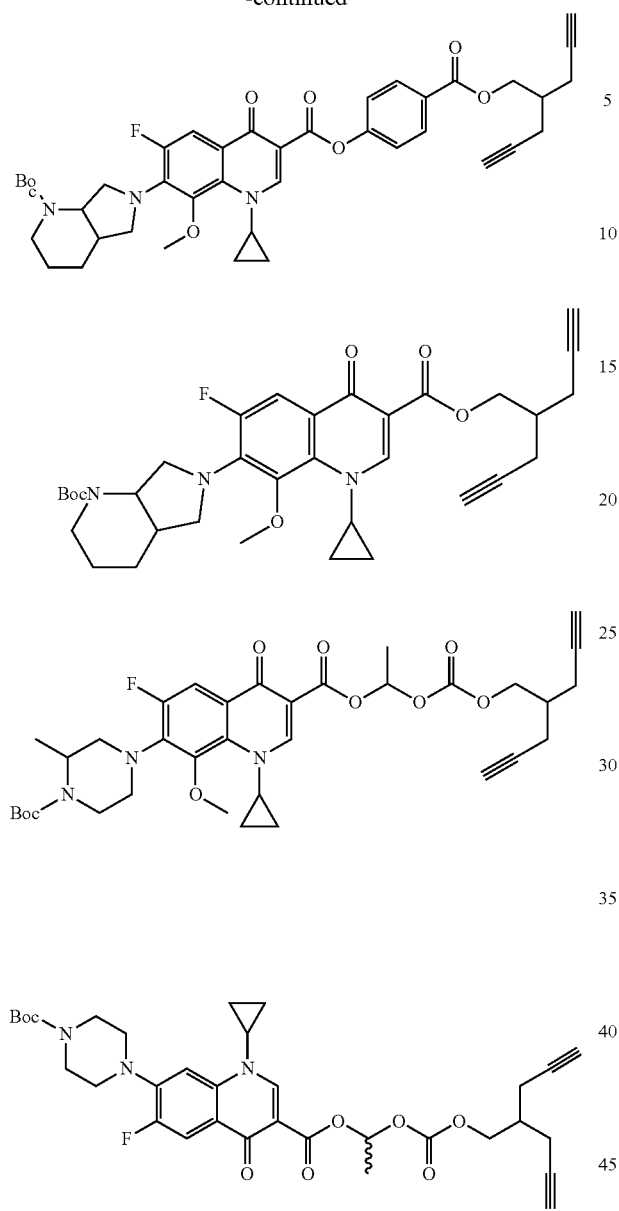
Examples of dialkyne, diazide and azide/alkyne monomer conjugates with NSAIDs as the pendant conjugated bioactive agent linked through the 1-carboxylic acid group are shown below:
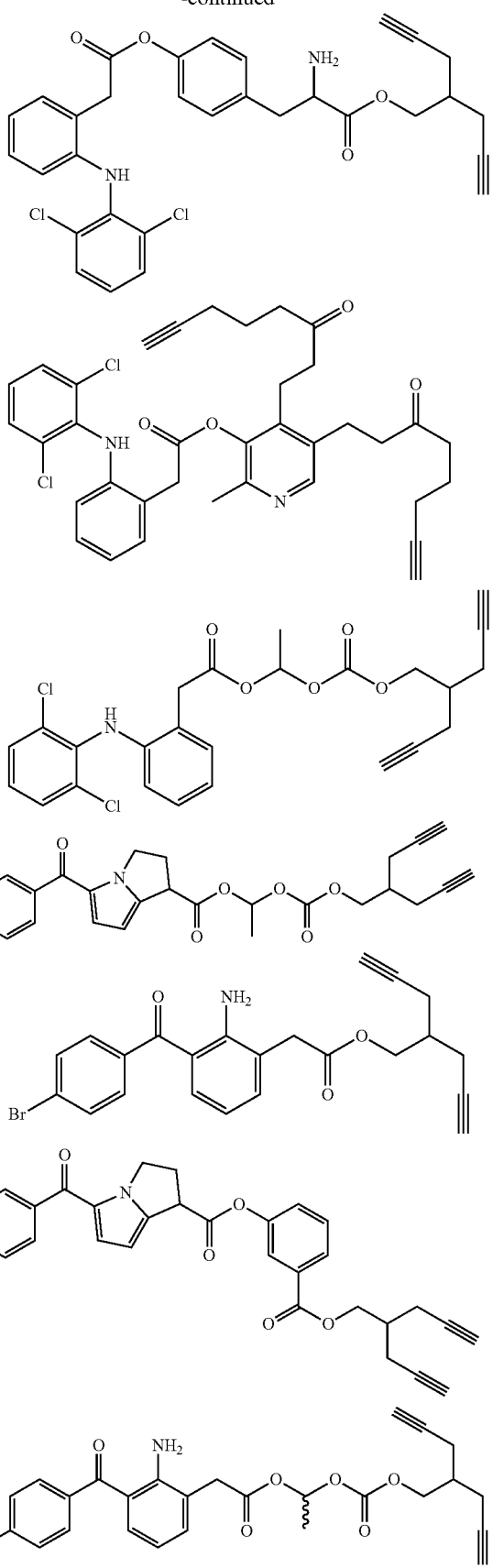

Monomer-bioactive agent conjugates of the invention may be prepared by covalently coupling a bioactive agent to a suitably functionalised alkyne or azide containing precursor compound. Some examples of alkyne precursor compounds that may be used to prepare monomer-bioactive agent conjugates of the invention are shown below:

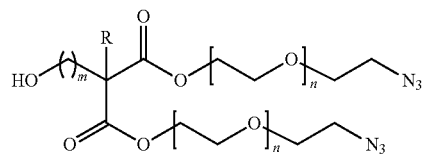

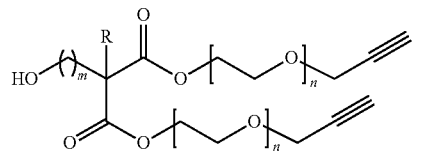

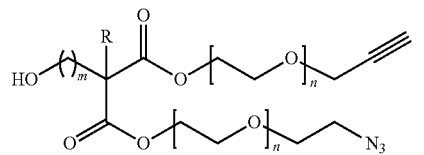

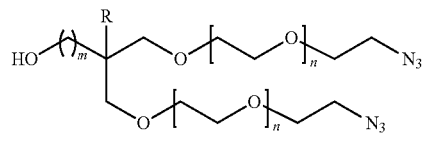

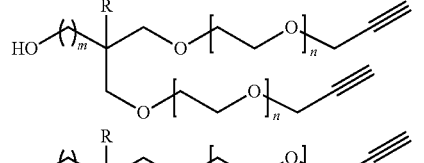

m = 0, 1   n = 2-100   R = H, alkyl

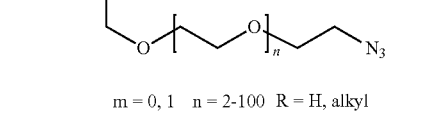

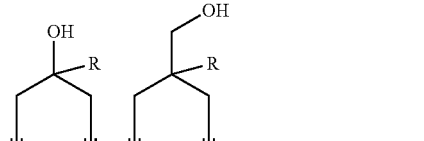

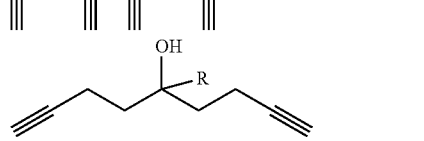

-continued

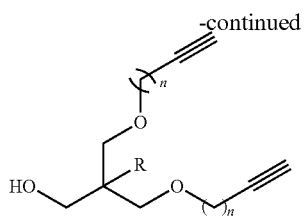

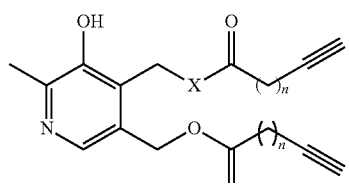

n = 0-12
X = O, NH

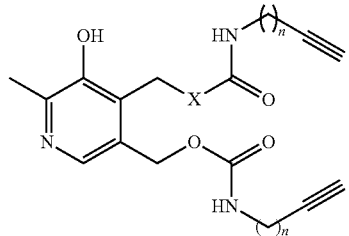

n = 0-12
X = O, NH

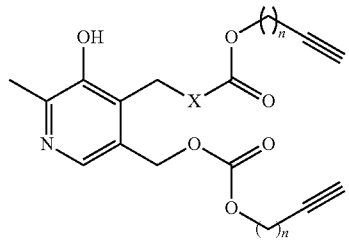

n = 0-12
X = O, NH

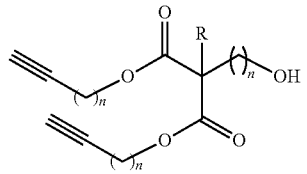

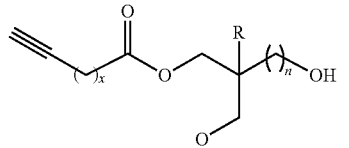

x = 0-12
n = 0, 1

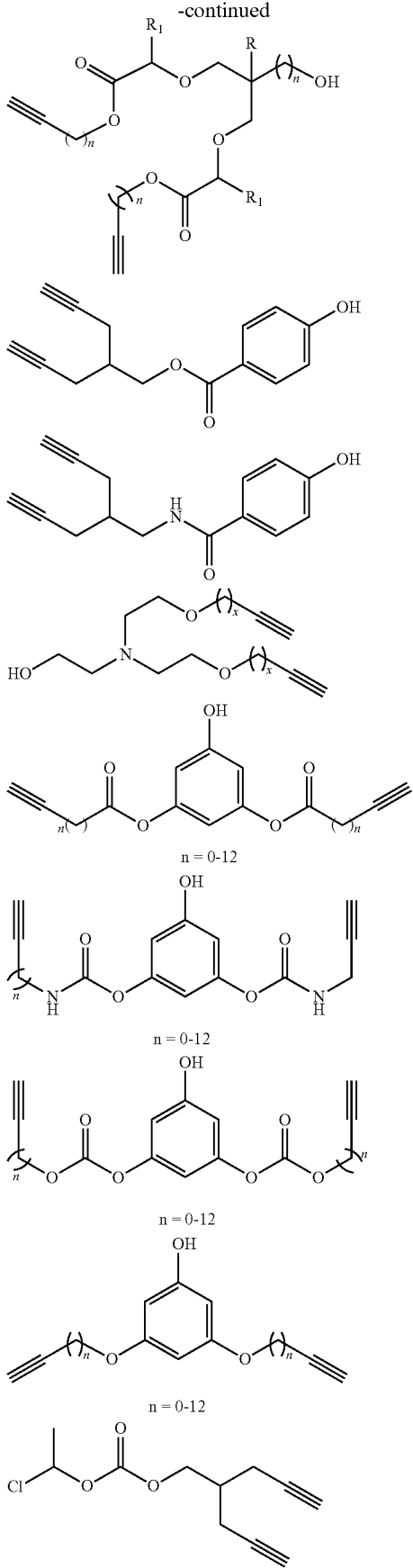
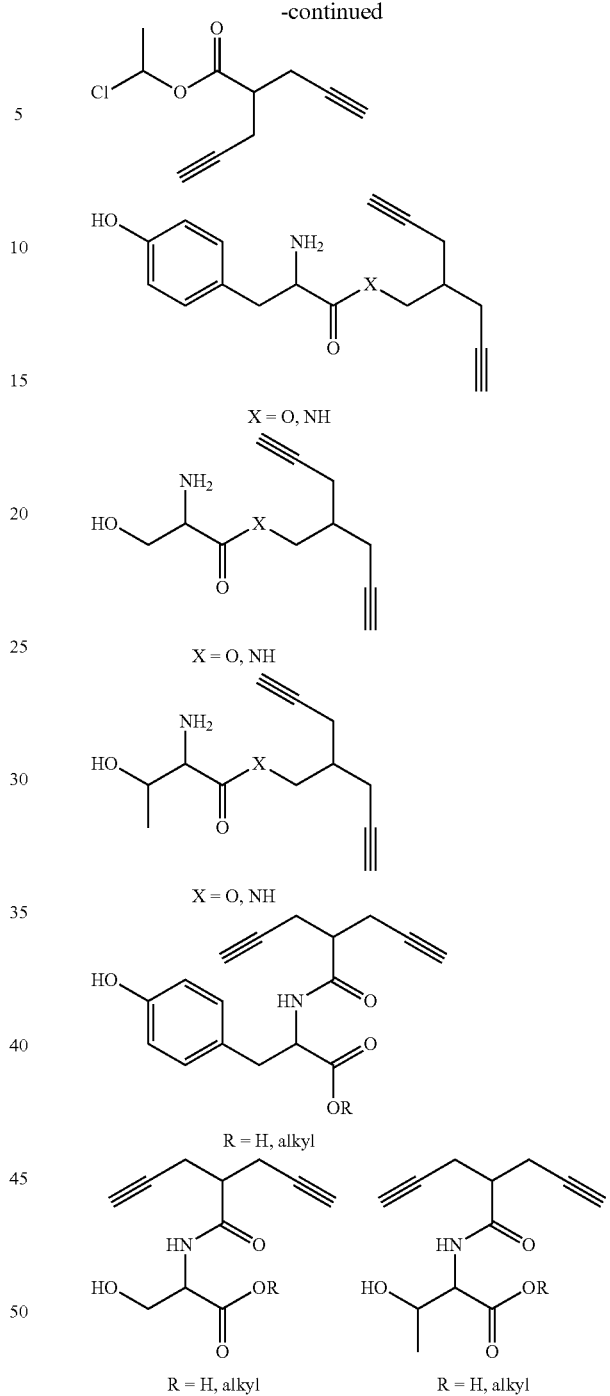

In the above dialkyne compounds, the hydroxyl functional groups are capable of covalently reacting with a complementary functional group (particularly an acid or acid derivative) in the bioactive agent, to allow the bioactive agent to be coupled to the dialkyne compound to produce a monomer-bioactive agent conjugate that may participate in click chemistry reactions. In the resulting monomer the ester group formed comprises the alcohol portion from the dialkyne and acyl portion (C(O)) from the bioactive agent. One skilled in the relevant art would appreciate that one or more of the alkyne functionalities in the above compounds may be replaced by azide functional groups.

In one set of embodiments, the monomer-bioactive agent conjugate of formula (IV) is preferably a dialkyne monomer. Accordingly, the group X in formula (IV) are each terminal functional groups comprising alkyne functionality. Monomer-bioactive agent conjugates comprising terminal functional groups comprising alkyne functionality are preferred as such monomer-bioactive agents are safer to process than their diazide counterparts.

As discussed above, in some embodiments, the polymer-bioactive agent conjugate of the invention can be obtained by polymerising at least one monomer of formula (IV) with at least one monomer of formula (V) described above.

In some embodiments, the polymer-bioactive agent conjugate of the invention is a copolymer of at least one monomer of formula (IV):

where:
X may be the same or different at each occurrence and represents a terminal functional group comprising an alkyne or an azide functionality;
Q is independently selected at each occurrence and may be present or absent and when present, represents a linking group;
R is an optionally substituted linear or branched hydrocarbon which may include optionally substituted aromatic hydrocarbon and heteroaromatic hydrocarbon;
Z is a cleavable linking group; and
D is a bioactive agent selected from the group consisting of quinolones and NSAIDs;
and at least one monomer of formula (V):

where:
A may be the same or different at each occurrence and represents a group comprising a terminal functional group comprising an alkyne or an azide functionality, wherein said terminal functional group is complementary to the terminal functional group of X;
L is an optionally substituted linker group; and
n is an integer and is at least 1.

The groups A, L and n in formula (V) are further discussed below.

The covalent reaction between a terminal functional group (X) on the monomer of formula (IV) with a complementary terminal functional group on the monomer of formula (V) produces a triazole moiety. Triazole moiety may be of formulae (II), (III) or (IX) as described herein. Preferably, the triazole moiety is a 1,4-regioisomer as represented by formulae (II), (IIa) and (IIb), or a 1,5-regiosiomer as represented by formulae (III), (IIIa) and (IIIb), as described herein. It will be understood by those skilled in the art that the 1,4-regioisomer can be formed using a copper catalyst during the reaction of the monomers and the 1,5-regioisomer can be formed using a rhuthenium catalyst during the reaction of the monomers (J. Am. Chem. Soc., 2005, 127 (46), pp 15998-15999, Ruthenium-Catalyzed Cycloaddition of Alkynes and Organic Azides, Zhang et al, Boren et al J Am Chem Soc 2008; 130: 8923-8930).

The triazole may also be formed through the use of metal-free, strain promoted azide-alkyne cycloaddition (SPAAC) and does not require a catalyst. The regiochemistry of SPAAC is mixed with both 1,4 and 1,5 1,2,3 triazoles being formed. The preparation of cycloalkyne and heterocyclic alkyne compounds and their use in SPAAC click chemistry has been described in a number of publications, including:

Jewett et al. "Cu-free click cycloaddition in chemical biology", Chem. Soc. Rev., 2010, 39, 1272-1279;

Baskin et al. "Copper-Free Click Chemistry: Bioorthogonal Reagents for Tagging Azides" Aldrichimica Acta, Vol. 43, No. 1 2010, 15-23;

Recer et al. "Click Chemistry beyond Metal-Catalyzed Cycloaddition" Angew. Chem. Int. Ed., 2009, 48, 4900-4908.

Almeida et al. "Thiacycloalkanes for copper-free click chemistry", Angewandte Chemie Int. Ed. 2012, 51, 2443-2447; and Sletten et al., "Ahydrophilic Azacyclooctyne for Cu-Free Click Chemistry Org. Let. Vol. 10, No. 14, 2009, 3097-3099.

The methods and compounds described in these references may be used in preparation of the cycloalkyne of formula XVI having a wide range of substituents without undue experimentation. The method of the invention may be used to provide a wide range of polymers of formula IX with triazole units such as in formula IV. It is an advantage of this embodiment that the copolymerization reaction to form triazole groups may in many cases take place without the need for a catalyst.

The monomers of formula (IV) and (V) may react with one another in a mole ratio of 1:1. In some embodiments, it may be desirable to have a molar excess of a monomer comprising terminal functional groups having alkynyl functionality. Without wishing to be limited by theory, it is thought that azide containing functional groups may be toxic to a biological environment. As a result, the use of a molar excess of monomer comprising alkynyl functional groups to prepare the conjugates may help to ensure that residual unreacted azide functional groups do not remain in the structure of the conjugates.

In the monomer of formula (V), A represents a group comprising a terminal functional group comprising an alkyne or an azide functionality. The azide or alkyne functionality present in terminal functional group of moiety "A" is complementary to the azide or alkyne functionality present in the terminal functional group of X in formula (IV), such that upon reaction of the functional groups in A and X under click reaction conditions, a triazole moiety is formed.

In the monomer of formula (V) n is an integer and is at least 1. In some embodiments, n is an integer selected from the group consisting of 1, 2, 3, 5, 6, 7 and 8. In one form, in the monomer of formula (V) n is 1 or 2. The monomer of formula (V) comprises at least two A moieties, which may be the same or different at each occurrence.

When n is 1, the monomer of formula (V) is difunctional and comprises two A moieties. When n is 2 or more, the monomer of formula (V) is multifunctional and comprises 3 or more A moieties. In such embodiments, the monomer of formula (V) may be a branched monomer. Three or more A moieties may be present when L is branched. Monomers of formula (V) comprising at least three terminal functional groups have the potential to provide branched architectures for the polymer conjugates of the invention. When n is 3 or more, the monomer of formula (V) is multifunctional and comprises 4 or more A moieties. In such embodiments, the monomer of formula (V) may be a cross-linking monomer. Four or more A moieties may be present. Monomers of formula (V) comprising at least four terminal functional groups have the potential to provide cross-linked architectures for the polymer conjugates of the invention.

As used herein, the term "group comprising a terminal functional group" encompasses embodiments where the group represents the terminal functional group per se, as well as embodiments where the terminal functional group is part of a larger chemical group.

The moiety "L" in formula (V) represents an optionally substituted linker group. In some embodiments L may be a divalent group. Alternatively, L may be mulitvalent and be a branched group. When a monomer of formula (IV) and (V) copolymerise, L forms a linker segment in the polymer backbone of the conjugate.

In some embodiments, polymer-bioactive agent conjugates of the invention are formed with a monomer of formula (V), where L is a linker group comprising a linker moiety selected from the group consisting of optionally substituted linear or branched aliphatic hydrocarbon, optionally substituted carbocyclyl, optionally substituted heterocyclyl, optionally substituted aryl, optionally substituted heteroaryl, and an optionally substituted polymeric segment.

In some embodiments of a monomer of formula (V), L comprises a biodegradable polymer. Biodegradable polymers may include at least one biodegradable moiety selected from the group consisting of an ester, an amide, a urethane, a urea and a disulfide moiety.

In some embodiments of a monomer of formula (V), L comprises a polymer selected from the group consisting of a polyether, a polyester, a polyamide, a polyurethane, and copolymers thereof.

In some embodiments of a monomer of formula (V), L comprises a functional group selected from the group consisting of an amide, ether, ester, urethane, urea, and carbonate ester.

In some embodiments of a monomer of formula (V), n is from 1 to 8 such as 1, 2 or 3.

In some embodiments of a monomer of formula (IV), Q is present and said Q comprises a functional group selected from the group consisting of an amide, ether, ester, urethane, urea, and carbonate ester functional group.

In some embodiments of a monomer of formula (IV), Q is present and each Q-X is independently selected from the following group:

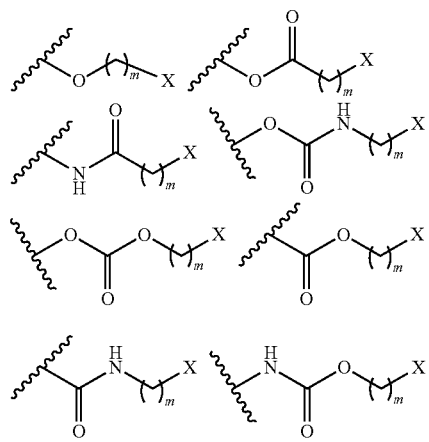

In some embodiments of a monomer of formula (IV), each Q-X is a group of formula (VII):

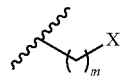

(VII)

where:

X is a terminal functional group selected from the group consisting of an alkyne and an azide; and m is an integer in the range of from 0 to 10, preferably in the range of from 1 to 5.

In some embodiments of a monomer of formula (IV), R is an optionally substituted linear or branched hydrocarbon having from 1 to 12 carbon atoms.

In some embodiments, polymer-bioactive agent conjugates of the invention are formed when at least one monomer of formula (IV) is reacted with a monomer for formula (V) such that the drug is pendant to a triazole-containing polymer backbone according to formula (I).

In one form of the invention, two or more monomers of formula (IV) are reacted with a monomer of formula (V). In such embodiments, the monomers of formula (IV) may contain different bioactive agents (D), such that the resulting polymer conjugate contains a mixture of different bioactive agents. The different bioactive agents may, for example, be a mixture of a quinolone and an NSAID.

In some embodiments, polymer-bioactive agent conjugates of the invention are formed when a monomer of formula (IV) is reacted with a complementary monomer of formula (IV) such that the bioactive agent is pendant to a triazole-containing polymer backbone according to formula (Ib).

In some embodiments, L may comprise a linker moiety selected from the group consisting of optionally substituted linear or branched aliphatic hydrocarbon, optionally substituted carbocyclyl, optionally substituted heterocyclyl, optionally substituted aryl, optionally substituted heteroaryl, an optionally substituted polymeric segment, and combinations thereof.

Optionally substituted linear or branched aliphatic hydrocarbon linker moieties may be selected from optionally substituted $C_1$ to $C_{20}$, $C_1$ to $C_{10}$ or $C_1$ to $C_6$ linear or branched aliphatic hydrocarbons. The aliphatic hydrocarbons may be saturated or unsaturated hydrocarbon.

Optionally substituted carbocyclyl linker moieties may have from 3 to 12, 3 to 8 or 5 to 6 carbon ring members.

Optionally substituted heterocyclyl linker moieties may have from 3 to 12, 3 to 8 or 5 to 6 ring members and 1, 2, 3, 4 or more heteroatoms as a part of the ring. The heterotoms may be independently selected from the group consisting of O, N and S.

Optionally substituted aryl linker moieties may have from 3 to 12, 3 to 8 or 5 to 6 carbon ring members and at least one unsaturation.

Optionally substituted heteroaryl linker moieties may have from 3 to 12, 3 to 8 or 5 to 6 ring members and 1, 2, 3, 4 or more heteroatoms as a part of the ring. The heterotoms may be independently selected from the group consisting of O, N and S. The heteroaryl linker moiety also has at least one unsaturation.

Optionally substituted polymeric linker moieties may comprise any suitable polymer or copolymer. In some embodiments, it can be desirable for the polymeric moiety to comprise a biocompatible and/or biodegradable polymer. One skilled in the relevant art would be able to select suitable biocompatible and/or biodegradable polymers.

Exemplary biocompatible polymers may include polyethers, polyesters, polyamides, polyurethanes, and copolymers thereof, such as poly(ether-esters), polyurethane-ethers), poly(urethane-esters), poly(ester-amides) and the like. Preferred biocompatible polymers are polyethers, polyesters, polyurethanes, and copolymers thereof.

Exemplary polyethers include polymers of $C_2$ to C4 alkylene diols, such as polyethylene glycol and polypropylene glycol, preferably polyethylene glycol.

Exemplary polyesters include polycaprolactone, poly(lactic acid), poly(glycolic acid) and poly(lactic-co-glycolic acid).

In one form, the polymeric linker moiety may comprise a biodegradable polymer. In general, biodegradable polymers comprise at least one biodegradable moiety. The biodegradable moiety may be selected from the group consisting of an ester, an amide, a urethane and a disulfide moiety. The biodegradable polymers comprise a combination of such moieties. One skilled in the relevant art would understand that such biodegradable moieties are capable of undergoing degradation or cleavage in a biological or physiological environment.

Optionally substituted polymeric linker moieties may be of any suitable molecular weight, and the desired molecular weight may depend on the type of polymer and its properties. In some embodiments, L comprises a polymeric moiety having a molecular weight of not more than 1,500.

In one set of embodiments, L comprises a polyether linker moiety derived from polyethylene glycol (PEG). The polyether segment may be derived from a PEG of suitable molecular weight. In some embodiments, the PEG has a molecular weight in the range of from about 200 to 10,000, preferably from about 200 to about 3,000.

More specifically, L comprises a linear polyether linker moiety derived from polyethylene glycol (PEG) with a molecular weight of 400 g/mol, 1,000 g/mol or 3,000 g/mol. L also comprises 3-arm or 4-arm branched polyether linker moieties derived from polyethylene glycol (PEG) with a molecular weight of 450 g/mol, 800 g/mol, 1,000 g/mol, 2,000 g/mol or 8,000 g/mol.

In one set of embodiments, L comprises a linker moiety derived from lysine, including the ethyl ester of lysine such as ethyl-2,6-bis(((3-azidopropoxy)carbonyl)amino)hexanoate (ELDN$_3$) the di(1-pentynol)urethane of the ethyl ester of lysine and the di(1-pentynol)urethane of the 1-pentynol ester of lysine.

In some embodiments, the group "L" in the formula (V) may comprise a functional group. The functional group may be selected from the group consisting of an amide, ether, ester, urethane, urea, and carbonate ester functional group. Such functional groups will generally be cleavable functional groups, which can degrade in a biological environment.

In one set of embodiments, L comprises a linker moiety and a functional group.

In some embodiments, the monomer of formula (V) may have a structure of formula (Va):

 (Va)

where:

A may be the same or different at each occurrence and represents a group comprising a terminal functional group comprising an alkyne or an azide functionality, wherein the alkyne or azide functionality in the terminal functional group is complementary to the alkyne or azide functionality in a terminal functional group X present on a monomer of formula (IV);

Y represents a functional group;

B may be present or absent and when present represents an optionally substituted linker moiety; and n is 1 or 2, In some embodiments, the monomer of formula (V) may have a structure of formula (Vb):

 (Vb)

where:

A may be the same or different at each occurrence and represents a group comprising a terminal functional group comprising an alkyne or an azide functionality, wherein the alkyne or azide functionality in the terminal functional group is complementary to the alkyne or azide functionality in a terminal functional group X present on a monomer of formula (IV);

Y may be the same or different at each occurrence and represents a functional group;

B represents an optionally substituted linker moiety; and n is at least 1, such as 1 to 8 and preferably n is 1, 2 or 3.

In some embodiments of formula (Vb), B represents a linear linker moiety (such as linear aliphatic linker moiety) and n is at least 1. In such embodiments, B comprises three only two —Y-A substituent groups.

In some embodiments of formula (Vb), B represents a branched linker moiety (such as branched aliphatic linker moiety) and n is 2 or 3 or more. In such embodiments, B comprises three or 4 or more —Y-A substituent groups respectively.

In some embodiments of formula (Vb), B represents an optionally substituted polymeric linker moiety. The polymeric linker moiety may comprise a biocompatible and/or biodegradable polymer as described herein. In one set of embodiments B preferably comprises a polyether, polyester, polyamide, polyurethane, or copolymer thereof.

In one set of embodiments of formulae (Vb), B is a polymeric linker moiety derived from polyethylene glycol (PEG). The polyethylene glycol moiety preferably has a molecular weight in the range of from about 200 to 10,000, more preferably from about 200 to 3000.

More specifically, B comprises a linear polyether linker moiety derived from polyethylene glycol (PEG) with a molecular weight of 400 g/mol, 1,000 g/mol or 3,000 g/mol. B also comprises 3-arm or 4-arm branched polyether linker moieties derived from polyethylene glycol (PEG) with a molecular weight of 450 g/mol, 800 g/mol, 1,000 g/mol, 2,000 g/mol or 8,000 g/mol.

The group Y in formulae (Va) and (Vb) may be independently selected from the group consisting of an amide, ether, ester, urethane, urea, and carbonate ester functional group, preferably a ester or urethane functional group.

In monomers of formulae (Va) and (Vb), the combination of the moieties B and Y together form the linker group L, as shown in formula (V).

Some specific examples of monomers of formula (V) that may be used to prepare polymer-bioactive agent conjugates of the invention is shown in Table 4:

TABLE 4
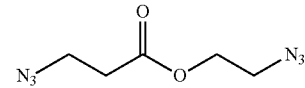 [SMILES: [N-]=[N+]=NCCOC(=O)CCN=[N+]=[N-]]
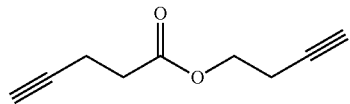
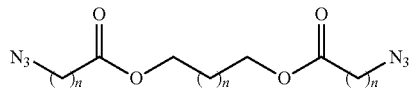
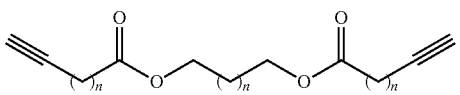
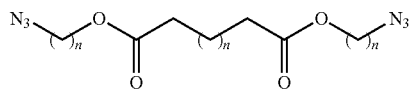
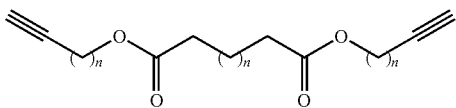
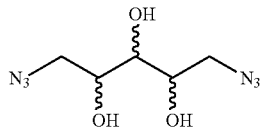 [SMILES: [N-]=[N+]=NCC(O)C(O)C(O)CN=[N+]=[N-]]
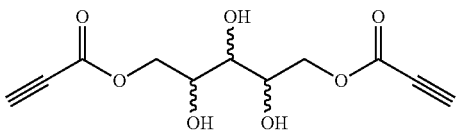 [SMILES: C#CC(=O)OCC(O)C(O)C(O)COC(=O)C#C]
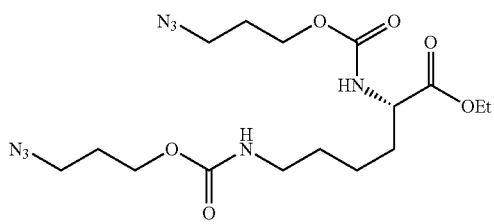 [SMILES: CCOC(=O)[C@H](CCCCNC(=O)OCCCN=[N+]=[N-])NC(=O)OCCCN=[N+]=[N-]]
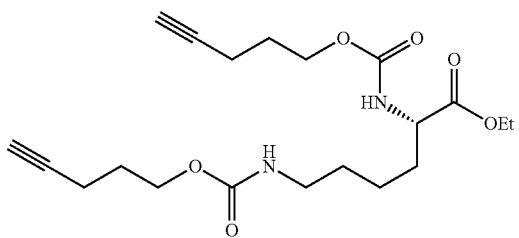 [SMILES: C#CCCCOC(=O)NCCCC[C@H](NC(=O)OCCCC#C)C(=O)OCC]

TABLE 4-continued
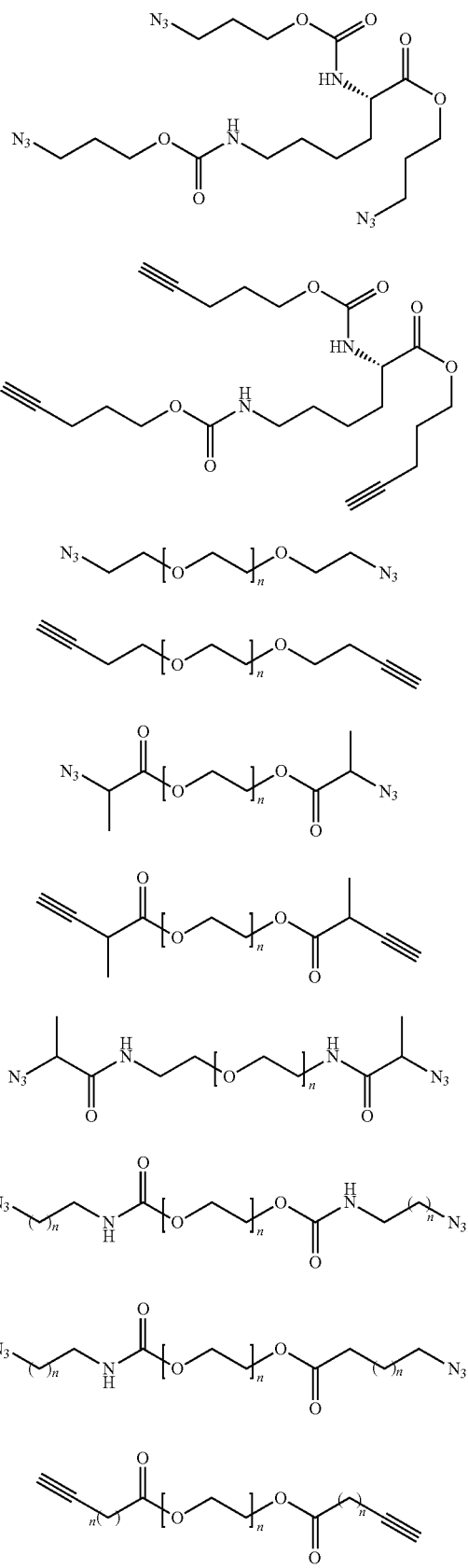

TABLE 4-continued
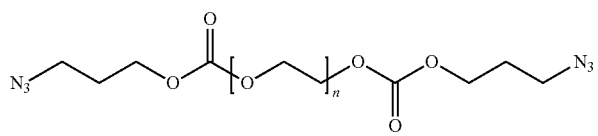
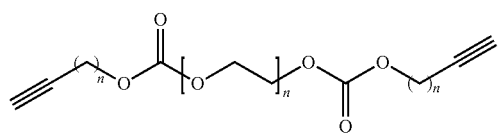
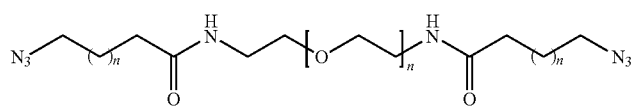
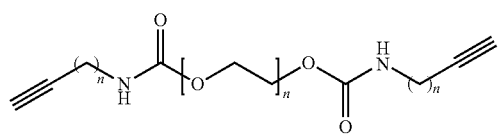
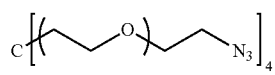
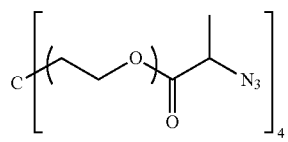
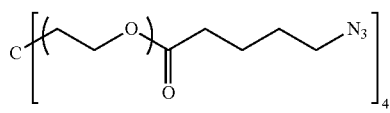
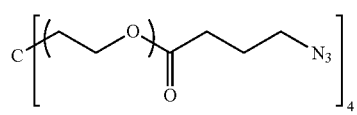
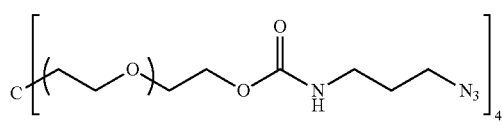
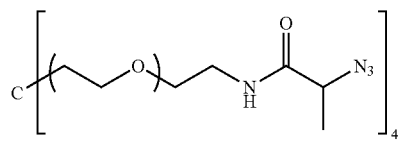
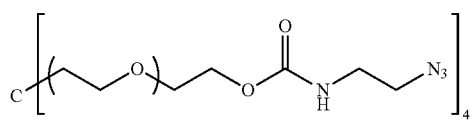
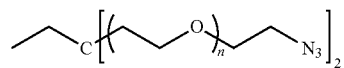

TABLE 4-continued
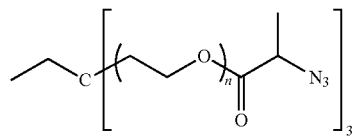
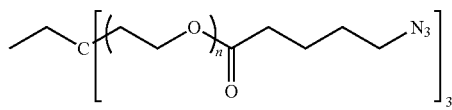
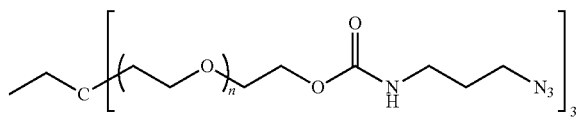
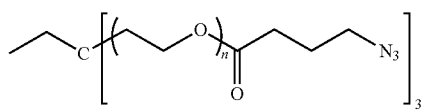
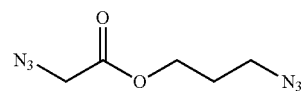
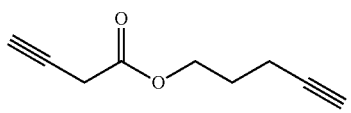
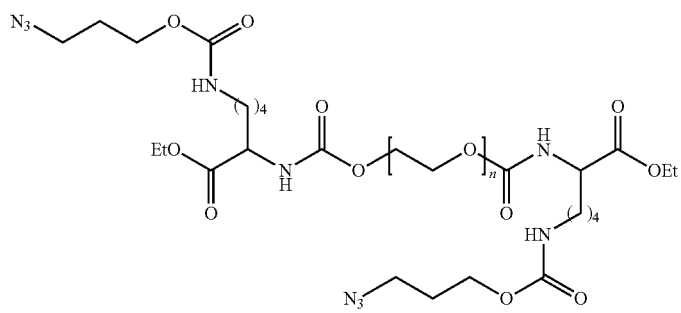
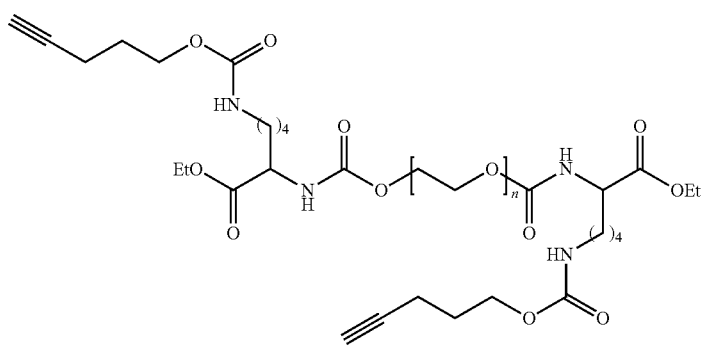

TABLE 4-continued
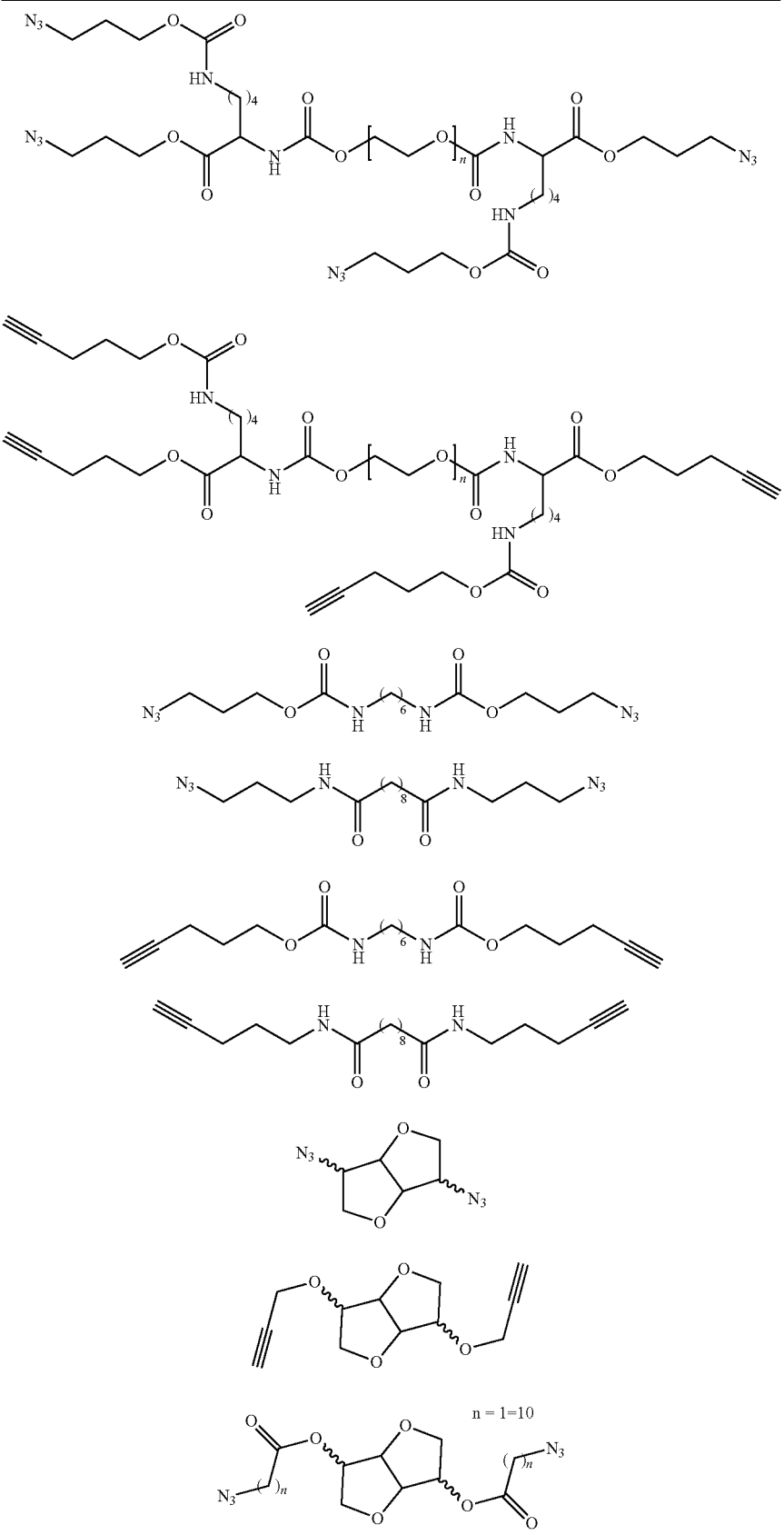

TABLE 4-continued
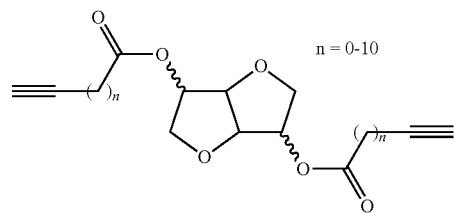
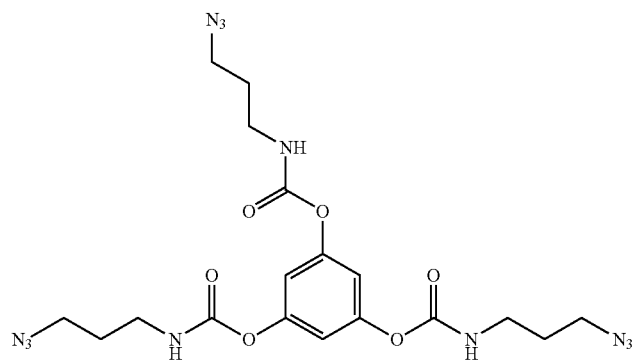 [SMILES: [N-]=[N+]=NCCCNC(=O)Oc1cc(OC(=O)NCCCN=[N+]=[N-])cc(OC(=O)NCCCN=[N+]=[N-])c1]
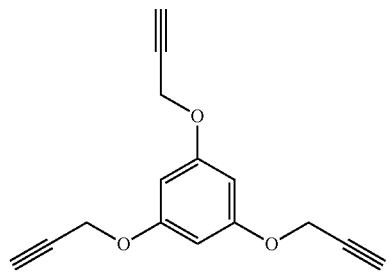 [SMILES: C#CCOc1cc(OCC#C)cc(OCC#C)c1]
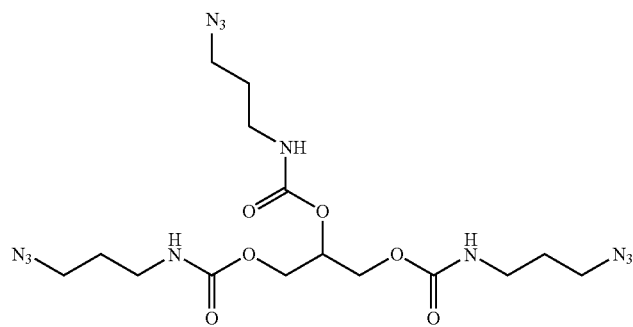 [SMILES: [N-]=[N+]=NCCCNC(=O)OCC(COC(=O)NCCCN=[N+]=[N-])OC(=O)NCCCN=[N+]=[N-]]
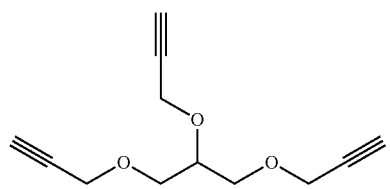

In some structures shown in Table 3, n represents the number of repeating units and is an integer that may be selected from 0 and at least 1 and can be the same or different at each occurrence.

An example of a polymer-bioactive agent conjugate of the invention formed with a dialkyne monomer of formula (IV) and a diazide monomer of formula (V) is shown in Scheme 1 below:

Scheme 1

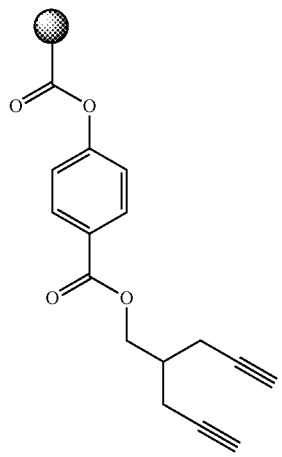

+

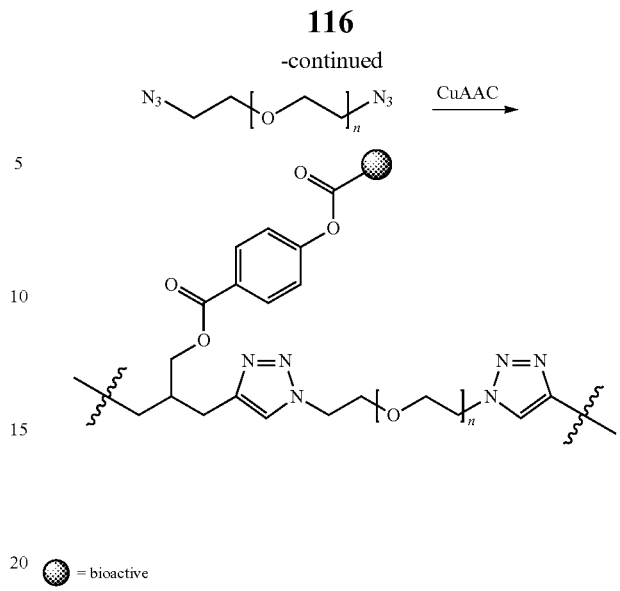

Another example of a polymer-bioactive agent conjugate of the invention formed with a dialkyne monomer of formula (IV) and a diazide monomer of formula (V) is shown in Scheme 2 below:

Scheme 2

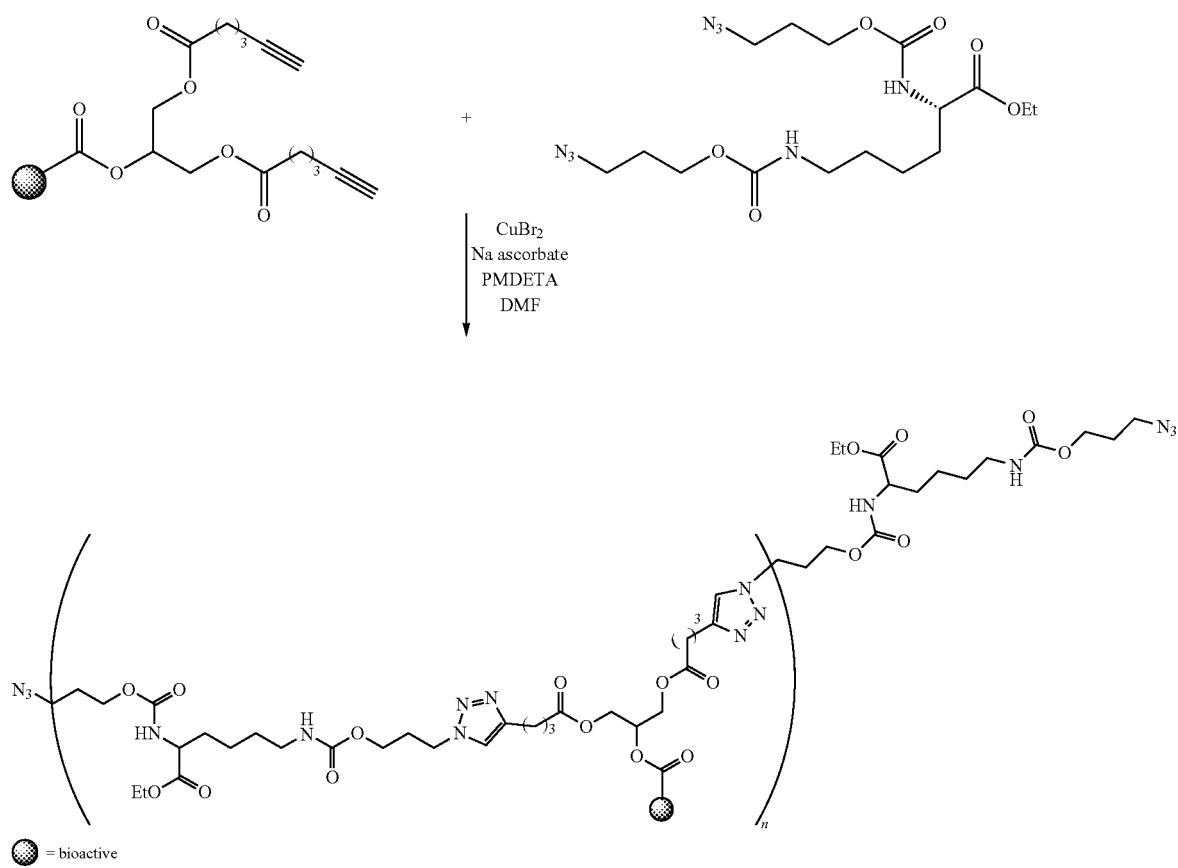

An example of a polymer-bioactive agent conjugate of the invention formed with a diazide monomer formula (IV) and a dialkyne monomer of formula (V) is shown in Scheme 3 below:

Scheme 3

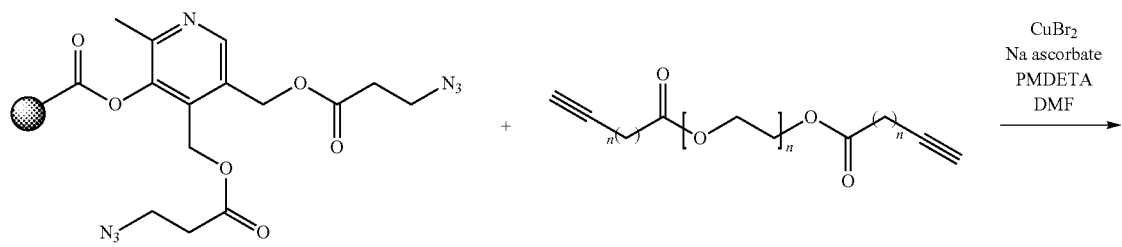

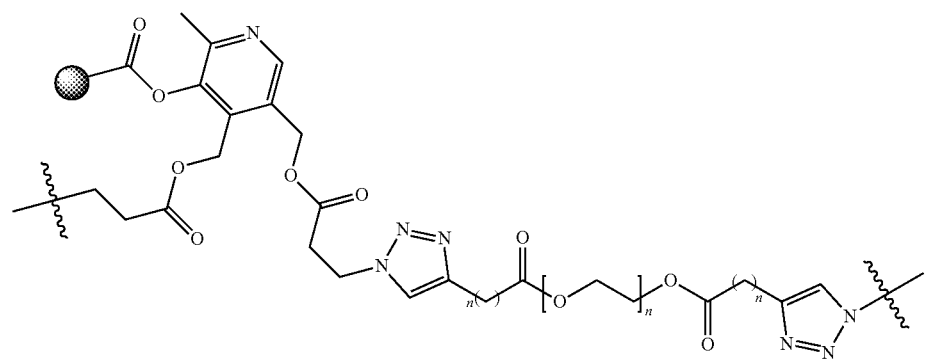

= bioactive

Scheme 4 illustrating general structures of polymer-bioactive agent conjugates in accordance with embodiments of the invention that are formed with co-monomers comprising different terminal functional groups and under different click chemistry reaction conditions.

Scheme 4

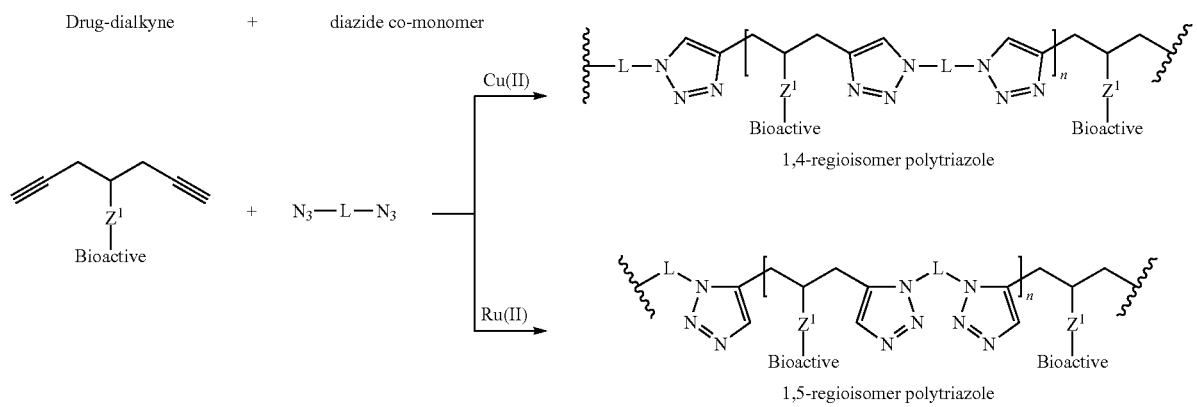

Drug-diazide + dialkyne co-monomer

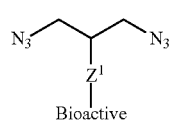
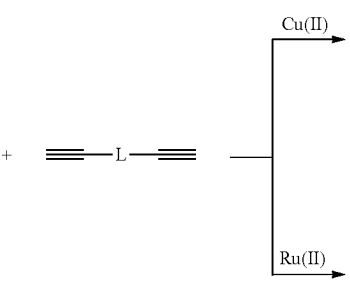

1,4-regioisomer polytriazole

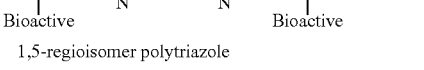

1,5-regioisomer polytriazole

Drug-bifunctional alkyne/azide
+
bifunctional alkyne/azide co-monomer

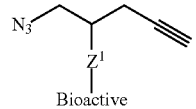
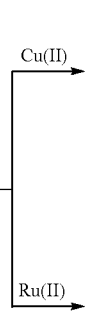
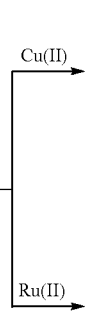

1,4-regioisomer polytriazole 1,5-regioisomer polytriazole

One skilled in the relevant art would understand that the constituent components of each monomer, for example the cleavable linking group of the monomer of formula (IV) or the linker group of the monomer of formula (V), can be varied to allow the properties of the polymer-bioactive agent conjugate to be tailored to suit particular applications.

It will be understood that in embodiments in which the integer n in the monomer of formula V (which may be in the form such as Va or Vb) has a value of 2 or more (such as 2 to 8, 2, 3 or 4 or 2 or 3) the monomer is a cross-linker (also referred to as a branching monomer). In some embodiments, the polymer-bioactive agent conjugate according to any one of the embodiments described herein comprises at least about 33 mol % of such cross-linker monomer having formula (V) wherein n is two or more. In this embodiment it is preferred that the theoretical average molecular weights between crosslinks ($M_c$) lower than 2,000 g/mol and a theoretical crosslink density ($v=1/(2M_c)$) higher than 0.5 mmol/g.

Polymer conjugates of the invention may contain more than one type of bioactive agent.

Polymer conjugates of the invention may contain more than one type of linker segment in the polymer backbone.

Some specific examples of monomer-bioactive agent conjugates, and co-monomers that may be used in the preparation of polymer-bioactive agent conjugates of the invention are shown below:

Monomer-Bioactive Agent Conjugates

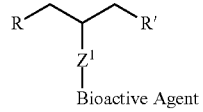

R = R' = interchangeably a group including an alkyne or azide

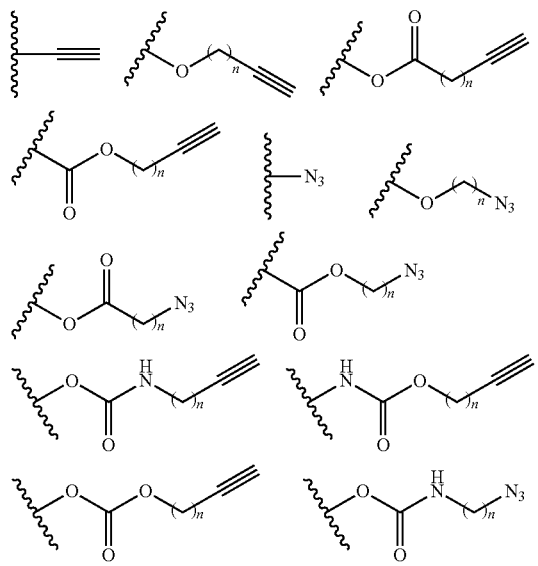

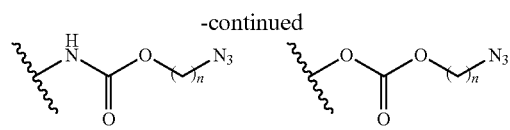

Co-Monomers

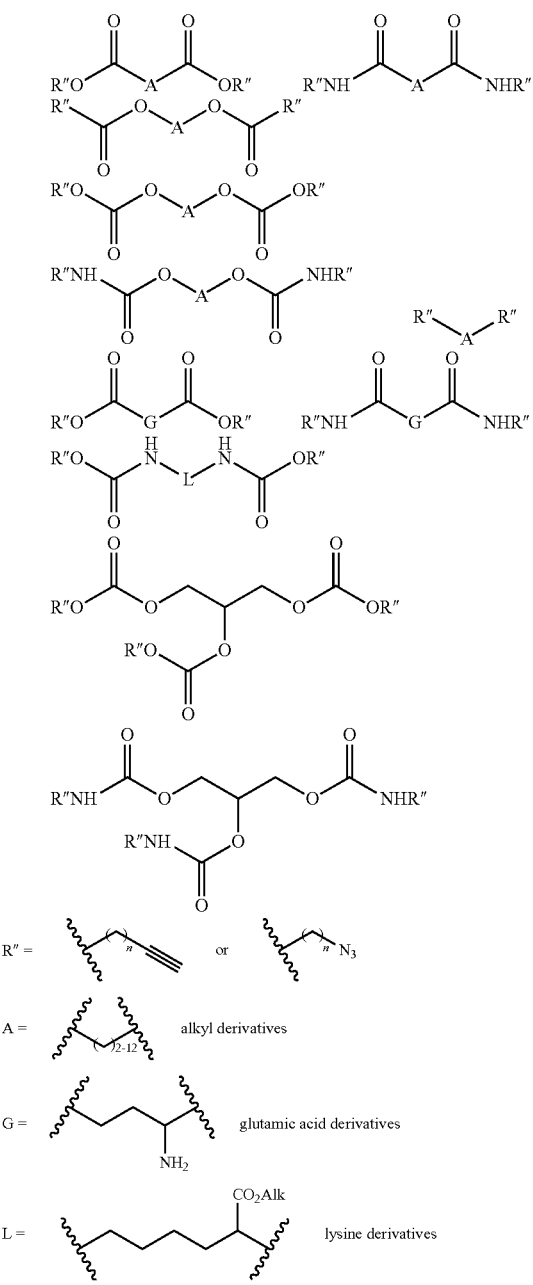

As discussed above, polymer-bioactive agent conjugates of the invention may comprise a moiety of formulae (VIa), (VIb) or (VIc). Moieties of formulae (VIa), (VIb) and (VIc) may be formed when a monomer of formula (IV) polymerises with a monomer of complementary functionality. The monomer of complementary functionality may be a monomer of formula (V), or it may be a further monomer of formula (IV). As illustrated above, moieties of formulae (VIa), (VIb) and (VIc) comprise Q and in the case of formulae (VIa) and (VIb), also comprise L.

Polymer-bioactive agent conjugates of the invention may be a copolymer of a mixture of monomers, such as for example, a mixture of two or more monomer conjugates of formula (IV), optionally, or additionally, with a mixture of two or more complementary monomers of formula (V). The ability to use a monomer composition comprising a mixture of different types of monomer can allow the properties of the polymer conjugates to be tailored for different applications. For example, the copolymerisation of at least two different monomer conjugates of formula (IV), where the monomer conjugates comprise quinolones and NSAIDs as the bioactive agent D, can allow a single polymer conjugate comprising a mixture of quinolones and NSAIDs as pendant bioactive agents to be obtained.

When Q and L comprise functional groups, conjugates of the invention may comprise a polymer backbone having a plurality of cleavable functional groups. The cleavable functional groups will generally form part of the polymer backbone and may be located on either one side or both sides of a triazole moiety. Cleavage of the functional groups in the polymer backbone may therefore release a triazole containing fragment when polymer conjugates of the invention biodegrade. For example, when Q and/or L comprises ester functional groups, a triazole fragment produced as a by-product of polymer degradation could be a dihydroxy triazole, a diacid triazole or hydroxyl-acid triazole, depending on the direction of the ester.

One of the advantages of the polymer drug conjugate is that it allows a relatively high proportion of bioactive NSAID and or quinolone monomers to be included. For example in one embodiment the conjugate includes at least 30 mol % bioactive monomers selected from the group consisting of quinolone conjugated monomers, NSAID conjugated monomers and mixtures of these monomers. Preferably the proportion of said bioactive monomers is at least 40 mol %, more preferably at least 50 mol %. In manuy cases we have achieved at least 60 mol % of said bioactive monomers. The use of cross-linking agents as hereinbefore discussed is useful in some embodiments in optimising the proportion of bioactive monomers.

The invention also provides a method for preparing a polymer-bioactive agent conjugate comprising as part of its polymer backbone a moiety of general formula (I):

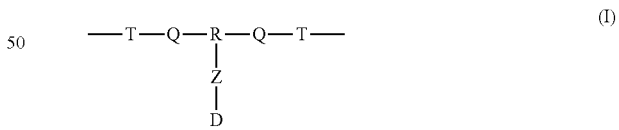

by reacting at least one monomer of formula (IV):

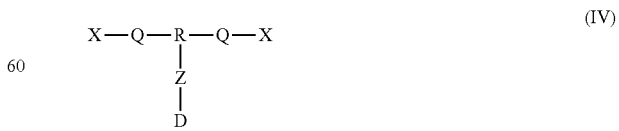

with at least one complementary monomer of formula (V):

under click cycloaddition reaction conditions.

In embodiments of the invention, click cycloaddition reactions may be catalyzed by a metal. Exemplary metals include copper (e.g. Cu(I)) which may be generated in situ from Cu(II) and ascorbic acid), and ruthenium (e.g. Ru(II)). Other metals that can be used include, but are not limited to, Ag, Ni, Pt, Pd, Rh, and Ir. In addition a metal free, strain promoted azide-alkyne cycloaddition (SPAAC). In this embodiment, no metal catalyst is required as the alkyne is activated by means of incorporation of the alkyne functionality into a strained ring.

In some embodiments, one or more further monomers may be employed in the synthesis of the polymer-bioactive conjugates of the invention. When used, the one or more further monomers may act as chain extenders, to increase the molecular weight or to tailor the properties of the polymer backbone, for example, by introducing flexibility or hard or soft segments into the polymer backbone. In order to be incorporated into the polymer backbone, the one or more further monomers will be required to have terminal functional groups selected from alkyne and azide functional groups. Depending on the nature of the terminal functional group, the one or more further monomers will be capable of reacting with at least one co-monomer selected from the group consisting of a formula (IV) and a monomer of formula (V).

It is possible to some extent to control the molecular weight of the polymer-bioactive agent conjugate, its degree of branching (through control of monomer functionality) and its end group functionality by adjusting the molar ratio and the functionality of the monomers employed in the conjugate synthesis.

Irrespective of the manner in which the polymer-bioactive agent conjugates are prepared, all repeat units that make up the polymer backbone will be coupled via a triazole moiety.

In one embodiment, the methods of the invention allow the formation of biodegradable moieties with multiple bioactive agents, known loadings, evenly distributed bioactive agents in the polymer chain, predetermined relative proportions and predetermined relative positions.

In some embodiments, particularly with respect to quinolones it is advantageous in order to obtain high yield of polymer product to protect nucleophilic groups such as primary and secondary amine groups in order to inhibit side reactions. Suitable protecting groups such as Boc (tert-butyloxycarbonyl) and their use in protecting nucleophilic groups which are not intended to take place in reactions, is well known in the art. In the present case the protection may be carried out of the amine group of quinolones such as moxifloxacin, gatifloxacin, ciprofloxacin, norfloxacin, besifloxacin or their mixtures prior to forming the monomer conjugate. The protecting group may in some cases be removed prior to polymerisation or following polymerisation to form the quinolone-polymer conjugate. The optimum step for removal may be determined without undue experimentation. The protected monomer-quinolone conjugates and protected quinolone-polymer are useful intermediates in the preparation of the quinolone polymer conjugates. Accordingly in a further embodiment there is provided bioactive-polymer conjugates and bioactive monomer conjugates where the bioactive comprises an amine such as a primary or secondary amine protected by a protecting group such as Boc. Specific examples include polymer conjugates of formula (I), (II) and monomer conjugates of formula (V) wherein the D (particularly where D, D1 and/or D2 are a quinolone such as a fluoroquinolone) comprises a primary or secondary amine which is protected by a protecting group such as Boc. In more specific examples at least one of D, D1 and D2 is selected from the group consisting of Boc-moxifloxacin, Boc-ciprafloxacin, Boc-gatifloxacin, Boc-norfloxacin and Boc-besifloxacin.

Polymer-bioactive agent conjugates in accordance with the invention can advantageously be prepared such that they are suitable for administration to a subject (i.e. suitable for in vivo applications).

According to one embodiment there is provided a method of delivering a bioactive agent to a subject, the method comprising administering to the subject a polymer-bioactive agent conjugate in accordance with the invention.

By the polymer conjugate being "suitable" for administration to a subject is meant that administration of the conjugate to a subject will not result in unacceptable toxicity, including allergenic responses and disease states. By the term "subject" is meant either an animal or human subject.

By "administration" of the conjugate to a subject is meant that the composition is transferred to the subject such that the bioactive agent will be released. The quinolones and NSAIDs are intended to use in the treatment of eye disorders associated with increased intraocular pressure, such as glaucoma, it is preferred that the polymer conjugate is administered to an affected eye of a subject. Administration to the eye may be by way of intracameral or subconjunctival administration.

The polymer conjugates may be provided in particulate form and blended with a pharmacologically acceptable carrier to facilitate administration. By "pharmacologically acceptable" is meant that the carrier is suitable for administration to a subject in its own right. In other words, administration of the carrier to a subject will not result in unacceptable toxicity, including allergenic responses and disease states. The term "carrier" refers to the vehicle with which the conjugate is contained prior to being administered.

As a guide only, a person skilled in the art may consider "pharmacologically acceptable" as an entity approved by a regulatory agency of a federal or state government or listed in the US Pharmacopeia or other generally recognised pharmacopeia for use in animals, and more particularly humans. Suitable pharmacologically acceptable carriers are described in Martin, Remington's Pharmaceutical Sciences, 18th Ed., Mack Publishing Co., Easton, Pa., (1990).

The polymer bioactive agent conjugates may also form part of or be formed into an article or device, or be applied as a coating on an article or device, and implanted in a subject. By being "implanted" is meant that the article or device is totally or partly introduced medically into a subject's body and which is intended to remain there after the procedure.

Suitable dosage amounts of the bioactive agents and dosing regimens of the polymer conjugates can be determined by a physician and may depend on the particular condition being treated, the rate of release of the agent form the polymer backbone, the severity of the condition as well the general age, health and weight of the subject.

The form of the polymer-bioactive agent conjugate may be adjusted to be suited to the required application such as a coating, film, pellet, capsule, fibres, laminate, foam etc. The difference in the form of the conjugate provides a means to alter the release profile of the bioactive agent. For example the amount of polymer and bioactive agent may be the same in two different structures however the differences in the surface area to volume, rates of hydration and diffusion paths from the different physical forms or structures can result in different rates of bioactive agent release from essentially the same polymer.

The adjustment of the form of the polymer conjugate to suit the application and further to adjust the form to further control bioactive agent release provides an additional advantage over purely compositional and polymer structural means to control the release profile of the bioactive agent.

Some of the compositional structural means to control the release of the bioactive agent include: controlling the loading of the bioactive; composition of the other comonomers to adjust criteria such as hydrophobicity, flexibility, susceptibility to degradation, ability of the fragments to autocatalyse the polymer degradation, thermal stability of the polymer, mouldability, polymer solubility to assist casting etc.

In one set of embodiments, the bioactive agent may be released from the polymer conjugate such that it provides for a sustained bioactive delivery system. Such a delivery system may in its simplest form be the polymer conjugate provided in a desired shape, for example a pellet or more intricate shape. To promote surface area contact of the polymer conjugate under physiological conditions or with a biological environment, it may also be provided in the form of a foamed product or a coating on substrate.

By "sustained bioactive moiety delivery" is meant that the bioactive agent is released from the conjugate over a period of time, for example over a period of 10 or more minutes, 30 or more minutes, 60 or more minutes, 2 or more hours, 4 or more hours, 12 or more hours, 24 or more hours, 2 or more days, 5 or more days, 10 or more days, 30 or more days, 2 or more months, 4 or more months or over 6 or more months.

Polymer-bioactive agent conjugates of the present invention may be incorporated into drug delivery systems, therapeutic articles, devices or preparations, and pharmaceutical products for the treatment of ocular hypertension.

The polymer-bioactive agent conjugates of the present invention may be blended with one or more other polymers (for example, biodegradable polymers).

The present invention also provides a sustained drug delivery system comprising a polymer-bioactive agent conjugate of the invention. In one embodiment, the sustained drug delivery system may be in the form of an implant. The sustained drug delivery system may enable the quinolones and/or NSAID to be administered over a sustained period of time, such as for example, for at least 15 days, for at least 30 days, for at least 45 days, for at least 60 days, or for at least 90 days. A sustained release drug delivery system may be a more convenient way to administer the quinolones and/or NSAID, as it enables therapeutic levels of the drug to be continuously administered over an extended period time and allows the drug therapy schedule to be matched with a patient's visitation schedule to a medical or health practitioner.

Polymer-bioactive agent conjugates in accordance with the invention can be formed into an article or device. The article or device may be fabricated in a range of forms. Suitably, the article or device is a medical device, preferably an ocular implant. The polymer conjugates in accordance with the invention can also be incorporated or made into coatings for target in vitro and in vivo applications.

The polymer-bioactive agent conjugates in accordance with the invention can be formed into an article or device that is suitable for administration to the eye.

In some embodiments, a polymer-bioactive agent conjugate may be in the form of a solid article (such as a particle, rod or pellet), a semi-solid, a deformable solid, a gel, or a liquid, for placement in the eye of the subject.

In another aspect, the present invention provides an ocular implant for the treatment of glaucoma comprising a polymer-bioactive agent conjugate of any one of the embodiments described herein.

In one form, the implant is a rod-shaped and is able to be housed within the lumen of a needle, such as a 20 to 23 gauge needle. The outer diameter of the implant would be less than 0.5 mm, preferably about 0.4 mm and more preferably 0.3 mm. The length of the implant can be selected to deliver the required dose of drug.

The implant can be of a number of different structural forms. The ocular implant could be a solid, a semi-solid or even a gel. A solid implant would comprise material with a glass transition temperature (as measured by differential scanning calorimetry) above 37° C., a semi-solid would have a glass transition temperature at or just below 25-37° C. A gel could be formed by appropriate formulation of the polymer conjugate with an appropriate plasticiser. In one set of embodiments, the implant could be a hydrogel.

In yet another aspect the present invention provides an injectable article for placement in an eye of the subject, wherein the injectable article comprises a polymer-bioactive agent conjugate of any one of the embodiments described herein. In one form, the injectable article is an injectable gel.

It is contemplated that an ocular implant may be a bi-component polymer structure where the polymer-bioactive agent conjugate can either be incorporated in the outer or inner layers of the bi-component structure. Incorporating the polymer-bioactive agent conjugate in the outer layer could be done to give a measured dose. Additionally the inner polymer layer could be to provide structural integrity to allow the delivery via the needle. Additionally the inner polymer could be designed to degrade either faster or slower than the polymer conjugate layer. This could be to alter the rate of bioerosion or the implant.

Possible means for producing rod-shaped implants include:

Melt extrusion of the polymer-bioactive agent conjugate or a material containing the polymer-bioactive agent conjugate through a shaped die.

Simultaneous bi-component extrusion of the polymer-bioactive agent conjugate and other materials forming the outer or inner layers through an appropriate die.

Sequential overcoating extrusion of one polymer later with another. For example a core polymer fibre of PLGA could be melt overcoated with a polymer containing the polymer-bioactive agent conjugate.

It is also possible to solution coat an appropriate inner polymer carrier material (e.g. PLGA) with a solution containing the polymer-bioactive agent conjugate.

In another aspect, the present invention provides an ocular implant for the treatment of ocular infections in a subject comprising a polymer-drug conjugate of any one of the embodiments described herein. In some embodiments, the implant is in the form of a solid, semi-solid, gel or liquid suitable for placement in the eye of the subject.

In yet another aspect the present invention provides a pharmaceutical product for the treatment of ocular infections in a subject, said pharmaceutical product comprising a polymer-bioactive agent conjugate of any one of the embodiments described herein. The pharmaceutical product may be an ocular implant or drug delivery system for the treatment of ocular infections. In one form, the pharmaceutical product is an implant in the form of a solid article, semi-solid, deformable solid, gel (including hydrogel), or liquid for placement in the eye of a subject.

In yet another aspect the present invention provides an injectable article for placement in an eye of the subject, wherein the injectable article comprises a polymer-bioactive agent conjugate of any one of the embodiments described herein. In one form, the injectable article is in the form of a gel.

In another aspect, there is provided a method for the treatment of ocular infections in a subject suffering infection in one or both eyes, the method comprising administering a polymer-bioactive agent conjugate of any one of the embodiments described herein to an eye afflicted with the infection.

In one set of embodiments, the polymer-bioactive agent conjugate is contained in a solid article and method comprises implanting the article in an affected eye of a subject. In one set of embodiments, the method comprises depositing the solid article in the lumen of a needle and injecting the article into the eye from the needle.

In another aspect, there is provided use of a polymer-bioactive agent conjugate of any one of the embodiments described herein in the manufacture of a pharmaceutical product for the treatment of ocular infections. In one set of embodiments, the pharmaceutical product is in the form of an ocular implant. The ocular implant is a solid article and may be injectable.

In this specification "optionally substituted" is taken to mean that a group may or may not be substituted or fused (so as to form a condensed polycyclic group) with one, two, three or more of organic and inorganic groups (i.e. the optional substituent) including those selected from: alkyl, alkenyl, alkynyl, carbocyclyl, aryl, heterocyclyl, heteroaryl, acyl, aralkyl, alkaryl, alkheterocyclyl, alkheteroaryl, alkcarbocyclyl, halo, haloalkyl, haloalkenyl, haloalkynyl, haloaryl, halocarbocyclyl, haloheterocyclyl, haloheteroaryl, haloacyl, haloaryalkyl, hydroxy, hydroxyalkyl, hydroxyalkenyl, hydroxyalkynyl, hydroxycarbocyclyl, hydroxyaryl, hydroxyheterocyclyl, hydroxyheteroaryl, hydroxyacyl, hydroxyaralkyl, alkoxyalkyl, alkoxyalkenyl, alkoxyalkynyl, alkoxycarbocyclyl, alkoxyaryl, alkoxyheterocyclyl, alkoxyheteroaryl, alkoxyacyl, alkoxyaralkyl, alkoxy, alkenyloxy, alkynyloxy, aryloxy, carbocyclyloxy, aralkyloxy, heteroaryloxy, heterocyclyloxy, acyloxy, haloalkoxy, haloalkenyloxy, haloalkynyloxy, haloaryloxy, halocarbocyclyloxy, haloaralkyloxy, haloheteroaryloxy, haloheterocyclyloxy, haloacyloxy, nitro, nitroalkyl, nitroalkenyl, nitroalkynyl, nitroaryl, nitroheterocyclyl, nitroheteroayl, nitrocarbocyclyl, nitroacyl, nitroaralkyl, amino ($NH_2$), alkylamino, dialkylamino, alkenylamino, alkynylamino, arylamino, diarylamino, aralkylamino, diaralkylamino, acylamino, diacylamino, heterocyclamino, heteroarylamino, carboxy, carboxyester, amido, alkylsulphonyloxy, arylsulphenyloxy, alkylsulphenyl, arylsulphenyl, thio, alkylthio, alkenylthio, alkynylthio, arylthio, aralkylthio, carbocyclylthio, heterocyclylthio, heteroarylthio, acylthio, sulfoxide, sulfonyl, sulfonamide, aminoalkyl, aminoalkenyl, aminoalkynyl, aminocarbocyclyl, aminoaryl, aminoheterocyclyl, aminoheteroaryl, aminoacyl, aminoaralkyl, thioalkyl, thioalkenyl, thioalkynyl, thiocarbocyclyl, thioaryl, thioheterocyclyl, thioheteroaryl, thioacyl, thioaralkyl, carboxyalkyl, carboxyalkenyl, carboxyalkynyl, carboxycarbocyclyl, carboxyaryl, carboxyheterocyclyl, carboxyheteroaryl, carboxyacyl, carboxyaralkyl, carboxyesteralkyl, carboxyesteralkenyl, carboxyesteralkynyl, carboxyestercarbocyclyl, carboxyesterarayl, carboxyesterheterocyclyl, carboxyesterheteroaryl, carboxyesteracyl, carboxyesteraralkyl, amidoalkyl, amidoalkenyl, amidoalkynyl, amidocarbocyclyl, amidoaryl, amidoheterocyclyl, amidoheteroaryl, amidoacyl, amidoaralkyl, formylalkyl, formylalkenyl, formylalkynyl, formylcarbocyclyl, formylaryl, formylheterocyclyl, formylheteroaryl, formylacyl, formylaralkyl, acylalkyl, acylalkenyl, acylalkynyl, acylcarbocyclyl, acylaryl, acylheterocyclyl, acylheteroaryl, acylacyl, acylaralkyl, sulfoxidealkyl, sulfoxidealkenyl, sulfoxidealkynyl, sulfoxidecarbocyclyl, sulfoxidearyl, sulfoxideheterocyclyl, sulfoxideheteroaryl, sulfoxideacyl, sulfoxidearalkyl, sulfonylalkyl, sulfonylalkenyl, sulfonylalkynyl, sulfonylcarbocyclyl, sulfonylaryl, sulfonylheterocyclyl, sulfonylheteroaryl, sulfonylacyl, sulfonylaralkyl, sulfonamidoalkyl, sulfonamidoalkenyl, sulfonamidoalkynyl, sulfonamidocarbocyclyl, sulfonamidoaryl, sulfonamidoheterocyclyl, sulfonamidoheteroaryl, sulfonamidoacyl, sulfonamidoaralkyl, nitroalkyl, nitroalkenyl, nitroalkynyl, nitrocarbocyclyl, nitroaryl, nitroheterocyclyl, nitroheteroaryl, nitroacyl, nitroaralkyl, cyano, sulfate and phosphate groups.

Preferred optional substituents include the aforementioned reactive functional groups or moieties, polymer chains and alkyl, (e.g. $C_{1-6}$ alkyl such as methyl, ethyl, propyl, butyl, cyclopropyl, cyclobutyl, cyclopentyl or cyclohexyl), hydroxyalkyl (e.g. hydroxymethyl, hydroxyethyl, hydroxypropyl), alkoxyalkyl (e.g. methoxymethyl, methoxyethyl, methoxypropyl, ethoxymethyl, ethoxyethyl, ethoxypropyl etc) alkoxy (e.g. $C_{1-6}$ alkoxy such as methoxy, ethoxy, propoxy, butoxy, cyclopropoxy, cyclobutoxy), halo, trifluoromethyl, trichloromethyl, tribromomethyl, hydroxy, phenyl (which itself may be further substituted e.g., by $C_{1-6}$ alkyl, halo, hydroxy, hydroxy$C_{1-6}$ alkyl, $C_{1-6}$ alkoxy, halo$C_{1-6}$alkyl, cyano, nitro OC(O)$C_{1-6}$ alkyl, and amino), benzyl (wherein benzyl itself may be further substituted e.g., by $C_{1-6}$ alkyl, halo, hydroxy, hydroxy$C_{1-6}$alkyl, $C_{1-6}$ alkoxy, halo$C_{1-6}$ alkyl, cyano, nitro OC(O)$C_{1-6}$ alkyl, and amino), phenoxy (wherein phenyl itself may be further substituted e.g., by $C_{1-6}$ alkyl, halo, hydroxy, hydroxy$C_{1-6}$ alkyl, $C_{1-6}$ alkoxy, halo$C_{1-6}$ alkyl, cyano, nitro OC(O)$C_{1-6}$ alkyl, and amino), benzyloxy (wherein benzyl itself may be further substituted e.g., by $C_{1-6}$ alkyl, halo, hydroxy, hydroxy$C_{1-6}$ alkyl, $C_{1-6}$ alkoxy, halo$C_{1-6}$ alkyl, cyano, nitro OC(O)$C_{1-6}$ alkyl, and amino), amino, alkylamino (e.g. $C_{1-6}$ alkyl, such as methylamino, ethylamino, propylamino etc), dialkylamino (e.g. $C_{1-6}$ alkyl, such as dimethylamino, diethylamino, dipropylamino), acylamino (e.g. NHC(O)$CH_3$), phenylamine (wherein phenyl itself may be further substituted e.g., by $C_{1-6}$ alkyl, halo, hydroxy hydroxy$C_{1-6}$ alkyl, $C_{1-6}$ alkoxy, halo$C_{1-6}$ alkyl, cyano, nitro OC(O)$C_{1-6}$ alkyl, and amino), nitro, formyl, —C(O)-alkyl (e.g. $C_{1-6}$ alkyl, such as acetyl), O—C(O)-alkyl (e.g. $C_{1-6}$alkyl, such as acetyloxy), benzoyl (wherein the phenyl group itself may be further substituted e.g., by $C_{1-6}$ alkyl, halo, hydroxy hydroxy$C_{1-6}$ alkyl, $C_{1-6}$ alkoxy, halo$C_{1-6}$ alkyl, cyano, nitro OC(O)$C_{1-6}$ alkyl, and amino), replacement of $CH_2$ with C=O, $CO_2H$, $CO_2$alkyl (e.g. $C_{1-6}$ alkyl such as methyl ester, ethyl ester, propyl ester, butyl ester), $CO_2$phenyl (wherein phenyl itself may be further substituted e.g., by $C_{1-6}$ alkyl, halo, hydroxy, hydroxyl $C_{1-6}$ alkyl, $C_{1-6}$ alkoxy, halo $C_{1-6}$ alkyl, cyano, nitro OC(O)$C_{1-6}$ alkyl, and amino), $CONH_2$, CONHphenyl (wherein phenyl itself may be further substituted e.g., by $C_{1-6}$ alkyl, halo, hydroxy, hydroxyl $C_{1-6}$ alkyl, $C_{1-6}$ alkoxy, halo $C_{1-6}$ alkyl, cyano, nitro OC(O)$C_{1-6}$ alkyl, and amino), CONHbenzyl (wherein benzyl itself may be further substituted e.g., by $C_{1-6}$ alkyl, halo, hydroxy hydroxyl $C_{1-6}$ alkyl, $C_{1-6}$ alkoxy, halo $C_{1-6}$ alkyl, cyano, nitro OC(O)$C_{1-6}$ alkyl, and amino), CONHalkyl (e.g. $C_{1-6}$ alkyl such as methyl amide, ethyl amide, propyl amide, butyl amide) CONHdialkyl (e.g. $C_{1-6}$ alkyl) aminoalkyl (e.g., HN $C_{1-6}$ alkyl-, $C_{1-6}$alkylHN—$C_{1-6}$ alkyl- and ($C_{1-6}$ alkyl)$_2$N—$C_{1-6}$ alkyl-), thioalkyl (e.g., HS $C_{1-6}$ alkyl-), carboxyalkyl (e.g., $HO_2CC_{1-6}$ alkyl-), carboxyesteralkyl (e.g., $C_{1-6}$ alkylO$_2$CC$_{1-6}$ alkyl-), amidoalkyl (e.g., $H_2N(O)CC_{1-6}$ alkyl-, $H(C_{1-6}$ alkyl)N(O)CC$_{1-6}$ alkyl-), formylalkyl (e.g., OHCC$_{1-6}$alkyl-), acylalkyl (e.g., $C_{1-6}$ alkyl(O)CC$_{1-6}$ alkyl-), nitroalkyl (e.g., $O_2NC_{1-6}$ alkyl-), sulfoxidealkyl (e.g., $R^3(O)SC_{1-6}$ alkyl, such as $C_{1-6}$ alkyl(O)SC$_{1-8}$ alkyl-), sulfonylalkyl (e.g., $R^3(O)_2SC_{1-6}$ alkyl- such as $C_{1-6}$ alkyl(O)$_2$SC$_{1-6}$ alkyl-), sulfonamidoalkyl (e.g., 2HRN(O)SC$_{1-6}$ alkyl, $H(C_{1-6}$ alkyl)N(O)SC$_{1-6}$ alkyl-), It is understood that the compounds of the present invention (including monomers and polymers) may exist in one or more stereoisomeric forms (eg enantiomers, diastereomers). The present invention includes within its scope all of these stereoisomeric forms either isolated (in for example enantiomeric isolation), or in combination (including racemic mixtures).

The following examples are intended to illustrate the scope of the invention and to enable reproduction and comparison. They are not intended to limit the scope of the disclosure in any way.

EXAMPLES

The examples are described with reference to the drawings.

In the drawings:

FIG. 1 Is a graph showing the release of levofloxacin from linear (Example 29) and cross-linked (Example 30, Example 31, Example 32) drug polytriazole conjugates.

FIG. 2 is a graph showing the cumulative release of levofloxacin from polytriazole conjugates. Levofloxacin is conjugated to the polymer backbone through either a p-hydroxybenzoic acid (Example 38, Example 39, Example 40) or pyridoxine (Example 41, Example 42, Example 43) linker with a linear polymer architecture (Example 40, Example 43) or cross-linked polymer architecture (Example 38, Example 39, Example 41, Example 42).

Figure 1:
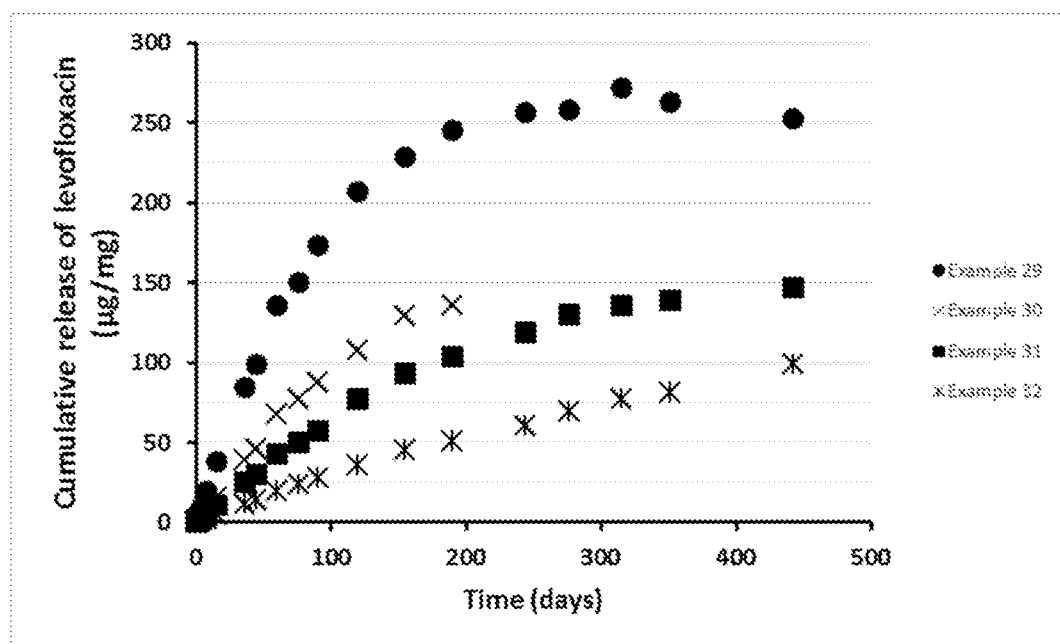
Figure 2:
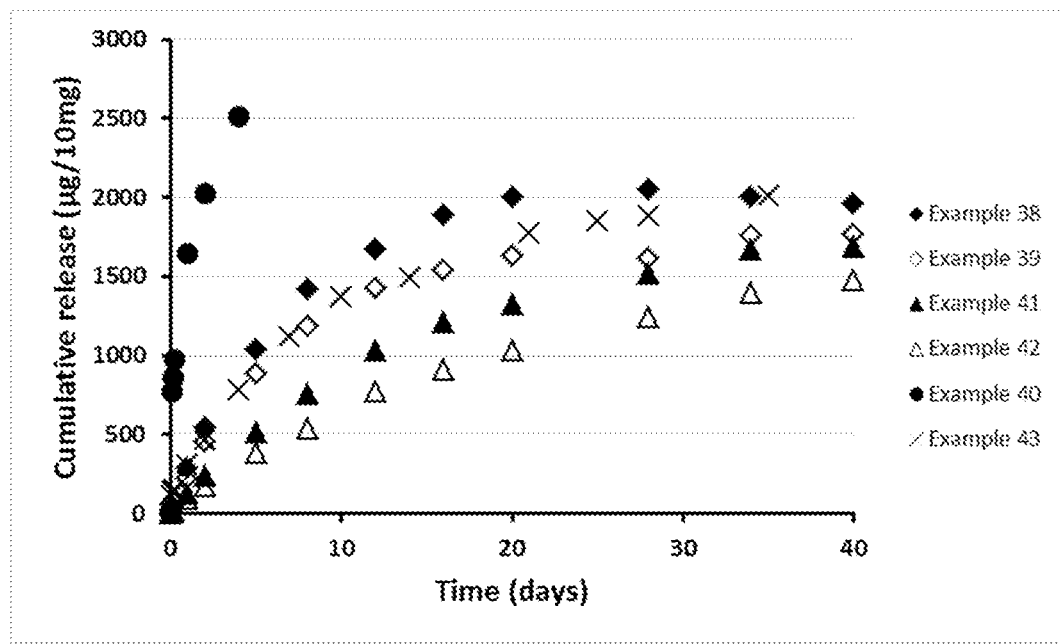
Figure 3:
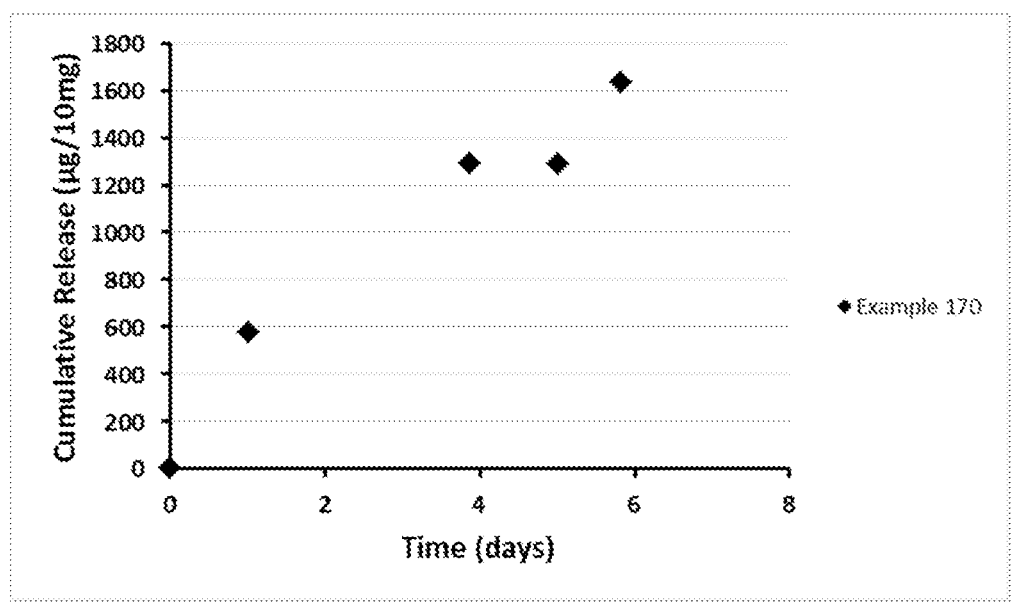
FIG. 3 is a graph showing the cumulative release of moxifloxacin from a linear polytriazole conjugate with moxifloxacin conjugated to the polymer backbone through an [(alkoxycarbonyl)oxy]alkyl ester linkage (Example 170).
Figure 4:
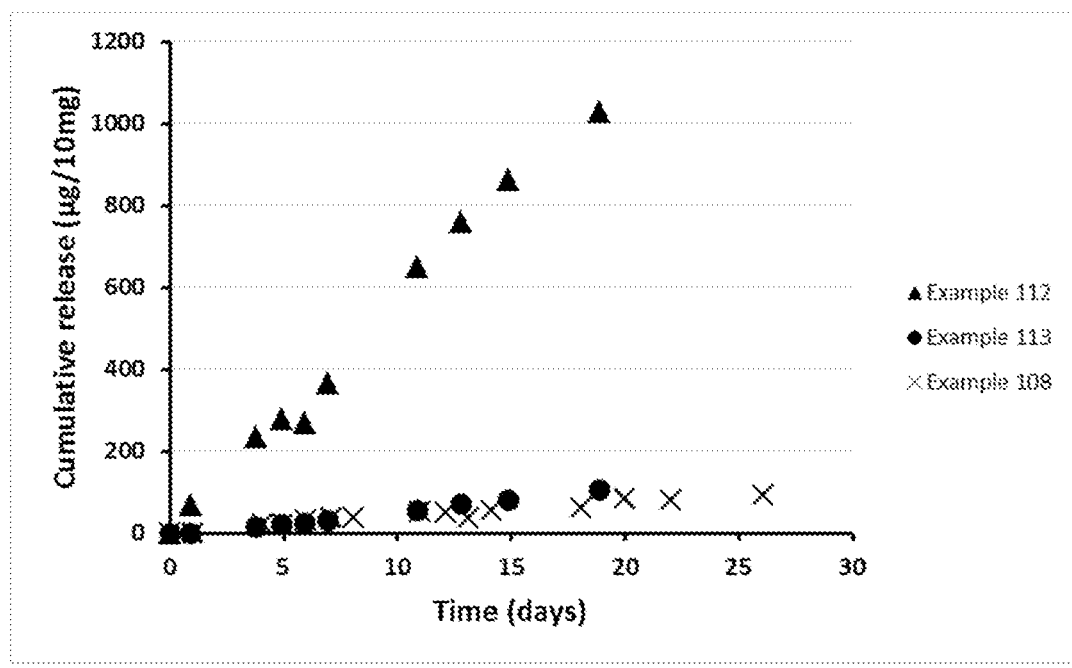
FIG. 4 is a graph showing the cumulative release of diclofenac from linear polytriazole conjugates. Diclofenac is conjugated to the polymer with an alkyl ester linkage (Example 108) and an aryl ester linkage (Example 112, Example 113,), Example 112 was produced with an ethyl lysine based co-monomer, whereras, Example 113 was produced with a more hydrophilic PEG based co-monomer.
Figure 5:
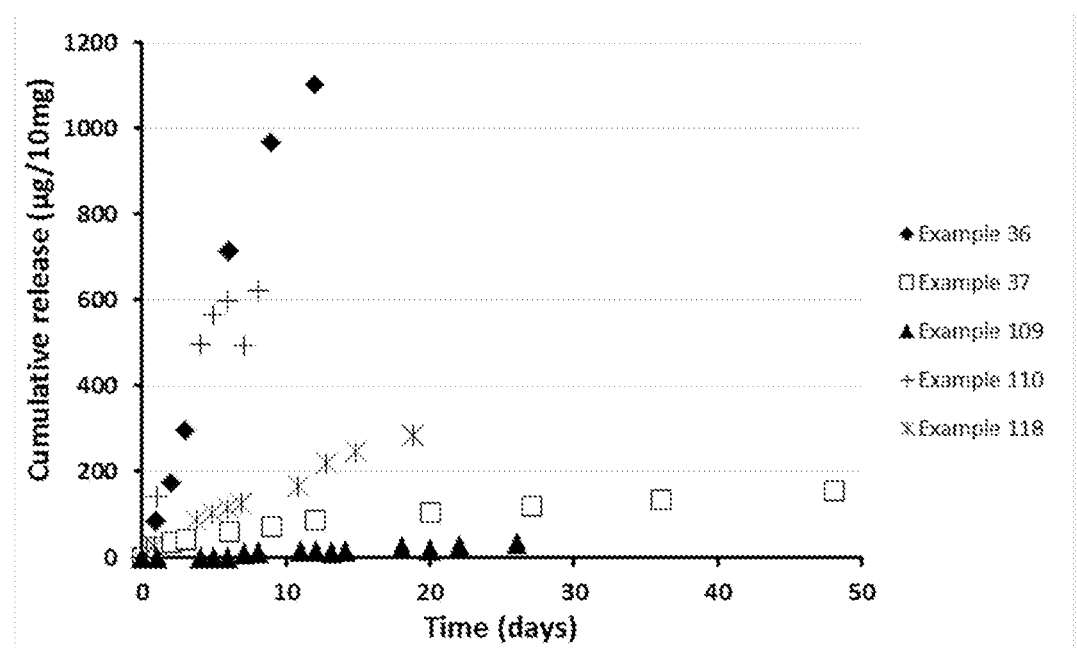
FIG. 5 is a graph showing the cumulative release of diclofenac from cross-linked polytriazole hydrogel conjugates. Diclofenac is conjugated to the polymer with an alkyl ester linkage (Example 109), an aryl ester linkage (Example 36, Example 37, Example 110) and an [(alkoxycarbonyl)oxy]alkyl ester (Example 118).
Figure 6:
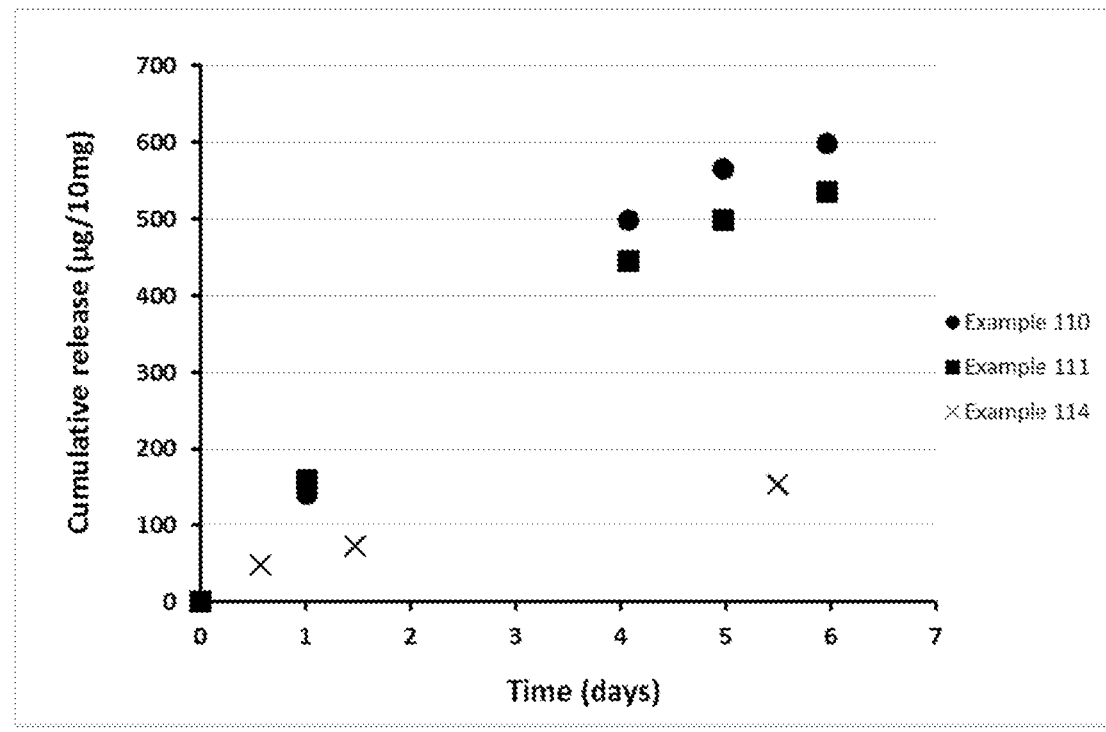

FIG. 6 is a graph showing the cumulative release of diclofenac from cross-linked polytriazole hydrogel conjugates. In each case diclofenac is conjugated to the polymer with a p-hydroxybenzoic acid linkage. Example 110 was produced with a 4-arm PEG azide, whereras, Example 111 was produced with a 4-arm PEG azide that contains an ester moiety and Example 114 was produced with a 4-arm PEG azide that contains a carbamate moiety.

Figure 7:
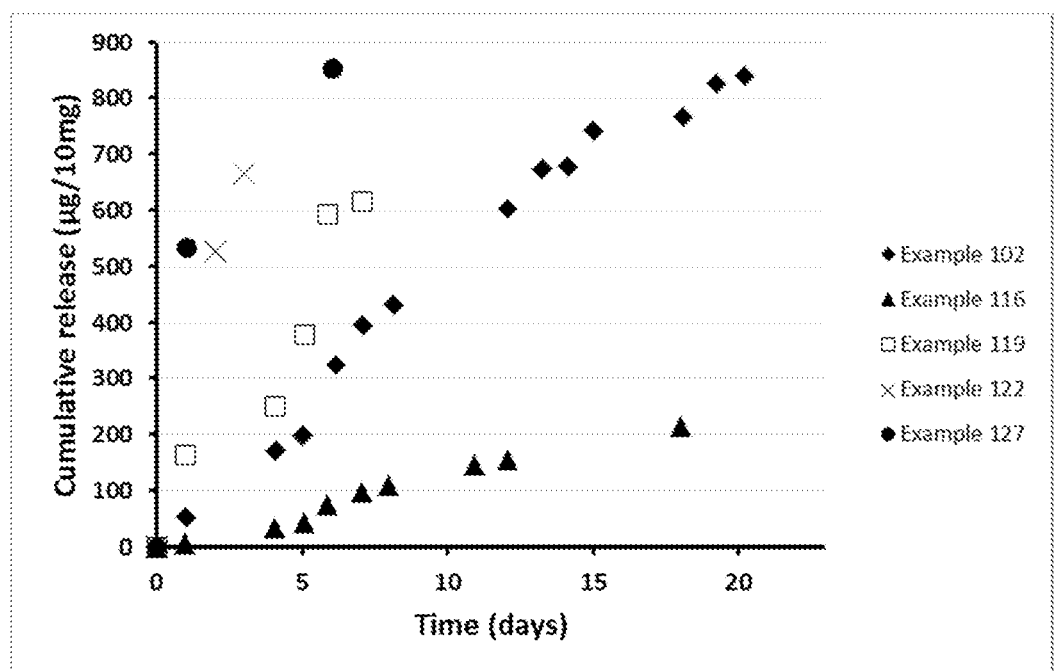

FIG. 7 is a graph showing the cumulative release of ketorolac from polytriazole conjugates. Ketorolac is conjugated to the polymer with an alkyl ester linkage (Example 102, Example 116) and an aryl ester linkage (Example 119, Example 122, Example 127). Example 102 and Example 127 have linear polymer architecture, whereas, Example 116, Example 119 and Example 122 have a cross-linked hydrogel polymer architecture.

Figure 8:
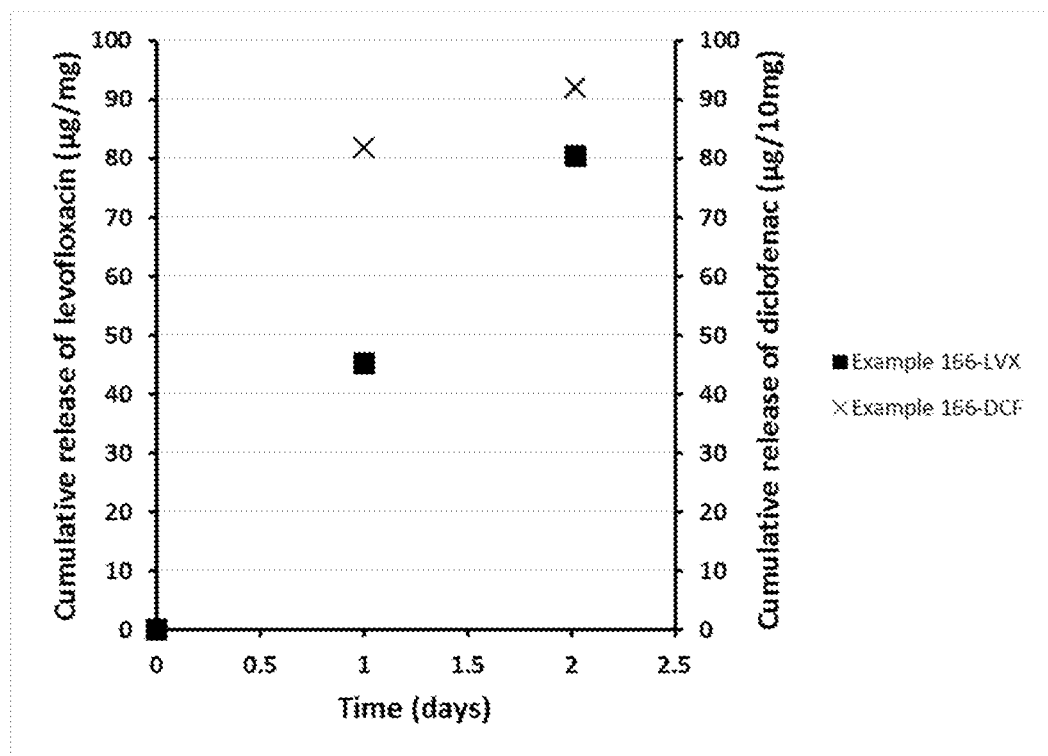

FIG. 8 is a graph showing the cumulative release of levofloxacin and diclofenac from a linear polytriazole conjugate with levofloxacin and diclofenac covalently attached to a common polymer backbone (Example 166). Levofloxacin and diclofenac are both conjugated to the polymer backbone through a p-hydroxybenzoic acid linker.

Figure 9:
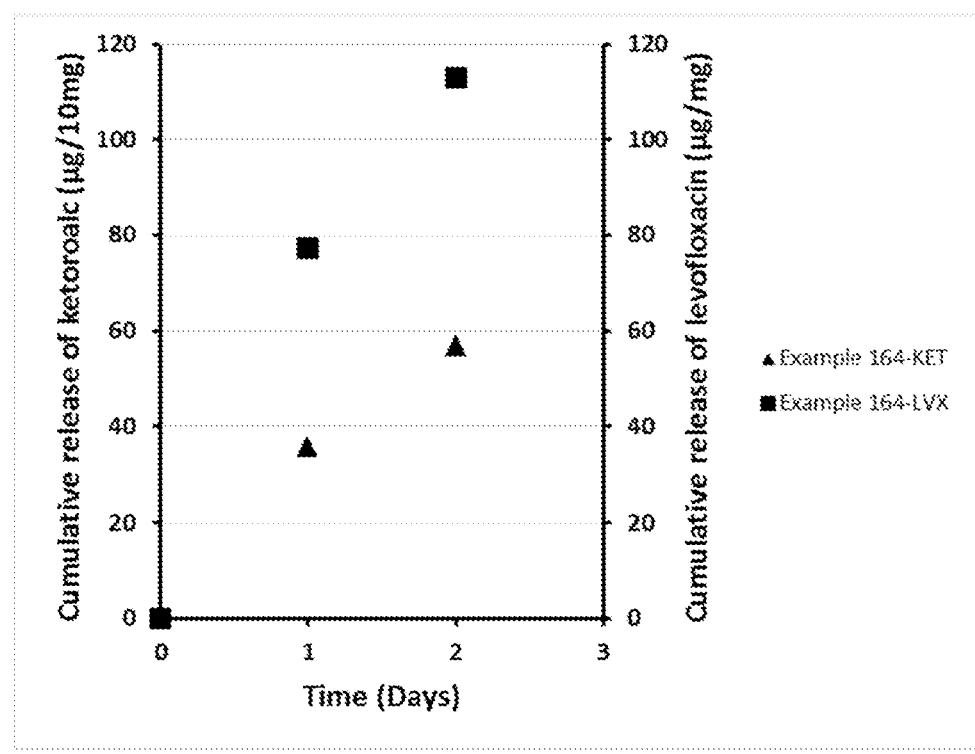

FIG. 9 is a graph showing the cumulative release of levofloxacin and ketorlac from a linear polytriazole conjugate with levofloxacin and ketorolac covalently attached to a common polymer backbone (Example 164). Levofloxacin and ketorolac are both conjugated to the polymer backbone through a p-hydroxybenzoic acid linker.

EXPERIMENTAL PROCEDURES

General

The following compounds necessary for the invention were prepared according to literature methods or unless otherwise described using techniques well known to those skilled in the art.

2-(Prop-2-yn-1-yl)pent-4-yn-1-ol (CAS 432027-96-8); (2-Hydroxypropane-1,3-diyl bis(hex-5-ynoate) (CAS16-27101-87-4); 2-(Prop-2-yn-1-yl)pent-4-yn-1-yl 4-hydroxybenzoate (CAS1627101-89-6) [2-(Prop-2-yn-1-yl)pent-4-yn-1-yl 3-hydroxybenzoate was prepared in the same manner]; 4-Hydroxy-N-(2-(prop-2-yn-1-yl)pent-4-yn-1-yl) benzamide (CAS1627101-91-yl); (5-Hydroxy-6-methylpyridine-3,4-diyl)bis(methylene) bis(hex-5-ynoate) (CAS1627101-92-1) [(5-Hydroxy-6-methylpyridine-3,4-diyl)bis(methylene) bis(hept-6-ynoate) was prepared in the same manner]; 1,3-Bis(prop-2-yn-1-yloxy)propan-2-ol (CAS 16169-22-5) were all prepared according to the procedure described in WO 2014134689 A1, Sep. 12, 2014. N-Boc Moxifloxacin (CAS 925684-42-yl), N-Boc Gatifloxacin (CAS 925684-44-2), N-Boc Ciprofloxacin (CAS 93594-48-yl) and N-Boc Besifloxacin were all prepared following literature procedures (US2008/287396 A-1, 2008)

Preparation of Monomer-Bioactive Agent Conjugates

The monomer-bioactive agents of this invention may be prepared by methods well known to those skilled in the art and as described in the synthesis and experimental procedures for representative compounds shown below.

Preparation of Example 2: 4-(((2-(prop-2-yn-1-yl)pent-4-yn-1-yl)oxy)carbonyl)phenyl 9-fluoro-3-methyl-10-(4-methylpiperazin-1-yl)-7-oxo-2,3-dihydro-7H-[1,4]oxazino[2,3,4-ij]quinoline-6-carboxylate To an ice cold solution of levofloxacin (500.0 mg, 1.38 mmol) and NEt$_3$ (250 µL, 1.78 mmol) in anhydrous DCM (30 mL), ethyl chloroformate (158 µL, 1.65 mmol) was added in one portion. The reaction mixture was stirred at 0° C. for 1 h and to it was added 2-(prop-2-yn-1-yl)pent-4-yn-1-yl-4-hydroxybenzoate (368 mg, 1.52 mmol). The reaction was allowed to warm to room temperature and then stirred further for 18 h. The reaction was quenched with H$_2$O (20 mL), extracted with CH$_2$Cl$_2$ (2×20 mL), washed with H$_2$O (2×20 mL) and brine (20 mL). Combined organic extracts dried over anhydrous Na$_2$SO$_4$, filtered and concentrated under reduced pressure. Flash chromatography over silica gel (0-30% DCM/MeOH gradient elution) gave the title compound as a pale yellow solid (375 mg, 0.64 mmol, 46%).

Preparation of Example 3: 2-((9-fluoro-3-methyl-10-(4-methylpiperazin-1-yl)-7-oxo-2,3-dihydro-7H-[1,4]oxazino[2,3,4-ij]quinoline-6-carbonyl)oxy)propane-1,3-diyl bis(hex-5-ynoate)

2-hydroxypropane-1,3-diyl bis(hex-5-ynoate) (0.667 g, 2.38 mmol, 1.0 e.q.), levofloxacin (1.03 g, 2.86 mmol, 1.2 e.q.), HBTU (1.08 g, 2.86 mmol, 1.2 e.q) were dissolved in 25 mL anhydrous dichloromethane. Triethylamine (0.963 g, 9.52 mmol, 4.0 e.q.) was added slowly into the reaction mixture and stirred for 72 hours at room temperature. The crude material was purified directly via column chromatography on silica gel (10% methanol in DCM) to give the product as a yellow oil (0.718 g).

Preparation of Example 4: 2-(prop-2-yn-1-yl)pent-4-yn-1-yl (S)-9-fluoro-3-methyl-10-(4-methylpiperazin-1-yl)-7-oxo-2,3-dihydro-7H-[1,4]oxazino[2,3,4-ij]quinoline-6-carboxylate To a solution of levofloxacin (1.0 g, 2.767 mmol) and di-tert-butyl dicarbonate (0.785 g, 3.597 mmol) in anhydrous DCM (20 mL), 4-dimethylamino pyridine (33.8 mg, 0.2767 mmol) was added. The mixture was stirred at room temperature for 16 h. The solvent was removed in vacuo and the residue passed through a plug of silica. Flash chromatography (0-30% dichloromethane/methanol gradient elution) gave the title compound as a yellow solid (0.510 g, 40%).

Preparation of Example 9: 1-((((2-(Prop-2-yn-1-yl)pent-4-yn-1-yl)oxy)carbonyl)oxy)ethyl (3S)-9-fluoro-3-methyl-10-(4-methylpiperazin-1-yl)-7-oxo-2,3-dihydro-7H-[1,4]oxazino[2,3,4-ij]quinoline-6-carboxylate 1-Chloroethyl (2-(prop-2-yn-1-yl)pent-4-yn-1-yl) carbonate

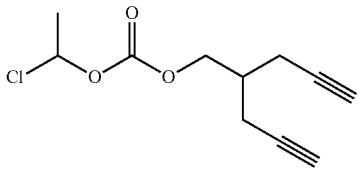

To an ice cold solution of 2-(prop-2-yn-1-yl)pent-4-yn-1-ol (2.0 g, 16.37 mmol) and DMAP (3.0 g, 24.55 mmol) in anhydrous dichloromethane (60 mL), was added 1-chloroethyl chloroformate (3.4 mL, 31.4 mmol). The reaction mixture was allowed to warm to room temperature and stirred for 18 h. The solvent was removed under reduced pressure. The crude was slurried with ethyl acetate and passed through a plug of silica. The title compound was isolated as a clear amber coloured liquid (3.01 g, 80% yield). $^1$H NMR (400 MHz, CDCl$_3$) δ 6.43 (q, J=5.8 Hz, 1H), 4.31 (d, J=6.1 Hz, 2H), 2.48-2.36 (m, 4H), 2.25-2.14 (m, 1H), 2.03 (t, J=2.6 Hz, 2H), 1.84 (d, J=5.8 Hz, 3H).

To a suspension of levofloxacin (0.280 g, 0.88 mmol) in anhydrous DMF, potassium carbonate (0.475 g, 3.44 mmol) and a solution of 1-chloroethyl (2-(prop-2-yn-1-yl)pent-4-yn-1-yl) carbonate (0.339 g, 1.5 mmol) in anhydrous DMF (5 mL) was added. The reaction mixture was stirred at room temperature for 4 days with the exclusion from light. The reaction mixture was extracted with ethyl acetate and washed with water and brine. The organic phase was then dried over Na$_2$SO$_4$, filtered and concentrated and dried in vacuo. The crude residue was purified on the automated flash chromatography using 0%-30% MeOH in DCM gradient elution to give a 1:1 diastereomer of the title compound as a clear colourless oil (0.1146 g, 27% yield).

Preparation of Example 47: 6-(1-cyclopropyl-6-fluoro-8-methoxy-3-(((2-methyl-4,5-bis(((2-(prop-2-yn-1-yloxy)propanoyl)oxy)methyl) pyridin-3-yl) oxy)carbonyl)-4-oxo-1,4-dihydroquinolin-7-yl) octahydro-1H-pyrrolo[3,4-b]pyridin-1-ium 2,2,2-trifluoroacetate

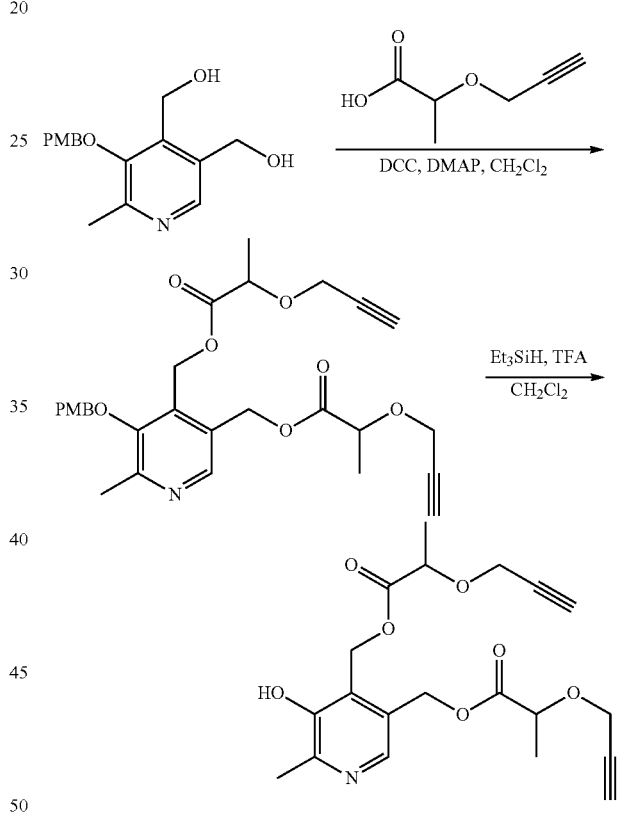

To a solution of (5-((4-methoxybenzyl)oxy)-6-methylpyridine-3,4-diyl)dimethanol (1.77 g, 6.12 mmol), 2-(prop-2-yn-1-yloxy)propanoic acid (1.93 g, 15.1 mmol) and DMAP (54.8 mg, 0.449 mmol) in CH$_2$Cl$_2$ (70 mL) was added DCC (3.06 g, 14.8 mmol) in one portion. The reaction was stirred at rt for 17 h before the resulting precipitate was removed by filtration. The filtrate was concentrated under reduced pressure and the residue purified by flash chromatography (20%-100% EtOAc/petrol gradient elution) to give (5-((4-methoxybenzyl)oxy)-6-methylpyridine-3,4-diyl)bis (methylene) bis(2-(prop-2-yn-1-yloxy)propanoate) (2.84 g, 5.57 mmol, 91%). R$_f$=0.40 (50% EtOAc/petrol) $^1$H NMR (400 MHz, CDCl$_3$) δ 8.35 (s, 1H), 7.38-7.31 (m, 2H), 6.94-6.89 (m, 2H), 5.31-5.24 (m, 4H), 4.84 (s, 2H), 4.33-4.13 (m, 6H), 2.58 (s, 3H), 2.44 (t, J=2.4 Hz, 1H), 2.40 (t, J=2.4 Hz, 1H), 1.42 (d, J=6.9 Hz, 3H), 1.40 (d, J=6.9 Hz, 3H). $^{13}$C NMR (100 MHz, CDCl$_3$) δ 172.4, 172.3, 160.1, 154.6, 152.1, 145.7, 135.7, 130.1, 129.2, 128.2, 114.3, 78.92, 78.89, 76.4, 75.4, 73.11, 73.07, 62.0, 57.9, 57.3, 55.5, 20.1, 18.59, 18.56. Et$_3$SiH (1.0 mL, 6.3 mmol) was added to a stirred solution of (5-((4-methoxybenzyl)oxy)-6-methyl-pyridine-3,4-diyl)bis(methylene) bis(2-(prop-2-yn-1-yloxy)propanoate) (2.84 g, 5.57 mmol) in CH$_2$Cl$_2$ (100 mL). The resultant solution was stirred at rt for 10 min before TFA (2.4 mL, 31 mmol) was added dropwise. The reaction mixture was stirred at rt for 18 h before the volatiles were removed under reduced pressure. The residue was dissolved (CH$_2$Cl$_2$), washed (sat. aq. NaHCO$_3$, then H$_2$O, then brine), dried (Na$_2$SO$_4$), filtered and concentrated under reduced pressure. Flash chromatography (20%-100% EtOAc/petrol gradient elution) gave (5-hydroxy-6-methylpyridine-3,4-diyl)bis(methylene) bis(2-(prop-2-yn-1-yloxy)propanoate) (1.93 g, 4.96 mmol, 89%). R$_f$=0.60 (EtOAc) $^1$H NMR (400 MHz, CDCl$_3$) δ 8.14 (s, 1H), 7.86 (br s, 1H), 5.32 (s, 2H), 5.27 (s, 2H), 4.33-4.24 (m, 4H), 4.18 (ddd, J=16.0, 6.0, 2.4 Hz, 2H), 2.53 (s, 3H), 2.43 (t, J=2.4 Hz, 1H), 2.33 (t, J=2.4 Hz, 1H), 1.43 (d, J=4.9 Hz, 1H), 1.42 (d, J=4.9 Hz, 1H).

To a 0° C. solution of N-Boc-moxifloxacin (1.05 g, 2.09 mmol) in CH$_2$Cl$_2$ (30 mL) was added NEt$_3$ (380 µL, 2.73 mmol) followed by ethyl chloroformate (240 µL, 2.52 mmol). The resulting mixture was stirred at 0° C. for 50 min before a solution of (5-hydroxy-6-methylpyridine-3,4-diyl) bis(methylene) bis(2-(prop-2-yn-1-yloxy)propanoate) (883.4 mg, 2.27 mmol) in CH$_2$Cl$_2$ (20 mL) was added via cannula. The mixture was stirred at 0° C. for 1 h before allowing to warm to rt and stirring for a further 18 h. The reaction was quenched (H$_2$O), extracted (CH$_2$Cl$_2$), washed (H$_2$O, then brine), dried (Na$_2$SO$_4$), filtered and concentrated under reduced pressure. Flash chromatography (20%-100% EtOAc/petrol gradient elution) gave (5-((7-(1-(tert-butoxy-carbonyl)octahydro-6H-pyrrolo[3,4-b]pyridin-6-yl)-1-cyclopropyl-6-fluoro-8-methoxy-4-oxo-1,4-dihydroquinoline-3-carbonyl)oxy)-6-methylpyridine-3,4-diyl)bis(methylene) bis(2-(prop-2-yn-1-yloxy)propanoate) (1.46 g, 1.67 mmol, 80%) as a white crystalline solid. R$_f$=0.60 (EtOAc)

To a solution of (5-((7-(1-(tert-butoxycarbonyl)octa-hydro-6H-pyrrolo[3,4-b]pyridin-6-yl)-1-cyclopropyl-6-fluoro-8-methoxy-4-oxo-1,4-dihydroquinoline-3-carbonyl) oxy)-6-methylpyridine-3,4-diyl)bis(methylene) bis(2-(prop-2-yn-1-yloxy)propanoate) (281.5 mg, 0.322 mmol) in CH$_2$Cl$_2$ (3 mL) was added a solution of 20% TFA/CH$_2$Cl$_2$ (6 mL). The reaction was stirred at rt for 2.5 h before CH$_2$Cl$_2$ and H$_2$O were added. The product was extracted (CH$_2$Cl$_2$), washed (H$_2$O, then brine), dried (Na$_2$SO$_4$), filtered and concentrated under reduced pressure to give 6-(1-cyclopropyl-6-fluoro-8-methoxy-3-(((2-methyl-4,5-bis(((2-(prop-2-yn-1-yloxy)propanoyl)oxy)methyl)pyridin-3-yl)oxy)carbonyl)-4-oxo-1,4-dihydroquinolin-7-yl)octahydro-1H-pyrrolo[3,4-b]pyridin-1-ium 2,2,2-trifluoroacetate (230.4 mg, 0.260 mmol, 81%).

Preparation of Example 11: 2-(prop-2-yn-1-yl)pent-4-yn-1-yl 4-(2-(2-((2,6-dichlorophenyl)amino) phenyl)acetoxy)benzoate To a chilled (0° C.) solution of diclofenac free acid (202.3 mg, 0.683 mg), 2-(prop-2-yn-1-yl)pent-4-yn-1-yl 4-hydroxybenzoate (194.7 mg, 0.804 mmol) and DMAP (10.1 mg, 0.083 mmol) in DCM (15 mL) was added dropwise over 5 min a solution of DCC (173.1 mg, 0.839 mmol) in DCM (10 mL) before the resulting mixture was allowed to gradually warm to rt and stirred for 20 h. The resulting precipitate was removed by filtration and the filtrate was concentrated under reduced pressure. Flash chromatography (0-100% EtOAc/petrol gradient elution) gave 2-(prop-2-yn-1-yl)pent-4-yn-1-yl 4-(2-(2-((2,6-dichlorophenyl)amino)pheny)acetoxy)benzoate (317.7 mg, 0.610 mmol, 89%).

Preparation of Example 12: (S)-2-(prop-2-yn-1-yl) pent-4-yn-1-yl 2-((tert-butoxycarbonyl)amino)-3-(4-(2-(2-((2,6-dichlorophenyl)amino)phenyl)acetoxy) phenyl)propanoate Building Block: (S)-2-(prop-2-yn-1-yl)pent-4-yn-1-yl 2-((tert-butoxycarbonyl)amino)-3-(4-hydroxyphenyl)propanoate

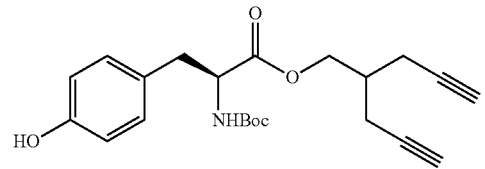 [SMILES: C#CCC(CC#C)COC(=O)[C@H](Cc1ccc(O)cc1)NC(=O)OC(C)(C)C]

NaH (60% disp., 163.1 mg, 4.08 mmol) was added to a cooled (0° C.) solution of N-Boc-(L)-Tyrosine (1.27 g, 4.51 mmol) in DMF (25 mL) and the mixture allowed to warm to rt and stirred for 15 min. A solution of 2-(prop-2-yn-1-yl)pent-4-yn-1-yl methanesulfonate (650.0 mg, 3.25 mmol) in DMF (10 mL) was added via cannula and the mixture was stirred at rt for 46 h. The mixture was heated at 50° C. for 71 h, then 60° C. for 24 h, followed by 70° C. for 48 h, then 80° C. for 23 h before allowing to cool to rt. EtOAc and MeOH were added, followed by sat. aq. NaHCO$_3$. The product was extracted (EtOAc), washed (H$_2$O, then brine), dried (Na$_2$SO$_4$), filtered and concentrated under reduced pressure. Flash chromatography (0-100% EtOAc/hexane gradient elution) gave (S)-2-(prop-2-yn-1-yl)pent-4-yn-1-yl 2-((tert-butoxycarbonyl)amino)-3-(4-hydroxyphenyl) propanoate (921 mg, 2.39 mmol, 74%). (ESI-MS: m/z=384.2 [M−H]$^−$). $^1$H NMR (400 MHz, CDCl$_3$): δ 7.01 (m, 2H), 6.76 (m, 2H), 4.97 (d, J=8.0 Hz, 1H), 4.53 (dd, J=14.0, 6.0 Hz, 1H), 4.19 (dd, J=11.1, 6.0 Hz, 1H), 4.16 (dd, J=11 6.4 Hz, 1H), 3.01 (d, J=6.0 Hz, 1H), 2.30 (m, 4H), 2.08 (m, 1H), 1.97 (t, J=2.6 Hz, 2H), 1.43 (s, 9H). $^{13}$C NMR (100 MHz, CDCl$_3$) δ 172.04, 155.27, 154.96, 130.60, 127.95, 115.68, 80.97, 80.88, 80.25, 70.76, 66.13, 54.77, 37.81, 36.26, 28.45, 19.96, 19.92.

To a cooled (0° C.) solution of diclofenac (301.3 mg, 1.02 mmol), (S)-2-(prop-2-yn-1-yl)pent-4-yn-1-yl 2-((tert-butoxycarbonyl)amino)-3-(4-hydroxyphenyl)propanoate (383.3 mg, 0.994 mmol) and DMAP (14.2 mg, 0.116 mmol) in anhydrous DCM (20 mL) was added dropwise a solution of DCC (291.3 mg, 1.41 mmol) in anhydrous DCM (15 mL) according to the procedure outlined in the preparation of Example 11. Flash chromatography (0-100% EtOAc/hexane gradient elution) gave (S)-2-(prop-2-yn-1-yl)pent-4-yn-1-yl 2-((tert-butoxycarbonyl)amino)-3-(4-(2-(2-((2,6-dichloro-phenyl)amino)phenyl)acetoxy)phenyl)propanoate as a white solid (483.9 mg, 0.73 mmol, 74%).

Preparation of Example 13: (S)-2-(prop-2-yn-1-yl) pent-4-yn-1-yl 2-amino-3-(4-(2-(2-((2,6dichlorophenyl)amino)phenyl)acetoxy)phenyl) propanoate A mixture of (S)-2-(prop-2-yn-1-yl)pent-4-yn-1-yl 2-((tert-butoxycarbonyl)amino)-3-(4-(2-(2-((2,6-dichlorophenyl)amino)phenyl)acetoxy)phenyl)propanoate (480 mg) and 2M HCl in Et$_2$O (15 mL) was stirred at 0° C. for 1.5 h, before allowing to warm to rt and stirring for a further 2 h. The solvent was removed under reduced pressure and EtOAc and sat. aq. NaHCO$_3$ were added to the residue. The product was extracted (EtOAc), washed (brine), dried (Na$_2$SO$_4$), filtered and concentrated under reduced pressure. The crude material was resubjected to stirring in 2M HCl in Et$_2$O for a further 2 h before the solvent was removed under reduced pressure. EtOAc and sat. aq. NaHCO$_3$ were added, the product extracted (EtOAc), washed (brine), dried (Na$_2$SO$_4$), filtered and concentrated under reduced pressure. Flash chromatography (0-30% MeOH/DCM gradient elution) gave (S)-2-(prop-2-yn-1-yl)pent-4-yn-1-yl 2-amino-3-(4-(2-(2-((2,6-dichlorophenyl)amino)phenyl)acetoxy)phenyl)propanoate as a white solid (235.2 mg, 58%).

Preparation of Example 14: 1-((((2-(Prop-2-yn-1-yl) pent-4-yn-1-yl)oxy)carbonyl)oxy)ethyl 2-(2-((2,6-dichlorophenyl)amino)phenyl)acetate Diclofenac sodium salt (322.9 mg, 1.01 mmol) was added to a stirred 0° C. solution of 1-chloroethyl (2-(prop-2-yn-1-yl)pent-4-yn-1-yl) carbonate (404.3 mg, 1.77 mmol) in DMF (10 mL). The reaction was stirred at 0° C. for 1 h before being allowed to warm to rt and stirring for a further 14 days. EtOAc and sat. aq. NaHCO$_3$ were added, the product was extracted (EtOAc), washed (H$_2$O, then brine), dried (Na$_2$SO$_4$), filtered and concentrated under reduced pressure. Flash chromatography (0%-100% EtOAc/petrol gradient elution) gave 1-((((2-(prop-2-yn-1-yl)pent-4-yn-1-yl)oxy)carbonyl)oxy)ethyl 2-(2-((2,6-dichlorophenyl)amino) phenyl)acetate (212.2 mg, 0.435 mmol, 43%).

Preparation of Example 80: 2-(prop-2-yn-1-yl)pent-4-yn-1-yl 2-(2-amino-3-(4-bromobenzoyl)phenyl) acetate Bromfenac (200.5 mg) was dried azeotropically from toluene (188.3 mg bromfenac after drying, 0.564 mmol) before dissolving in DMF (5 mL). The mixture was cooled to 0° C. before NaH (60% disp. in mineral oil, 22.9 mg, 0.573 mmol) was added and the mixture stirred at 0° C. for 30 min. A solution of 2-(prop-2-yn-1-yl)pent-4-yn-1-yl methanesulfonate (408.5 mg, 2.03 mmol) in DMF (5 mL) was added via cannula and the resulting solution was allowed to stir at 0° C. for 30 min before allowing to warm to rt and stirring for an additional 19 h. The mixture was heated to 40° C. and stirred for 49 h, before heating at 50° C. for an additional 71 h. The reaction was allowed to cool to rt. EtOAc and sat. aq. NH$_4$Cl were added, the product extracted (EtOAc), washed (H$_2$O, then brine), dried (Na$_2$SO$_4$), filtered and concentrated under reduced pressure. Flash chromatography (0%-100% EtOAc/petrol gradient elution) gave 2-(prop-2-yn-1-yl)pent-4-yn-1-yl 2-(2-amino-3-(4-bromobenzoyl)phenyl)acetate (71.7 mg, 0.164 mmol, 29%) as a brown oil.

Preparation of Example 86: 3-(((2-(prop-2-yn-1-yl) pent-4-yn-1-yl)oxy)carbonyl)phenyl 5-benzoyl-2,3-dihydro-1H-pyrrolizine-1-carboxylate To a solution of 5-benzoyl-2,3-dihydro-1H-pyrrolizine-1-carboxylic acid (0.3 g, 1.175 mmol), 2-(prop-2-yn-1-yl) pent-4-yn-1-yl 3-hydroxybenzoate (0.312 g, 1.293 mmol) and DHAP (15 mg, 0.117 mmol) in CH$_2$Cl$_2$ (20 mL) was added DCC (0.242 g, 1.175 mmol) in one portion. The reaction was stirred at room temperature for 17 h. The solvent was removed under reduced pressure. The crude was slurried with ethyl acetate and the suspended solids filtered through a plug of silica. The filtrate was concentrated under reduced pressure and the residue purified by flash chromatography (0%-50% EtOAc/petrol gradient elution) to give 3-(((2-(prop-2-yn-1-yl)pent-4-yn-1-yl)oxy)carbonyl)phenyl 5-benzoyl-2,3-dihydro-1H-pyrrolizine-1-carboxylate as amber coloured viscous oil (0.4 g, 71%)

Using the methods described above the monomer bioactive agents in Table 5 and 6 were also prepared.

TABLE 5

Examples of MONOMER-BIOACTIVE AGENT CONJUGATES: FLUOROQUINOLONES

| Ex | Structure/Name | Appearance | $^1$H (CDCl$_3$) unless otherwise stated) δ (ppm) | $^{13}$C (CDCl$_3$) (unless otherwise stated) δ (ppm) | ESI MS ([M + H]+) |
|---|---|---|---|---|---|
| 1 | 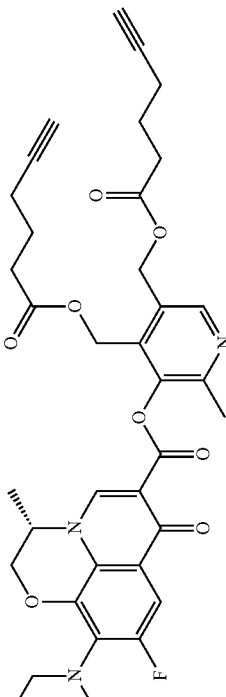<br>(5-((9-fluoro-3-methyl-10-(4-methyl)piperazin-1-yl)-7-oxo-2,3-dihydro-7H-[1,4]oxazino[2,3,4-ij]quinoline-6-carbonyl)oxy)-6-methylpyridine-3,4-diyl)bis(methylene) bis(hex-5-ynoate) | pale yellow solid | δ 8.50 (s, 1H), 8.45 (s, 1H), 7.76 (d, J = 12.4 Hz, 1H), 5.25 (t, J = 13.1 Hz, 4H), 4.45-4.31 (m, 3H), 3.44-3.30 (m, 4H), 2.53 (d, J = 16.4 Hz, 4H), 2.51-2.34 (m, 10H), 2.26 (td, J = 6.9, 2.7 Hz, 2H), 2.17 (td, J = 7.0, 2.6 Hz, 2H), 1.94 (dt, J = 23.0, 2.7 Hz, 2H), 1.84 (tt, J = 17.5, 8.7 Hz, 2H), 1.74 (q, J = 7.2 Hz, 2H), 1.63 (t, J = 6.6 Hz, 3H). | δ 172.83, 172.69, 172.60, 163.62, 157.40, 154.93, 153.77, 147.75, 146.31, 145.06, 139.81, 139.74, 135.88, 132.39, 132.25, 131.48, 129.45, 123.81, 123.78, 123.69, 108.14, 106.55, 83.38, 83.17, 69.51, 69.30, 68.31, 61.48, 57.39, 55.84, 55.21, 50.76, 50.72, 46.55, 32.85, 32.68, 23.55, 23.52, 20.05, 18.32, 17.94, 17.91. | 701.2 |
| 2 | 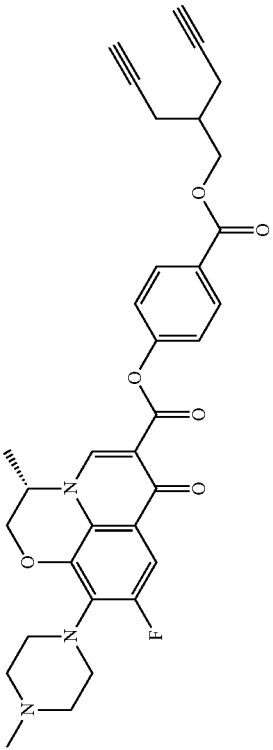<br>4-(((2-(prop-2-yn-1-yl)pent-4-yn-1-yl)oxy)carbonyl)phenyl 9-fluoro-3-methyl-10-(4-methylpiperazin-1-yl)-7-oxo-2,3-dihydro-7H-[1,4]oxazino[2,3,4-ij]quinoline-6-carboxylate | pale yellow solid | δ 8.41 (s, 1H), 8.12-8.04 (m, 2H), 7.64 (d, J = 12.4 Hz, 1H), 7.33-7.27 (m, 2H), 4.46-4.32 (m, 5H), 3.44-3.28 (m, 4H), 2.50 (ddd, J = 14.7, 12.6, 10.0 Hz, 8H), 2.40-2.24 (m, 4H), 2.03 (t, J = 2.6 Hz, 2H), 1.57 (d, J = 6.7 Hz, 3H). | δ 172.85, 172.82, 165.75, 163.64, 157.26, 154.86, 154.80, 146.10, 139.76, 139.69, 132.29, 132.15, 131.23, 127.48, 123.74, 123.50, 123.42, 122.24, 108.35, 106.14, 105.90, 81.00, 70.71, 68.23, 65.90, 55.83, 55.18, 50.67, 46.54, 36.57, 20.16, 18.37 | 586.2 |

TABLE 5-continued

Examples of MONOMER-BIOACTIVE AGENT CONJUGATES: FLUOROQUINOLONES

| Ex | Structure/Name | Appearance | $^1$H (CDCl$_3$) unless otherwise stated) δ (ppm) | $^{13}$C (CDCl$_3$) (unless otherwise stated) δ (ppm) | ESI MS ([M + H]+) |
|---|---|---|---|---|---|
| 3 | 2-((9-fluoro-3-methyl-10-(4-methyl-piperazin-1-yl)-7-oxo-2,3-dihydro-7H-[1,4]oxazino[2,3,4-ij]quinoline-6-carbonyl)oxy)propane-1,3-diyl bis(hex-5-ynoate) | Yellow oil | δ$_H$ 1.55 (d, 3H, J = 8 Hz), 1.83 (m, 4H), 1.93 (m, 2H), 2.25 (m, 4H), 2.37 (s, 3H), 2.52 (m, 4H), 2.56 (s, 4H), 3.35 (dd, 4H, J = 8 Hz), 4.30 (m, 4H), 4.48 (m, 3H), 5.45 (m, 1H), 7.70 (d, 1H, 32 Hz), 8.26 (s, 1H) ppm. | — | — |
| 4 | 2-(prop-2-yn-1-yl)pent-4-yn-1-yl 9-fluoro-3-methyl-10-(4-methylpiperazin-1-yl)-7-oxo-2,3-dihydro-7H-[1,4]oxazino[2,3,4-ij]quinoline-6-carboxylate | yellow solid | (DMSO) δ 8.60 (s, 1H), 7.43 (d, J = 12.7 Hz, 1H), 4.73 (q, J = 6.6 Hz, 1H), 4.50 (dd, J = 11.3, 1.7 Hz, 1H), 4.32 (dd, J = 11.3, 2.1 Hz, 1H), 4.26-4.12 (m, 2H), 3.29-3.15 (m, 4H), 2.90 (t, J = 2.5 Hz, 2H), 2.48-2.35 (m, 8H), 2.22 (s, 3H), 2.18-2.02 (m, 1H), 1.40 (d, J = 6.7 Hz, 3H). | (DMSO) δ 171.43, 171.41, 164.66, 156.33, 153.90, 146.29, 140.33, 140.26, 130.76, 130.62, 123.81, 123.02, 122.94, 108.41, 103.85, 103.61, 81.65, 81.63, 72.78, 68.02, 64.45, 55.27, 53.68, 50.08, 50.04, 46.01, 36.10, 19.22, 17.65. | 465.9 |
| 5 | | white flaky solid | δ 8.63 (s, 1H), 8.44 (s, 1H), 7.83 (dd, J = 11.0, 7.4 Hz, 1H), 5.38-5.12 (m, 4H), 4.90-4.64 (m, 1H), 4.11-3.97 (m, 2H), 3.99-3.89 (m, 1H), 3.91-3.76 (m, 1H), 3.59 (s, 3H), 3.38 (d, J = 19.5 Hz, 1H), 3.22 (d, J = 9.5 Hz, 1H), 2.85 (dd, J = 28.3, 17.7 Hz, 1H), 2.55-2.42 (m, 5H), 2.40 (dd, J = 16.7, 9.3 Hz, 2H), 2.31-2.12 (m, 5H), 2.01-1.86 (m, 2H), 1.89-1.65 (m, 7H), 1.47 (d, J = 3.9 Hz, 11H), 1.34-0.75 (m, 4H). | δ 172.65, 172.62, 172.59, 172.57, 163.36, 155.39, 153.77, 151.78, 151.48, 147.67, 145.12, 141.61, 136.22, 136.11, 135.93, 133.34, 129.34, 122.13, 122.05, 109.13, 108.90, 108.04, 83.32, 83.15, 80.19, 77.48, 77.36, 77.16, 76.84, 69.48, 69.26, 61.51, 60.99, 57.47, 56.41, 56.33, 52.58, 48.62, 40.00, 39.51, 35.73, 32.84, 32.64, 28.57, 25.49, 24.30, 23.54, 23.49, 20.01, 17.92, 17.88, 10.51, 8.56. | 841.4 |

TABLE 5-continued

Examples of MONOMER-BIOACTIVE AGENT CONJUGATES: FLUOROQUINOLONES

| Ex | Structure/Name | Appearance | $^1$H (CDCl$_3$) unless otherwise stated) δ (ppm) | $^{13}$C (CDCl$_3$) (unless otherwise stated) δ (ppm) | ESI MS ([M + H]+) |
|---|---|---|---|---|---|
| 6 | (5-((7-(1-(tert-butoxycarbonyl)octahydro-6H-pyrrolo[3,4-b]pyridin-6-yl)-1-cyclopropyl-6-fluoro-8-methoxy-4-oxo-1,4-dihydroquinoline-3-carbonyl)oxy)-6-methylpyridine-3,4-diyl)bis(methylene) bis(hex-5-ynoate) | pale yellow solid | δ 8.73 (s, 1H), 8.46 (s, 1H), 7.74 (d, J = 14.0 Hz, 1H), 5.26 (d, J = 27.5 Hz, 4H), 4.07-3.77 (m, 5H), 3.71 (t, J = 8.8 Hz, 1H), 3.31 (d, J = 12.7 Hz, 1H), 2.96 (t, J = 10.0 Hz, 1H), 2.67 (d, J = 4.3 Hz, 1H), 2.52-2.44 (m, 5H), 2.40 (t, J = 7.4 Hz, 2H), 2.32-2.13 (m, 4H), 2.01-1.70 (m, 10H), 1.30-0.77 (m, 4H). | δ 172.75, 172.72, 172.68, 172.57, 162.88, 162.60, 162.25, 153.55, 151.73, 147.58, 144.93, 136.09, 135.40, 135.29, 133.40, 129.64, 109.01, 108.74, 107.80, 83.28, 83.18, 69.52, 69.36, 61.73, 61.44, 57.36, 54.98, 53.75, 52.70, 42.25, 40.04, 35.02, 32.85, 32.66, 23.56, 23.51, 21.82, 19.92, 18.31, 17.94, 17.89, 9.89, 9.15. | 741 |
| | 6-(3-(((4,5-bis((hex-5-ynoyloxy)methyl)-2-methylpyridin-3-yl)oxy)carbonyl)-1-cyclopropyl-6-fluoro-8-methoxy-4-oxo-1,4-dihydroquinolin-7-yl)octahydro-1H-pyrrolo[3,4-b]pyridin-1-ium 2,2,2-trifluoroacetate | | | | |
| 7 | 4-(((2-(prop-2-yn-1-yl)pent-4-yn-1-yl)oxy)carbonyl)phenyl 7-(1-(tert-butoxycarbonyl)octahydro-6H-pyrrolo[3,4-b]pyridin-6-yl)-1-cyclopropyl-6-fluoro-8-methoxy-4-oxo-1,4-dihydroquinoline-3-carboxylate | white flaky solid | δ 8.73 (s, J = 17.7 Hz, 1H), 8.15-8.03 (m, 2H), 7.86 (d, J = 14.0 Hz, 1H), 7.32 (d, J = 8.7 Hz, 2H), 4.78 (s, J = 51.2 Hz, 1H), 4.41 (d, J = 6.1 Hz, 2H), 4.12-4.00 (m, 2H), 4.01-3.93 (m, 1H), 3.85 (td, J = 9.9, 2.0 Hz, 1H), 3.59 (s, J = 11.7 Hz, 3H), 3.37 (t, J = 14.0 Hz, 1H), 3.23 (d, J = 9.2 Hz, 1H), 2.88 (t, J = 11.3 Hz, 1H), 2.49 (dd, J = 6.5, 2.6 Hz, 4H), 2.27 (ddd, J = 14.2, 12.1, 6.1 Hz, 3H), 2.04 (d, J = 2.5 Hz, 2H), 1.87-1.65 (m, 2H), 1.48 (s, J = 8.6 Hz, 11H), 1.32-1.19 (m, 2H), 1.18-0.98 (m, 2H), 0.90-0.75 (m, 1H). | δ 172.53, 172.50, 165.69, 163.67, 155.29, 154.80, 151.45, 141.38, 136.32, 136.21, 133.35, 131.08, 127.32, 122.20, 121.64, 121.56, 108.97, 108.73, 108.13, 80.90, 80.12, 77.36, 77.24, 77.04, 76.72, 70.57, 65.76, 60.96, 56.36, 56.29, 52.54, 48.54, 40.02, 39.26, 36.47, 35.60, 28.46, 25.36, 24.19, 20.04, 10.48, 8.46. | 726 |

TABLE 5-continued

Examples of MONOMER-BIOACTIVE AGENT CONJUGATES: FLUOROQUINOLONES

| Ex | Structure/Name | Appearance | $^1$H (CDCl$_3$) unless otherwise stated) δ (ppm) | $^{13}$C (CDCl$_3$) (unless otherwise stated) δ (ppm) | ESI MS ([M + H]+) |
|---|---|---|---|---|---|
| 8 | 6-(1-cyclopropyl-6-fluoro-8-methoxy-4-oxo-3-((4-(((2-(prop-2-yn-1-yl)pent-4-yn-1-yl)oxy)carbonyl)phenoxy)carbonyl)-1,4-dihydroquinolin-7-yl)octahydro-1H-pyrrolo[3,4-b]pyridin-1-ium 2,2,2-trifluoroacetate | pale yellow solid | δ 8.72 (s, 1H), 8.14-8.02 (m, 2H), 7.41-7.22 (m, 3H), 4.42 (d, J = 6.1 Hz, 2H), 4.02 (dd, J = 18.6, 6.0 Hz, 2H), 3.94-3.83 (m, 2H), 3.75 (t, J = 9.9 Hz, 1H), 3.61 (t, J = 7.8 Hz, 1H), 3.55 (s, 3H), 3.46-3.35 (m, 1H), 2.99 (t, J = 10.5 Hz, 1H), 2.64 (d, J = 3.9 Hz, 1H), 2.49 (dd, J = 6.5, 2.6 Hz, 4H), 2.42-2.24 (m, 1H), 2.03 (dt, J = 10.0, 2.9 Hz, 2H), 1.99-1.65 (m, 4H), 1.29-1.19 (m, 1H), 1.16-0.96 (m, 1H), 0.87-0.75 (m, 1H), 0.12-0.01 (m, 1H). | δ 173.31, 165.77, 162.51, 154.60, 151.64, 141.04, 135.60, 133.23, 131.27, 127.60, 122.22, 121.52, 121.43, 108.39, 107.67, 81.04, 70.72, 65.94, 61.35, 55.03, 54.35, 52.31, 42.64, 40.14, 36.60, 35.22, 21.63, 20.18, 18.15, 10.11, 8.99. | 626 |
| 9 | 1-(((2-(Prop-2-yn-1-yl)pent-4-yn-1-yl)oxy)carbonyl)oxy)ethyl (3S)-9-fluoro-3-methyl-10-(4-methylpiperazin-1-yl)-7-oxo-2,3-dihydro-7H-[1,4]oxazino[2,3,4-ij]quinoline-6-carboxylate | clear colourless oil | δ 8.17 (d, J = 9.3 Hz, 1H), 7.36 (dd, J = 21.7, 12.5 Hz, 1H), 6.97 (q, J = 5.5 Hz, 1H), 4.65-4.44 (m, 1H), 4.40-4.17 (m, 4H), 3.43-3.27 (m, 4H), 2.66-2.48 (m, 4H), 2.44-2.37 (m, 4H), 2.36 (s, 3H), 2.25-2.13 (m, 1H), 2.05-1.97 (m, 2H), 1.64 (dd, J = 5.4, 3.9 Hz, 3H), 1.54-1.45 (m, 3H). | δ 172.67, 172.64, 172.44, 172.42, 163.43, 162.59, 157.09 (d, J($^{13}$C-$^{19}$F) = 10.5 Hz), 154.63 (d, J($^{13}$C-$^{19}$F) = 10.4 Hz), 153.06 (d, J($^{13}$C-$^{19}$F) = 16.3 Hz), 145.76 (d, J($^{13}$C-$^{19}$F) = 42.3 Hz), 139.76, 139.70, 132.00, 131.96, 131.85, 131.82, 123.54, 123.49, 123.18, 123.09, 105.40 (d, J($^{13}$C-$^{19}$F) = 14.0 Hz), 91.91 (d, J($^{13}$C-$^{19}$F) = 15.1 Hz), 70.84, 70.81, 70.76, 68.99, 68.95, 68.13, 55.72, 54.91, 50.52, 50.48, 46.38, 36.35, 19.87, 19.85, 19.83, 19.80, 19.78, 18.50. | 554 |
| 44 | | White flaky solid | δ 8.68 (s, 1H), 8.46 (s, 1H), 7.90-7.79 (m, 1H), 5.39-5.14 (m, 4H), 4.79 (s, 1H), 4.07-3.83 (m, 5H), 3.60 (s, 3H), 3.40 (d, J = 17.5 Hz, 1H), 3.23 (d, J = 9.3 Hz, 1H), 2.87 (d, J = 10.7 Hz, 1H), 2.51 (d, J = 19.5 Hz, 3H), 2.42-2.09 (m, 8H), 1.97 (t, J = 2.6 Hz, 1H), 1.91-1.85 (m, 1H), 1.77-1.44 (m, 17H), 1.35-1.22 (m, 1H), 1.20-1.09 (m, 1H), 1.10-0.98 (m, 1H), 0.93-0.80 (m, 1H). | | |

TABLE 5-continued

Examples of MONOMER-BIOACTIVE AGENT CONJUGATES: FLUOROQUINOLONES

| Ex | Structure/Name | Appearance | $^1$H (CDCl$_3$) unless otherwise stated) δ (ppm) | $^{13}$C (CDCl$_3$) (unless otherwise stated) δ (ppm) | ESI MS ([M + H]+) |
|---|---|---|---|---|---|
| 45 | (5-((7-(1-(tert-butoxycarbonyl)octahydro-6H-pyrrolo[3,4-b]pyridin-6-yl)-1-cyclopropyl-6-fluoro-8-methoxy-4-oxo-1,4-dihydroquinoline-3-carbonyl)oxy)-6-methylpyridine-3,4-diyl)bis(methylene) bis(hept-6-ynoate) | Pale yellow flaky solid | (DMSO) δ 8.75 (s, 1H), 8.45 (s, 1H), 7.62 (d, J = 14.3 Hz, 1H), 5.20 (d, J = 54.8 Hz, 4H), 4.13-3.94 (m, 2H), 3.88 (s, J = 16.9 Hz, 1H), 3.79 (dt, J = 9.5, 4.7 Hz, 1H), 3.70 (t, J = 7.9 Hz, 1H), 3.60 (s, 3H), 3.54-3.45 (m, 1H), 3.32 (s, 1H), 3.23 (d, J = 12.9 Hz, 1H), 2.97 (t, J = 10.0 Hz, 1H), 2.75 (t, J = 2.6 Hz, 1H), 2.71-2.58 (m, 2H), 2.41-2.31 (m, 5H), 2.21 (dd, J = 15.1, 7.8 Hz, 2H), 2.16 (td, J = 7.0, 2.7 Hz, 2H), 2.03 (td, J = 7.0, 2.6 Hz, 2H), 1.89-1.66 (m, 4H), 1.61 (dt, J = 15.4, 7.5 Hz, 2H), 1.44 (dt, J = 9.7, 7.3 Hz, 4H), 1.38-1.26 (m, 2H), 1.21-1.14 (m, 1H), 1.12-0.95 (m, 2H), 0.87 (s, 1H). | — | — |
| 46 | 6-(3-(((4,5-bis((hept-6-ynoyloxy)methyl)-2-methylpyridin-3-yl)oxy)carbonyl)-1-cyclopropyl-6-fluoro-8-methoxy-4-oxo-1,4-dihydroquinolin-7-yl)octahydro-1H-pyrrolo[3,4-b]pyridin-1-ium 2,2,2-trifluoroacetate | white crystalline solid | δ 8.67 (s, 1H), 8.48 (s, 1H), 7.84 (d, J = 14.1 Hz, 1H), 5.37-5.30 (m, 4H), 4.78 (s, 1H), 4.32-4.03 (m, 8H), 3.94 (m, 1H), 3.84 (td, J = 9.6, 1.8 Hz, 1H), 3.60 (q, 3H), 3.37 (m, 1H), 3.23 (d, J = 9.4 Hz, 1H), 2.88 (t, J = 11.5 Hz, 1H), 2.50 (s, 3H), 2.44 (t, J = 2.4 Hz, 1H), 2.39 (t, J = 2.4 Hz, 1H), 2.25 (m, 1H), 1.83-1.75 (m, 2H), 1.52-1.44 (m, 1H), 1.42 (d, J = 6.9 Hz, 3H), 1.35 (d, J = 6.9 Hz, 3H), 1.28 (m, 1H), 1.14 (m, 1H), 1.05 (m, 1H), 0.86 (m, 1H). | δ 172.6, 172.3, 172.2, 163.6, 155.4, 154.1, 151.6, 147.7, 145.3, 141.9, 136.3, 132.2, 135.5, 133.4, 129.0, 122.3, 122.2, 109.2, 108.9, 108.1, 80.2, 79.2, 78.9, 75.5, 75.1, 73.3, 73.1, 61.9, 61.1, 57.9, 57.43, 57.38, 56.5, 56.4, 52.7, 48.7, 40.0, 39.5, 35.8, 28.6, 25.6, 24.3, 20.1, 18.6, 18.5, 10.5, 8.6. | — |
| | (5-((7-(1-(tert-butoxycarbonyl)octahydro-6H-pyrrolo[3,4-b]pyridin-6-yl)-1-cyclopropyl-6-fluoro-8-methoxy-4-oxo-1,4-dihydroquinoline-3-carbonyl)oxy)-6-methylpyridine-3,4-diyl)bis(methylene) bis(2-(prop-2-yn-1-yloxy)propanoate) | | | | |

TABLE 5-continued

Examples of MONOMER-BIOACTIVE AGENT CONJUGATES: FLUOROQUINOLONES

| Ex | Structure/Name | Appearance | $^1$H (CDCl$_3$) unless otherwise stated) δ (ppm) | $^{13}$C (CDCl$_3$) (unless otherwise stated) δ (ppm) | ESI MS ([M + H]+) |
|---|---|---|---|---|---|
| 47 | 6-(1-cyclopropyl-6-fluoro-8-methoxy-3-(((2-methyl-4,5-bis(((2-(prop-2-yn-1-yloxy)propanoyl)oxy)methyl)pyridin-3-yl)oxy)carbonyl)-4-oxo-1,4-dihydroquinolin-7-yl)octahydro-1H-pyrrolo[3,4-b]pyridin-1-ium 2,2,2-trifluoroacetate | — | δ 10.48 (s, 1H), 9.30 (s, 1H), 8.71 (s, 1H), 8.48 (s, 1H), 7.75 (d, J = 10.3 Hz, 1H), 5.37 (s, 2H), 5.32 (s, 2H), 4.32-4.05 (m, 8H), 4.00-3.81 (m, 4H), 3.72 (m, 2H), 3.62 (s, 3H), 3.33 (m, 1H), 2.98 (t, J = 10.3 Hz, 1H), 2.66 (m, 1H), 2.48 (s, 3H), 2.44 (t, J = 2.4 Hz, 1H), 2.42 (t, J = 2.4 Hz, 1H), 2.02 (m, 1H), 1.84 (m, 1H), 1.42 (d, J = 6.9 Hz, 3H), 1.34 (d, J = 6.9 Hz, 3H), 1.21-1.03 (m, 3H), 0.95 (m, 1H). | δ 172.6, 172.3, 172.2, 163.2, 154.7, 154.0, 152.3, 151.8, 147.7, 145.1, 142.0, 141.9, 135.5, 135.4, 135.3, 133.4, 129.1, 122.7, 109.1, 108.9, 108.0, 79.1, 78.9, 75.5, 75.3, 73.3, 73.1, 62.0, 61.8, 57.8, 57.40, 57.38, 54.8, 53.5, 53.4, 53.2, 42.1, 40.0, 35.0, 21.9, 20.0, 18.6, 18.5, 9.9, 9.2. | — |
| 48 | 1-((((2-(prop-2-yn-1-yl)pent-4-yn-1-yl)oxy)carbonyl)oxy)ethyl 7-(1-(tert-butoxycarbonyl)octahydro-6H-pyrrolo[3,4-b]pyridin-6-yl)-1-cyclopropyl-6-fluoro-8-methoxy-4-oxo-1,4-dihydroquinoline-3-carboxylate | Flaky yellow solid | DMSO δ 8.45 (s, 1H), 7.54 (dd, J = 14.1, 0.5 Hz, 1H), 6.88-6.72 (m, 1H), 4.66 (d, J = 7.1 Hz, 1H), 4.23-4.09 (m, 2H), 4.06-3.93 (m, 2H), 3.89 (d, J = 12.5 Hz, 1H), 3.74 (t, J = 9.7 Hz, 1H), 3.57 (d, J = 0.8 Hz, 3H), 3.31-3.22 (m, 1H), 3.20 (d, J = 10.1 Hz, 1H), 2.97-2.76 (m, 3H), 2.30 (dt, J = 24.8, 11.4 Hz, 4H), 2.28-2.11 (m, 1H), 2.11-1.98 (m, 1H), 1.81-1.62 (m, 2H), 1.55 (t, J = 6.7 Hz, 3H), 1.41 (s, 9H), 1.23-1.07 (m, 1H), 1.04 (tdd, J = 24.3, 10.9, 7.4 Hz, 1H), 1.00-0.71 (m, 2H). | | |

TABLE 5-continued

Examples of MONOMER-BIOACTIVE AGENT CONJUGATES: FLUOROQUINOLONES

| Ex | Structure/Name | Appearance | $^1$H (CDCl$_3$) unless otherwise stated) δ (ppm) | $^{13}$C (CDCl$_3$) (unless otherwise stated) δ (ppm) | ESI MS ([M + H]+) |
|---|---|---|---|---|---|
| 49 | 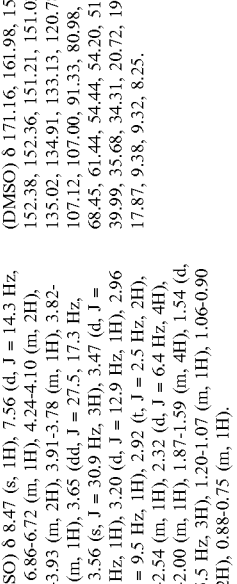<br>6-(1-cyclopropyl-6-fluoro-8-methoxy-4-oxo-3-((1-(((2-(prop-2-yn-1-yl)pent-4-yn-1-yl)oxy)carbonyl)oxy)ethoxy)carbonyl)-1,4-dihydroquinolin-7-yl)octahydro-1H-pyrrolo[3,4-b]pyridin-1-ium 2,2,2-trifluoroacetate | Off white solid | (DMSO) δ 8.47 (s, 1H), 7.56 (d, J = 14.3 Hz, 1H), 6.86-6.72 (m, 1H), 4.24-4.10 (m, 2H), 4.08-3.93 (m, 2H), 3.91-3.78 (m, 1H), 3.82-3.68 (m, 1H), 3.65 (dd, J = 27.5, 17.3 Hz, 1H), 3.56 (s, J = 30.9 Hz, 3H), 3.47 (d, J = 10.4 Hz, 1H), 3.20 (d, J = 12.9 Hz, 1H), 2.96 (d, J = 9.5 Hz, 1H), 2.92 (t, J = 2.5 Hz, 2H), 2.69-2.54 (m, 1H), 2.32 (d, J = 6.4 Hz, 4H), 2.14-2.00 (m, 1H), 1.87-1.59 (m, 4H), 1.54 (d, J = 5.5 Hz, 3H), 1.20-1.07 (m, 1H), 1.06-0.90 (m, 2H), 0.88-0.75 (m, 1H). | (DMSO) δ 171.16, 161.98, 153.49, 152.38, 152.36, 151.21, 151.02, 141.02, 135.02, 134.91, 133.13, 120.78, 107.23, 107.12, 107.00, 91.33, 80.98, 73.01, 68.45, 61.44, 54.44, 54.20, 51.47, 41.88, 39.99, 35.68, 34.31, 20.72, 19.42, 18.98, 17.87, 9.38, 9.32, 8.25. | 593.9 |
| 50 | 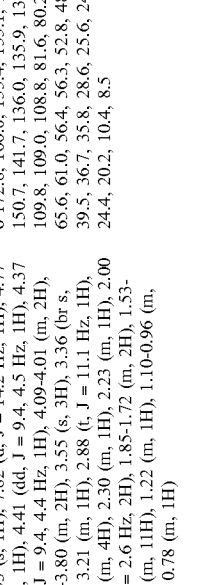<br>2-(prop-2-yn-1-yl)pent-4-yn-1-yl 7-(1-(tert-butoxycarbonyl)octahydro-6H-pyrrolo[3,4-b]pyridin-6-yl)-1-cyclopropyl-6-fluoro-8-methoxy-4-oxo-1,4-dihydroquinoline-3-carboxylate | white crystalline solid | δ 8.53 (s, 1H), 7.82 (d, J = 14.2 Hz, 1H), 4.77 (br s, 1H), 4.41 (dd, J = 9.4, 4.5 Hz, 1H), 4.37 (dd, J = 9.4, 4.4 Hz, 1H), 4.09-4.01 (m, 2H), 3.90-3.80 (m, 2H), 3.55 (s, 3H), 3.36 (br s, 1H), 3.21 (m, 1H), 2.88 (t, J = 11.1 Hz, 1H), 2.53 (m, 4H), 2.30 (m, 1H), 2.23 (m, 1H), 2.00 (t, J = 2.6 Hz, 2H), 1.85-1.72 (m, 2H), 1.53-1.42 (m, 1H), 1.22 (m, 1H), 1.10-0.96 (m, 2H), 0.78 (m, 1H) | δ 172.8, 166.0, 155.4, 155.1, 152.6, 150.7, 141.7, 136.0, 135.9, 133.5, 122.4, 109.8, 109.0, 108.8, 81.6, 80.2, 70.3, 65.6, 61.0, 56.4, 56.3, 52.8, 48.6, 39.6, 39.5, 36.7, 35.8, 28.6, 25.6, 24.4, 20.2, 24.4, 20.2, 10.4, 8.5 | — |
| 51 | 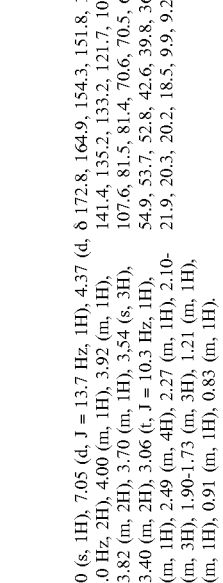<br>6-(1-cyclopropyl-6-fluoro-8-methoxy-4- | — | δ 8.50 (s, 1H), 7.05 (d, J = 13.7 Hz, 1H), 4.37 (d, J = 6.0 Hz, 2H), 4.00 (m, 1H), 3.92 (m, 1H), 3.88-3.82 (m, 2H), 3.70 (m, 1H), 3.54 (s, 3H), 3.53-3.40 (m, 2H), 3.06 (t, J = 10.3 Hz, 1H), 2.61 (m, 1H), 2.49 (m, 4H), 2.27 (m, 1H), 2.10-1.99 (m, 3H), 1.90-1.73 (m, 3H), 1.21 (m, 1H), 1.09 (m, 1H), 0.91 (m, 1H), 0.83 (m, 1H). | δ 172.8, 164.9, 154.3, 151.8, 150.5, 141.4, 135.2, 133.2, 121.7, 108.8, 107.9, 107.6, 81.5, 81.4, 70.6, 70.5, 65.6, 61.5, 54.9, 53.7, 52.8, 42.6, 39.8, 36.6, 35.3, 21.9, 20.3, 20.2, 18.5, 9.9, 9.2. | — |

TABLE 5-continued

Examples of MONOMER-BIOACTIVE AGENT CONJUGATES: FLUOROQUINOLONES

| Ex | Structure/Name | Appearance | ¹H (CDCl₃) unless otherwise stated) δ (ppm) | ¹³C (CDCl₃) (unless otherwise stated) δ (ppm) | ESI MS ([M + H]+) |
|---|---|---|---|---|---|
| 52 | oxo-3-(((2-(prop-2-yn-1-yl)pent-4-yn-1-yl)oxy)carbonyl)-1,4-dihydroquinolin-7-yl)octahydro-1H-pyrrolo[3,4-b]pyridin-1-ium 2,2,2-trifluoroacetate | White solid | (DMSO) δ 8.88 (s, 1H), 8.17-8.02 (m, 2H), 7.88 (d, J = 11.0 Hz, 1H), 7.47-7.32 (m, 2H), 6.66 (d, J = 7.7 Hz, 1H), 4.31 (dd, J = 10.6, 4.9 Hz, 3H), 3.55 (s, 1H), 3.40-3.23 (m, 2H), 3.23 (dd, J = 18.4, 5.3 Hz, 2H), 2.93 (t, J = 2.6 Hz, 2H), 2.44 (dd, J = 6.6, 2.6 Hz, 4H), 2.29-2.11 (m, 1H), 1.95-1.59 (m, 5H), 1.61-1.44 (m, 1H), 1.30 (s, J = 23.0 Hz, 9H), 1.24-0.90 (m, 4H). | — | — |
| 53 | 4-(((2-(prop-2-yn-1-yl)pent-4-yn-1-yl)oxy)carbonyl)phenyl (R)-7-(3-((tert-butoxycarbonyl)amino)azepan-1-yl)-8-chloro-1-cyclopropyl-6-fluoro-4-oxo-1,4-dihydroquinoline-3-carboxylate | White solid | (DMSO) δ 8.90 (s, 1H), 8.16-8.04 (m, 2H), 7.92 (d, J = 10.7 Hz, 4H), 7.46-7.30 (m, 2H), 4.43-4.19 (m, 3H), 3.69-3.34 (m, 3H), 3.37-3.05 (m, 2H), 2.93 (t, J = 2.6 Hz, 2H), 2.44 (dd, J = 6.5, 2.5 Hz, 4H), 2.29-2.14 (m, 1H), 2.14-1.98 (m, 1H), 1.87 (dd, J = 29.8, 25.8 Hz, 2H), 1.81-1.53 (m, 3H), 1.31-0.89 (m, 4H). | (DMSO) δ 171.11, 164.91, 161.53, 158.20, 155.73, 154.39, 154.00, 143.61, 143.46, 136.55, 130.88, 127.51, 127.44, 126.89, 123.49, 122.41, 111.30, 111.07, 108.18, 81.36, 72.90, 65.50, 54.86, 53.65, 51.78, 40.55, 35.85, 32.27, 28.22, 21.50, 19.36, 10.98, 10.53. | 617.9 |

TABLE 5-continued

Examples of MONOMER-BIOACTIVE AGENT CONJUGATES: FLUOROQUINOLONES

| Ex | Structure/Name | Appearance | $^1$H (CDCl$_3$) unless otherwise stated) δ (ppm) | $^{13}$C (CDCl$_3$) (unless otherwise stated) δ (ppm) | ESI MS ([M + H]+) |
|---|---|---|---|---|---|
| 54 | (R)-1-(8-chloro-1-cyclopropyl-6-fluoro-4-oxo-3-((4-(((2-(prop-2-yn-1-yl)pent-4-yn-1-yl)oxy)carbonyl)phenoxy)carbonyl)-1,4-dihydroquinolin-7-yl)azepan-3-aminium 2,2,2-trifluoroacetate | White flaky solid | δ 8.83 (s, 1H), 8.47 (s, 1H), 8.11 (d, J = 10.7 Hz, 1H), 5.43-5.13 (m, 5H), 4.36-4.20 (m, 1H), 3.86 (s, J = 40.2 Hz, 1H), 3.62 (d, J = 14.4 Hz, 1H), 3.19 (t, J = 8.0 Hz, 3H), 2.53-2.46 (m, 5H), 2.40 (t, J = 7.4 Hz, 2H), 2.26 (td, J = 6.9, 2.6 Hz, 2H), 2.19 (td, J = 7.0, 2.6 Hz, 2H), 2.04-1.90 (m, 3H), 1.90-1.69 (m, 9H), 1.36 (s, 9H), 1.33-1.18 (m, 2H), 1.11-0.95 (m, 2H). | δ 172.60, 172.47, 172.20, 162.70, 159.71, 157.21, 155.23, 153.55, 153.42, 145.16, 136.70, 129.82, 113.07, 112.83, 109.09, 83.28, 83.13, 79.11, 77.36, 69.50, 69.29, 61.35, 57.26, 53.75, 50.47, 40.72, 35.67, 32.86, 32.67, 29.31, 28.51, 23.58, 23.56, 22.02, 19.69, 17.94, 17.91, 11.66, 11.30. | — |
| 55 | (R)-(5-((7-(3-((tert-butoxycarbonyl)amino)azepan-1-yl)-8-chloro-1-cyclopropyl-6-fluoro-4-oxo-1,4-dihydroquinoline-3-carbonyl)oxy)-6-methylpyridine-3,4-diyl)bis(methylene) bis(hex-5-ynoate)<br><br>CF$_3$COO$^-$ (R)-1-(3-(((4,5-bis((hex-5-ynoyloxy)methyl)-2-methylpyridin-3-yl)oxy) | White solid | (DMSO) δ 8.95 (s, 1H), 8.47 (s, 1H), 7.94 (d, J = 10.8 Hz, 1H), 7.86 (s, 3H), 5.28 (s, J = 31.8 Hz, 2H), 5.15 (s, 2H), 4.38-4.24 (m, 1H), 3.57-3.11 (m, 5H), 2.79 (t, J = 2.6 Hz, 1H), 2.71 (t, J = 2.6 Hz, 1H), 2.44 (t, J = 7.4 Hz, 2H), 2.37 (s, 3H), 2.29 (t, J = 7.4 Hz, 2H), 2.19 (td, J = 7.1, 2.6 Hz, 2H), 2.08 (td, J = 7.1, 2.6 Hz, 3H), 1.98-1.56 (m, 9H), 1.29-1.11 (m, 2H), 1.09-0.90 (m, 2H). | (DMSO) δ 172.03, 171.87, 171.15, 161.25, 158.27, 155.79, 154.06, 152.54, 147.39, 144.27, 143.67, 143.52, 136.57, 135.66, 129.58, 127.59, 127.52, 123.61, 111.36, 111.13, 107.71, 83.50, 83.43, 71.65, 71.43, 60.92, 56.91, 54.90, 53.69, 51.77, 40.58, 32.27, 32.21, 31.97, 28.23, 23.33, 23.26, 21.50, 19.31, 17.04, 16.96, 10.96, 10.51. | 732.9 |

TABLE 5-continued

Examples of MONOMER-BIOACTIVE AGENT CONJUGATES: FLUOROQUINOLONES

| Ex | Structure/Name | Appearance | ¹H (CDCl₃) unless otherwise stated) δ (ppm) | ¹³C (CDCl₃) (unless otherwise stated) δ (ppm) | ESI MS ([M + H]+) |
|---|---|---|---|---|---|
| | carbonyl)-8-chloro-1-cyclopropyl-6-fluoro-4-oxo-1,4-dihydroquinolin-7-yl) azepan-3-aminium 2,2,2-trifluoroacetate | | | | — |
| 56 | 4-(((2-(prop-2-yn-1-yl)pent-4-yn-1-yl)oxy)carbonyl)phenyl 7-(4-(tert-butoxycarbonyl)-3-methylpiperazin-1-yl)-1-cyclopropyl-6-fluoro-8-methoxy-4-oxo-1,4-dihydroquinoline-3-carboxylate | White flaky solid | δ 8.71 (s, 1H), 8.12-8.05 (m, 1H), 7.91 (d, J = 12.4 Hz, 1H), 7.34-7.28 (m, 1H), 4.41 (d, J = 6.1 Hz, 2H), 4.36 (dd, J = 11.3, 4.3 Hz, 1H), 4.01-3.89 (m, 2H), 3.75 (s, J = 7.8 Hz, 3H), 3.44-3.17 (m, 5H), 2.55-2.42 (m, 4H), 2.37-2.23 (m, 1H), 2.03 (t, J = 2.6 Hz, 2H), 1.50 (s, 9H), 1.34 (d, J = 6.7 Hz, 3H), 1.23-1.15 (m, 2H), 1.03-0.91 (m, 2H). | δ 172.69, 165.79, 163.52, 157.47, 154.98, 154.95, 154.90, 151.63, 145.89, 145.84, 139.25, 139.14, 133.11, 131.21, 127.54, 125.42, 125.34, 122.26, 109.47, 109.24, 108.70, 81.04, 80.03, 70.67, 65.93, 63.23, 55.55, 55.51, 51.15, 51.11, 47.55, 39.89, 39.52, 36.67, 28.61, 20.21, 15.66, 9.67, 9.51. | |
| 57 | 4-(1-cyclopropyl-6-fluoro-8-methoxy-4-oxo-3-((4-(((2-(prop-2-yn-1-yl)pent-4-yn-1-yl)oxy)carbonyl)phenoxy)carbonyl)-1,4-dihydroquinolin-7-yl)-2-methyl-piperazin-1-ium 2,2,2-trifluoroacetate | Pale yellow solid | (DMSO) δ 9.22 (s, 1H), 8.84 (s, J = 30.9 Hz, 1H), 8.75 (s, J = 8.6 Hz, 1H), 8.09 (d, J = 8.7 Hz, 2H), 7.70 (d, J = 12.1 Hz, 1H), 7.37 (d, J = 8.7 Hz, 2H), 4.33 (d, J = 5.9 Hz, 2H), 4.20-3.97 (m, 1H), 3.82 (s, J = 9.6 Hz, 3H), 3.38 (ddd, J = 78.3, 24.6, 12.2 Hz, 8H), 2.93 (t, J = 2.5 Hz, 2H), 2.44 (dd, J = 6.5, 2.5 Hz, 4H), 2.30-2.09 m, 1H), 1.27 (d, J = 6.3 Hz, 3H), 1.17-0.93 (m, 4H). | (DMSO) δ 171.33, 164.93, 161.88, 156.62, 154.52, 154.15, 152.01, 146.67, 146.63, 136.72, 136.60, 132.74, 130.85, 126.80, 125.22, 125.14, 122.44, 107.37, 107.14, 81.36, 72.90, 65.49, 62.95, 53.42, 51.07, 46.75, 43.24, 39.10, 35.85, 19.35, 15.43, 8.90, 8.81. | |

TABLE 5-continued

Examples of MONOMER-BIOACTIVE AGENT CONJUGATES: FLUOROQUINOLONES

| Ex | Structure/Name | Appearance | $^1$H (CDCl$_3$) unless otherwise stated) δ (ppm) | $^{13}$C (CDCl$_3$) (unless otherwise stated) δ (ppm) | ESI MS ([M + H]+) |
|---|---|---|---|---|---|
| 58 | (5-((7-(4-(tert-butoxycarbonyl)-3-methylpiperazin-1-yl)-1-cyclopropyl-6-fluoro-8-methoxy-4-oxo-1,4-dihydroquinoline-3-carbonyl)oxy)-6-methylpyridine-3,4-diyl)bis(methylene) bis(hex-5-ynoate) | White flaky solid | δ 8.72 (s, 1H), 8.45 (s, 1H), 7.92 (d, J = 12.4 Hz, 1H), 5.26 (d, J = 22.4 Hz, 4H), 4.36 (d, J = 7.0 Hz, 1H), 3.97 (td, J = 7.3, 3.7 Hz, 2H), 3.76 (s, 3H), 3.51-3.35 (m, 2H), 3.37-3.18 (m, 3H), 2.57-2.33 (m, 7H), 2.22 (dtd, J = 30.5, 6.9, 2.6 Hz, 4H), 1.94 (dt, J = 22.9, 2.6 Hz, 2H), 1.89-1.70 (m, 4H), 1.50 (s, J = 2.9 Hz, 9H), 1.34 (d, J = 6.7 Hz, 3H), 1.19 (dd, J = 7.2, 1.7 Hz, 2H), 1.07-0.92 (m, 2H). | δ 172.60, 172.51, 163.19, 157.52, 155.04, 154.90, 153.25, 151.74, 145.98, 145.93, 145.41, 139.28, 139.16, 133.11, 130.06, 125.52, 125.44, 109.53, 109.30, 108.15, 80.04, 69.53, 69.29, 63.24, 61.31, 57.38, 55.56, 55.52, 51.13, 51.09, 47.55, 39.94, 39.51, 32.85, 32.67, 28.61, 23.59, 23.55, 19.48, 17.95, 17.92, 15.66, 9.66, 9.51. | 815.3 |
| 59 | 4-(3-(((4,5-bis((hex-5-ynoyloxy)methyl)-2-methyl pyridin-3-yl)oxy)carbonyl)-1-cyclopropyl-6-fluoro-8-methoxy-4-oxo-1,4-dihydroquinolin-7-yl)-2-methylpiperazin-1-ium 2,2,2-trifluoroacetate | Pale yellow solid | (DMSO) δ 9.20 (s, 1H), 8.83 (s, J = 14.0 Hz, 1H), 8.79 (s, 1H), 8.47 (s, J = 11.1 Hz, 1H), 7.73 (d, J = 12.1 Hz, 1H), 5.28 (s, 2H), 5.14 (s, 2H), 4.17-4.00 (m, 1H), 3.83 (s, J = 14.8 Hz, 3H), 3.47 (dt, J = 21.9, 12.1 Hz, 5H), 3.33-3.09 (m, 2H), 2.75 (dt, 3 = 31.4, 2.6 Hz, 2H), 2.51-2.37 (m, 2H), 2.36 (s, J = 11.7 Hz, 3H), 2.29 (t, J = 7.3 Hz, 2H), 2.13 (dtd, J = 51.7, 7.1, 2.6 Hz, 4H), 1.63 (dp, J = 58.9, 7.2 Hz, 4H), 1.27 (d, J = 6.3 Hz, 3H), 1.17-0.87 (m, 4H). | (DMSO) δ 170.99, 161.55, 158.13, 155.66, 153.45, 152.34, 143.50, 143.35, 136.49, 127.56, 127.50, 123.45, 111.29, 111.06, 108.20, 91.51, 80.98, 73.02, 68.50, 54.83, 53.63, 51.79, 40.45, 35.67, 32.28, 28.18, 21.48, 19.40, 18.98, 10.94, 10.46. | 716.3 ([M + 2H]+) |

TABLE 5-continued

Examples of MONOMER-BIOACTIVE AGENT CONJUGATES: FLUOROQUINOLONES

| Ex | Structure/Name | Appearance | ¹H (CDCl₃) unless otherwise stated) δ (ppm) | ¹³C (CDCl₃) (unless otherwise stated) δ (ppm) | ESI MS ([M + H]+) |
|---|---|---|---|---|---|
| 60 | 1-((((2-(prop-2-yn-1-yl)pent-4-yn-1-yl)oxy)carbonyl)oxy)ethyl 7-(4-(tert-butoxycarbonyl)-3-methylpiperazin-1-yl)-1-cyclopropyl-6-fluoro-8-methoxy-4-oxo-1,4-dihydroquinoline-3-carboxylate | Flaky yellow solid | δ 8.56 (s, 1H), 7.87 (d, J = 12.4 Hz, 1H), 6.99 (q, J = 5.4 Hz, 1H), 4.33 (s, J = 17.4 Hz, 1H), 4.28-4.20 (m, 2H), 4.01-3.82 (m, 2H), 3.71 (s, 3H), 3.52-3.10 (m, 5H), 2.46-2.31 (m, 4H), 2.25-2.09 (m, 1H), 2.06-1.95 (m, 2H), 1.66 (d, J = 5.4 Hz, 3H), 1.49 (s, 9H), 1.29 (dd, J = 28.4, 7.3 Hz, 3H), 1.21-1.05 (m, 2H), 1.01-0.85 (m, 2H). | δ 172.66, 163.12, 157.35, 154.91, 154.87, 153.16, 151.16, 145.83, 139.06, 138.95, 135.05, 125.43, 109.41, 109.18, 108.75, 92.07, 80.88, 80.82, 80.00, 70.72, 70.68, 68.97, 63.18, 55.52, 51.15, 51.11, 47.55, 39.68, 39.52, 36.46, 28.61, 19.91, 19.88, 19.84, 15.65, 9.59, 9.46. | — |
| 61 | 4-(1-cyclopropyl-6-fluoro-8-methoxy-4-oxo-3-((1-(((2-(prop-2-yn-1-yl)pent-4-yn-1-yl)oxy)carbonyl)oxy)ethoxy)carbonyl)-1,4-dihydroquinolin-7-yl)-2-methylpiperazin-1-ium 2,2,2-trifluoroacetate CF₃COO⁻ | Pale yellow solid | (DMSO) δ 9.61 (s, 1H), 9.32 (s, 1H), 8.51 (s, 1H), 7.65 (d, J = 12.2 Hz, 1H), 6.80 (q, J = 5.3 Hz, 1H), 4.31-4.08 (m, 2H), 4.09-3.93 (m, 1H), 3.79 (s, 3H), 3.62-3.22 (m, 6H), 3.15 (d, J = 8.2 Hz, 1H), 2.92 (t, J = 2.3 Hz, 2H), 2.32 (d, J = 6.2 Hz, 4H), 2.07 (dt, J = 12.7, 6.3 Hz, 1H), 1.55 (d, J = 5.4 Hz, 3H), 1.27 (t, J = 14.3 Hz, 3H), 1.14-0.87 (m, 4H). | (DMSO) δ 171.20, 161.88, 156.48, 154.02, 152.35, 151.43, 146.54, 146.50, 136.70, 136.58, 132.71, 125.16, 125.08, 107.30, 107.14, 107.08, 91.39, 80.98, 73.02, 68.46, 62.90, 53.29, 51.00, 46.63, 43.07, 39.61, 35.67, 19.41, 18.98, 15.37, 8.81. | 590.2 ([M + Na]+) |

TABLE 5-continued

Examples of MONOMER-BIOACTIVE AGENT CONJUGATES: FLUOROQUINOLONES

| Ex | Structure/Name | Appearance | ¹H (CDCl₃) unless otherwise stated) δ (ppm) | ¹³C (CDCl₃) (unless otherwise stated) δ (ppm) | ESI MS ([M + H]+) |
|---|---|---|---|---|---|
| 62 | 1-((((2-(prop-2-yn-1-yl)oxy)carbonyl)ethyl 7-((R)-3-((tert-butoxycarbonyl)amino)azepan-1-yl)-8-chloro-1-cyclopropyl-6-fluoro-4-oxo-1,4-dihydroquinoline-3-carboxylate | Flaky yellow solid | δ 8.65 (s, 1H), 8.06 (d, J = 10.8 Hz, 1H), 6.98 (qd, J = 5.3, 1.0 Hz, 1H), 5.31 (d, J = 5.5 Hz, 1H), 4.31-4.13 (m, 3H), 3.83 (s, 1H), 3.58 (d, J = 14.2 Hz, 1H), 3.26-3.03 (m, 3H), 2.45-2.30 (m, 4H), 2.26-2.08 (m, 1H), 2.06-1.96 (m, 2H), 2.00-1.88 (m, 2H), 1.87-1.70 (m, 4H), 1.66 (d, J = 5.4 Hz, 3H), 1.34 (s, 9H), 1.28-1.14 (m, 2H), 1.02-0.80 (m, 2H). | δ 172.28, 162.57, 159.54, 157.04, 155.25, 153.12, 152.93, 145.05, 136.62, 128.48, 123.52, 113.00, 112.76, 109.64, 92.12, 80.80, 70.74, 70.70, 69.02, 57.07, 53.70, 50.39, 40.44, 36.45, 35.67, 29.33, 28.50, 21.99, 19.89, 19.87, 19.83, 11.63, 11.22. | — |
| 63 | CF₃COO⁻<br>(3R)-1-(8-chloro-1-cyclopropyl-6-fluoro-4-oxo-3-((1-(((2-(prop-2-yn-1-yl)pent-4-yn-1-yl)oxy)carbonyl)oxy)ethoxy)carbonyl)-1,4-dihydroquinolin-7-yl)azepan-3-aminium 2,2,2-trifluoroacetate | Pale yellow solid | (DMSO) δ 8.66 (s, 1H), 7.88 (d, J = 10.8 Hz, 1H), 7.80 (s, 2H), 6.81 (q, J = 5.3 Hz, 1H), 4.34-4.22 (m, 1H), 4.17 (dd, J = 6.1, 1.7 Hz, 2H), 3.52-3.27 (m, 3H), 3.16 (dt, J = 21.4, 6.3 Hz, 2H), 2.91 (t, J = 2.6 Hz, 2H), 2.40-2.23 (m, 4H), 2.14-1.99 (m, 2H), 1.97-1.78 (m, 2H), 1.72 (dd, J = 19.3, 8.9 Hz, 2H), 1.67-1.49 (m, 4H), 1.24-1.09 (m, 2H), 1.03-0.83 (m, 2H). | (DMSO) δ 170.99, 161.55, 158.13, 155.66, 153.45, 152.34, 143.50, 143.35, 136.49, 127.56, 127.50, 123.45, 111.29, 111.06, 108.20, 91.51, 80.98, 73.02, 68.50, 54.83, 53.63, 51.79, 40.45, 35.67, 32.28, 28.18, 21.48, 19.40, 18.98, 10.94, 10.46. | 586.2 |

TABLE 5-continued

Examples of MONOMER-BIOACTIVE AGENT CONJUGATES: FLUOROQUINOLONES

| Ex | Structure/Name | Appearance | $^1$H (CDCl$_3$) unless otherwise stated) δ (ppm) | $^{13}$C (CDCl$_3$) (unless otherwise stated) δ (ppm) | ESI MS ([M + H]+) |
|---|---|---|---|---|---|
| 64 | 4-((2-(prop-2-yn-1-yl)pent-4-yn-1-yl)oxy)carbonyl)phenyl 7-(4-(tert-butoxycarbonyl)piperazin-1-yl)-1-cyclopropyl-6-fluoro-4-oxo-1,4-dihydroquinoline-3-carboxylate | White solid | δ 8.64 (s, 1H), 8.07 (ddd, J = 19.3, 9.6, 7.8 Hz, 3H), 7.34-7.27 (m, 3H), 4.40 (t, J = 11.9 Hz, 2H), 3.71-3.59 (m, 4H), 3.52-3.43 (m, 1H), 3.29-3.18 (m, 4H), 2.53-2.43 (m, 4H), 2.36-2.25 (m, 1H), 2.03 (dd, J = 3.3, 1.9 Hz, 2H), 1.50 (s, 9H), 1.39-1.31 (m, 2H), 1.21-1.14 (m, 2H). | δ 172.96, 165.79, 163.59, 155.00, 154.93, 154.76, 152.46, 149.16, 144.84, 144.74, 138.12, 131.20, 127.50, 123.46, 123.39, 122.26, 113.81, 113.58, 109.19, 105.29, 105.27, 81.04, 80.38, 70.67, 65.93, 50.07, 36.67, 34.92, 28.57, 20.22, 8.37. | — |
| 65 | 4-(1-cyclopropyl-6-fluoro-4-oxo-3-((4-(((2-(prop-2-yn-1-yl)pent-4-yn-1-yl)oxy)carbonyl)phenoxy)carbonyl)-1,4-dihydroquinolin-7-yl)piperazin-1-ium 2,2,2-trifluoroacetate | Yellow solid | (DMSO) δ 8.93 (s, 2H), 8.71 (s, J = 6.5 Hz, 1H), 8.18-8.01 (m, 2H), 7.86 (d, J = 13.1 Hz, 1H), 7.53 (d, J = 7.4 Hz, 1H), 7.43-7.31 (m, 2H), 4.33 (d, J = 5.9 Hz, 2H), 3.84-3.66 (m, 1H), 3.47 (d, J = 5.5 Hz, 4H), 3.34 (s, 4H), 2.93 (t, J = 2.6 Hz, 2H), 2.44 (dd, J = 6.6, 2.6 Hz, 4H), 2.32-2.10 (m, 1H), 1.39-1.20 (m, 2H), 1.21-1.07 (m, 2H). | | 555.9 |

TABLE 5-continued

Examples of MONOMER-BIOACTIVE AGENT CONJUGATES: FLUOROQUINOLONES

| Ex | Structure/Name | Appearance | $^1$H (CDCl$_3$) unless otherwise stated) δ (ppm) | $^{13}$C (CDCl$_3$) (unless otherwise stated) δ (ppm) | ESI MS ([M + H]+) |
|---|---|---|---|---|---|
| 66 | (5-((7-(4-(tert-butoxycarbonyl)piperazin-1-yl)-1-cyclopropyl-6-fluoro-4-oxo-1,4-dihydroquinoline-3-carbonyl)oxy)-6-methylpyridine-3,4-diyl)bis(methylene) bis(hex-5-ynoate) | White flaky solid | δ 8.69 (s, 1H), 8.45 (s, 1H), 8.07 (dd, J = 18.0, 10.9 Hz, 1H), 7.38-7.28 (m, 1H), 5.27 (d, J = 18.6 Hz, 4H), 3.75-3.60 (m, 4H), 3.57-3.42 (m, 1H), 3.37-3.15 (m, 4H), 2.55-2.33 (m, 7H), 2.22 (dtd, J = 32.6, 6.9, 2.6 Hz, 4H), 2.00-1.87 (m, 2H), 1.89-1.67 (m, 4H), 1.50 (s, 9H), 1.45-1.28 (m, 2H), 1.27-1.14 (m, 2H). | δ 172.89, 172.64, 172.55, 163.46, 154.99, 154.76, 153.77, 152.51, 149.28, 147.76, 145.11, 144.93, 144.83, 138.22, 135.90, 129.45, 123.56, 123.49, 113.96, 113.73, 108.88, 105.27, 80.41, 69.48, 69.25, 61.50, 57.42, 50.12, 34.96, 32.90, 32.73, 28.57, 23.62, 23.58, 20.03, 17.97, 17.93, 8.39. | 771.9 |
| 67 | 4-(3-((4,5-bis((hex-5-ynoyloxy)methyl)-2-methylpyridin-3-yl)oxy)carbonyl)-1-cyclopropyl-6-fluoro-4-oxo-1,4-dihydroquinolin-7-yl)piperazin-1-ium 2,2,2-trifluoroacetate | Yellow solid | (DMSO) δ 9.01 (s, 2H), 8.75 (s, J = 21.6 Hz, 1H), 8.47 (s, J = 10.0 Hz, 1H), 7.88 (d, J = 13.1 Hz, 1H), 7.55 (d, J = 7.4 Hz, 1H), 5.28 (s, 2H), 5.15 (s, J = 24.3 Hz, 2H), 3.82-3.67 (m, 1H), 3.48 (d, J = 5.3 Hz, 4H), 3.35 (s, J = 14.0 Hz, 4H), 2.79 (t, J = 2.6 Hz, 1H), 2.70 (t, J = 2.6 Hz, 1H), 2.44 (t, J = 7.4 Hz, 2H), 2.37 (s, 3H), 2.29 (t, J = 7.4 Hz, 2H), 2.19 (td, J = 7.1, 2.6 Hz, 2H), 2.07 (td, J = 7.2, 2.6 Hz, 2H), 1.70 (p, J = 7.2 Hz, 2H), 1.55 (p, J = 7.3 Hz, 2H), 1.30 (d, J = 7.0 Hz, 2H), 1.17 (s, J = 22.5 Hz, 2H). | — | 670.9 |

TABLE 5-continued

Examples of MONOMER-BIOACTIVE AGENT CONJUGATES: FLUOROQUINOLONES

| Ex | Structure/Name | Appearance | ¹H (CDCl₃) unless otherwise stated) δ (ppm) | ¹³C (CDCl₃) (unless otherwise stated) δ (ppm) | ESI MS ([M + H]+) |
|---|---|---|---|---|---|
| 68 | 2-(prop-2-yn-1-yl)pent-4-yn-1-yl 7-(4-(tert-butoxycarbonyl)piperazin-1-yl)-1-cyclopropyl-6-fluoro-4-oxo-1,4-dihydroquinoline-3-carboxylate | Pale yellow solid | δ 8.52 (s, 1H), 8.03 (d, J = 13.2 Hz, 1H), 7.26 (d, J = 7.0 Hz, 1H), 4.40 (d, J = 6.1 Hz, 2H), 3.74-3.56 (m, 4H), 3.49-3.30 (m, 1H), 3.28-3.11 (m, 4H), 2.60-2.44 (m, 4H), 2.40-2.20 (m, 1H), 2.01 (t, 2H), 1.49 (s, 9H), 1.32 (q, J = 6.7 Hz, 2H), 1.13 (q, J = 6.7 Hz, 2H). | δ 173.10, 166.01, 154.78, 152.33, 148.45, 144.67, 144.56, 138.18, 123.56, 123.49, 113.75, 113.52, 110.47, 105.14, 105.11, 81.55, 80.37, 70.37, 65.68, 50.10, 36.71, 34.67, 28.57, 20.17, 8.32. | 536.3 |
| 69 | CF₃COO⁻ 4-(1-cyclopropyl-6-fluoro-4-oxo-3-(((2-(prop-2-yn-1-yl)pent-4-yn-1-yl)oxy)carbonyl)-1,4-dihydroquinolin-7-yl)piperazin-1-ium 2,2,2-trifluoroacetate | Yellow solid | (DMSO) δ 8.95 (s, 2H), 8.38 (s, 1H), 7.75 (d, J = 13.3 Hz, 1H), 7.40 (d, J = 7.4 Hz, 1H), 4.13 (d, J = 6.0 Hz, 2H), 3.65-3.54 (m, 1H), 3.37 (d, J = 5.5 Hz, 4H), 3.26 (s, J = 18.4 Hz, 4H), 2.83 (t, J = 2.6 Hz, 2H), 2.37-2.26 (m, 4H), 2.03 (ddd, J = 17.0, 11.6, 5.3 Hz, 1H), 1.21-1.12 (m, 2H), 1.03-0.94 (m, 2H). | | 435.9 ([M⁺]) |

TABLE 5-continued

Examples of MONOMER-BIOACTIVE AGENT CONJUGATES: FLUOROQUINOLONES

| Ex | Structure/Name | Appearance | $^1$H (CDCl$_3$) unless otherwise stated) δ (ppm) | $^{13}$C (CDCl$_3$) (unless otherwise stated) δ (ppm) | ESI MS ([M + H]+) |
|----|----------------|------------|---------------------------------------------------|-------------------------------------------------------|-------------------|
| 70 | 2-(prop-2-yn-1-yl)pent-4-yn-1-yl 7-(4-(tert-butoxycarbonyl)-3-methylpiperazin-1-yl)-1-cyclopropyl-6-fluoro-8-methoxy-4-oxo-1,4-dihydroquinoline-3-carboxylate | Pale yellow solid | δ 8.56 (s, 1H), 7.87 (d, J = 12.5, 1H), 4.38 (d, J = 8.2 Hz, 2H), 4.33 (s, 1H), 3.98-3.80 (m, 2H), 3.71 (s, J = 13.2 Hz, 3H), 3.50-3.13 (m, 5H), 2.61-2.47 (m, 4H), 2.37-2.22 (m, 1H), 2.00 (t, J = 2.6 Hz, 2H), 1.49 (s, 9H), 1.33 (d, J = 6.8 Hz, 3H), 1.20-1.01 (m, 2H), 0.97-0.83 (m, 2H). | δ 172.77, 165.80, 157.27, 154.92, 154.79, 150.86, 145.78, 138.89, 138.78, 133.14, 125.71, 125.63, 110.02, 109.34, 109.11, 81.54, 79.98, 70.37, 65.63, 63.14, 55.58, 55.53, 51.17, 51.13, 47.58, 39.55, 39.47, 38.78, 36.71, 28.61, 20.16, 15.65, 9.55, 9.44. | 579.9 |
| 71 | 4-(1-cyclopropyl-6-fluoro-8-methoxy-4-oxo-3-((((2-(prop-2-yn-1-yl)pent-4-yn-1-yl)oxy)carbonyl)-1,4-dihydroquinolin-7-yl)-2-methylpiperazin-1-ium 2,2,2-trifluoroacetate · CF$_3$COO$^-$ | Pale yellow solid | (DMSO) δ 8.99-8.78 (m, 2H), 8.53 (s, J = 12.1 Hz, 1H), 7.68 (d, J = 12.2 Hz, 1H), 4.21 (d, J = 5.9 Hz, 2H), 3.99 (m, 1H), 3.80 (s, 3H), 3.69-3.10 (m, 6H), 2.92 (t, J = 2.5 Hz, 2H), 2.48-2.34 (m, 4H), 2.18-2.06 (m, 1H), 1.28 (d, 3H), 1.22-1.01 (m, 4H). | — | 479.9 |

TABLE 5-continued

Examples of MONOMER-BIOACTIVE AGENT CONJUGATES: FLUOROQUINOLONES

| Ex | Structure/Name | Appearance | ¹H (CDCl₃) unless otherwise stated) δ (ppm) | ¹³C (CDCl₃) (unless otherwise stated) δ (ppm) | ESI MS ([M + H]+) |
|---|---|---|---|---|---|
| 72 | 3-(((2-(prop-2-yn-1-yl)pent-4-yn-1-yl)oxycarbonyl)phenyl 9-fluoro-3-methyl-10-(4-methylpiperazin-1-yl)-7-oxo-2,3-dihydro-7H-[1,4]oxazino[2,3,4-ij]quinoline-6-carboxylate | Pale yellow solid | (DMSO) δ 8.91 (s, 1H), 7.98-7.86 (m, 1H), 7.86-7.73 (m, 1H), 7.62 (t, J = 7.9 Hz, 1H), 7.58-7.47 (m, 1H), 7.45 (d, J = 12.6 Hz, 1H), 4.78 (q, J = 6.6 Hz, 1H), 4.61-4.46 (m, 1H), 4.35 (dd, J = 14.5, 4.0 Hz, 3H), 3.41-3.11 (m, 7H), 2.92 (t, J = 2.6 Hz, 2H), 2.47-2.34 (m, 8H), 2.29-2.08 (m, 4H), 1.45 (d, J = 6.7 Hz, 3H). | (DMSO) δ 171.56, 171.53, 164.88, 162.40, 156.44, 154.01, 150.75, 147.35, 140.42, 140.35, 131.00, 130.86, 130.83, 129.92, 127.25, 126.43, 123.70, 122.83, 122.73, 106.98, 103.94, 103.71, 81.35, 72.91, 68.08, 65.75, 55.27, 53.97, 50.08, 50.04, 45.99, 35.77, 19.36, 17.68. | 585.9 |
| 73 | 2-(prop-2-yn-1-yl)pent-4-yn-1-yl (R)-7-(3-((tert-butoxycarbonyl)amino)azepan-1-yl)-8-chloro-1-cyclopropyl-6-fluoro-4-oxo-1,4-dihydroquinoline-3-carboxylate | White crystalline solid | δ 8.67 (s, 1H), 8.07 (d, J = 10.9 Hz, 1H), 5.35 (br s, 1H), 4.40 (d, J = 6.1 Hz, 2H), 3.85 (br s, 1H), 3.59 (d, J = 14.2 Hz, 2H), 3.24-3.11 (m, 3H), 2.52 (dd, J = 6.6, 2.3 Hz, 4H), 2.30 (m, 1H), 2.01 (t, J = 2.6 Hz, 2H), 1.97 (m, 1H), 1.88-1.67 (m, 5H), 1.34 (s, 9H), 1.26 (m, 2H), 0.93 (m, 2H). | δ 172.39, 172.37, 165.2, 159.5, 157.0, 155.3, 152.7, 144.1, 136.7, 128.7, 123.5, 113.0, 112.7, 110.8, 81.5, 79.1, 70.4, 65.8, 57.09, 57.05, 53.7, 50.4, 40.3, 36.7, 35.7, 29.4, 28.5, 22.0, 20.2, 11.6, 11.2. | 597.9 |

TABLE 5-continued

Examples of MONOMER-BIOACTIVE AGENT CONJUGATES: FLUOROQUINOLONES

| Ex | Structure/Name | Appearance | $^1$H (CDCl$_3$) unless otherwise stated) δ (ppm) | $^{13}$C (CDCl$_3$) (unless otherwise stated) δ (ppm) | ESI MS ([M + H]+) |
|---|---|---|---|---|---|
| 74 | 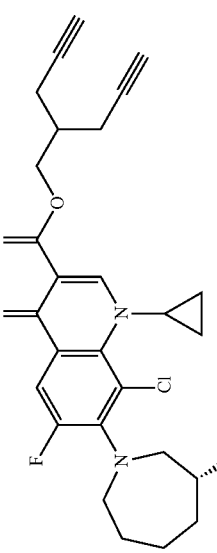<br>(R)-1-(8-chloro-1-cyclopropyl-6-fluoro-4-oxo-3-(((2-(prop-2-yn-1-yl)pent-4-yn-1-yl)oxy)carbonyl)-1,4-dihydroquinolin-7-yl)azepan-3-aminium 2,2,2-trifluoroacetate | White crystalline solid | δ 8.58 (s, 1H), 8.07 (br s, 3H) 7.61 (d, J = 10.8 Hz, 1H), 4.32 (m, 2H), 4.14 (m, 1H), 3.86-3.67 (m, 3H), 2.81 (m, 2H), 2.46 (m, 4H), 2.25 (m, 2H), 2.11 (m, 1H), 2.04 (m, 2H), 1.98-1.72 (m, 4H), 1.29 (m, 1H), 1.19 (m, 1H), 0.92 (m, 1H), 0.79 (m, 1H). | | 497.9 |

TABLE 6

Examples of MONOMER-BIOACTIVE AGENT CONJUGATES: NSAIDs

| Ex | Structure/Name | Appearance | $^1$H (CDCl$_3$) unless otherwise stated) δ (ppm) | $^{13}$C (CDCl$_3$) (unless otherwise stated) δ (ppm) | ESI MS ([M + H]+) |
|---|---|---|---|---|---|
| 10 | (5-(2-(2-((2,6-dichlorophenyl)amino)phenyl)acetoxy)-6-methylpyridine-3,4-diyl)bis(methylene) bis(hex-5-ynoate) | white solid | δ 8.44 (s, 1H), 7.42-7.31 (m, 3H), 7.18 (td, J = 7.8, 1.5 Hz, 1H), 7.06-6.96 (m, 2H), 6.75 (s, 1H), 6.59 (d, J = 8.0 Hz, 1H), 5.28 (s, J = 5.6 Hz, 2H), 5.13 (s, 2H), 4.15 (s, 2H), 2.47 (t, J = 7.4 Hz, 2H), 2.33-2.18 (m, 7H), 2.10 (td, J = 6.9, 2.7 Hz, 2H), 1.96 (t, J = 2.7 Hz, 1H), 1.90 (t, J = 2.6 Hz, 1H), 1.84 (p, J = 7.0 Hz, 2H), 1.67 (p, J = 7.1 Hz, 2H). | δ 172.62, 172.50, 170.03, 153.30, 148.27, 144.79, 142.81, 137.75, 135.86, 131.19, 129.65, 129.60, 129.06, 128.72, 124.47, 123.28, 122.55, 118.76, 83.21, 83.15, 69.50, 69.32, 61.32, 56.89, 38.11, 32.84, 32.32, 23.54, 23.39, 19.51, 17.93, 17.80. | 635 |
| 11 | 2-(prop-2-yn-1-yl)pent-4-yn-1-yl 4-(2-(2-((2,6-dichlorophenyl)amino)phenyl)acetoxy)benzoate | — | δ 8.06 (m, 2H), 7.36-7.33 (m, 3H), 7.21-7.16 (m, 3H), 7.02 (td, J = 7.5, 1.2 Hz, 1H), 6.99 (dd, J = 8.4, 8.0 Hz, 1H), 6.67 (br s, 1H), 6.60 (dd, J = 8.0, 1.0 Hz, 1H), 4.41 (d, J = 6.1 Hz, 2H), 4.07 (s, 2H), 2.47 (dd, J = 6.5, 2.6 Hz, 4H), 2.29 (m, 1H), 2.03 (t, J = 2.6 Hz, 2H) | δ 170.3, 165.6, 154.4, 142.8, 137.8, 131.4, 131.2, 129.6, 129.0, 128.6, 127.9, 124.4, 123.7, 122.5, 121.8, 118.8, 81.0, 70.7, 66.0, 38.7, 36.6, 20.2. | — |
| 12 | (S)-2-(prop-2-yn-1-yl)pent-4-yn-1-yl 2- | white solid | δ 7.36-7.31 (m, 3H), 7.19-7.12 (m, 3H), 7.06-6.96 (m, 4H), 6.75 (s, 1H), 6.58 (d, J = 7.9 Hz, 1H), 4.99 (d, J = 8.0 Hz, 1H), 4.57 (dd, J = 13.5, 6.3 Hz, 1H), 4.20 (dd, J = 11.0, 6.0 Hz, 1H), 4.15 (dd, J = 11.0, 6.2 Hz, 1H), 4.04 (s, 2H), 3.07 (d, J = 5.8 Hz, 2H), 2.29 (m, 4H), 2.07 (m, 1H), 1.99 (t, J = 2.6 Hz, 2H), 1.42 (2, 9H). | δ 171.74, 170.72, 149.81, 142.87, 137.90, 133.90, 131.16, 130.44, 129.64, 129.00, 128.41, 124.64, 124.28, 124.01, 122.42, 121.81, 118.68, 89.60, 80.83, 70.78, 70.73, 66.19, 54.57, 38.74, 37.99, 36.20, 28.44, 20.01. | — |

TABLE 6-continued

Examples of MONOMER-BIOACTIVE AGENT CONJUGATES: NSAIDs

| Ex | Structure/Name | Appearance | $^1$H (CDCl$_3$) unless otherwise stated) δ (ppm) | $^{13}$C (CDCl$_3$) (unless otherwise stated) δ (ppm) | ESI MS ([M + H]+) |
|---|---|---|---|---|---|
| 13 | ((tert-butoxycarbonyl)amino)-3-(4-(2-(2-((2,6-dichlorophenyl)amino)phenyl)acetoxy)phenyl)propanoate | white solid | δ 7.36-7.30 (m, 3H), 7.24-7.13 (m, 3H), 7.08-6.96 (m, 4H), 6.75 (s, 1H), 6.58 (d, J = 8.0 Hz, 1H), 4.18 (d, J = 6.1 Hz, 2H), 4.04 (s, 2H), 3.75 (dd, J = 7.3, 5.9 Hz, 1H), 3.06 (dd, J = 13.7, 5.8 Hz, 1H), 2.91 (dd, J = 13.7, 7.4 Hz, 1H), 2.31 (m, 4H), 2.09 (m, 1H), 7.00 (2 × t, J = 7.7 Hz, 2 × 1H). | δ 174.74, 170.78, 149.67, 142.86, 137.88, 134.94, 131.15, 130.41, 129.63, 128.99, 128.39, 124.28, 124.01, 122.41, 121.81, 118.66, 80.91, 80.87, 70.72, 70.70, 65.87, 55.85, 40.55, 38.73, 36.25, 20.02, 20.00. | — |
| | (S)-2-(prop-2-yn-1-yl)pent-4-yn-1-yl 2-amino-3-(4-(2-(2-((2,6-dichlorophenyl)amino)phenyl)acetoxy)phenyl)propanoate | | | | |
| 14 | 1-((((2-(Prop-2-yn-1-yl)pent-4-yn-1-yl)oxy)carbonyl)oxy)ethyl 2-(2-((2,6-dichlorophenyl)amino)phenyl)acetate | — | δ 7.34 (d, J = 8.1 Hz, 2H), 7.23 (dd, J = 7.5, 1.4 Hz, 1H), 7.13 (td, J = 7.7, 1.5 Hz, 1H), 6.98 (t, J = 8.1 Hz, 1H), 6.97 (t, J = 7.4, 0.8 Hz, H), 6.81 (q, J = 5.4 Hz, 1H), 6.60 (s, 1H), 6.56 (d, J = 8.0 Hz, 1H), 4.21(d, J = 6.2 Hz, H), 3.88 (d, J = 15.0 Hz, 1H), 3.82 (d, J = 15.0 Hz, 1H), 2.38 (ddd, J = 6.8, 2.4, 1.2 Hz, 4H), 2.14 (m, 1H), 2.03 (t, J = 2.7 Hz, 1H), 1.99 (t, J = 2.7 Hz, 1H), 1.54 (t, J = 2.7 Hz, 3H). | δ 170.4, 152.9, 142.9, 138.1, 131.1, 129.6, 129.0, 128.3, 124.19, 124.15, 122.5, 118.9, 92.2, 80.8, 80.7, 70.8, 70.7, 69.1, 38.4, 36.4, 19.9, 19.8, 19.7. | 487.8 |

TABLE 6-continued

Examples of MONOMER-BIOACTIVE AGENT CONJUGATES: NSAIDs

| Ex | Structure/Name | Appearance | $^1$H (CDCl$_3$) unless otherwise stated) δ (ppm) | $^{13}$C (CDCl$_3$) (unless otherwise stated) δ (ppm) | ESI MS ([M + H]+) |
|---|---|---|---|---|---|
| 75 | 1-((((2-(prop-2-yn-1-yl)pent-4-yn-1-yl)oxy)carbonyl)oxy)ethyl 5-benzoyl-2,3-dihydro-1H-pyrrolizine-1-carboxylate | yellow oil | Diastereomer 1: R$_f$ = 0.18 (20% EtOAc/petrol)δ 7.83-7.78 (m, 2H), 7.53 (m, 1H), 7.47-7.41 (m, 2H), 6.83-6.79 (m, 2H), 6.11 (dd, J = 4.0, 0.6 Hz, 1H), 4.57 (m, 1H), 4.44 (m, 1H), 4.27 (d, J = 6.2 Hz, 2H), 4.10 (m, 1H), 2.95 (m, 1H), 2.82 (m, 1H), 2.40 (ddd, J = 6.5, 2.5, 1.6 Hz, 4H), 2.19 (m, 1H), 2.02 (t, J = 2.7 Hz, 2H), 1.56 (d, J = 5.4 Hz, 3H), Diastereomer 2: R$_f$ = 0.15 (20% EtOAc/petrol)δ 7.84-7.79 (m, 2H), 7.53 (m, 1H), 7.48-7.40 (m, 1H), 6.85-6.78 (m, 2H), 6.10 (dd, J = 4.0, 0.8 Hz, 1H), 4.58 (m, 1H), 4.43 (m, 1H), 4.25 (dd, J = 8.7 Hz, 4.0 Hz, 1H), 4.21 (dd, J = 8.7 4.1 Hz), 4.09 (dd, J = 8.9, 6.1 Hz, 1H), 2.94 (m, 1H), 2.82 (m, 1H), 2.39 (t, J = 2.3 Hz, 2H), 2.37 (t, J = 2.3 Hz, 2H), 2.15 (m, 1H), 1.98 (t, J = 2.7 Hz, 1H), 1.97(t, J = 2.7 Hz, 1H), 1.57(d, J = 5.4 Hz, 3H). | δ 185.2, 169.3, 153.0, 141.6, 139.4, 131.6, 129.1, 128.3, 127.5, 125.1, 103.4, 92.2, 80.68, 80.65, 70.81, 70.79, 69.2, 47.6, 42.6, 36.4, 30.9, 19.84, 19.82, 19.6. | 447.9 |
| 76 | 2-(prop-2-yn-1-yl)pent-4-yn-1-yl 2-(2-((2,6-dichlorophenyl)amino)phenyl) acetate | colorless viscous oil | δ 7.39-7.30 (m, 2H), 7.25-7.19 (m, 1H), 7.18-7.07 (m, 1H), 7.01-6.90 (m, 2H), 6.88-6.73 (m, J = 30.0 Hz, 1H), 6.56 (dd, J = 8.0, 1.0 Hz, 1H), 4.24 (d, J = 6.3 Hz, 2H), 3.83 (s, J = 16.1 Hz, 2H), 2.45-2.30 (m, 4H), 2.26-2.10 (m, 1H), 2.01 (dt, J = 5.3, 2.7 Hz, 2H). | δ 172.30, 142.88, 138.01, 130.96, 129.72, 129.02, 128.22, 124.45, 174.19, 122.26, 118.57, 80.93, 70.65, 66.23, 38.62, 36.42, 20.01. | 399.8 |
| 77 | 2-(prop-2-yn-1-yl)pent-4-yn-1-yl 5-benzoyl-2,3-dihydro-1H-pyrrolizine-1-carboxylate | golden yellow viscous oil | δ 7.87-7.74 (m, 2H), 7.60-7.47 (m, 1H), 7.45 (ddt, J = 8.2, 6.7, 1.5 Hz, 2H), 6.83 (d, J = 4.0 Hz, 1H), 6.10 (dd, J = 4.0, 0.8 Hz, 1H), 4.63-4.50 (m, 1H), 4.51-4.40 (m, 1H), 4.34-4.17 (m, 2H), 4.14-4.04 (m, H), 3.02-2.86 (m, 1H), 2.87-2.73 (m, 1H), 2.39 (dt, J = 6.5, 2.6 Hz, 4H), 2.26-2.09 (m, 1H), 2.07-1.98 (m, 2H). | δ 185.16, 171.11, 142.21, 139.40, 131.56, 129.05, 128.30, 127.44, 175.09, 103.21, 80.81, 80.78, 70.78, 70.75, 66.30, 47.71, 42.74, 36.42, 31.09, 20.08, 20.07 | 359.9 |

TABLE 6-continued

Examples of MONOMER-BIOACTIVE AGENT CONJUGATES: NSAIDs

| Ex | Structure/Name | Appearance | $^1$H (CDCl$_3$) unless otherwise stated) δ (ppm) | $^{13}$C (CDCl$_3$) (unless otherwise stated) δ (ppm) | ESI MS ([M + H]+) |
|---|---|---|---|---|---|
| 78 | 2-(prop-2-yn-1-yl)pent-4-yn-1-yl 2-(1-(4-chlorobenzoyl)-5-methoxy-2-methyl-1H-indol-3-yl)acetate | pale yellow solid | δ 7.72-7.60 (m, 1H), 7.52-7.42 (m, 1H), 6.95 (d, J = 2.5 Hz, 1H), 6.87 (d, J = 9.0 Hz, 1H), 6.67 (dd, J = 9.0, 2.5 Hz, 1H), 4.19 (d, J = 6.1 Hz, 1H), 3.84 (s, 2H), 3.68 (s, 1H), 2.39 (s, J = 2.8 Hz, 2H), 2.30 (dd, J = 6.5, 2.7 Hz, 2H), 2.11 (dt, J = 12.7, 6.3 Hz, 1H), 1.99 (t, J = 2.6 Hz, 1H). | δ 170.68, 168.43, 156.31, 139.46, 136.02, 134.08, 131.33, 131.00, 130.70, 129.30, 115.15, 112.59, 112.00, 101.36, 80.87, 70.63, 65.81, 55.90, 36.42, 30.46, 19.96, 19.90, 13.43. | 463.9 |
| 79 | 2-(prop-2-yn-1-yl)pent-4-yn-1-yl 2-(4-isobutylphenyl)propanoate | colourless oil | δ 7.23-7.13 (m, 2H), 7.09 (d, J = 8.1 Hz, 2H), 4.14 (ddd, J = 29.5, 11.1, 6.1 Hz, 2H), 3.70 (q, J = 7.2 Hz, 1H), 2.45 (d, J = 7.2 Hz, 2H), 2.31-2.16 (m, 4H), 2.11-2.00 (m, 1H), 1.96 (dd, J = 4.7, 2.6 Hz, 2H), 1.90-1.76 (m, 1H), 1.50 (d, J = 7.2 Hz, 3H), 0.89 (d, J = 6.6 Hz, 3H). | δ 174.57, 140.77, 137.83, 129.50, 127.28, 81.05, 70.42, 65.37, 45.30, 45.18, 36.48, 30.33, 22.51, 19.85, 19.82, 18.35. | — |
| 80 | 2-(prop-2-yn-1-yl)pent-4-yn-1-yl 2-(2-amino-3-(4-bromobenzoyl)phenyl)acetate | brown oil | δ 7.61-7.58 (m, 2H), 7.52-7.49 (m, 2H), 7.36 (dd, J = 8.1, 1.5 Hz, 1H), 7.27 (dd, J = 7.6 Hz, 1.6 Hz, 1H), 6.61 (dd, J = 8.0 Hz, 7.4 Hz, 1H), 6.50 (s, 2H), 4.22 (d, J = 6.2 Hz, 2H), 3.63 (s, 2H), 2.34 (dd, J = 6.4, 2.7 Hz, 4H), 2.14 (m, 1H), 2.00 (t, J = 2.7 Hz, 2H). | δ 198.1, 171.0, 149.9, 139.1, 136.4, 134.2, 131.5, 131.0, 126.1, 120.5, 118.9, 115.6, 80.8, 70.7, 66.2, 38.6, 36.3, 20.0. | 437.8 |

TABLE 6-continued

Examples of MONOMER-BIOACTIVE AGENT CONJUGATES: NSAIDs

| Ex | Structure/Name | Appearance | $^{1}$H (CDCl$_3$) unless otherwise stated) δ (ppm) | $^{13}$C (CDCl$_3$) (unless otherwise stated) δ (ppm) | ESI MS ([M + H]+) |
|---|---|---|---|---|---|
| 81 | 4-(((2-(prop-2-yn-1-yl)pent-4-yn-1-yl)oxy)carbonyl)phenyl 5-benzoyl-2,3-dihydro-1H-pyrrolizine-1-carboxylate | Yellow brown solid | R$_f$ = 0.17 (20% EtOAc/petrol) δ 8.10-8.07 (m, 2H), 7.85-7.82 (m, 2H), 7.57-7.45 (m, 3H), 7.22-7.18 (m, 2H), 6.87 (d, J = 4.0 Hz, 1H), 6.25 (dd, J = 4.0, 0.8 Hz, 1H), 4.65 (ddd, J = 12.2, 8.5, 5.7 Hz, 1H), 4.53 (ddd, J = 12.3, 8.4, 5.8 Hz, 1H), 4.42 (d, J = 6.1 Hz, 1H), 4.35 (dd, J = 8.7, 5.4 Hz, 1H), 3.08 (m, 1H), 2.94 (m, 1H), 2.48 (dd, J = 6.5, 2.7 Hz, 1H), 2.30 (m, 1H), 2.03 (t, J = 2.6 Hz, 2H). | δ 185.3, 169.3, 165.5, 154.5, 141.3, 139.3, 131.7, 131.4, 129.1, 128.4, 128.1, 127.8, 125.1, 121.6, 103.4, 81.0, 70.7, 66.1, 47.7, 42.9, 36.6, 30.9, 20.2. | 479.9 |
| 82 | (5-((5-benzoyl-2,3-dihydro-1H-pyrrolizine-1-carbonyl)oxy)-6-methylpyridine-3,4-diyl)bis(methylene) bis(hex-5-ynoate) | golden yellow viscous oil | δ 8.46 (s, 1H), 7.92-7.78 (m, 2H), 7.61-7.39 (m, 3H), 6.90 (dd, J = 14.6, 4.0 Hz, 1H), 6.26 (dd, J = 4.0, 0.6 Hz, 1H), 5.45-4.99 (m, 4H), 4.74-4.47 (m, 2H), 4.41 (dd, J = 8.8, 5.0 Hz, 1H), 3.21-2.88 (m, 2H), 2.56-2.30 (m, 5H), 2.30-2.14 (m, 4H), 1.99-1.90 (m, 2H), 1.91-1.67 (m, 4H). | δ 185.26, 172.57, 172.38, 168.99, 152.84, 147.68, 144.83, 140.68, 139.18, 136.28, 131.74, 130.16, 129.06, 128.37, 127.82, 125.02, 103.69, 83.07, 69.53, 61.18, 56.76, 47.71, 42.71, 32.84, 32.51, 31.37, 23.57, 23.46, 19.47, 17.94, 17.87. | 596 |
| 83 | (5-((2-(4-isobutylphenyl)propanoyl)oxy)-6-methylpyridine-3,4-diyl)bis(methylene) bis(hex-5-ynoate) | colourless oil | δ 8.39 (s, 1H), 7.33 (d, J = 8.1 Hz, 2H), 7.15 (d, J = 8.1 Hz, 2H), 5.41-5.22 (m, 2H), 5.02 (s, 2H), 4.03 (q, J = 7.1 Hz, 11H), 2.52-2.43 (m, 4H), 2.36 (t, J = 7.2 Hz, 2H), 2.24 (qd, J = 7.1, 2.6 Hz, 4H), 2.05 (t, J = 12.7 Hz, 3H), 1.96 (m, 2H), 1.92-1.72 (m, 5H), 1.67 (d, J = 7.2 Hz, 3H), 0.89 (dd, J = 6.6, 0.5 Hz, 6H). | δ 172.55, 172.34, 172.16, 153.02, 147.06, 145.06, 141.56, 136.47, 136.33, 129.89, 129.74, 127.65, 83.18, 83.12, 69.49, 69.42, 61.24, 56.85, 45.27, 45.16, 32.83, 32.52, 30.32, 23.56, 23.51, 22.43, 22.41, 18.95, 17.93, 17.90, 17.86. | 546 |

TABLE 6-continued

Examples of MONOMER-BIOACTIVE AGENT CONJUGATES: NSAIDs

| Ex | Appearance | Structure/Name | $^1$H (CDCl$_3$) unless otherwise stated) δ (ppm) | $^{13}$C (CDCl$_3$) (unless otherwise stated) δ (ppm) | ESI MS ([M + H]+) |
|---|---|---|---|---|---|
| 84 | pale yellow solid | (5-(2-(1-(4-chlorobenzoyl)-5-methoxy-2-methyl-1H-indol-3-yl)acetoxy)-6-methylpyridine-3,4-diyl)bis(methylene) bis(hex-5-ynoate) | δ 8.45 (d, J = 2.9 Hz, 1H), 7.73-7.62 (m, 2H), 7.54-7.43 (m, 2H), 7.06 (d, J = 2.5 Hz, 1H), 6.85 (d, J = 9.0 Hz, 1H), 6.75-6.64 (m, 1H), 5.27 (s, 2H), 5.07 (s, 2H), 4.01 (s, 2H), 3.83 (d, J = 4.0 Hz, 3H), 2.48 (dd, J = 12.2, 4.7 Hz, 4H), 2.36-2.21 (m, 6H), 2.18 (ddd, J = 9.5, 6.3, 2.7 Hz, 2H), 1.98-1.91 (m, 2H), 1.90-1.79 (m, 2H), 1.78-1.67 (m, 2H). | δ 172.59, 172.38, 168.51, 168.42, 156.35, 153.05, 148.12, 144.78, 139.63, 136.68, 135.62, 133.89, 131.37, 131.04, 130.52, 129.75, 129.34, 115.23, 111.97, 111.39, 101.45, 83.17, 83.13, 69.48, 69.44, 61.26, 56.70, 55.87, 32.85, 32.44, 30.17, 23.57, 23.49, 19.61, 17.93, 17.85, 13.46. | 697.8 |
| 85 | Colourless viscous oil | 2-(prop-2-yn-1-yl) pent-4-yn-1-yl 3-(2-(((2,6-dichlorophenyl)amino)phenyl) acetoxy) benzoate | δ 7.98-7.87 (m, 1H), 7.76 (dd, J = 5.7, 4.0 Hz, 1H), 7.46 (t, J = 8.0 Hz, 1H), 7.41-7.29 (m, 4H), 7.17 (tt, J = 16.2, 8.1 Hz, 1H), 7.08-6.93 (m, 2H), 6.69 (s, 1H), 6.57 (dd, J = 26.4, 8.0 Hz, 1H), 4.41 (d, J = 6.1 Hz, 2H), 4.10 (d, J = 13.0 Hz, 2H), 2.44 (ddd, J = 13.8, 6.1, 2.9 Hz, 4H), 2.36-2.21 (m, 1H), 2.04-1.97 (m, 2H). | δ 170.53, 165.46, 150.75, 142.87, 137.91, 131.78, 131.21, 129.70, 129.67, 129.03, 128.56, 127.44, 126.57, 124.35, 123.82, 122.92, 122.56, 118.80, 80.99, 70.73, 66.25, 38.68, 36.58, 20.24. | — |

TABLE 6-continued

Examples of MONOMER-BIOACTIVE AGENT CONJUGATES: NSAIDs

| Ex | Structure/Name | Appearance | $^1$H (CDCl$_3$) unless otherwise stated) δ (ppm) | $^{13}$C (CDCl$_3$) (unless otherwise stated) δ (ppm) | ESI MS ([M + H]+) |
|----|---|---|---|---|---|
| 86 | 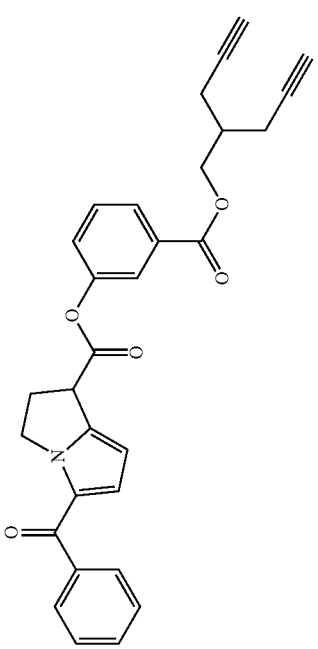<br>3-(((2-(prop-2-yn-1-yl)pent-4-yn-1-yl)oxy)carbonyl)phenyl 5-benzoyl-2,3-dihydro-1H-pyrrolizine-1-carboxylate | Amber coloured viscous oil | δ 7.93 (ddd, J = 18.7, 9.9, 8.7 Hz, 1H), 7.84 (dd, J = 5.2, 3.2 Hz, 2H), 7.79-7.74 (m, 1H), 7.62-7.42 (m, 4H), 7.36-7.29 (m, 1H), 6.88 (d, J = 4.0 Hz, 1H), 6.26 (dd, J = 4.0, 0.7 Hz, 1H), 4.71-4.60 (m, 1H), 4.59-4.47 (m, 1H), 4.48-4.32 (m, 3H), 3.09 (ddt, J = 14.1, 8.5, 5.7 Hz, 1H), 2.94 (dtd, J = 14.3, 8.6, 5.8 Hz, 1H), 2.47 (dd, J = 6.4, 2.5 Hz, 4H), 2.38-2.21 (m, 1H), 2.07-1.98 (m, 2H). | — | 479.9 |

TABLE 7
Prophetic Examples of MONOMER-BIOACTIVE AGENT CONJUGATES
| Ex | Structure |
|----|-----------|
| 87 | 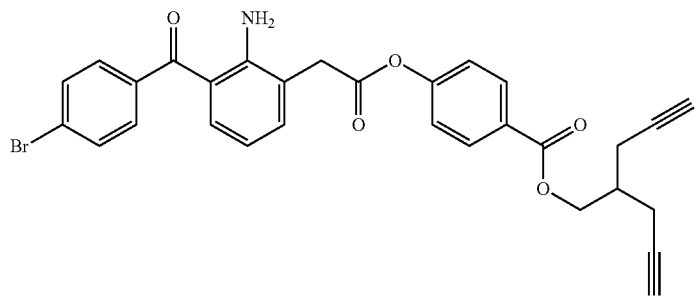 [SMILES: C#CCC(CC#C)COC(=O)c1ccc(OC(=O)Cc2cccc(C(=O)c3ccc(Br)cc3)c2N)cc1] |
| 88 | 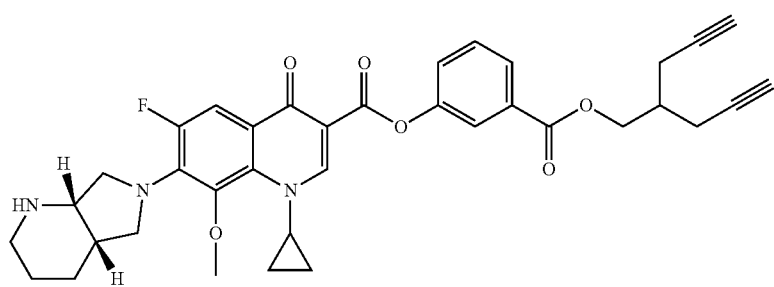 [SMILES: C#CCC(CC#C)COC(=O)c1cccc(OC(=O)c2cn(C3CC3)c3c(OC)c(N4C[C@@H]5CCCN[C@@H]5C4)c(F)cc3c2=O)c1] |
| 89 | 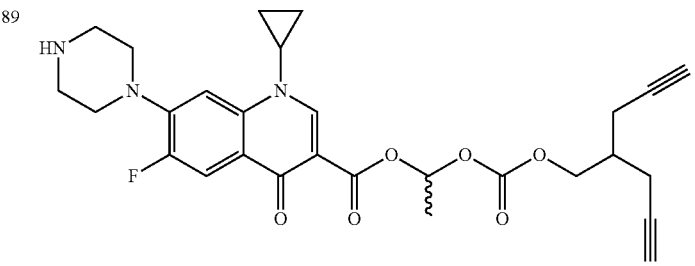 |
| 90 | 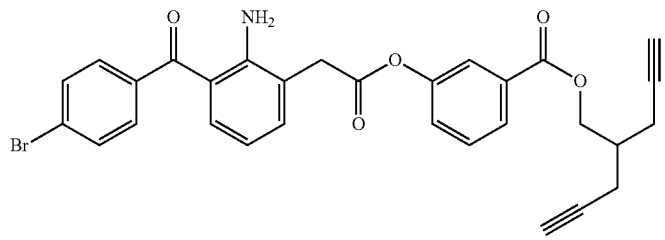 [SMILES: C#CCC(CC#C)COC(=O)c1cccc(OC(=O)Cc2cccc(C(=O)c3ccc(Br)cc3)c2N)c1] |
| 91 | 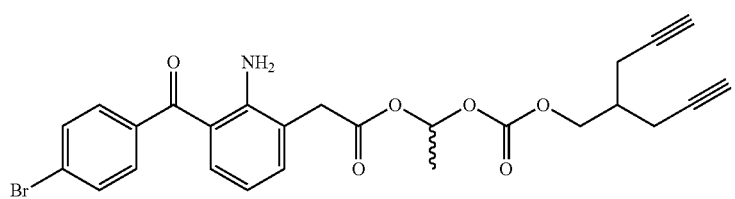 [SMILES: C#CCC(CC#C)COC(=O)OC(C)OC(=O)Cc1cccc(C(=O)c2ccc(Br)cc2)c1N] |

TABLE 7-continued
Prophetic Examples of MONOMER-BIOACTIVE AGENT CONJUGATES
Ex  Structure
92  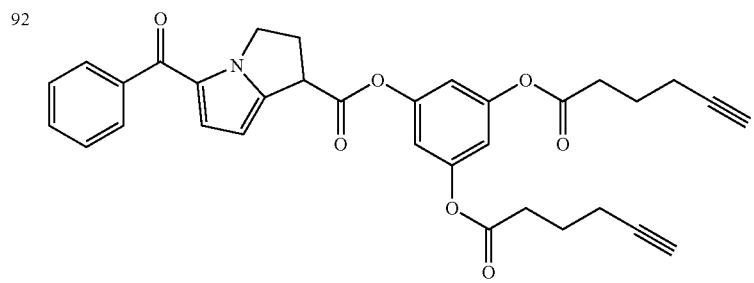
93  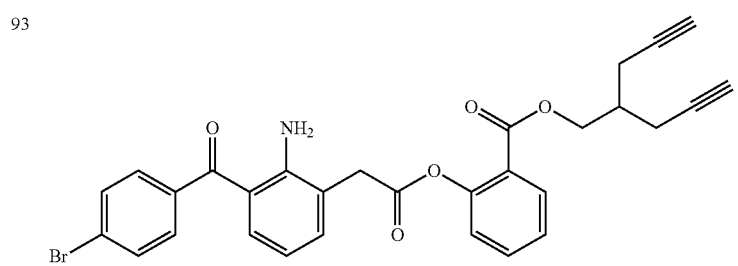
94  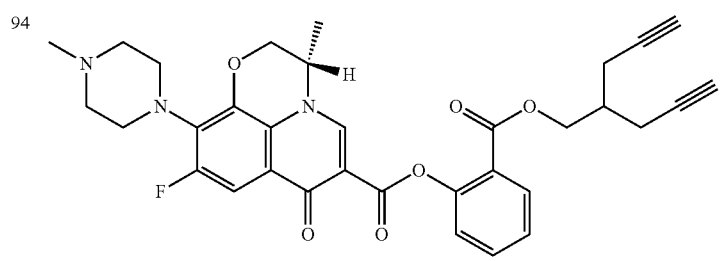
95  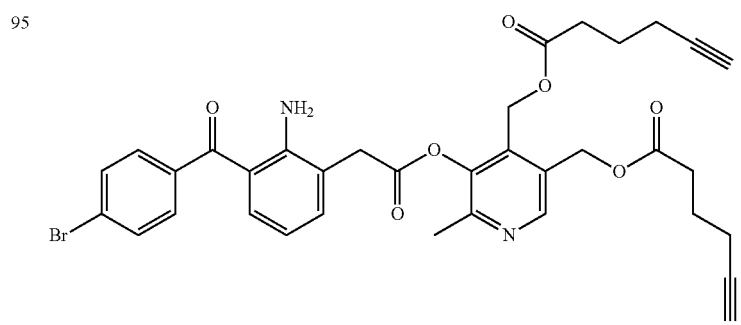
96  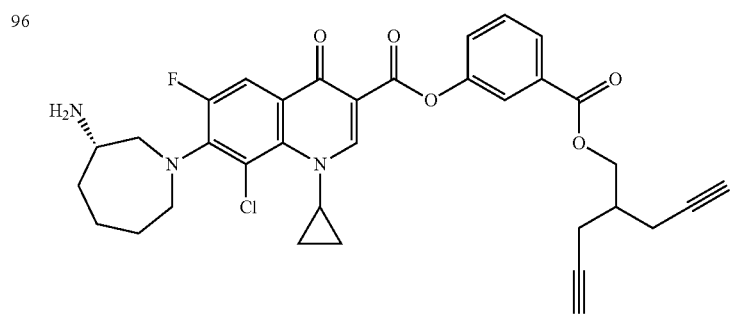

194
TABLE 7-continued
Prophetic Examples of MONOMER-BIOACTIVE AGENT CONJUGATES
| Ex | Structure |
|----|-----------|
| 97 | 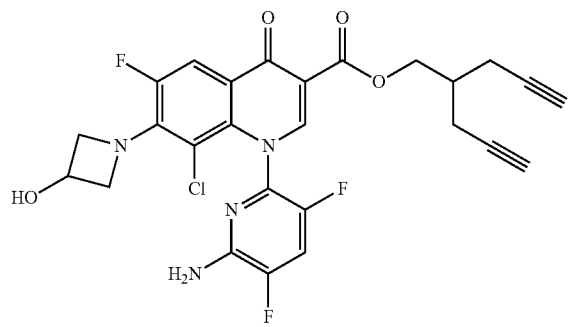 [SMILES: C#CCC(CC#C)COC(=O)c1cn(-c2nc(N)c(F)cc2F)c2c(Cl)c(N3CC(O)C3)c(F)cc2c1=O] |
| 98 | 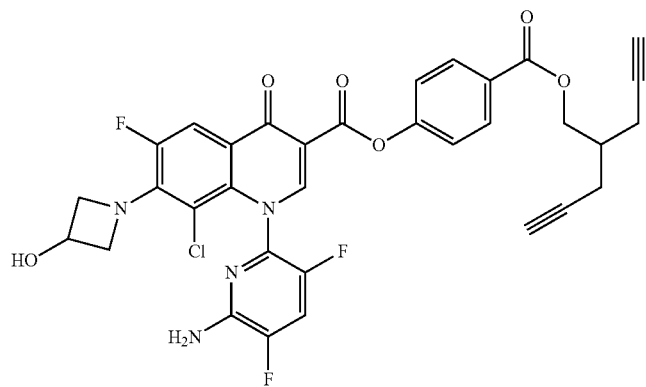 [SMILES: C#CCC(CC#C)COC(=O)c1ccc(OC(=O)c2cn(-c3nc(N)c(F)cc3F)c3c(Cl)c(N4CC(O)C4)c(F)cc3c2=O)cc1] |
| 99 | 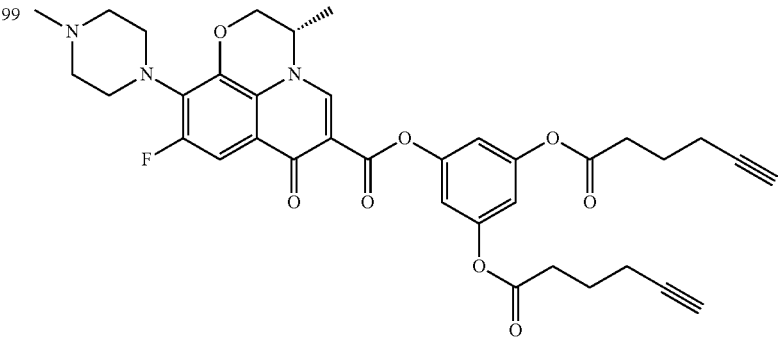 |
| 100 | 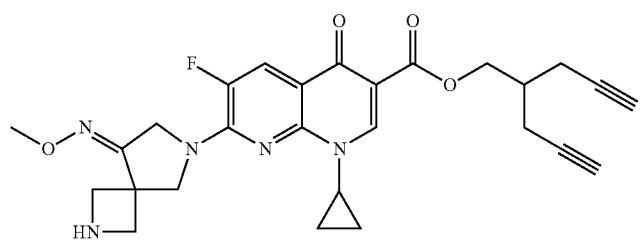 [SMILES: C#CCC(CC#C)COC(=O)c1cn(C2CC2)c2nc(N3C/C(=N/OC)C4(CNC4)C3)c(F)cc2c1=O] |

TABLE 7-continued

Prophetic Examples of MONOMER-BIOACTIVE AGENT CONJUGATES

| Ex | Structure |
|---|---|
| 101 | 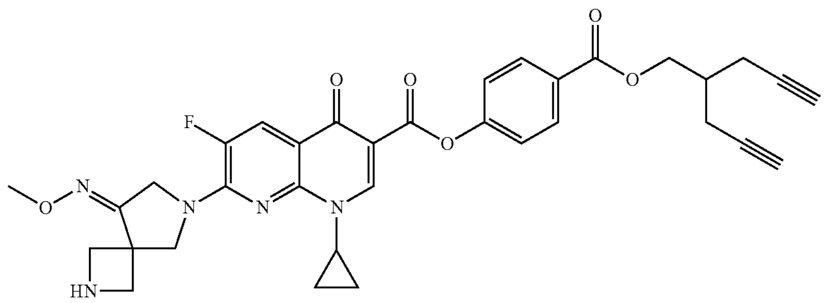 [SMILES: C#CCC(CC#C)COC(=O)c1ccc(OC(=O)c2cn(C3CC3)c3nc(N4C/C(=N/OC)C5(CNC5)C4)c(F)cc3c2=O)cc1] |

Preparation of Co-Monomers

Example 15

(S)-ethyl 2,6-bis(((3-azidopropoxy)carbonyl)amino)hexanoate was prepared in accordance with the procedure of Example 43 of International Publication WO2014/134689.

Example 16

Bis (3-azidopropyl) hexane-1,6-diyldicarbamate was prepared in accordance with the procedure of Example 44 of International Publication WO2014/134689.

Example 17: Synthesis of 4-Arm PEG$_{2000}$-Carbamate Tetraazide Co-Monomer

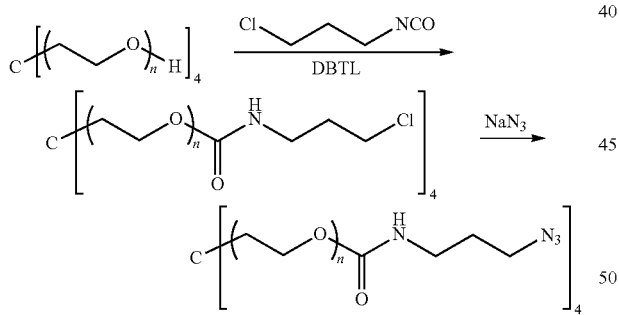

4-arm PEG$_{2000}$-OH (6 g, 3 mmol), dibutyltin dilaurate (0.19 g, 0.3 mmol) and dichloromethane (18 mL) were introduced in a RBF equipped with a septum and a magnetic bar. 3-chloropropyl isocyanate (2.15 g, 18.0 mmol) was added dropwise and the mixture was stirred during 24 h at room temperature. The solvent was evaporated and the product analysed by $^1$H NMR and MALDI-TOF spectroscopies.

4-arm PEG$_{2000}$-OCONH—C$_3$H$_6$—Br (4.56 g, 3.91 mmol), NaN$_3$ (10.2, 157 mmol) and DMF (120 mL) were introduced to a round-bottom flask. The solution was stirred during 48 h at 50° C. The solvent was evaporated, the mixture solubilised in EtOAc (50 mL) and filtered, washed with brine (25 mL), dried over NaSO$_4$ and the solvent removed under vacuum. The product was purified by flash chromatography (EtOAc:Hex=40:60 to 100:0 then Acetone 100).

Example 18

2-azido-N-(3-azidopropyl)acetamide was prepared in accordance with the procedure of Example 46 of International Publication WO2014/134689.

Example 19

(S)-ethyl 2,6-bis(((prop-2-yn-1-yloxy)carbonyl)amino)hexanoate was prepared in accordance with the procedure of Example 47 of International Publication WO2014/134689.

Example 20

PEG3000-dilysine diazide co-monomer was prepared in accordance with the procedure of Example 43 of International Publication WO2014/134689.

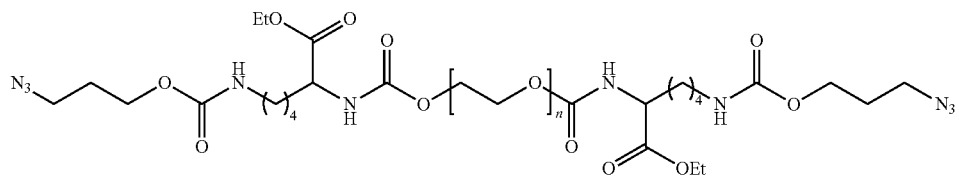

Example 21

PEG3000-dilysine dipropargyl co-monomer was prepared in accordance with the procedure of Example 49 of International Publication WO2014/134689.

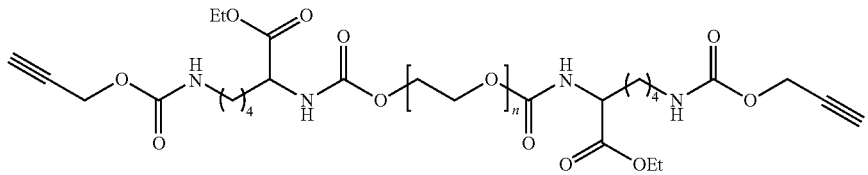

Example 22: Synthesis of 4-Arm PEG$_{2000}$-Ester Tetraazide Co-Monomer

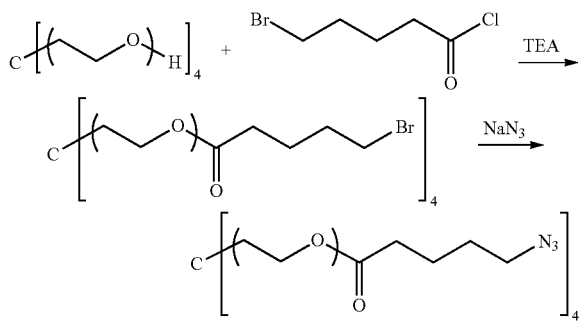

4-arm PEG$_{2000}$OH (5.0 g, 2.5 mmol), TEA (2.23 g, 3.1 ml, 22 mmol, 8.8 eq) and DCM (50 mL) were introduced to a round-bottom flask equipped with a stir bar and placed under nitrogen. The solution was stirred and cooled down to 0° C. Then, a mixture of 5-bromovaleryl chloride (3.99 g, 2.68 ml, 20.0 mmol, 8 eq) in 10 mL of DCM was added dropwise. The solution was stirred overnight and allowed to warm up to room temperature. After filtration, 30 mL of brine was added to the mixture and the aqueous phase was washed three times with DCM (3×100 ml). The organic phases were combined, dried over MgSO$_4$ and the solvent removed under vacuum. The product was purified by column chromatography (EtOAc:Hex=40:60 to 100:0, then acetone 100).

4-arm PEG$_{2000}$-Br, (4.36 g. 1.64 mmol), NaN$_3$ (4.27 g, 65.7 mmol and DMF (50 mL) were introduced to a round-bottom flask. The solution was stirred during 24 h at room temperature. The solvent was evaporated, the mixture solubilised in acetone and filtered. Then, acetone was evaporated, brine (50 mL) was added and the mixture was washed with ethyl acetate (3×50 mL). The organic phases were combined, dried over MgSO$_4$ and dried under vacuum.

Example 23: Synthesis of poly(ethylene glycol) bis(azide)$_{400}$

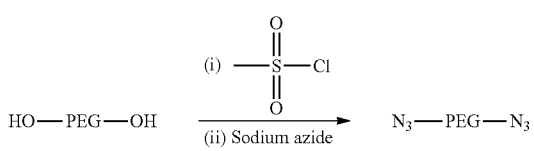

Poly(ethylene glycol)$_{400}$ (3.00 g, 7.50 mmol) was reacted with methanesulfonyl chloride (1.72 g, 15.0 mmol) and triethylamine (1.69 g, 16.7 mmol) in 25 mL anhydrous DCM at room T under argon atmosphere for 48 hours. The insoluble material was filtered off and the crude mixture was dried in vacuo to give the product as a white solid (3.92 g, 93.3%). The identity and purity were confirmed by $^1$H NMR spectrum and MALDI-ToF.

Poly(ethylene glycol) bis(methane sulfonate)$_{400}$ (3.90 g, 6.99 mmol) was reacted with sodium azide (4.54 g, 69.9 mmol) in 20 mL of DMF at 60° C. for 48 hour. Removal of the solid via filtration and drying of the solution in vacuo yield the desired product, poly(ethylene glycol) bis(azide)$_{400}$, as a yellow oil (1.59 g, 50.8%), which was confirmed via $^1$H NMR and MALDI-ToF.

Example 24: Synthesis of 3-(1,3-bis(pro-2-ynyloxy)propan-2-yloxy)prop-1-yne

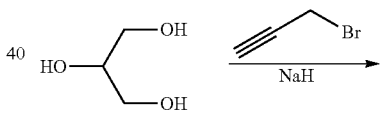

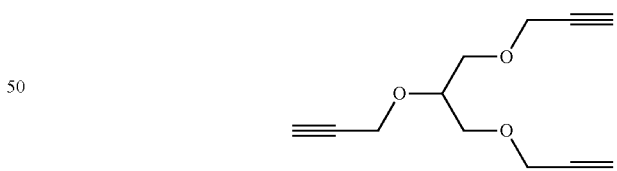

The trialkyne (3-(1,3-bis(pro-2-ynyloxy)propan-2-yloxy)prop-1-yne) was prepared by reacting glycerol (1.00 g, 10.9 mmol) with propylene bromide (4.43 g, 37.2 mmol) in the presence of sodium hydride (1.49 g, 37.2 mmol) in 15 mL of anhydrous DMF for 72 hours. The product was purified using column chromatography using 2:1 hexane:ethyl acetate solution and dried in vacuo to yield the desired product as clear yellow oil (0.123 g, 5.52%) and was confirmed via $^1$H NMR spectroscopy.

Example 25: Preparation of poly(ethyleneglycol) bis(4-((3S,4S)-(3,4-dimethoxy)azacyclooct-5-yn-1-yl)-4-oxobutanoate)

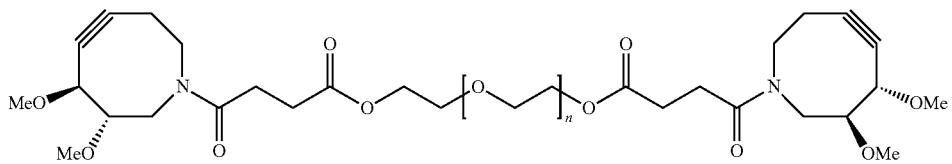

DCC (2.2 eq) can be added to a solution of a polyethylene glycol (1 eq), 4-((3S,4S)-(3,4-dimethoxy)azacyclooct-5-yn-1-yl)-4-oxobutanoic acid (2.5 eq) and DMAP (0.1 eq) in DCM. Precipitation of the crude material can provide the title compound poly(ethyleneglycol) bis(4-((3S,4S)-(3,4-dimethoxy)azacyclooct-5-yn-1-yl)-4-oxobutanoate).

Example 26: Preparation of (S)-ethyl 2,6-bis(((((1R,8S,9r)-1,8-dimethylbicyclo[6.1.0]non-4-yn-9-yl)methoxy)carbonyl)amino)hexanoate

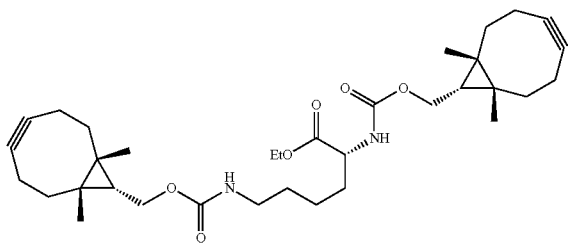 [SMILES: CCOC(=O)[C@@H](CCCCNC(=O)OC[C@@H]1[C@]2(C)CCC#CCC[C@]12C)NC(=O)OC[C@@H]1[C@]2(C)CCC#CCC[C@]12C]

A solution of (S)-ethyl 2,6-diisocyanatohexanoate (1 eq), ((1R,8S,9r)-1,8-dimethylbicyclo[6.1.0]non-4-yn-9-yl)methanol (2.2 eq) and dibutyltin dilaurate (catalytic, ~0.05 eq.) in anhydrous DCM can be reacted together. The solvent can be removed under reduced pressure and flash chromatography of the crude material can provide the title compound.

Example 27: Preparation of (S)-ethyl 2,6-bis((((1R,8S,9s)-bicyclo[6.1.0]non-4-yn-9-ylmethoxy)carbonyl)amino)hexanoate

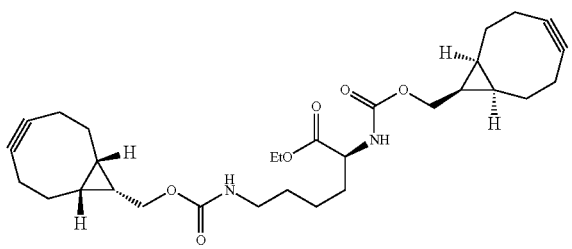 [SMILES: CCOC(=O)[C@H](CCCCNC(=O)OC[C@@H]1[C@@H]2CCC#CCC[C@@H]21)NC(=O)OC[C@@H]1[C@@H]2CCC#CCC[C@@H]21]

A solution of (S)-ethyl 2,6-diisocyanatohexanoate (1 eq), (1R,8S,9s)-bicyclo[6.1.0]non-4-yn-9-ylmethanol (2.2 eq) and dibutyltin dilaurate (catalytic, ~0.05 eq.) in anhydrous DCM can be reacted together. The solvent can be removed under reduced pressure and flash chromatography of the crude material can provide the title compound.

Preparation of Polymer-Bioactive Agent Conjugates

The polymer-bioactive agent conjugates of this invention may be prepared by the methods described below in the experimental procedures for representative conjugates as well as methods known to those skilled in the art, Method 1: Copper (Cu(II)) Catalysed Azide-Alkyne Cycloaddition (CuAAC) 'Click' Reaction (a) Polymer Conjugate Prepared With Dialkyne-Bioactive Agent Conjugate Monomer Preparation of Example 102

Example 77 (43.8 mg, 0.122 mmol, 1 eq), Example 23 (65.6 mg, 0.122, 1 eq) and sodium ascorbate (5.93 mg, 0.055 mmol, 045 eq) were placed into a 4 mL vial fitted with a stirrer bar and then sealed with a suba seal. 0.5 mL of anhydrous DMF pre-purged with $N_2$ was introduced into the vial and the mixture was stirred to form a clear solution under constant flow of $N_2$. 0.2 mL of $CuBr_2$ (4.07 mg, 0.018 mmol, 0.15 eq) and PMDETA (3.17 mg, 0.018 mmol, 0.15 eq) stock solution (20 mg/mL in DMF purged with $N_2$) was subsequently added into the reaction mixture and the solution was stirred for 24 hours at room T under constant flow of $N_2$. At the end of the reaction, the solution was diluted with 3 mL of THF and passed through a column of neutral alumina. The column was washed further with 10 mL of THF followed by 10 mL of DCM to collect the remaining polymers. The solution was then concentrated to around 1 mL and then precipitated into 40 mL of hexane to give clear greyish tacky oil upon drying in vacuo.

(b) Polymer Conjugate Prepared With Diazide-Bioactive Agent Conjugate Monomer.

The diazide-bioactive agent conjugate monomer (1 eq.) and a dialkyne co-monomer (1 eq.) are dissolved in the solvent of choice. The solution is purged with inert gas for 30 minutes before copper (II) bromide ($CuBr_2$) (0.05 mol eq.), PMDETA (0.05 mol eq.) and sodium ascorbate (0.15 mol eq.) are added into the solution. The heterogeneous mixture is stirred vigorously overnight at room temperature until complete consumption of starting materials, as indicated by TLC. The mixture is diluted with water and any precipitate that forms is collected. Purification of the product by precipitation from DMF and further purification on Sephadex LH-20 gives the title polymer-bioactive agent conjugate. The polymer-bioactive agent conjugates are analysed by IR, $^1$H NMR and $^{13}$C NMR and GPC (c) Polymer Conjugate Prepared With Dialkyne-Bioactive Agent Conjugate Monomer With Additives (Linear).

The dialkyne-bioactive agent conjugate monomer and diazide co-monomer 1 and diazide co-monomer 2 are dissolved in the solvent of choice, keeping an equimolar ratio between the number of alkyne units and azide units. The solution is purged with inert gas for 30 minutes before copper (II) bromide ($CuBr_2$) (005 mol eq.), PMDETA (0.05 mol eq.) and sodium ascorbate (0.15 mol eq.) are added into the solution. The heterogeneous mixture is stirred overnight under inert gas atmosphere and at room temperature for 24 hours. The reaction mixture is then passed through a column of basic alumina to remove the $CuBr_2$ catalyst, and then concentrated in vacuo before being precipitated several times in excess of diethyl ether to afford the desired polymer a solid. The polymer-bioactive agent conjugates are analysed by $^1H$ NMR and GPC.

(d) Polymer Conjugate Prepared With Two Different Dialkyne-Bioactive Agent Conjugate Monomers Preparation of Example 165

Example 2 (35.65 mg, 0.061 mmol, 0.5 eq), Example 77.01 (21.9 mg, 0.061 mmol, 0.5 eq), Example 23 (65.5 mg, 0.122 mmol, 1 eq) were placed into a 4 mL vial fitted with a stirrer bar and then sealed with a suba seal. 0.5 mL of anhydrous DMF pre-purged with $N_2$ was introduced into the vial and the mixture was stirred to form a clear solution under constant flow of $N_2$. 0.2 mL of $CuBr_2$ (4.07 mg, 0.018 mmol, 0.15 eq) and PMDETA (3.17 mg, 0.018 mmol, 0.15 eq) stock solution (20 mg/mL in DMF purged with $N_2$) was subsequently added into the reaction mixture and the solution was stirred for 24 hours at room T under constant flow of $N_2$. At the end of the reaction, the solution was diluted with 3 mL of THF and passed through a column of neutral alumina. The column was washed further with 10 mL of THF followed by 10 mL of DCM to collect the remaining polymers. The solution was then concentrated to around 1 mL and then precipitated into 40 mL of diethyl ether to give brownish tacky oil upon drying in vacuo.

(e) Polymer Conjugate Prepared With Alkyne-Azide-Bioactive Agent Conjugate Monomer (Drug Monomer Only)

The alkyne-azide bioactive agent conjugate monomer (1 eq.) is dissolved in the solvent of choice. The solution is purged with inert gas for 30 minutes before copper (II) bromide ($CuBr_2$) (0.05 mol eq.), PMDETA (0.05 mol eq.) and sodium ascorbate (0.15 mol eq.) are added into the solution. The heterogeneous mixture is stirred vigorously overnight until complete consumption of starting materials, as indicated by TLC. The mixture is diluted with water and any precipitate that forms is collected. Purification of the product by precipitation from DMF and further purification on Sephadex LH-20 gives the title polymer-bioactive agent conjugate. The polymer-bioactive agent conjugates are analysed by IR, $^1H$ NMR and $^{13}C$ NMR and GPC (f) Polymer Conjugate Prepared With Alkyne-Azide-Bioactive Agent Conjugate Monomer (and Co-Monomer)

The alkyne-azide-bioactive agent conjugate monomer (1 eq.) and an alkyne-azide co-monomer (1 eq.) are dissolved in the solvent of choice. The solution is purged with inert gas for 30 minutes before copper (11) bromide ($CuBr_2$) (0.05 mol eq.), PMDETA (0.05 mol eq.) and sodium ascorbate (0.15 mol eq.) are added into the solution. The heterogeneous mixture is stirred vigorously overnight until complete consumption of starting materials, as indicated by TLC. The mixture is diluted with water and any precipitate that forms is collected. Purification of the product by precipitation from DMF and further purification on Sephadex LH-20 gives the title polymer-bioactive agent conjugate. The polymer-bioactivea agent conjugates are analysed by IR, $^1H$ NMR and $^{13}C$ NMR and GPC.

(g) Polymer Conjugate Prepared With Dialkyne-Bioactive Conjugate Monomer and Cross Linker The dialkyne-bioactive agent conjugate monomer, a diazide co-monomer 1 and a trialkyne co-monomer monomer 2 are dissolved in solvent of choice, while keeping an overall equimolar ratio of alkyne to azide. The solution is purged with inert gas for 30 minutes before copper (II) bromide ($CuBr_2$) (0.05 mol eq.), PMDETA (0.05 mol eq.) and sodium ascorbate (0.15 mol eq.) are added into the solution. The heterogeneous mixture is stirred overnight under inert gas atmosphere and at room T for 24 hours. The reaction mixture is then passed through a column of basic alumina to remove the $CuBr_2$ catalyst, and then concentrated in vacuo before being precipitated several times in excess amount of DEE to afford the desired polymer as solids. The polymer-bioactive agent conjugates are analysed by $^1H$ NMR and GPC.

(h) Polymer Conjugate Prepared With Dialkyne-Bioactive Conjugate Monomer and Azide Monomer Cross Linker Preparation of Example 105

Example 77 (43.8 mg, 0.122 mmol, 1 eq), 4-arm $PEG_{2000}$-$N_3$ (121.9 mg, 0.061 mmol, 0.5 eq) and sodium ascorbate (5.93 mg, 0.055 mmol, 0.45 eq) were placed into a 4 mL vial fitted with a stirrer bar and then sealed with a suba seal. 0.5 mL of DMF pre-purged with $N_2$ was introduced into the vial and the mixture was stirred to form a clear solution under constant flow of $N_2$. 0.2 mL of $CuBr_2$ (4.07 mg, 0.018 mmol, 0.15 eq) and PMDETA (3.17 mg, 0.018 mmol, 0.15 eq) stock solution (20 mg/mL in DMF purged with $N_2$) was subsequently added into the reaction mixture and the solution was stirred at room T under constant flow of $N_2$ to form a gel within an hour. The gel was isolated and dialysed in acetonitrile (50 mL×4) to remove the copper and dried in vacuo to give dark coloured sticky gel.

Method 2: Copper (Cu(1)) Catalysed Azide-Alkyne Cycloaddition (CuAAC) 'Click' Reaction a) Polymer Conjugate Prepared With Dialkyne-Bioactive Agent Conjugate Monomer Preparation of Example 112

Example 11 (63.4 mg, 0.122 mmol, 1 eq), Example 23 (65.5 mg, 0.122 mmol, 1 eq) were placed into a 4 mL vial fitted with a stirrer bar and then sealed with a suba seal. 0.5 mL of toluene pre-purged with $N_2$ was introduced into the vial and the mixture was stirred to form a clear solution under constant flow of $N_2$. 0.2 mL of CuBr (2.62 mg, 0.018 mmol, 0.15 eq) and PMDETA (3.17 mg, 0.018 mmol, 0.15 eq) stock solution (20 mg/mL in toluene, stirred for 30 minutes under $N_2$ prior to use) was subsequently added into the reaction mixture and the solution was stirred for 24 hours at room T under constant flow of $N_2$. At the end of the reaction, the solution was diluted with 3 mL of THF and passed through a column of neutral alumina. The column was washed further with 10 mL of THF followed by 10 mL of DCM to ensure all polymer were collected. The solution was then concentrated to around 1 mL and then precipitated into 40 mL of diethyl ether to give clear yellowish tacky oil upon drying in vacuo.

b) Cross-Linked Click Polymer Conjugate Prepared With Dialkyne-Drug Conjugate Monomer and Cross-Linker Preparation of Example 114

Example 11 (63.4 mg, 0.122 mmol, 1 eq), C-(PEG-OCONH—$C_3H_6$—$N_3$)$_4$ (74.2 mg, 0.061 mmol, 0.5 eq) were placed into a 4 mL vial fitted with a stirrer bar and then sealed with a suba seal. 0.5 mL of toluene pre-purged with $N_2$ was introduced into the vial and the mixture was stirred to form a clear solution under constant flow of $N_2$. 0.2 mL of CuBr (2.62 mg, 0.018 mmol, 0.15 eq) and PMDETA (3.17 mg, 0.018 mmol, 0.15 eq) stock solution (20 mg/mL in toluene, stirred for 30 minutes under $N_2$ prior to use) was subsequently added into the reaction mixture and the solution was stirred at room T under constant flow of $N_2$ to form a gel within an hour. The gel was isolated and dialysed in acetonitrile (50 mL×4) to remove the copper and dried in vacuo to give off white brittle solid. Yield=78.6 mg.

c) Polymer Conjugate Prepared With Two Different Dialkyne-Bioactive Agent Conjugate Monomers Preparation of Example 164

Example 2 (35.65 mg, 0.061 mmol, 0.5 eq), Example 77 (21.9 mg, 0.061 mmol, 0.5 eq), Example 23 (65.5 mg, 0.122 mmol, 1 eq) were placed into a 4 mL vial fitted with a stirrer bar and then sealed with a suba seal. 0.5 mL of toluene pre-purged with $N_2$ was introduced into the vial and the mixture was stirred at 50° C. to form a clear solution under constant flow of $N_2$. 0.2 mL of CuBr (2.62 mg, 0.018 mmol, 0.15 eq) and PMDETA (3.17 mg, 0.018 mmol, 0.15 eq) stock solution (20 mg/mL in toluene, stirred for 30 minutes under $N_2$ prior to use) was subsequently added into the reaction mixture and the solution was stirred at 50° C. for 1 hour followed by stirring at room T for 23 hours, under constant flow of $N_2$. At the end of the reaction, the solution was diluted with 3 mL of THF and passed through a column of neutral alumina. The column was washed further with 10 mL of THF followed by 10 mL of DCM to ensure all polymer were collected. The solution was then concentrated to around 1 mL and then precipitated into 40 mL of diethyl ether to give greenish slightly tacky solid upon drying in vacuo.

Method 3: Ruthenium-Catalyzed Click Reaction

The 1,5 disubstituted 1,2,3 triazole containing polymers can be formed using a procedure described in Zhang et al. *J. Am. Chem. Soc.*, 2005, 127 (46), pp 15998-15999, (a) Polymer Conjugate Prepared With Dialkyne-Bioactive Agent Conjugate Monomer The dialkyne-bioactive agent conjugate monomer (1 eq.), a diazide co-monomer (1 eq.) and Cp*RuCl(PPh$_3$)$_2$ is dissolved in the solvent of choice (benzene, THF DMF or dioxane) and allowed to stir at 60-80° C. until reaction is complete. Progress of the reaction is monitored by $^1$H NMR or TLC. The mixture is diluted with water and any precipitate that forms is collected. Purification of the product by precipitation from diethyl ether and further purification on Sephadex LH-20 gives the title polymer-bioactive agent conjugate. The polymer-bioactive agent conjugates are analysed by IR, $^1$H NMR and $^{13}$C NMR and GPC.

(b) Polymer Conjugate Prepared With Diazide-Bioactive Agent Conjugate Monomer

The diazide-bioactive agent conjugate monomer (1 eq.) and a dialkyne co-monomer (1 eq.) and Cp*RuCl(PPh$_3$)$_2$ are dissolved in the solvent of choice (benzene, THF, DMF or dioxane) and allowed to stir at 60-80° C. until reaction is complete. Progress of the reaction is monitored by $^1$H NMR or TLC. The mixture is diluted with water and any precipitate that forms is collected. Purification of the product by precipitation from diethyl ether and further purification on Sephadex LH-20 gives the title polymer-bioactive agent conjugate. The polymer-bioactive agent conjugates are analysed by IR, $^1$H NMR and $^{13}$C NMR and GPC.

(c) Polymer Conjugate Prepared With Azide-Alkyne-Bioactive Agent Conjugate Monomer The azide-alkyne-bioactive agent conjugate monomer and Cp*RuCl(PPh$_3$)$_2$ are dissolved in the solvent of choice (benzene, THF DMF or dioxane) and allowed to stir at 60-80° C. until reaction is complete. Progress of the reaction is monitored by $^1$H NMR or TLC. The mixture is diluted with water and any precipitate that forms is collected. Purification of the product by precipitation from diethyl ether and further purification on Sephadex LH-20 gives the title polymer-bioactive agent conjugate. The polymer-bioactive agent conjugates are analysed by IR, $^1$H NMR and $^{13}$C NMR and GPC.

(d) Polymer Conjugate Prepared With Dialkyne-Bioactive Agent Conjugate Monomer

The dialkyne-bioactive agent conjugate monomer (1 eq.), a diazide co-monomer (1 eq.) and Cp*RuCl(PPh$_3$)$_2$ is dissolved in the solvent of choice (benzene, THF DMF or dioxane) and allowed to stir at 60-80° C. until reaction is complete. The mixture is diluted with water and any precipitate that forms is collected. Purification of the product by precipitation from diethyl ether and further purification on Sephadex LH-20 gives the title polymer-bioactive agent conjugate.

Method 4: Strain Promoted Azide Alkyne Cycloaddition a) Polymer Conjugate Prepared With Dicycloalkyne-Bioactive Agent Conjugate Monomer and Diazide Co Monomer The dicycloalkyne-bioactive agent conjugate monomer substrate and the diazide monomer substrate can be dissolved separately in a solvent (CH$_3$CN or DMF) and mixed in a 1:1 ratio. The reaction mixture can be stirred for 12 h at room temperature. The mixture may be diluted with water and any precipitate that forms collected. Purification of the product by precipitation from DMF and diethyl ether and further purification on Sephadex LH-20 will give the title polymer-bioactive agent conjugate.

b) Polymer Conjugate Prepared With Diazide-Bioactive Agent Conjugate Monomer and Dialkyne (Cyclooctyne) Co-Monomer A diazide-bioactive agent conjugate monomer and a dicycloalkyne co-monomer can be dissolved separately in solvent (CH$_3$CN or DMF) and reacted using the same procedure as described for Method 4 a)

Using the above methods the polymers in Table 8 were prepared.

Method 5: Post Polymerisation Deprotection

Polymers prepared using any of the methods described above from bioactive agent monomer conjugates that contain a protecting group can have the protecting group removed post-polymersiation.

Preparation of Example 131

To a solution of Example 131 (72.0 mg) in CH$_2$Cl$_2$ (3.0 mL) was added TFA (1.00 mL, 13.1 mmol) dropwise. The mixture was stirred at rt for 2 h before the mixture was concentrated under reduced pressure and dried under vacuum overnight to give Example 169 (94.7 mg).

Using this method the polymers in Table 9 were prepared.

TABLE 8

Examples of Click Polymers

| Example | Drug | Drug-monomer 1 mmol (mg) | Co-Monomer 1 mmol (mg) | Co-Monomer 2 mmol (mg) | Production Method (solvent) | Characterisation |
|---|---|---|---|---|---|---|
| 28 | LVX | Example 3 (124) | Example 15 (80.1) | — | DMF, Cu(II) Click. | Mn = 5.83 kDa, Mw = 7.23 kDa PDI = 1.24 |
| 29 | LVX | Example 3 (124) | Example 15 (80.1) | — | DMF, Cu(II) Click. | Mn = 5.46 kDa, Mw = 7.04 kDa PDI = 1.29 |
| 30 | LVX | Example 3 (144) | Example 15 (120) | Example 24 (0.5) | DMF, Cu(II) Click. | Mn = 6.85 kDa, Mw = 8.50 kDa PDI = 1.24 |
| 31 | LVX | Example 3 (114) | Example 15 (120) | Example 24 (16.1) | DMF, Cu(II) Click. | Mn = 10.1 kDa, Mw = 16.8 kDa PDI = 1.66 |
| 32 | LVX | Example 3 (74.8) | Example 15 (120) | Example 24 (24.7) | DMF, Cu(II) Click | Mn = 29.4 kDa, Mw = 69.6 kDa PDI = 2.37 |
| 33 | LVX | Example 3 (124.7) | Example 16 (74) | — | DMF Cu(II) Click | |
| 34 | DCF | Example 13 (60) | Example 23 (54.3) | — | Toluene Cu(I) click | Mn = 3.93 kDa, Mw = 6.81 kDa PDI = 1.73 |
| 35 | DCF | Example 10 (51) | Example 23 (40.9) | — | Toluene Cu(I) click | Mn = 16.6 kDa, Mw = 42.4 kDa PDI = 2.55 |
| 36 | DCF | Example 10 (60) | $(N_3-PEG_{500})_4-C$ (94.4) | — | Toluene Cu(I) click | N/A Cross-linked |
| 37 | DCF | Example 13 (60) | $(N_3-PEG_{500})_4-C$ (106.5) | — | Toluene Cu(I) click | N/A Cross-linked |
| 38 | LVX | Example 2 0.127 (75.0) | $(N_3-PEG_{500})_4-C$ 0.0634 (129.8) | — | DMF, Cu(II) Click. | N/A Cross-linked |
| 39 | LVX | Example 2 0.127 (75.0) | Example 22 0.0634 (159.4) | — | DMF, Cu(II) Click. | N/A Cross-linked |
| 40 | LVX | Example 2 0.127 (75.0) | Example 23 0.127 (69.3) | — | DMF, Cu(II) Click. | Mn = 5.5 kDa, Mw = 11.6 kDa PDI = 2.10 |
| 41 | LVX | Example 1 0.127 (89.0) | $(N_3-PEG_{500})_4-C$ 0.0634 (126.1) | — | DMF, Cu(II) Click. | N/A Cross-linked |
| 42 | LVX | Example 1 0.127 (90.8) | Example 22 0.0634 (165.7) | — | DMF, Cu(II) Click. | N/A Cross-linked |
| 43 | LVX | Example 1 0.127 (88.9) | Example 23 0.127 (69.3) | — | DMF, Cu(II) Click. | Mn = 7.3 kDa, Mw = 12.5 kDa PDI = 1.71 |
| 102 | KET | Example 77 0.122 (43.8) | Example 23 0.122 (65.6) | — | DMF, Cu(II) Click | Mn = 5.04 kDa, Mw = 10.6 kDa PDI = 2.11 |
| 103 | IBU | Example 79 0.122 (37.8) | Example 23 0.122 (65.6) | — | DMF, Cu(II) Click | Mn = 4.14 kDa, Mw = 10.7 kDa PDI = 2.59 |
| 104 | IND | Example 78 0.122 (54.6) | Example 23 0.122 (65.6) | — | DMF, Cu(II) Click | Mn = 4.49 kDa, Mw = 11.5 kDa PDI = 2.57 |
| 105 | KET | Example 77 0.122 (43.8) | $(N_3-PEG_{500})_4-C$ 0.061 (121.9) | — | DMF, Cu(II) Click | N/A Cross-linked |
| 106 | IBU | Example 79 0.122 (37.8) | $(N_3-PEG_{500})_4-C$ 0.061 (121.9) | — | DMF, Cu(II) Click | N/A Cross-linked |
| 107 | IND | Example 78 0.122 (54.6) | $(N_3-PEG_{500})_4-C$ 0.061 (121.9) | — | DMF, Cu(II) Click | N/A Cross-linked |
| 108 | DCF | Example 76 0.122 (48.8) | Example 23 0.122 (65.6) | — | DMF, Cu(II) Click | Mn = 4.35 kDa, Mw = 11.6 kDa PDI = 2.67 |
| 109 | DCF | Example 760.122 (48.8) | $(N_3-PEG_{500})_4-C$ 0.061 (121.9) | — | DMF, Cu(II) Click | N/A Cross-linked |
| 110 | DCF | Example 11 0.122 (63.5) | $(N_3-PEG_{500})_4-C$ 0.061 (121.9) | — | DMF, Cu(II) Click | N/A Cross-linked |
| 111 | DCF | Example 11 0.122 (63.5) | Example 22 0.061 (143.3) | — | DMF, Cu(II) Click | N/A Cross-linked |
| 112 | DCF | Example 11 0.122 (63.5) | Example 23 0.122 (65.6) | — | Toluene, Cu(I) Click | Mn = 5.15 kDa, Mw = 6.89 kDa PDI = 1.34 |
| 113 | DCF | Example 11 0.122 (63.5) | $ELDN_3$ 0.122 (52.2) | — | Toluene, Cu(I) Click | Mn = 7.46 kDa, Mw = 12.1 kDa PDI = 1.61 |
| 114 | DCF | Example 11 0.122 (63.5) | $C-(PEG-OCONH-C_3H_6-N_3)_4$ 0.061 (74.2) | — | Toluene, Cu(I) Click | N/A Cross-linked |

TABLE 8-continued

Examples of Click Polymers

| Example | Drug | Drug-monomer 1 mmol (mg) | Co-Monomer 1 mmol (mg) | Co-Monomer 2 mmol (mg) | Production Method (solvent) | Characterisation |
|---|---|---|---|---|---|---|
| 115 | DCF | Example 11 0.122 (63.5) | C—(PEG$_{500}$—NHCO—C$_2$H$_4$—N$_3$)$_4$— 0.061 (148.4) | — | Toluene, Cu(I) Click | N/A Cross-linked |
| 116 | KET | Example 77 0.122 (43.8) | (N$_3$—PEG$_{500}$)$_4$—C 0.061 (121.9) | — | Toluene, Cu(I) Click | N/A Cross-linked |
| 117 | DCF | Example 11 0.061 (31.6) | C—(PEG—OCONH—C$_3$H$_6$—N$_3$)$_4$ 0.030 (37.0) | — | DMF, Cu(II) Click | N/A Cross-linked |
| 118 | DCF | Example 14 0.122 (59.5) | (N$_3$—PEG$_{500}$)$_4$—C 0.061 (121.9) | — | DMF, Cu(II) Click | N/A Cross-linked |
| 119 | KET | Example 82 0.122 (72.4) | (N$_3$—PEG$_{500}$)$_4$—C 0.061 (121.9) | — | DMF, Cu(II) Click | N/A Cross-linked |
| 120 | IBU | Example 83 0.122 (66.5) | (N$_3$—PEG$_{500}$)$_4$—C 0.061 (121.9) | — | DMF, Cu(II) Click | N/A Cross-linked |
| 121 | IND | Example 84 0.122 (84.9) | (N$_3$—PEG$_{500}$)$_4$—C 0.061 (121.9) | — | DMF, Cu(II) Click | N/A Cross-linked |
| 122 | KET | Example 81 0.090 (41.8) | (N$_3$—PEG$_{500}$)$_4$—C 0.045 (89.9) | — | DMF, Cu(II) Click | N/A Cross-linked |
| 123 | KET | Example 81 0.090 (41.8) | C—(PEG$_{500}$—NHCO—C$_2$H$_4$—N$_3$)$_4$— 0.045 (109.6) | — | DMF, Cu(II) Click | N/A Cross-linked |
| 124 | IBU | Example 83 0.090 (49.0) | Example 23 0.090 (48.3) | — | DMF, Cu(II) Click | Mn = 11.7 kDa, Mw = 16.4 kDa PDI = 1.41 |
| 125 | IND | Example 84 0.090 (62.6) | Example 23 0.090 (48.3) | — | DMF, Cu(II) Click | Mn = 7.98 kDa, Mw = 12.9 kDa PDI = 1.62 |
| 126 | DCF | Example 14 0.122 (59.5) | Example 23 0.122 (65.5) | — | Toluene, Cu(I) Click | Mn = 11.5 kDa, Mw = 20.1 kDa PDI = 3.22 |
| 127 | KET | Example 82 0.122 (72.4) | Example 23 0.122 (65.5) | — | Toluene, Cu(I) Click | Mn = 1.90 kDa, Mw = 9.30 kDa PDI = 4.88 |
| 128 | KET | Example 81 0.122 (56.7) | Example 23 0.122 (65.5) | — | Toluene, Cu(I) Click | Mn = 2.77 kDa, Mw = 8.92 kDa PDI = 3.22 |
| 129 | Boc-MOX | Example 50 0.122 (73.9) | Example 23 0.122 (65.5) | — | DMF, Cu(II) Click | Mn = 6.01 kDa, Mw = 11.5 kDa PDI = 1.91 |
| 130 | Boc-MOX | Example 5 0.122 (102.5) | Example 23 0.122 (65.5) | — | DMF, Cu(II) Click | Mn = 6.67 kDa, Mw = 10.2 kDa PDI = 1.55 |
| 131 | Boc-MOX | Example 7 0.122 (88.5) | Example 23 0.122 (65.5) | — | DMF, Cu(II) Click | Mn = 6.67 kDa, Mw = 13.8kDa PDI = 2.07 |
| 132 | Boc-MOX | Example 48 0.122 (76.7) | Example 23 0.122 (65.5) | — | DMF, Cu(II) Click | Mn = 5.93 kDa, Mw = 9.82 kDa PDI = 1.65 |
| 133 | GATI | Example 61 0.122 (83.1) | Example 23 0.122 (65.5) | — | DMF, Cu(II) Click | Mn = 9.48 kDa, Mw = 27.0 kDa PDI = 2.85 |
| 134 | BESI | Example 63 0.122 (85.4) | Example 23 0.122 (65.5) | — | DMF, Cu(II) Click | Mn = 5.97 kDa, Mw = 16.1 kDa PDI = 2.70 |
| 135 | BESI | Example 55 0.122 (103.3) | Example 23 0.122 (65.5) | — | DMF, Cu(II) Click | Mn = 10.5 kDa, Mw = 28.8 kDa PDI = 2.74 |
| 136 | GATI | Example 61 0.122 (83.1) | (N$_3$—PEG$_{500}$)$_4$—C 0.061 (121.9) | — | DMF, Cu(II) Click | N/A Cross-linked |
| 137 | BESI | Example 63 0.122 (85.4) | (N$_3$—PEG$_{500}$)$_4$—C 0.061 (121.9) | — | DMF, Cu(II) Click | N/A Cross-linked |
| 138 | BESI | Example 55 0.122 (103.3) | (N$_3$—PEG$_{500}$)$_4$—C 0.061 (121.9) | — | DMF, Cu(II) Click | N/A Cross-linked |
| 139 | BROM | Example 80 0.122 (53.4) | Example 23 0.122 (65.5) | — | Toluene, Cu(I) Click | Mn = 12.9 kDa, Mw = 43.0 kDa PDI = 3.32 |
| 140 | Boc-MOX | Example 50 0.122 (73.9) | (N$_3$—PEG$_{500}$)$_4$—C 0.061 (121.9) | — | DMF, Cu(II) Click | N/A Cross-linked |
| 141 | Boc-MOX | Example 5 0.122 (102.5) | (N$_3$—PEG$_{500}$)$_4$—C 0.061 (121.9) | — | DMF, Cu(II) Click | N/A Cross-linked |
| 142 | Boc-MOX | Example 7 0.122 (88.5) | (N$_3$—PEG$_{500}$)$_4$—C 0.061 (121.9) | — | DMF, Cu(II) Click | N/A Cross-linked |
| 143 | Boc-MOX | Example 48 0.122 (76.7) | (N$_3$—PEG$_{500}$)$_4$—C 0.061 (121.9) | — | DMF, Cu(II) Click | N/A Cross-linked |
| 144 | LVX | Example 4 0.122 (71.4) | (N$_3$—PEG$_{500}$)$_4$—C 0.061 (121.9) | — | DMF, Cu(II) Click | N/A Cross-linked |

TABLE 8-continued

Examples of Click Polymers

| Example | Drug | Drug-monomer 1 mmol (mg) | Co-Monomer 1 mmol (mg) | Co-Monomer 2 mmol (mg) | Production Method (solvent) | Characterisation |
|---|---|---|---|---|---|---|
| 145 | GATI | Example 57 0.122 (87.0) | (N$_3$—PEG$_{500}$—)$_4$—C 0.061 (121.9) | — | DMF, Cu(II) Click | N/A Cross-linked |
| 146 | Boc-CIPRO | Example 66 0.122 (94.0) | (N$_3$—PEG$_{500}$—)$_4$—C 0.061 (121.9) | — | DMF, Cu(II) Click | N/A Cross-linked |
| 147 | LVX | Example 4 0.122 (71.4) | Example 23 0.122 (65.5) | — | DMF, Cu(II) Click | Mn = 7.31 kDa, Mw = 18.7 kDa PDI = 2.56 |
| 148 | MOX | Example 51 0.122 (75.5) | Example 23 0.122 (65.5) | — | DMF, Cu(II) Click | Mn = 5.43 kDa, Mw = 32.0 kDa PDI = 5.89 |
| 149 | GATI | Example 57 0.122 (87.0) | Example 23 0.122 (65.5) | — | DMF, Cu(II) Click | Mn = 4.47 kDa, Mw = 10.0 kDa PDI = 2.24 |
| 150 | Boc-CIPRO | Example 68 0.122 (65.3) | Example 23 0.122 (65.5) | — | DMF, Cu(II) Click | Mn = 6.34 kDa, Mw = 12.1 kDa PDI = 1.91 |
| 151 | Boc CIPRO | Example 64 0.122 (79.9) | Example 23 0.122 (65.5) | — | DMF, Cu(II) Click | Mn = 5.69 kDa, Mw = 11.3 kDa PDI = 1.99 |
| 152 | Boc-GATI | Example 56 0.122 (85.3) | Example 23 0.122 (65.5) | — | DMF, Cu(II) Click | Mn = 7.36 kDa, Mw = 13.1 kDa PDI = 1.77 |
| 153 | KET | Example 86 0.122 (58.4) | Example 23 0.122 (65.5) | — | Toluene, Cu(I) Click | Mn = 18.2 kDa, Mw = 96.1 kDa PDI = 5.28 |
| 154 | DCF | Example 85 0.122 (63.4) | Example 23 0.122 (65.5) | — | Toluene, Cu(I) Click | Mn = 12.2 kDa, Mw = 22.7 kDa PDI = 1.85 |
| 155 | LVX | Example 72 0.122 (71.4) | Example 23 0.122 (65.5) | — | DMF, Cu(II) Click | Mn = 4.76 kDa, Mw = 10.7 kDa PDI = 2.25 |
| 156 | MOX | Example 6 0.135 (100.0) | (N$_3$—PEG$_{500}$—)$_4$—C 0.0675 (135.0) | | DMF, Cu(II) Click | N/A Cross-linked |
| 157 | MOX | Example 45 0.122 (94.0) | Example 23 0.122 (65.6) | | DMF, Cu(II) Click | Mn = 8.9 kDa, Mw = 24.7 kDa PDI = 2.77 |
| 158 | MOX | Example 45 0.122 (94.0) | (N$_3$—PEG$_{500}$—)$_4$—C 0.0611 (122.2) | | DMF, Cu(II) Click | N/A Cross-linked |
| 159 | Boc-MOX | Example 44 0.122 (113.3) | Example 23 0.122 (65.6) | | DMF, Cu(II) Click | Mn = 7.9 kDa, Mw = 13.7 kDa PDI = 1.73 |
| 160 | Boc-MOX | Example 44 0.122 (113.3) | (N$_3$—PEG$_{500}$—)$_4$—C 0.0611 (122.2) | | DMF, Cu(II) Click | N/A Cross-linked |
| 161 | Boc-MOX | Example 46 0.122 (106.5) | (N$_3$—PEG$_{500}$—)$_4$—C 0.0611 (122.2) | | DMF, Cu(II) Click | N/A Cross-linked |
| 162 | MOX | Example 8 0.165 (103.0) | Example 22 0.0823 (184.1) | | DMF, Cu(II) Click | N/A Cross-linked |
| 163 | MOX | Example 8 0.1493 (93.4) | (N$_3$—PEG$_{500}$—)$_4$—C 0.0746 (149.2) | | DMF, Cu(II) Click | N/A Cross-linked |
| 164 | LVX + KET | Example 2 0.061 (35.7) | Example 77 0.061 (21.9) | N$_3$—PEG$_{400}$—N$_3$ 0.122 (65.5) | Toluene, Cu(I) Click | Mn = 16.2 kDa, Mw = 57.8 kDa PDI = 3.57 |
| 165 | LVX + KET | Example 2 0.061 (35.7) | Example 77 0.061 (21.9) | N$_3$—PEG$_{400}$—N$_3$ 0.122 (65.5) | DMF, Cu(II) Click | Mn = 4.21 kDa, Mw = 11.0 kDa PDI = 2.33 |
| 166 | LVX + DCF | Example 2 0.061 (35.7) | Example 11 0.061 (31.7) | N$_3$—PEG$_{400}$—N$_3$ 0.122 (65.5) | Toluene, Cu(I) Click | Mn = 13.7 kDa, Mw = 31.8 kDa PDI = 2.33 |

TABLE 9

Examples of Click Polymers: Post polymerisation deprotection

| Ex. No | Drug | Starting polymer | Amount |
|---|---|---|---|
| 167 | Moxifloxacin | Example 129 | 43.6 |
| 168 | Moxifloxacin | Example 130 | 66.5 |
| 169 | Moxifloxacin | Example 131 | 94.7 |
| 170 | Moxifloxacin | Example 132 | 67.7 |
| 171 | Ciprofloxacin | Example 150 | 141.3 |
| 172 | Ciprofloxacin | Example 151 | 119.6 |
| 173 | Gatifloxacin | Example 152 | 128.7 |

Using the above methods the polymers shown in Table ZZ may also be prepared.

TABLE 10

| Ex. No | Drug | Drug-monomer conjugate | Drug-monomer conjugate 2 | Co-Monomer 1 | Co-Monomer 2 | Method of Synthesis (solvent) |
|---|---|---|---|---|---|---|
| 174 | MOX | Example 8 | — | $N_3$—$CH(CH_3)$—OCO—$PEG_{400}$—OCO—$CH(CH_3)$—$N_3$ | — | Click, DMF or ACN |
| 175 | MOX | Example 6 | — | Example 23 | Example 15 | Click, DMF or ACN |
| 176 | MOX | Example 6 | — | Example 23 | — | Click, DMF or ACN |
| 177 | MOX | Example 8 | — | $N_3$—$CH(CH_3)$—OCO—$PEG_{400}$—OCO—$CH(CH_3)$—$N_3$ | — | Click, DMF or ACN |
| 178 | MOX | Example 8 | — | $C_2H_5$—C—[PEG—OCO—$CH(CH_3)$—$N_3$]$_3$ | Example 15 | Click, DMF or ACN |
| 179 | MOX | Example 6 | — | $C_2H_5$—C—(PEG—$N_3$)$_3$ | — | Click, DMF or ACN |
| 180 | MOX | Example 6 | — | $C_2H_5$—C—(PEG—$N_3$)$_3$ | Example 15 | Click, DMF or ACN |
| 181 | MOX | Example 8 | — | C—[PEG—OCO—$CH(CH_3)$—$N_3$]$_4$ | — | Click, DMF or ACN |
| 182 | LVX | Example 9 | — | $N_3$—$CH(CH_3)$—OCO—$PEG_{400}$—OCO—$CH(CH_3)$—$N_3$ | — | Click, DMF or ACN |
| 183 | LVX | Example 9 | — | $C_2H_5$—C—[PEG—OCO—$CH(CH_3)$—$N_3$]$_3$ | — | Click, DMF or ACN |
| 184 | LVX | Example 9 | — | C—[PEG—OCOO—$C_3H_6$—$N_3$]$_4$ | — | Click, DMF or ACN |
| 185 | DCF | Example 14 | — | $N_3$—$CH(CH_3)$—OCO—$PEG_{400}$—OCO—$CH(CH_3)$—$N_3$ | — | Click, Toluene |
| 186 | DCF | Example 14 | — | $C_2H_5$—C—[PEG—OCO—$CH(CH_3)$—$N_3$]$_3$ | — | Click, Toluene |
| 187 | DCF | Example 14 | — | C—[PEG—OCOO—$C_3H_6$—$N_3$]$_4$ | — | Click, Toluene |
| 188 | LVX + DCF | Example 2 | Example 10 | C—[PEG—OCOO—$C_3H_6$—$N_3$]$_4$ | — | Click, Toluene |
| 189 | MOX + DCF | Example 6 | Example 10 | C—[PEG—OCOO—$C_3H_6$—$N_3$]$_4$ | — | Click, Toluene |
| 190 | MOX + DCF | Example 8 | Example 10 | Example 23 | — | Click, Toluene |
| 191 | LVX + DCF | Example 9 | Example 14 | C—[PEG—OCOO—$C_3H_6$—$N_3$]$_4$ | — | Click, Toluene |
| 192 | BESI | Example 53 | — | Example 23 | — | Click, DMF |
| 193 | BESI | Example 53 | — | C—(PEG—$N_3$)$_4$ | — | Click, DMF |
| 194 | BESI | Example 74 | — | Example 23 | — | Click, DMF |
| 195 | BESI | Example 74 | — | C—(PEG—$N_3$)$_4$ | — | Click, DMF |
| 196 | GATI | Example 71 | — | Example 23 | — | Click, DMF |
| 197 | GATI | Example 71 | — | C—(PEG—$N_3$)$_4$ | — | Click, DMF |
| 198 | GATI | Example 59 | — | Example 23 | — | Click, DMF |
| 199 | GATI | Example 59 | — | C—(PEG—$N_3$)$_4$ | — | Click, DMF |
| 200 | CIPRO | Example 69 | — | Example 23 | — | Click, DMF |
| 201 | CIPRO | Example 69 | — | C—(PEG—$N_3$)$_4$ | — | Click, DMF |
| 202 | CIPRO | Example 65 | — | Example 23 | — | Click, DMF |
| 203 | CIPRO | Example 65 | — | C—(PEG—$N_3$)$_4$ | — | Click, DMF |
| 204 | CIPRO | Example 89 | — | Example 23 | — | Click, DMF |
| 205 | CIPRO | Example 89 | — | C—(PEG—$N_3$)$_4$ | — | Click, DMF |

TABLE 10-continued

| Ex. No | Drug | Drug-monomer conjugate | Drug-monomer conjugate 2 | Co-Monomer 1 | Co-Monomer 2 | Method of Synthesis (solvent) |
|---|---|---|---|---|---|---|
| 206 | CIPRO | Example 67 | | Example 23 | — | Click, DMF |
| 207 | CIPRO | Example 67 | | C—(PEG—N$_3$)$_4$ | — | Click, DMF |
| 208 | KET | Example 75 | | Example 23 | | Click, DMF |
| 209 | KET | Example 75 | | C—(PEG—N$_3$)$_4$ | | Click, DMF |
| 210 | BROM | Example 91 | | Example 23 | | Click, Toluene |
| 211 | BROM | Example 91 | | C—(PEG—N$_3$)$_4$ | | Click, Toluene |
| 212 | BROM | Example 87 | | Example 23 | | Click, Toluene |
| 213 | BROM | Example 87 | | C—(PEG—N$_3$)$_4$ | | Click, Toluene |
| 214 | BROM | Example 80 | | C—(PEG—N$_3$)$_4$ | | Click, Toluene |
| 215 | BROM | Example 95 | | Example 23 | | Click, Toluene |
| 216 | BROM | Example 95 | | C—(PEG—N$_3$)$_4$ | | Click, Toluene |

Drug Release Method

Polymers were tested for in vitro drug release following guidelines recommended by the International Organisation of Standardisation. The samples were suspended on a wire mesh, immersed in 0.067 M isotonic phosphate buffer (IPB) pH 7.4 and incubated at 37° C. with continuous stirring.

Aliquots of the receptor solution were collected for HPLC analysis at predetermined time points and replaced with an equal volume of IPB. The experimental endpoint was reached when cumulative amount of bioactive drug released remained unchanged (within a margin of error) for at least three time points.

Quantification of Release Products and Impurities

The amount of bioactive drug measured from the samples during drug release was quantified by reverse phase high performance liquid chromatography (HPLC) with a UV absorbance detector. Several assays were developed for HPLC analysis. The chromatographic conditions and detection wavelength used are outlined in Table 11 below.

TABLE 11

Summary of HPLC assay conditions used in the quantification of drug release from drug polymer conjugates. The retention time of the drug is also specified for each analytical method.

| Assay | Column | Mobile Phase | Flow rate (mL/min) | Wavelength (nm) | Retention time of APIs (min) |
|---|---|---|---|---|---|
| 1) LVX | Phenomenex Kinetex EVO C18 Column 150 × 4.6 mm; 5 μm, 100 Å | Acetonitrile:50 mM phosphate buffer pH 2.5 17:83 | 1.0 | 290 | 2.25 |
| 2) MOX | Phenomenex Kinetex EVO C18 Column 150 × 4.6 mm; 5 μm, 100 Å | Mobile phase A Acetonitrile:water:triethylamine 15:85:06 pH 2.5 Mobile phase B Acetonitrile:water:triethylamine 70:30:06 pH 2.5 | 1.0 | 295 | 2.66 |
| 3) DCF | Waters Symmetry ® C18 150 × 3.9 mm; 5 μm, 100 Å | Acetonitrile:Water:Acetic Acid 57:43:1 | 1.0 | 275 | 5.15 |
| 4) BESI, GATI, Boc-MOX, CIPRO | Phenomenex Kinetex EVO C18 Column 150 × 4.6 mm; 5 μm, 100 Å | Mobile phase A Acetonitrile:water:triethylamine 15:85:06 pH 2.5 Mobile phase B Acetonitrile:water:triethylamine 70:30:06 pH 2.5 | 1.0 | Besi: 297 Gati: 297 Boc-Mox: 295 Cipro: 297 | Besi: 8.50 Gati: 3.50 Boc-Mox 14.7 Cipro: 2.40 |

TABLE 11-continued

Summary of HPLC assay conditions used in the quantification of drug release from drug polymer conjugates. The retention time of the drug is also specified for each analytical method.

| Assay | Column | Mobile Phase | Flow rate (mL/min) | Wavelength (nm) | Retention time of APIs (min) |
|---|---|---|---|---|---|
| 5) KET, BROM | Gracesmart R18, 5 µm, 150 × 4.6 mm | Acetonitrile:water:triethylamine 45:55:06 pH 3 | 1.0 | KET: 313 Brom: 227 | KET: 3.60 Brom: 7.50 |
| 6) LVX/DCF | Phenomenex Kinetex EVO C18 Column 150 × 4.6 mm; 5 µm, 100 Å | Mobile phase A Acetonitrile:water:Formic Acid 15:85:005 Mobile phase B Acetonitrile:water:Formic Acid 60:40:005 | 1.0 | LVX: 290 DCF: 275 | LVX: 1.60 DCF: 12.7 |
| 7) LVX/KET | Gracesmart R18, 5 µm, 150 × 4.6 mm | Mobile phase A Acetonitrile:water:Formic Acid 15:85:005 Mobile phase B Acetonitrile:water:Formic Acid 60:40:005 | 1.0 | LVX: 290 KET: 313 | LVX: 6.0 KET: 10.80 |

The following table shows the amount of release of levofloxacin from polytriazole conjugates of levofloxacin, moxifloxacin, besifloxacin and gatifloxacin. The release experiment was conducted according to the method described above. A known sample of material was placed in 15.0 ml of isotonic phosphate buffer (pH 7.4, 37° C.) for release period. The amount of drug released was determined by means of HPLC according to methods described above.

| | Fluoroquinolone | Sample Amount (mg) | Release Period (days) | Amount Released (µg) | Average Release Rate for period (µg/10 mg/24 hours) | Percentage of Theoretical Drug Load Released |
|---|---|---|---|---|---|---|
| 38 | Levofloxacin | 14.16 | 5 | 1464 | 206.7 | 45.8 |
| 40 | | 12.39 | 4 | 3111 | 627.7 | 72.4 |
| 29 | | 9.39 | 8 | 185 | 24.6 | 5.8 |
| 170 | Moxifloxacin | 13.36 | 5.8 | 2232 | 288.0 | 44.9 |
| 134 | Besifloxacin | 9.04 | 7.8 | 173 | 24.5 | 6.4 |
| 135 | | 16.04 | 7.8 | 93.5 | 7.5 | 2.1 |
| 133 | Gatifloxacin | 6.94 | 7.8 | 1441 | 266.2 | 73.5 |
| 145 | | 13.63 | 3 | 402 | 98.3 | 18.3 |

Drug Release Method

Polytriazole conjugates of the invention were tested for in vitro drug release following guidelines recommended by the International Organisation of Standardisation. A known mass of each sample was suspended on a wire mesh, immersed in 0.067 M isotonic phosphate buffer (IPB) pH 7.4 and incubated at 37° C. with continuous stirring.

Aliquots of the receptor solution were collected for HPLC analysis at predetermined time points and replaced with an equal volume IPB. The experimental endpoint was reached when cumulative amount of levofloxacin released remained unchanged (within a margin of error) for at least three time points.

The following table outlines the sample weight for polytriazole conjugate tested.

| Examples | Sample Weights (mg) |
|---|---|
| 29 | 9.39 |
| 30 | 9.82 |
| 31 | 9.68 |
| 32 | 10.34 |
| 38 | 14.16 |
| 39 | 18.21 |
| 40 | 12.39 |
| 41 | 16.58 |
| 42 | 15.87 |
| 43 | 16.65 |
| 170 | 13.63 |
| 133 | 6.94 |
| 145 | 13.63 |
| 134 | 9.04 |
| 135 | 16.4 |
| 108 | 11.49 |
| 112 | 8.86 |
| 113 | 9.01 |
| 102 | 9.6 |
| 116 | 17.07 |
| 119 | 13.9 |
| 122 | 12.03 |
| 127 | 2.65 |
| 36 | 17.4 |
| 37 | 17.3 |
| 109 | 12.13 |
| 110 | 10.49 |
| 111 | 13.28 |
| 118 | 11.68 |
| 114 | 10.96 |
| 164 | 12.07 |
| 166 | 10.08 |

The invention claimed is:

1. A polymer-bioactive agent conjugate comprising:
    a polymer backbone comprising a plurality of triazole moieties; and
    a plurality of releasable bioactive agents covalently bonded to and pendant from the polymer backbone via a cleavable ester group,
    wherein the bioactive agent are selected from quinolone, NSAIDs, and mixtures thereof.

2. A polymer-bioactive agent conjugate according to claim 1, having a backbone comprising a plurality of moieties of formula (I):

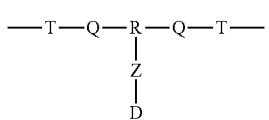 (I)

where:

T represents a triazole moiety;

Q is independently selected at each occurrence and may be present or absent and when present represents a linking group;

R is selected from the group consisting of optionally substituted linear or branched hydrocarbon and optionally substituted aromatic or heteroaromatic hydrocarbon;

Z is a cleavable linking group forming an ester with the bioactive agent; and

D is the bioactive agent selected from quinolones and NSAIDs.

3. A polymer-bioactive agent conjugate according to claim 2, wherein the polymer backbone comprises at least one moiety selected from formula (IIa), (IIb) and (IIIa) and (IIIb):

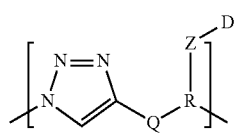 (IIa)

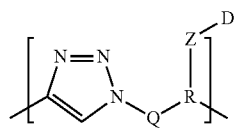 (IIb)

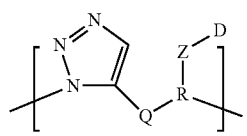 (IIIa)

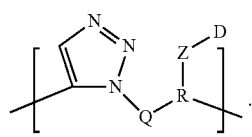 (IIIb)

4. A polymer-bioactive agent conjugate according to claim 2, wherein the quinolone analogue is conjugated to the polymer backbone via an ester linking group formed with the carboxylic acid of at least one of the quinolone and NSAID active agents.

5. A polymer-bioactive agent conjugate according to claim 4, wherein the bioactive agent comprises a plurality of quinolones conjugated to the polymer backbone via at least one ester group selected from alkyl ester, aryl ester, (acyloxy)alkyl ester, and [(aryloxycarbonyl)oxy]alkyl ester linking groups.

6. A polymer-bioactive agent conjugate according to claim 5, wherein the bioactive agent is selected from quinolone antibiotics of formula (Xi) or (Xii):

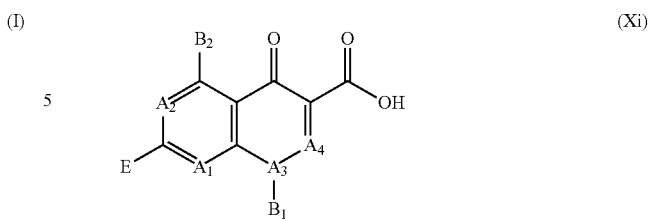

wherein:

A$_1$ is selected from N or —CY$_1$— where Y$_1$ is hydrogen, halogen, alkyl, haloalkyl, —O— alkyl, halo(C$_1$ to C$_4$alkoxy), —S-alkyl, nitrile, an amine, an amino radical, NO$_2$, and the group wherein Y$_1$ forms a bridge with B$_1$;

A$_2$ is selected from N or —CY$_2$— where Y$_2$ is selected from hydrogen, halogen, alkyl, —O— alkyl, —S-alkyl, an amine, an amino radical, NO$_2$ and the group wherein Y$_2$ forms a bridge with E;

A$_3$ is selected from N or —C—;

A$_4$ is selected from N, —CB$_3$ wherein B$_3$ is H or together with B$_1$ forms a bridge —B$_3$—B$_1$— wherein B$_3$ is —S— and B$_1$ is —CH(B$_4$)— where B$_4$ is H or methyl;

B$_1$ is selected from hydrogen, alkyl, substituted alkyl, optionally substituted cycloalkyl, aryl, substituted aryl, heteroaryl, substituted heteroaryl; —O-alkyl; and wherein B$_1$ may form a bridge with A$_1$ or, when A$_4$ is CB$_3$, a bridge with B$_3$, wherein in the bridge —B$_3$—B$_1$— the group B$_3$ is —S— and B$_1$ is —CH (B$_4$)— where B$_4$ is H or methyl;

B$_2$ is hydrogen, halogen, —OH, —CH$_3$, or an amino radical;

E is selected from hydrogen; halogen; alkyl; optionally substituted aryl; alkoxy; amino radical; and the group wherein A$_2$ forms a bridge with E.

7. A polymer-bioactive agent conjugate according to claim 6, wherein the quinolone antibiotics are of formula Xi wherein A$_3$ is N and A$_2$ is —CY$_2$— wherein Y$_2$ is fluoro.

8. A polymer-bioactive agent conjugate according to claim 2, wherein the active agent is a quinolone selected from alatrofloxacin, amifloxacin avarofloxacin, balofloxacin, besifloxacin, cadazolid, cinoxacin, ciprofloxacin clinafloxacin, danofloxacin, delafloxacin, dextrofloxacin, difloxacin, DS-8587, enoxacin, enrofloxacin, finafloxacin, fleroxacin, flumequine, garenoxacin, gatifloxacin, gemifloxacin, grepafloxacin, ibafloxacin, KRP AM1977X, KRP-AM1977Y, levofloxacin, lomefloxacin, marbofloxacin, miloxacin, moxifloxacin, nadifloxacin, (S)-nadifloxacin (WCK771), nalidixic acid, nemonoxacin, norfloxacin, ofloxacin, orbifloxacin, oxolinic acid, ozenoxacin, pazufloxacin, pefloxacin, pipemidic acid, piromidic acid, pradofloxacin, prulifloxacin, rosoxacin, rufloxacin, sarafloxacin, sitafloxacin, sparfloxacin, temafloxacin, tosufloxacin, trovafloxacin, ulifloxacin, WCK 2349, and zabofloxacin.

9. A polymer-bioactive agent conjugate according to claim 2, wherein the active agent is a quinolone selected from besifloxacin, boc-moxifloxacin, ciprofloxacin, ofloxacin, levofloxacin ((S)-ofloxacin), dextrofloxacin ((R)-ofloxacin), gatifloxacin, and moxifloxacin.

10. A polymer-bioactive agent conjugate according to claim 2, wherein the bioactive agent comprises NSAIDs conjugated to the polymer backbone via at least one ester group selected from an alkyl ester, aryl ester, (acyloxy)alkyl ester, and [(aryloxycarbonyl)oxy]alkyl ester linking group formed with the 1-COOH moiety of the carboxylic acid NSAID.

11. A polymer-bioactive agent conjugate according to claim 10, wherein the bioactive agent is an NSAID of formula (XX)

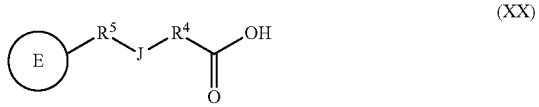

(XX)

where:
E represents an optionally substituted ring system;
J is selected from the group consisting of a bond or a functional group;
$R^4$ and $R^5$ are each independently selected from the group consisting of a bond and an optionally substituted aliphatic.

12. A polymer-bioactive agent conjugate according to claim 2, wherein D is the acid residue of a carboxylic acid NSAID selected from aceclofenac, alminoprofen, amfenac, bromfenac, carprofen, diclofenac, enfenamic acid, etodolac, flufenamic acid, meclofenamic acid, mefenamic acid, niflumic acid, tolfenamic acid, bendazac, benoxaprofen, bermoprofen, bucloxic acid, butibufen, cinmetacin, clidanac, clopirac, dexibuprofen, dexketoprofen, felbinac, fenbufen, fenclozic acid, fenoprofen, fentiazac, flunoxaprofen, flunixin, flurbiprofen, ibuprofen, indomethacin, isofezolac, isoxepac, ketoprofen, licofelone, lonazolac, loxoprofen, lumiracoxib, metiazinic acid, mofezolac, naproxen, oxaprozin, pirazolac, pirprofen, pranoprofen, protizinic acid, sulindac, suprofen, tiaprofenic acid, tolmetin, bermoprofen, bucloxic acid, isoxepac, ketoprofen, loxoprofen, zaltoprofen, balsalazide, fendosal, olsalazine, ximoprofen, mesalamine, sulfasalazine, acetylsalicylsalicylic acid, alclofenac, aspirin, benoxaprofen, 5-bromosalicylic acid acetate, cinchophen, diacerein, dipyrocetyl, fosfosal, ibufenac, indoprofen, clometacin, ketorolac, zomepirac, actarit, clonixin, salicylamide O-acetic acid, diflunisal, gentisic acid, and salsalate.

13. A polymer-bioactive agent conjugate according to claim 2, wherein the bioactive agent is the acid residue of a carboxylic acid NSAID selected from bromfenac, diclofenac, and ketorolac.

14. A polymer bioactive conjugate according to claim 2, wherein Z is of formula selected from the group consisting of:

(R)—O-(D); (i)

(R)-J-Ar—O-(D); (ii)

(R)-J-C1-C12alkylene-O-(D); (iii)

(R)-J-Ar-J-C1-C12alkylene-O-(D); (iv)

(R)-J-C1-C12alkylene-J-Ar—O-(D); and (v)

(R)-J-C1-C12alkylene-J-Ar-Q-C1-C12alkylene-O-(D); (vi)

wherein:
(R) indicates the end of the linking group bonded to the R group in the polymer backbone and (D) indicates the end of the linking group bonded to the quinolone drug;
Ar is optionally substituted aromatic or heteroaromatic hydrocarbon; and
J is selected from —O—, —C(O)—, —O—C(O)—, —O—C(O)—O—, —C(O)—O—, —C(O)OC(O)—, —C(O)NRaC(O)—, —OC(O)NRa—, —NRaC(O)O—, —NRa—, —NRaC(O)NRa—, —NRaC(O)—, —C(O)NRa—, —S—, —O—C(S)—, —C(S)—O—, —S—C(O)—, —C(O)—S—, —NRaC(S)—, and —C(S)NRa—,
where Ra is hydrogen or C1 to C6 alkyl.

15. A polymer-bioactive agent conjugate according to claim 1, which is a copolymer of at least one monomer of formula (IV):

(IV)

where:
X may be the same or different at each occurrence and represents a terminal functional group comprising an alkyne or an azide;
Q is independently selected at each occurrence and may be present or absent and when present, represents a linking group;
R is selected from the group consisting of optionally substituted linear or branched hydrocarbon and optionally substituted aromatic or heteroaromatic hydrocarbon;
Z is a cleavable linking group forming an ester with the bioactive agent; and
D is a bioactive agent selected from the group consisting of quinolones and NSAIDs;
and a monomer of formula (V):

A-L-[-A]$_n$ (V)

where:
A may be the same or different at each occurrence and represents a group comprising a terminal functional group comprising an alkyne or an azide functionality, wherein said terminal functional group is complementary to the terminal functional group of X;
L is an optionally substituted linker group; and
n is an integer and is at least 1.

16. A polymer-bioactive agent conjugate according to claim 15, wherein in the monomer of formula (V), L comprises a linker moiety selected from optionally substituted linear or branched aliphatic hydrocarbon, optionally substituted carbocyclyl, optionally substituted heterocyclyl, optionally substituted aryl, optionally substituted heteroaryl, and an optionally substituted polymeric segment.

17. A polymer-bioactive agent conjugate according to claim 15, wherein in the monomer of formula (V), L comprises a polymer selected from a polyether, a polyester, a polyurethane, and copolymers thereof.

18. A polymer-bioactive agent conjugate according to claim 15, wherein in the monomer of formula (V), n is 2 or 3.

19. A polymer-bioactive agent conjugate according to claim 15, wherein the monomer of formula (V), L comprises a functional group selected from the group consisting of an amide, ether, ester, urethane, urea, and carbonate ester.

20. A polymer-bioactive agent conjugate according to claim 15, wherein in the monomer of formula (IV), Q is present and each Q-X is independently selected from:

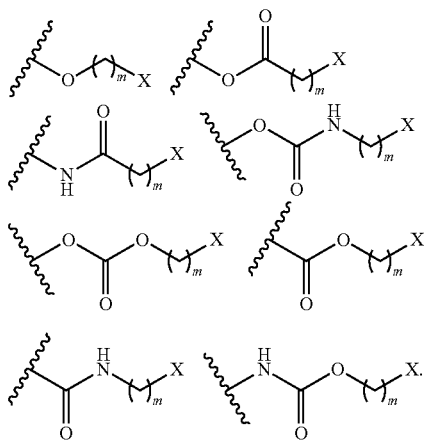

21. A polymer-bioactive agent conjugate according to claim 15, wherein in the monomer of formula (IV), each Q-X is a group of formula (VII):

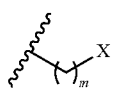

where:

X is a terminal functional group comprising an alkyne or an azide functionality; and m is an integer in the range of from 0 to 10.

22. A polymer-bioactive agent conjugate according to claim 15, wherein in the monomer of formula (IV), R is selected from the group consisting of optionally substituted linear or branched hydrocarbon having from 1 to 12 carbon atoms and

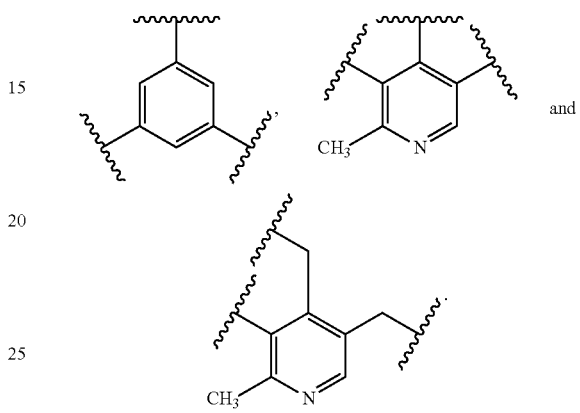

23. A polymer-bioactive agent conjugate according to claim 15, wherein L comprises a polyether linker moiety derived from polyethylene glycol.

24. The polymer-bioactive agent conjugate of claim 23 wherein the polyethylene glycol has a molecular weight in the range of 200 to 3000.

* * * * *